(12) United States Patent
Matharu

(10) Patent No.: US 11,460,406 B2
(45) Date of Patent: Oct. 4, 2022

(54) METHOD FOR IDENTIFYING AND TREATING CANCER

(71) Applicant: Maninder Singh Matharu, Las Vegas, NV (US)

(72) Inventor: Maninder Singh Matharu, Las Vegas, NV (US)

(*) Notice: Subject to any disclaimer, the term of this patent is extended or adjusted under 35 U.S.C. 154(b) by 628 days.

(21) Appl. No.: 16/503,635

(22) Filed: Jul. 5, 2019

(65) Prior Publication Data

US 2021/0003507 A1    Jan. 7, 2021

(51) Int. Cl.
*G01N 21/64* (2006.01)
*C12N 15/82* (2006.01)
*C07K 14/47* (2006.01)

(52) U.S. Cl.
CPC ..... *G01N 21/6486* (2013.01); *C12N 15/8212* (2013.01)

(58) Field of Classification Search
None
See application file for complete search history.

(56) References Cited

PUBLICATIONS

Faust N, et al. Insertion of Enhanced Green Fluorescent Protein into the Lysozyme Gene Creates Mice with Green Fluorescent Granulocytes and Macrophages. Blood, Jul. 15, 2000, vol. 96 No. 2, pp. 719-726.
Abbasi Meysam, et al. Recent Attempts at RNAi-Mediated P-Glycoprotein Downregulation for Reversal of Multidrug Resistance in Cancer. Medicinal Research Reviews Apr. 26, 2010, vol. 33 No. 1 pp. 33-53.
Doceul V, et al. Repulsion of Superinfecting Virions: A Mechanism for Rapid Virus Spread. Science, Feb. 12, 2010, vol. 327(5967), pp. 873-876.

*Primary Examiner* — Suzanne M Noakes
*Assistant Examiner* — Jae W Lee
(74) *Attorney, Agent, or Firm* — Bayramoglu Law Offices LLC

(57) ABSTRACT

A new system for identification and treatment against cancer, specifically the mutation or deletion of an antioncogene. An ideal candidate is a patient with family history for hereditary mutations in a known antioncogene. The first method of this system identifies the mutation of a patient's at-risk antioncogene by causing a natural fluorescence only when the specific at-risk antioncogene has mutated or deleted. The second method of this system utilizes a virus to attack and dissolve cancer cells with special markers to avoid the damage to normal cells, thereby achieving the purpose of treating cancer.

4 Claims, 2 Drawing Sheets

Specification includes a Sequence Listing.

| 1 | A fluorescent gene is added to a genome in normal cells to express a fluorescent protein. 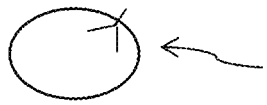 |

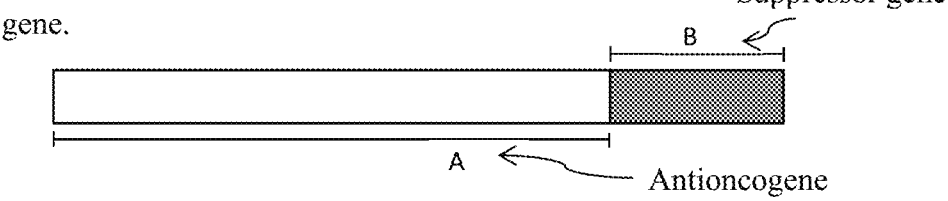

| 2 | A suppressor gene is added adjacent to an antioncogene to suppress the fluorescent gene. |

Normal cell (+fluorescent gene+ suppressor gene)

| 3 | The antioncogene deteriorates, so does the suppressor gene. |

| 4 | The fluorescent protein is expressed on the cancer cells, but not on the normal cells with an antioncogene intact. |

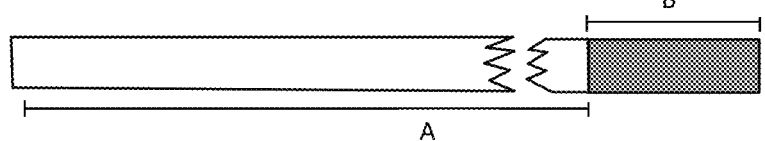

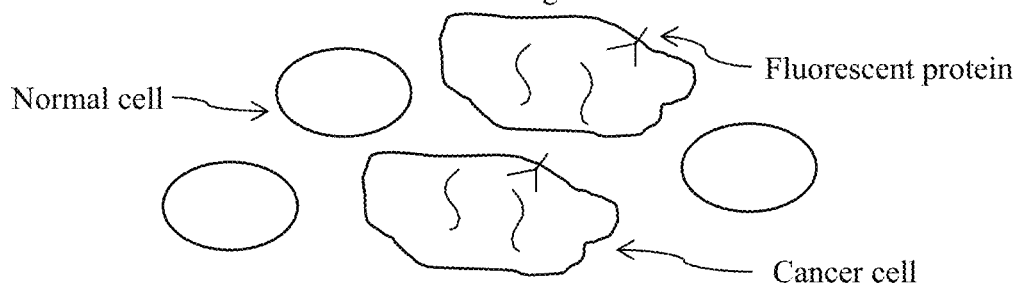

| 5 | The fluorescent protein is detected for identification of a cancer. |

FIG. 1

1. An actin tail is expressed in normal cells, via addition to an at-risk antioncogene.

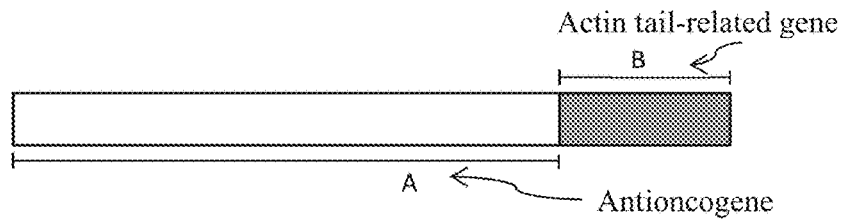
Actin tail-related gene
B
A
Antioncogene

2. The antioncogene deteriorates, so does the actin tail-related gene.

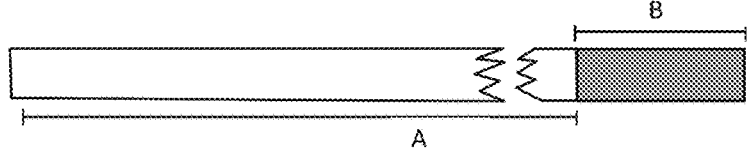
B
A

3. The actin tail is no longer expressed on the cancer cells, but stays expressed on normal cells with an antioncogene intact.

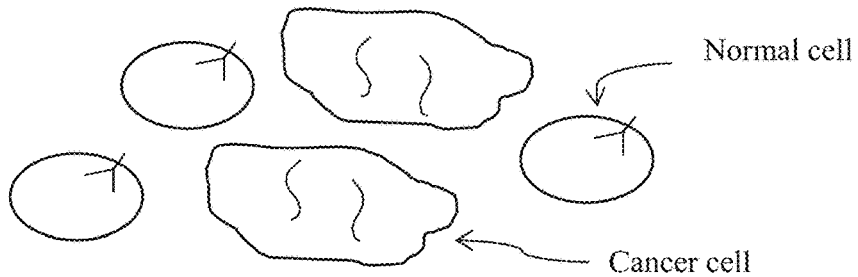
Normal cell

Cancer cell

4. Viruses with actin tail-skipping are administered to avoid damage to most normal cells.

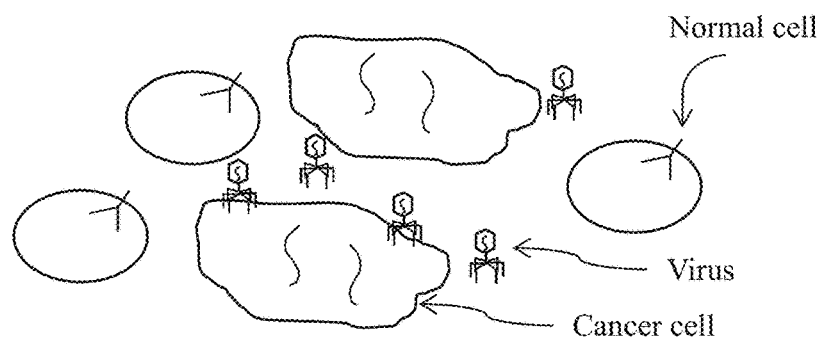
Normal cell

Virus

Cancer cell

5. Once the cancer cells are reduced via viral therapy and chemotherapy, immune boosters are added to help flush out the viruses.

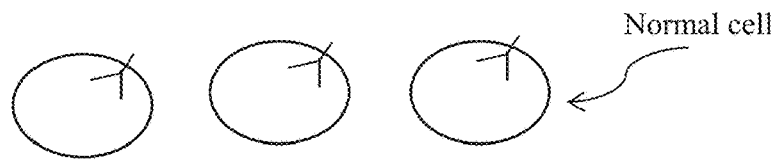
Normal cell

FIG. 2

METHOD FOR IDENTIFYING AND TREATING CANCER

TECHNICAL FIELD

The present invention relates to the field of cancer therapy, and specifically relates to a method for identifying and treating a cancer.

BACKGROUND

DNA, or deoxyribonucleic acid, is the hereditary material that lies within the nucleus of all cells in humans and other living organisms. Nearly every cell in a person's body has the same DNA. Genes, made up of DNA, act as instructions to make molecules called proteins, among other things, cell surface proteins. It is now feasible to manipulate genetic code, and thereby alter protein expression.

DNA genetic manipulation involves scientific procedures to add new DNA to or silence gene sequences in an organism. In general, DNA manipulation includes the following four steps:

(1) Gene identification;
(2) Coding of desired gene;
(3) Gene transfer into genome: via biolistic gene-gun, $CaPO_4$, dendrimers, lipsoma, cationic polymer, electroporation, cell squeezing, sonoporation, optical transfection, protoplast fusion, impalefection, nydrodynamic delivery, magnetofection, nucleofection, or viral transduction; and
(4) Incorporation. Gene splicing is used in the DNA manipulation, mainly including the steps of chemically snipping out sequences of DNA and adding new DNA.

The location of the genome into which a gene is placed is important for the context of this application. If a newly inserted "Gene Z" is inserted adjacent "Gene A" via, for example, zinc finger insertion, then naturally whatever happens to "Gene A" has a very high likelihood of happening to "Gene Z". If Gene A is mutated, deleted, or even enhanced in transcription, it is very likely that Gene Z will experience the same effect. However, if Gene Z is placed far away from Gene A, then naturally the two will have no relationship with each other. The co-regulation of adjacent genes will be utilized significantly in this application.

For the purpose of this application, it is important to give a preface on the finality of fluorescent labeling in scientific studies. Using fluorescent genes, such as Green Fluorescent Protein (GFP) gene and inserting them into genomes of cells in order to study them is a hallmark of many scientific studies. For example, after inserting the GFP gene into a genome, a cell will become fluorescent. This allows researchers to measure the quantities of that specific type of cell, by measuring the presence of GFP visualized. More details can be found in: Faust N, Varas F, Kelly L M, et al. Insertion of enhanced green fluorescent protein into the lysozyme gene creates mice with green fluorescent granulocytes and macrophages[J]. Blood, 2000, 96(2):719. Further, GFP can be suppressed by RNAi; inhibitory small RNA molecules that the body naturally uses in order to suppress genes. The insertion of sequence-specific RNAi into the genome is an important tactic used by contemporary scientists for both research and treatments alike. In this application, RNAi suppression will be used to suppress GFP. More details can be found in: Abbasi, Meysam, Afsaneh Lavasanifar, and Hasan Uluda, "Recent attempts at RNAi-mediated P-glycoprotein downregulation for reversal of multidrug resistance in cancer." *Medicinal research reviews* 33.1 (2013): 33-53.

In recent years, studies have found that vaccinia virus spreads throughout the body faster than one might expect. An explanation is that the vaccinia virus has evolved a mechanism by which infected cells repel vaccinia virions on actin tails toward neighboring cells: if the neighboring cell is uninfected, the virion enters and starts a new cycle of replication. Alternatively, if the cell is already infected then the infection is blocked, and a new actin tail is formed, propelling the virus further away until it reaches uninfected cells. Due to their capability to "skip over", and therefore not waste time on cells that have already been infected, vaccinia virus spreads across one cell faster than its replication cycle would permit. More details can be found in: Doceul V, Hollinshead M, Van d L L, et al. Repulsion of Superinfecting Virions: A Mechanism for Rapid Virus Spread[J]. Science, 2010, 327(5967):873-876. The actin tail left by the vaccinia will be referred to as the "skip protein" further in this application. Currently, the non-fatal vaccinia virus has been studied for this trait. It is very likely other viruses, especially those closely related to vaccinia, exhibit this same trait. The genes that can encode proteins to affect the formation of the actin tail includes:

A33R
The A33R gene encodes a protein A33 in vaccinia virus (strain Western Reserve) (VACV) (Vaccinia virus (strain WR)). The protein A33 Coordinates the incorporation of A36 into wrapped enveloped virion (EV) membranes and, subsequently, the production of actin tails. Therefore plays an essential role in efficient cell-to-cell spread of viral particles. The protein A33 has an amino acid sequence as shown in SEQ ID NO: 1.

A36R

The A36R gene encodes a protein A36 in vaccinia virus (strain Western Reserve) (VACV) (Vaccinia virus (strain WR)). The protein A36 is nvolved in the intracellular transport of virions to the host cell surface. Participates also in the formation of actin tails at the plasma membrane to allow efficient actin-based motility and thus cell to cell transmission of viral particles. Recruits host intersectin-1/ITSN1 and activates host CDC42 to drive ARP2/3-mediated actin polymerization. The protein A36 has an amino acid sequence as shown in SEQ ID NO: 2.

A common trait in all cancer cells is the deterioration of genetic material. In some cancers, the deterioration of a specific gene can be a sign indicative of cancer. In others, there are ranges of genes that have a strong corruptibility if a patient has cancer. Some genetic defects are inheritable; if a patient has a defect in a specific gene which causes cancer, a physician may recommend that the patients' child also get tested on that gene. A defective/cancerous gene could be derived due to the following: (1) Inheritance of faulty gene; (2) Destruction of gene via mutation or deletion of the gene; (3) Inheritance of traits that make it more likely for the destruction of gene to happen.

If a patient presents with a specific type of cancer, it is reasonable to assume there was damage to a foreknown antioncogene. An "antioncogene" is a gene that is critical to cell replication and DNA stability. An "Oncogene" is the mutated and defective iteration of the antioncogene. Oncogenes are responsible for the formation of cancer, as the result in unstoppable proliferation and misfunction of cells. In the beginning, cancers are localized to a specific part of the body and to a specific cell type. For example, if a patient has a mutation or deletion of an antioncogene, the malfunction of the antioncogene means a potential for cancer in whichever cells the antioncogene has malfunctioned.

The mutation or deletion of an antioncogene often has a significantly high level of genetic inheritance. This is how patients will be selected for the application of this method. All of the following are "risk genes/antioncogenes" (genes that, if damaged, increase the likelihood of cancer). These are common antioncogenes that are at risk for deterioration, but not all antioncogenes are listed below. The below will serve as examples for treatment.

BRCA1
Repairs DNA. A human gene. This gene encodes a nuclear phosphoprotein that plays a role in maintaining genomic stability, and it also acts as a tumor suppressor. The encoded protein combines with other tumor suppressors, DNA damage sensors, and signal transducers to form a large multi-subunit protein complex known as the BRCA1-associated genome surveillance complex (BASC). This gene product associates with RNA polymerase II, and through the C-terminal domain, also interacts with histone deacetylase complexes. This protein thus plays a role in transcription, DNA repair of double-stranded breaks, and recombination. Mutations in this gene are responsible for approximately 40% of inherited breast cancers and more than 80% of inherited breast and ovarian cancers. Alternative splicing plays a role in modulating the subcellular localization and physiological function of this gene. Many alternatively spliced transcript variants, some of which are disease-associated mutations, have been described for this gene, but the full-length natures of only some of these variants has been described. Females with a mutation of this gene have up to an 80% risk of developing breast cancer by age 90, 55% increased chance for developing ovarian cancer. If a female has breast cancer, there is a 1 out of 10 chance that it is due to BRCA1 or BRCA2 mutations. The human BRCA1 gene includes a wild type allele having a sequence shown in SEQ ID NO: 3, and the mutant alleles of the wild type allele.

BRCA2
Repairs DNA. BRCA2 is a human tumor suppressor gene (specifically, a caretaker gene), found in all humans; its protein, also called by the synonym breast cancer type 2 susceptibility protein, is responsible for repairing DNA. Females with a mutation of this gene have up to an 80% risk of developing breast cancer by age 90, 55% increased chance for developing ovarian cancer. If a female has breast cancer, there is a 1 out of 10 chance that it is due to BRCA1 or BRCA2 mutations. The human BRCA2 gene includes a wild type allele having a sequence shown in SEQ ID NO: 4, and the mutant alleles of the wild type allele.

MSH2
DNA Mismatch repair gene in humans. The MSH2 gene encodes a DNA mismatch repair protein Msh2 also known as MutS protein homolog 2 or MSH2 in humans, which is located on chromosome 2. MSH2 is a tumor suppressor gene and more specifically a caretaker gene that codes for a DNA mismatch repair (MMR) protein, MSH2, which forms a heterodimer with MSH6 to make the human MutSα mismatch repair complex. It also dimerizes with MSH3 to form the MutSβ DNA repair complex. MSH2 is involved in many different forms of DNA repair, including transcription-coupled repair, homologous recombination, and base excision repair. Mutations in this gene account for 40% of Hereditary nonpolyposis colorectal cancer (aka Lynch Syndrome) which is inherited in an autosomal dominant fashion. The human MSH2 gene includes a wild type allele having a sequence shown in SEQ ID NO: 5, and the mutant alleles of the wild type allele.

TP53
This is a tumor suppressor gene in humans. The TP53 gene is the most frequently mutated gene (>50%) in human cancer, indicating that the TP53 gene plays a crucial role in preventing cancer formation. TP53 gene encodes proteins that bind to DNA and regulate gene expression to prevent mutations of the genome. It is extremely important for this gene to be functional. More than 50% of human tumors contain a mutation/deletion of the TP53 gene. The human TP53 gene includes a wild type allele having a sequence shown in SEQ ID NO: 6, and the mutant alleles of the wild type allele.

Currently, cancer targeted therapy has become a research hotspot, which is one of the major modalities of medical treatment (pharmacotherapy) for cancer, others being hormonal therapy and cytotoxic chemotherapy. Contemporary treatment of cancer, such as chemotherapy, is extremely harmful to the human body as it is very difficult to specifically target cancer while avoiding the remainder of the body. Contemporary treatment also has other drawbacks: firstly, it cannot eradicate cancer, as cancer cells develop resistance; further, when cancer cells have metastasized, the targeted therapy is almost ineffective.

While it is possible to detect cancer overall through many biological markers, there is no universal procedure to measure the presence of any one specific type of cancer.

SUMMARY

The present invention provides a Preparative/Realized system which uniquely changes cancer treatment as it prepares the body genetically prior to the occurrence of cancer, and later creates an effective platform for targeting and termination of cancer cells, including a Preparative phase and a Realized phase with a co-dependent relation to each other; wherein Firstly, the Preparative phase includes a normal cell, antioncogene, a marker-related gene that can express a marker protein directly or express a protein to effect a formation of a marker protein, and a gene transfection method, wherein the marker-related gene is inserted into a genome of the normal cell containing the antioncogene by the gene transfection method in an expressive state or in a suppressive state, once the antioncogene deteriorates, the marker-related gene stops expressing the marker protein or expressing the protein to effect the formation of the marker protein if the marker-related gene is preset in the expressive state, or expresses the marker protein or expressing the protein to effect the formation of the marker protein if the marker-related gene is preset in the suppressive state. In the Preparative phase, the patient is identified to be at risk for deterioration of the known antioncogene, (such as BRCA1/2). As the deterioration of many antioncogenes have a model of genetic inheritance, this is determined by family history. Then a variety of gene transfer and modifications take place via the defined methods of transfer and modification below. These modifications prepare the patient and supervising physician for the possibility of cancer via providing easier detection and facilitating a significantly more effective treatment if the known antioncogene deteriorates.

Secondly, the Realized phase comprises a detecting method, wherein, if the marker-related gene is preset in the expressive state, once the marker protein is not detected by the detecting method, the normal cell turns into the cancer cell, and the cancer cell is caused by the deterioration of the antioncogene; or, if the marker-related gene is preset in the suppressive state, once the marker protein is detected by the detecting method, the normal cell turns into the cancer cell, and the cancer cell is caused by the deterioration of the antioncogene. The Realized phase begins upon realization of the deterioration of the prepared antioncogene. Due to modifications made in the preparative phase, the physician will accurately detect that the cancer originates specifically from the deterioration of the known oncogene and no other oncogene. Then, the supervising physician will administer treatments that are only feasible if the preparative phase takes place, as they depend on the presence of certain elements in the genome which will be described further into this reading. These elements are only present if the known antioncogene deteriorates.

The present invention provided a method for identifying a cancer caused by an antioncogene, including the following steps:

step 1) identifying the antioncogene that is at a risk for mutation, wherein a deterioration of the antioncogene causes a normal cell into a cancer cell;

step 2) inserting a fluorescent gene, as a marker-related gene, into a position in a genome of a patient by a gene transfection method, wherein, the fluorescent gene causes the normal cell to produce a fluorescent protein as a fluorescent marker, the position is different from a position of the antioncogene, and step 2) is performed immediately when the patient is determined to have the risk for the deterioration of the antioncogene;

step 3) inserting a suppressor gene adjacent to the antioncogene in the genome by the gene transfection method, wherein the suppressor gene suppresses the fluorescent gene; and step 4) performing a regular screen for a presence of the fluorescent marker in the patient; wherein the fluorescent marker is detected in the patient when the normal cell turns into the cancer cell, and the cancer cell is caused by the deterioration of the antioncogene.

Further, the antioncogene is at least one gene selected from the group consisting of human BRCA1, human BRCA2, human MSH2, human TP53, etc.

Further, the gene transfection method in step 2) is one or more gene transfer method selected from the group consisting of biolistic gene-gun, $CaPO_4$, dendrimers, liposma, cationic polymer, electroporation, cell squeezing, sonoporation, optical transfection, protoplast fusion, impalefection, nydrodynamic delivery, magnetofection, nucleofection, viral transduction, etc.

Further, the fluorescent gene in step 2) is Green Fluorescent Protein (GFP) gene.

The present invention further provided a method for treating a cancer caused by an antioncogene, including the following steps:

step 1) identifying the antioncogene that is at a risk for mutation, wherein a deterioration of the antioncogene causes normal cells of a patient into cancer cells; for example, certain antioncogenes, such as BRCA1 and BRCA2, have a very strong genetic link and patients with a family history of mutations in these antioncogenes are ideal candidates;

step 2) inserting at least one marker-related gene adjacent to the antioncogene in the normal cells by a gene transfection method, wherein the gene transfection method is performed immediately when the patient is determined to have the risk for the deterioration of the antioncogene, and as the antioncogene deteriorates, the at least one marker-related gene also deteriorates; the at least one marker-related gene express a marker protein directly or express a protein for a formation of a marker protein; if the at least one marker-related gene includes more than two genes, the more than two genes are placed beside each other in order to produce the marker protein.

step 3) when the marker protein is detected not to express on the cancer cells, administering a virus to attack and dissolve the cancer cells without the marker protein, wherein the normal cells are not attacked by the virus because the normal cells have the marker protein; and step 4) once the cancer cells are killed and decreased, implementing combination with chemotherapy and adding immune boosters to help flush out the virus.

Further, the antioncogene is at least one gene selected from the group consisting of human BRCA1, human BRCA2, human MSH2, human TP53, etc.

Further, the gene transfection method in step 2) is one gene transfer method selected from the group consisting of biolistic gene-gun, $CaPO_4$, dendrimers, lipsoma, cationic polymer, electroporation, cell squeezing, sonoporation, optical transfection, protoplast fusion, impalefection, nydrodynamic delivery, magnetofection, nucleofection, viral transduction, etc.

Further, the at least one marker-related gene in step 2) is a gene expressing a protein for a formation of an actin tail, the marker protein is the actin tail, and the virus attacks the cancer cells without the actin tail.

Furthermore, the at least one marker-related gene includes two genes of A33R encoding a protein A33 having an amino acid sequence shown in SEQ ID NO: 1 and A36R encoding a protein A36 having an amino acid sequence shown in SEQ ID NO: 2, and the two genes are placed beside each other in order to produce the actin tail.

Further, the virus in step 3) is vaccinia virus.

The beneficial effects of the present invention are as follows:

1. The method for identifying cancer provided by the present invention includes a gene insertion in order to accurately and immediately identify if there is a mutation of the antioncogene of concern. Therefore, measuring the presence of the specific type of cancer caused by the specific antioncogene is realized. This makes it possible for the supervising physician to confidently say not only that the patient has cancer, but that the patient has cancer in the known antioncogene. This results in a fast and extremely accurate method of identification of cancer and is unique in that it is the only procedure able to accurately state that the cancer has arrived from a specific gene.

2. The method for treating cancer provided by the present invention utilizes a virus to attack and dissolve cancer cells with special markers to avoid the damage to normal cells, thereby achieving the purpose of treating cancer.

BRIEF DESCRIPTION OF THE DRAWINGS

FIG. 1 is a flow diagram of a method for identifying a cancer caused by an antioncogene according to embodiment 1 in the present invention; and FIG. 2 is a flow diagram of a method for treating a cancer caused by an antioncogene according to embodiment 2 in the present invention.

DETAILED DESCRIPTION

As used in this specification and the appended claims, the singular forms "a", "an" and "the" include plural referents unless the context clearly indicates otherwise. Thus, for example, reference to "a protein" includes more than one protein, and reference to "a virus" includes more than one virus.

It is further to be understood that use of "or" means "and/or" unless stated otherwise. Similarly, "comprise," "comprises," "comprising" "include," "includes," and "including" are interchangeable and not intended to be limiting. Also, where descriptions of various embodiments use the term "comprising," those skilled in the art would understand that in some specific instances, an embodiment can be alternatively described using language "consisting essentially of" or "consisting of."

The foregoing general description, including the drawings, and the following detailed description are exemplary and explanatory only and are not restrictive of the present invention. The section headings used herein are for organizational purposes only and not to be construed as limiting the subject matter described.

Definitions

In reference to the present invention, the technical and scientific terms used in the descriptions herein will have the meanings commonly understood by one of ordinary skill in the art, unless specifically defined otherwise. Accordingly, the following terms are intended to have the following meanings:

"Gene" as used herein refers to a nucleic acid region, also referred to as a transcribed region, which expresses a polynucleotide, such as an RNA. The transcribed polynucleotide can have a sequence encoding a polypeptide, such as a functional protein, which can be translated into the encoded polypeptide when placed under the control of an appropriate regulatory region. A gene may comprise several operably linked fragments, such as a promoter, a 5' leader sequence, a coding sequence and a 3' nontranslated sequence, such as a polyadenylation site. A chimeric or recombinant gene is a gene not normally found in nature, such as a gene in which, for example, the promoter is not associated in nature with part or all of the transcribed DNA region. "Expression of a gene" refers to the process wherein a gene is transcribed into an RNA and/or translated into a functional protein.

"Gene transfer" refers to methods for introduction of recombinant or foreign DNA into host cells. The transferred DNA can remain non-integrated or preferably integrates into the genome of the host cell. Gene transfer can take place for example by transduction, using viral vectors, or by transformation of cells, using known methods, such as electroporation, protoplast fusion.

"Risk gene" refers to the antioncogene that the patient has a family history of mutations of.

"Therapeutically effective amount" refers to an amount effective, at dosages and for periods of time necessary, to achieve the desired therapeutic result. A therapeutically effective amount of a vaccinia virion or pharmaceutical composition may vary according to factors such as the disease state, age, sex, and weight of the individual, and the ability of the vaccinia virion or pharmaceutical composition to elicit a desired response in the individual. Dosage regimens may be adjusted to provide the optimum therapeutic response. A therapeutically effective amount is also typically one in which any toxic or detrimental effects of the vaccinia virion or pharmaceutical composition are outweighed by the therapeutically beneficial effects.

"Deterioration" of a gene refers to the mutation or deletion of that gene.

"Skip protein" refers to the actin tail that will tell the vaccinia virus to skip that cell and instead infect a cell not presenting this skip protein.

"Patient" refers to a mammal, such as a non-primate (e.g., cow, pig, horse, cat, dog, rat, etc.) or a primate (e.g., monkey or human). Preferably, the mammal is a domesticated animal, such as a dog, a cat, a mouse, a cow, a sheep, a goat, a horse, a pig, or a human subject. In some embodiments, the human is an adult patient. In some embodiments, the human is a pediatric patient.

"Deterioration" or "deteriorate" as used herein refers to damage, harm, lost or destroy of a structure and function of the described gene in the present invention.

"Gene transfection method" refers to a transfection method such as gene-gun, $CaPO_4$, dendrimers, lipsoma, cationic polymer, electroporation, cell squeezing, sonoporation, optical transfection, protoplast fusion, impalefection, nydrodynamic delivery, magnetofection, nucleofection, viral transduction, etc.

"Suppressor gene" refers to a gene that can express a protein to suppress a fluorescent protein expressed by a fluorescent gene.

"Marker-related gene" refers to a gene that can express a marker protein directly or express a protein to effect a formation of a marker protein.

The present invention provides a Preparative/Realized system which uniquely changes cancer treatment as it prepares the body genetically prior to the occurrence of cancer, and later creates an effective platform for targeting and termination of cancer cells, including a Preparative phase and a Realized phase with a co-dependent relation to each other; wherein Firstly, the Preparative phase includes a normal cell, antioncogene, a marker-related gene that can express a marker protein directly or express a protein to effect a formation of a marker protein, and a gene transfection method, wherein the marker-related gene is inserted into a genome of the normal cell containing the antioncogene by the gene transfection method in an expressive state or in a suppressive state, once the antioncogene deteriorates, the marker-related gene stops expressing the marker protein or expressing the protein to effect the formation of the marker protein if the marker-related gene is preset in the expressive state, or expresses the marker protein or expressing the protein to effect the formation of the marker protein if the marker-related gene is preset in the suppressive state. In the Preparative phase, the patient is identified to be at risk for deterioration of the known antioncogene, (such as BRCA1/2). As the deterioration of many antioncogenes have a model of genetic inheritance, this is determined by family history. Then a variety of gene transfer and modifications take place via the defined methods of transfer and modification below. These modifications prepare the patient and supervising physician for the possibility of cancer via providing easier detection and facilitating a significantly more effective treatment if the known antioncogene deteriorates.

Secondly, the Realized phase comprises a detecting method, wherein, if the marker-related gene is preset in the expressive state, once the marker protein is not detected by the detecting method, the normal cell turns into the cancer cell, and the cancer cell is caused by the deterioration of the antioncogene; or, if the marker-related gene is preset in the suppressive state, once the marker protein is detected by the detecting method, the normal cell turns into the cancer cell, and the cancer cell is caused by the deterioration of the antioncogene. The Realized phase begins upon realization of the deterioration of the prepared antioncogene. Due to modifications made in the preparative phase, the physician will accurately detect that the cancer originates specifically from the deterioration of the known oncogene and no other oncogene. Then, the supervising physician will administer treatments that are only feasible if the preparative phase takes place, as they depend on the presence of certain elements in the genome which will be described further into this reading. These elements are only present if the known prooncogene deteriorates.

The following embodiments will provide a detailed description on how to use the Preparative/Realized system of the present invention to identify or treat a cancer.

In embodiment 1, referring to FIG. 1, a method for identifying a cancer caused by an antioncogene is provided, including step 1) identifying the antioncogene that is at a risk for mutation, wherein a deterioration of the antioncogene causes a normal cell into a cancer cell; step 2) inserting a fluorescent gene, as a marker-related gene, into a position in a genome of a patient by a gene transfection method, wherein, the fluorescent gene causes the normal cell to produce a fluorescent protein as a fluorescent marker, the position of the fluorescent gene is different from a position of the antioncogene, and step 2) is performed immediately when the patient is determined to have the risk for the deterioration of the antioncogene; step 3) inserting a suppressor gene adjacent to the antioncogene in the genome by the gene transfection method, wherein the suppressor gene suppresses the fluorescent gene; and step 4) performing a regular screen for a presence of the fluorescent marker in the patient; wherein the fluorescent marker is detected in the patient when the normal cell turns into the cancer cell, and the cancer cell is caused by the deterioration of the antioncogene.

The antioncogene may be human BRCA1, human BRCA2, human MSH2, human TP53, etc.

The gene transfection method in step 2) may be biolistic gene-gun, $CaPO_4$, dendrimers, lipsoma, cationic polymer, electroporation, cell squeezing, sonoporation, optical transfection, protoplast fusion, impalefection, nydrodynamic delivery, magnetofection, nucleofection, viral transduction, etc.

The fluorescent gene in step 2) may be Green Fluorescent Protein (GFP) gene.

In embodiment 2, referring to FIG. 2, a method for treating a cancer caused by an antioncogene is provided, including step 1) identifying the antioncogene that is at a risk for mutation, wherein a deterioration of the antioncogene causes normal cells of a patient into cancer cells; for example, certain antioncogenes, such as BRCA1 and BRCA2, have a very strong genetic link and patients with a family history of mutations in these antioncogenes are ideal candidates; step 2) inserting at least one marker-related gene adjacent to the antioncogene in the normal cells by a gene transfection method, wherein the gene transfection method is performed immediately when the patient is determined to have the risk for the deterioration of the antioncogene, and as the antioncogene deteriorates, the at least one marker-related gene also deteriorates; the at least one marker-related gene express a marker protein directly or express a protein for a formation of a marker protein; if the at least one marker-related gene includes more than two genes, the more than two genes are placed beside each other in order to produce the marker protein; tep 3) when the marker protein is detected not to express on the cancer cells, administering a virus to attack and dissolve the cancer cells without the marker protein, wherein the normal cells are not attacked by the virus because the normal cells have the marker protein; and step 4) once the cancer cells are killed and decreased, implementing combination with chemotherapy and adding immune boosters to help flush out the virus.

The antioncogene may be human BRCA1, human BRCA2, human MSH2, human TP53, etc.

The gene transfection method in step 2) may be biolistic gene-gun, $CaPO_4$, dendrimers, lipsoma, cationic polymer, electroporation, cell squeezing, sonoporation, optical transfection, protoplast fusion, impalefection, nydrodynamic delivery, magnetofection, nucleofection, viral transduction, etc.

The at least one marker-related gene in step 2) may be a gene expressing a protein for a formation of an actin tail, the marker protein is the actin tail, and the virus attacks the cancer cells without the actin tail.

Further, the at least one marker-related gene includes two genes of A33R encoding a protein A33 having an amino acid sequence shown in SEQ ID NO: 1 and A36R encoding a protein A36 having an amino acid sequence shown in SEQ ID NO: 2, and the two genes are placed beside each other in order to produce the actin tail.

The virus in step 3) may be vaccinia virus.

It should be noted that while this applies to cancer, it can be applied to other diseases caused by genetic defects as well through the same mechanism of action. The above embodiments are only used to illustrate the technical solutions of the present invention, and are not intended to limit the present invention. Although the present invention has been described in detail with reference to the preferred embodiments, a person skilled in the art should understand that the present invention may be modified or equivalently substituted without departing from the spirit and scope of the present invention, which should be included within the scope of the appended claims.

What is claimed is:

1. A method for treating a cancer caused by an antioncogene, comprising the following steps:
   step 1) identifying the antioncogene that is at a risk for mutation, wherein a deterioration of the antioncogene causes normal cells of a patient into cancer cells;
   step 2) inserting at least one marker-related gene adjacent to the antioncogene in the normal cells by a gene transfection method, wherein the gene transfection method is performed immediately when the patient is determined to have the risk for the deterioration of the antioncogene, and as the antioncogene deteriorates, the at least one marker-related gene deteriorates as well; the at least one marker-related gene express a marker protein directly or express a protein for a formation of a marker protein; if the at least one marker-related gene includes more than two genes, the more than two genes are placed beside each other in order to produce the marker protein;
   step 3) when the marker protein is detected not to express on the cancer cells, administering a virus to attack and dissolve the cancer cells without the marker protein, wherein the normal cells are not attacked by the virus because the normal cells have the marker protein; and
   step 4) once the cancer cells are killed and decreased, implementing combination with chemotherapy and adding immune boosters to help flush out the virus,
   wherein the antioncogene is at least one gene selected from the group consisting of human BRCA1, human BRCA2, human MSH2, and human TP53, and
   wherein the at least one marker-related gene in step 2) is a gene expressing a protein for a formation of an actin tail, the marker protein is the actin tail, and the virus attacks the cancer cells without the actin tail.

2. The method of claim 1, wherein, the gene transfection method in step 2) is one gene transfer method selected from the group consisting of biolistic gene-gun, $CaPO_4$, dendrimers, lipsoma, cationic polymer, electroporation, cell squeezing, sonoporation, optical transfection, protoplast fusion, impalefection, nydrodynamic delivery, magnetofection, nucleofection, and viral transduction.

3. The method of claim 1, wherein, the at least one marker-related gene includes two genes of A33R encoding a protein A33 having an amino acid sequence shown in SEQ ID NO: 1 and A36R encoding a protein A36 having an amino acid sequence shown in SEQ ID NO: 2, and the two genes are placed beside each other in order to produce the actin tail.

4. The method of claim 1, wherein, the virus in step 3) is vaccinia virus.

* * * * *

SEQUENCE LISTING

```
<160> NUMBER OF SEQ ID NOS: 6

<210> SEQ ID NO 1
<211> LENGTH: 185
<212> TYPE: PRT
<213> ORGANISM: Unknown
<220> FEATURE:
<223> OTHER INFORMATION: A protein A33 encoded by the A33R gene in
      vaccinia virus (strain Western Reserve) (VACV) (Vaccinia virus
      (strain WR))
```

<400> SEQUENCE: 1

```
Met Met Thr Pro Glu Asn Asp Glu Gln Thr Ser Val Phe Ser Ala
1               5                  10                 15

Thr Val Tyr Gly Asp Lys Ile Gln Gly Lys Asn Lys Arg Lys Arg Val
            20                  25                  30

Ile Gly Leu Cys Ile Arg Ile Ser Met Val Ile Ser Leu Leu Ser Met
        35                  40                  45

Ile Thr Met Ser Ala Phe Leu Ile Val Arg Leu Asn Gln Cys Met Ser
    50                  55                  60

Ala Asn Glu Ala Ala Ile Thr Asp Ala Ala Val Ala Val Ala Ala Ala
65                  70                  75                  80

Ser Ser Thr His Arg Lys Val Ala Ser Ser Thr Thr Gln Tyr Asp His
                85                  90                  95

Lys Glu Ser Cys Asn Gly Leu Tyr Tyr Gln Gly Ser Cys Tyr Ile Leu
                100                 105                 110

His Ser Asp Tyr Gln Leu Phe Ser Asp Ala Lys Ala Asn Cys Thr Ala
            115                 120                 125

Glu Ser Ser Thr Leu Pro Asn Lys Ser Asp Val Leu Ile Thr Trp Leu
130                 135                 140

Ile Asp Tyr Val Glu Asp Thr Trp Gly Ser Asp Gly Asn Pro Ile Thr
145                 150                 155                 160

Lys Thr Thr Ser Asp Tyr Gln Asp Ser Asp Val Ser Gln Glu Val Arg
                165                 170                 175

Lys Tyr Phe Cys Val Lys Thr Met Asn
                180                 185
```

<210> SEQ ID NO 2
<211> LENGTH: 221
<212> TYPE: PRT
<213> ORGANISM: Unknown
<220> FEATURE:
<223> OTHER INFORMATION: A protein A36 econded by the A36R gene in vaccinia virus(strain Western Reserve) (VACV) (Vaccinia virus (strain WR))

<400> SEQUENCE: 2

```
Met Met Leu Val Pro Leu Ile Thr Val Thr Val Ala Gly Thr Ile
1               5                  10                  15

Leu Val Cys Tyr Ile Leu Tyr Ile Cys Arg Lys Lys Ile Arg Thr Val
            20                  25                  30

Tyr Asn Asp Asn Lys Ile Ile Met Thr Lys Leu Lys Lys Ile Lys Ser
        35                  40                  45

Ser Asn Ser Ser Lys Ser Ser Lys Ser Thr Asp Ser Glu Ser Asp Trp
    50                  55                  60

Glu Asp His Cys Ser Ala Met Glu Gln Asn Asn Asp Val Asp Asn Ile
65                  70                  75                  80

Ser Arg Asn Glu Ile Leu Asp Asp Ser Phe Ala Gly Ser Leu Ile
                85                  90                  95

Trp Asp Asn Glu Ser Asn Val Met Ala Pro Ser Thr Glu His Ile Tyr
                100                 105                 110

Asp Ser Val Ala Gly Ser Thr Leu Leu Ile Asn Asn Asp Arg Asn Glu
            115                 120                 125

Gln Thr Ile Tyr Gln Asn Thr Thr Val Val Ile Asn Glu Thr Glu Thr
130                 135                 140

Val Glu Val Leu Asn Glu Asp Thr Lys Gln Asn Pro Asn Tyr Ser Ser
```

```
            145                 150                 155                 160
Asn Pro Phe Val Asn Tyr Asn Lys Thr Ser Ile Cys Ser Lys Ser Asn
                165                 170                 175

Pro Phe Ile Thr Glu Leu Asn Asn Lys Phe Ser Glu Asn Asn Pro Phe
            180                 185                 190

Arg Arg Ala His Ser Asp Asp Tyr Leu Asn Lys Gln Glu Gln Asp His
                195                 200                 205

Glu His Asp Asp Ile Glu Ser Ser Val Val Ser Leu Val
        210                 215                 220

<210> SEQ ID NO 3
<211> LENGTH: 117143
<212> TYPE: DNA
<213> ORGANISM: Homo sapiens

<400> SEQUENCE: 3
```

| | | | | | |
|---|---|---|---|---|---|
| acggggtctc | gaaaaaagga | gaatgggatg | agaaggatat | atgggtagtg | tcatttttta | 60 |
| acttgcagat | ttcatcctag | tcttccagtt | atcgtttcct | agcactccat | gttcccaaga | 120 |
| tagtgtcacc | accccaagga | ctctctctca | ttttctttgc | ctgggccctc | tttctactga | 180 |
| ggagtcgtgg | ccttccatca | gtagaagccg | gatgttcttg | tgtccgaaat | tggtgggttc | 240 |
| ttggtctcac | tgacttcaag | aatgaagttg | cggaccctca | cggtgagtgg | tacagttctt | 300 |
| aaagatgatg | tgtccagagt | ttgttccttc | tgatgttcgg | acgtgttcag | agttacctcc | 360 |
| ttctggtgga | ttcgtggtct | cgctggcttc | aggagtgaag | ctgcagacct | tgcggtgag | 420 |
| tgttacagct | cttaaggcgg | catgtctgga | gtttgttcgt | tcctcccgtc | tggagttgtt | 480 |
| cattcctcct | ggtgggttcg | tggtctcgct | ggcttcagga | gtgaagctgc | agacctctgc | 540 |
| ggtcggtgtt | accagcagat | aaatgctatg | cggacccaaa | gagtgagcag | cagcaagatt | 600 |
| tattgcaaag | agcacaagaa | caaagcttcc | acagcgtgga | aggagaccag | agcgggttgc | 660 |
| tgctgctggc | tcaggcagcc | tgcatttttt | tttttttttt | tttttttttt | tgagatggag | 720 |
| tctccctctg | tcacccaggc | tggaatgcag | tggtgcaatc | tgggctcact | gcaagctccg | 780 |
| cctcccgggt | tcacgccatt | ctcctgcctc | aacctcccca | gtagagggga | ttacaggcac | 840 |
| ccaccaccgc | acccagctaa | tatttttgtct | ttttagtaga | gtcggggttt | cactgtgtta | 900 |
| gccaggatgg | tctcgatctc | ttgacctcgt | gatccacccc | tctaggcctc | ccaaattgct | 960 |
| gggattacag | gtgtgagcca | ctggcaccca | gcggggcagc | ctgcttttat | tcccttatct | 1020 |
| gaccccaccc | acatcctgtt | gattggtcca | ttttacagag | agctaattgg | tccgttttga | 1080 |
| cagggtgctg | attggtgcat | ttacaatccc | tgagctagat | atacacagag | tgctgattgg | 1140 |
| tgcatttaca | atcctctagc | tagacataaa | aattctccaa | gtccccacta | catttgctag | 1200 |
| acacagagca | ctgattggtg | cgtttacaaa | cctttagcta | gacacagagt | gctgattggt | 1260 |
| gcatttgcaa | accttgagct | agacacagag | cactgattgg | tgcatttaca | atccttagc | 1320 |
| tagacacaga | agttctccaa | gtgccccacca | gattagctag | atacagagtg | ctgattggtg | 1380 |
| catccccaaa | ccccaagcta | gacacagagt | gctgactggt | gcatataaaa | tcctcaggct | 1440 |
| agacataaaa | gttttccaag | tccccatctg | actcaggagc | ccagctggct | tcacctagtg | 1500 |
| gatcctgcgc | agggctgtgc | cgggcgcctg | cactcctctc | agcccttggg | cagtcgatgg | 1560 |
| gaccgggcgc | tgaggagcag | ggggcggtgc | ccgtcgggga | ggctcaggcc | acgctggagc | 1620 |
| tcacaggggt | tgggaggggg | ctcgggcatg | gcgggctgca | ggtcctgagc | cttgccctgt | 1680 |
| gcagggcggc | tggggcccgg | tgagaattca | agcggggtgc | aggcgggccg | gcagtgctgg | 1740 |

```
gggacccggc gcaccctctg cagctgctgg cccgggtgct aggcccctga ctgcccgggg    1800 ccggggtgc ggggcccgct gagcccgcgc ccacctggaa ctcgcgctgg ctggcgagcg    1860
ctgcgcgcag ccccagttcc cacacccgcc tctccctcca cacttcccccg caagcagagg   1920 gagccggctc tggcttcggc cagcccagag aggggccccc acagcgcagt ggcgggctga   1980
agggctcctc cagcacggcc agaatggacg ccaaggccga ggaggcgccg agagcgagcg   2040
agggctgcta gcacgttgtc acctcgcatt ctgaaccaca gactctccaa ctctccggcg   2100
cttttcgccc actcggtccc tcagaacacg aagggctctc tcatcctgtc actaaaacga   2160
ttagctgtcc ggagacacgg aaaaagtcgc ccctcttctt tgcaggattc ctcccttgaa   2220
cttctccaaa ccctcttagt gtgacgtgac cccaccccta gctaacccag gctgcttcct   2280
taccagcttc ccgcccctg gggaggcggc aatgcaaaga ccgtccgctg ccagctctgc    2340
cgctatctct gtggggtgaa tctaacatgg cggacaaaga cagtaactag tcccgtttct   2400
ccgcgttttc gccaagaaga ttggctctta ccacttgtcc ctcaaaacga ccaccccatt   2460
gactggtggc gattgcgtcg acggagacgg ggcaaaagca agctgaaccc gaaaaataac   2520
aaacactggg gctgaggggt ggaactacga gtgcgcagac atgggccaga gcgcatttcc   2580
cctgccccag gcaaattcgg cgctcactgc gtccccgcag gccactgacc ttacaagact   2640
acttgcccca gactcctggg gctggatggg aattgtagtc tccctaaaga gttgtacgta   2700 tcttttaag gcctagtttc tgctttcaaa atacgaaaac ataacactcc agtccataac    2760
tgttgacaag tacaagcgcg cacaggtctc caatctatcc actggatttc cgtgagaatt   2820
gtgcccgctc tggtattgga tgttcctctc cataagacta cagtttctaa ggaacactgt   2880
ggcgaagacc tttcattccg caacgcatgc tggaaataat tatttccctc cacccccca    2940 acaatcctta ttacttatat ttaccgaaac tggagacctc cattagggcg aaagagtgg    3000 gggattggga cctcttctta cgactgcttt ggacaatagg tagcgattct gaccttcgta   3060
cagcaattac tgtgatgcaa taagccgcaa ctggaagagt agaggctaga gggcaggcac   3120
tttatggcaa actcaggtag aattcttcct cttccgtctc tttccttttta cgtcatccgg   3180 gggcagactg ggtggccaat ccagagcccc gagagacgct tggctctttc tgtccctccc   3240
atcctctgat tgtaccttga tttcgtattc tgagaggctg ctgcttagcg gtagccccctt  3300 ggtttccgtg gcaacggaaa agcgcgggaa ttacagataa attaaaactg cgactgcgcg   3360
gcgtgagctc gctgagactt cctggacggg ggacaggctg tggggtttct cagataactg   3420
ggcccctgcg ctcaggaggc cttcaccctc tgctctgggt aaaggtagta gagtcccggg   3480
aaagggacag ggggcccaag tgatgctctg gggtactggc gtgggagagt ggatttccga   3540
agctgacaga tgggtattct ttgacggggg taggggcgg aacctgagag cgtaaggcg    3600 ttgtgaaccc tggggagggg ggcagtttgt aggtcgcgag ggaagcgctg aggatcagga   3660 aggggcact gagtgtccgt gggggaatcc tcgtgatagg aactgaaata tgccttgagg    3720
gggacactat gtctttaaaa acgtcggctg gtcatgaggt caggagttcc agaccagcct   3780
gaccaacgtg gtgaaactcc gtctctacta aaaatacaaa aattagccgg gcgtggtgcc   3840
gctccagcta ctcaggaggc tgaggcagga gaatcgctag aacccgggag gcggaggttg   3900
cagtgagccg agatcgcgcc attgcactcc agcctgggcg acagagcgag actgtctcaa   3960
aacaaaacaa aacaaaacaa aacaaaaaac accggctggt atgtatgaga ggatgggacc   4020
ttgtggaaga agaggtgcca ggaatatgtc tgggaagggg aggagacagg attttgtggg   4080
```

```
agggagaact taagaactgg atccatttgc gccattgaga aagcgcaaga gggaagtaga    4140
ggagcgtcag tagtaacaga tgctgccggc agggatgtgc ttgaggagga tccagagatg    4200
agagcaggtc actgggaaag gttaggggcg gggaggcctt gattggtgtt ggtttggtcg    4260
ttgttgattt tggttttatg caagaaaaag aaaacaacca gaaacattgg agaaagctaa    4320
ggctaccacc acctacccgg tcagtcactc ctctgtagct ttctctttct tggagaaagg    4380
aaaagaccca aggggttggc agcaatatgt gaaaaaattc agaatttatg ttgtctaatt    4440
acaaaaagca acttctagaa tctttaaaaa taaggacgt tgtcattagt tctttggttt     4500
gtattattct aaaaccttcc aaatcttaaa tttactttat tttaaaatga taaaatgaag    4560
ttgtcatttt ataaaccttt taaaaagata tatatatatg ttttctaat gtgttaaagt     4620
tcattggaac agaagaaat ggatttatct gctcttcgcg ttgaagaagt acaaaatgtc      4680
attaatgcta tgcagaaaat cttagagtgt cccatctggt aagtcagcac aagagtgtat    4740
taatttggga ttcctatgat tatctcctat gcaaatgaac agaattgacc ttacatacta    4800
gggaagaaaa gacatgtcta gtaagattag gctattgtaa ttgctgattt ccttaactga    4860
agaactttaa aaatatagaa aatgattcct tgttctccat ccactctgcc tctcccactc    4920
ctctcctttt caacacaaat cctgtggtcc gggaaagaca gggactctgt cttgattggt    4980
tctgcactgg ggcaggaatc tagtttagat taactggcat tttggctttt cttccagctc    5040
taaaacaagc tccatcactt gaaatggcaa aataaaatca tggatgaggc cgagggcggt    5100
ggcttatgcc tgtaatccca gcactttggg aggccaaggt ggtaggatca cgaggtcagg    5160
agatcgagac catcctggcc aacatggtga accccctct ccactaaaaa tacaaaaatt      5220
agctgggcgt agtggcatgt gcctgtaatc ccagctactc aggaggctga ggcaggagaa    5280
tcacttgaac caggaggcag atgttgctgt gagccaatat ggcaccactg aactccagcg    5340
acagagctaa actccatccc aaaaaaaaaa aaaaaaaaa aaaacatgg atgatcggtg       5400
tcgttgagag gataggtatt tggaagaacc tttgtttgaa actggctctg tacatacaat    5460
gaaattacat acttatttac atacaatgaa atgcagaggt ttttttttta tataggatct    5520
ctgtcgagag gctggagtgc agtggtgcta tcacagctca ctgcagcctc aacctcgtca    5580
ggctcaagca atcctcccac ctcagcctcc agagtagcag ggacgatagg tgtgcaccac    5640
catgcccagc taattttgt attttttttt cttttttga gatggagtct tgctctgttg       5700
cccaggctgg agtgcagtgg cgcgatctca gctcactgca aactctgcct cccgggttca    5760
tgccattctt ctgcctgagc ctcctgaata gctgggacta caagcaccca ctaccacgcc    5820
cggctaattt tttgtatttt tttttctttt ttagtagagg cgggatttca ccgtgttagc    5880
caggatagtc ttgatctcct gaccttgtga tccacccgcc tggcctccc aaagtgctag     5940
gattacaggc ataagccact gcgtccagcc attcttgtat ttttctgttg tagagatagg    6000
gttttgctat gttggccatg ctggtctcaa actcctgacc tcaagtgatc taccctccct    6060
tggcctctca aggtgctggg attacaggcc tgagccattg cacccagcca tggtctaaaa    6120
atcttgattg aaataccacc ttttcatttc cagacacccc tatttaaaat taccacaccc    6180
ccagcacaca cttatcttc tattcctgct gcttctccat aacactgatt actagctgac      6240
attctatgta atgtatccat tttttatctc tagtcccaca gaatgtaaac tccaggatgg    6300
gattttgtt ttgttacat acatctgtat gttcagtagt tagaacggta cttgggacct      6360
agttgccact caataaacat ttgtcaaata aataataaac taaactaaat tagttctta     6420
atttttaa atatggtgat ggttagtagt gagtaacatt caaaaaataa gttgaaaagt       6480
```

```
tgtaccattg cctcttaccc acaataaaaa agggtaaatt cttttctgct ttatgaaagt    6540
tgtttttcat atttgaagtc aagttaatca gattaaggaa aatgtatgtt gtgttttcag    6600
agcgatacaa gatttataaa taaccatcct ctcccttgcc cttcaacatt atagctaaac    6660
aaaaataaga ggaaaacagg attcacaatt tatcaattta ttgaaaatca gagccagaga    6720
agcaggaaat gacattgtag gaaaaaactg cttttgaaaa agcacaaaac ttactcatga    6780
caatcagtga tcaggaaaat cctcaatagt gtggcatttg gatacattta tgtttcattt    6840
ccatgggaga gagtcataaa aataggatgt tctttctcat tctggcaaat taaaccatca    6900
attaaaaact cagatacata aaaattaaag atgtaagaat gaaaatgcta aattgttatt    6960
ttcaatcaac tattatgttt tctagctttt cattgctttt ttctgtttcc tgttaagatt    7020
aatttctttt ttttttttt ttttttttt tgagacagac tttggctctt gttgcccagg    7080
ctggagtgca gtggcacaat ctcggctcac tacaacctcc acctcccggg ttcaagcaat    7140
tctgctgcct cagcctccgg agtacctggg attgcaggca tgtgccatca ccagctaa     7200 ttttgtattt ttagtagaga cagggtttct ccatattggt caggttggtc tcgaactcct    7260
gacctcaggt gatcctcctg ccttggcctc cgaaagtgct gggattacag gcgtgagcca    7320
ccgctcccag acttttttgtt ttgttttgtt ttgtttttttt gagacacggt ctcgctctgc    7380
tgcctaggct ggagtgcagt ggcacgatct tggctcactg ccagctccga ctcccgggtt    7440
caggccattc tcctgcctca gcctcccgag tagctgggac tacaggcgcc caccactatg    7500
cccggctaat ttttttgtatt tttagtagag acggggtttc accatgttag ccaagatggt    7560
ctcgatctcc tgaccttgtg atccacccgc ctcagccttc caaagtgctg ggattacagt    7620
cctgagccac tgcgcccggc ctggaccttt ttttttcggg gtgggggggtt ggagtctggc    7680 tctgtcgccc aggctggagt gcagtggcgc atcttggct cactgcaacc tccgcctgcc    7740
aggttcaagt tcaagcgctt ctcctgcctc agcctcctga gtagctggga ttataggcgc    7800
acgccaccgt ggccggctaa ttttttgtattt ttagtagaga tagggttttca tcacgttggt    7860 caggctggtc ttgaagtcct gatctcgtga tccacccgcc tcggccttcc aaagtgctgg    7920
cgtgagccac tgcgcctggc ttaagattaa ttttttgtttg ttttgttttt gagacggagt    7980
ctcgctcttt cacccaggcc ggagtgcagt ggcgccatct cggctcactg caagctccgc    8040
ctcccgggtt cacgccattc tcctgcctcg gcccccaag tagctgggac tacaggcgtc    8100
caccaccacg cccggctaat ttttttgtatt tttagtagag acggggttttc accgtgttag    8160 ccaggatggt ctccacttcc tgacctcgtg atccgcccac ctcggcctcc caaagtgctg    8220
ggattacagg cgtgagccac cgcgcccggc cttaagatta attttttatgg tgttttacat    8280 tcatttgtat ggaaagttct aggatagggga tcatatttca cttcctttta atatagtaca    8340
gtatagcaca atttgcagtt atgtcttaat atgtgatcag gaatgatcat gactggaaac    8400
agtgttattt gtggtagcta tagggtaggt aaggttttca gcctgtttta ggtttcttga    8460
actaaaattc cttctgctgt cttctaagtc aatattggca gctatttctg acaattggta    8520 gttcttttgta actttttacc tatgactata acatttttga ctttcagaag aatttgctaa    8580
aatgtgttcc ccggtgggtt gttgttttttc aacctaaacc tagctgcttt ttccagtcac    8640
ttatccgtat tggaagctca aaatgcaaat atacagtagg cctaaaatat tgcctggttt    8700
gaaaagtgtt taaatatttt gaatcatttt tatagtaaac atttactctc atcaggacct    8760 agaagggggaa catttaatt ttttttctttt tcccttttca cagtcttcct tcaacattca    8820
```

```
ttaccttttt acatatcgga gttttcatct gttcaaagtt tgtgtttaca gtgtgtttat   8880
atagtttaga ttataattac catactgaaa tataattgtt tcagaattga gtcagtggtg   8940
agaatgaaag ccatctggta tgataactga atccaatttt tcttttacgg agaatttctt   9000
tgaaatgtag cttatctcag aaatagggat ttagtaacca atcagagttt tctttgtcaa   9060
ggttgttttt cttttaaag tcacatttgg tcccagtaat aataccaatg ttggtacaag    9120
ttatctcagg ttgtgaagca ttttcccaa gtcatctcag gttgtgaagc attttcccaa    9180
gtagcattta atttattct tgcaatagcc caaggagtct ggcagggtga atggcaagag    9240
aaggaaacag gttcaggtag agtggttagc ccaaggtggc tctgcttata tacacaactg   9300
gtagtagaaa cccagcctcc tgacttagtt cattgttttt cttttcactg ccctgtgcta   9360
tgtcaaaaac cccatgatta caagagttgt attacaaccc ttcacaataa ggttactgtc   9420
cacaagcttt tcttgtgatc cttttctttt ttttttttct ttttttgaga tggattctct   9480
gtcacccagg ctggcccgcc ttggcctccc aaaatgctgg gattacagcg tgagccaccg   9540
cacctggccc ttgtgatcct tttctaaaaa gttaaatatt taaggaaaaa accacattct   9600
tgtcacactg ccaggttagt cgttctttga tatcttgcct ggactttatc caaaaaatcc   9660
gtttcaaaaa ttcacattta gagctaagtg tagtggctca cgcctgtaat cccggtcgag   9720
gcagatggat cacttgaggt caggacttca agaccagcct gggcaatatg gtgaaacccc   9780
ttccctacca aaaatacaaa aaattagcc gggtgtggca gcacgcgcct gtagtcccag    9840
ctacttggaa tgctgaggca caagaatcac ttcaatccga gaggcagagg ttgcagtgag   9900
ccaagaccac accactgcac tccagcctga gcagcagagt gagtgagact ccatctccaa   9960
aaaaaaaaaa aaaggttcac attcagaaga aagctaaagg ccgggtatag tagctcacac  10020
ctgtaatccc agcactttgg gaagccgaag caggaagatt gcttgatgcc aggcattcaa  10080
gaccagcatg ggcatcatag tgagatcctg tctctacaaa aattaattaa cattaaaaat  10140
taaaagatg gctggcatgg tggctcactc ctgtaatccc agtactttgg gaggccaagg   10200
catggtggtg catgcctta gtcccagcta ctcgggaggc tgaggcagga gaatcacttg    10260
aattcaggag gcggaggtta cagagagccg agatggtgcc actgcactcc agcctgggcg  10320
acagaacgag actctgtctg aaaaaaaaaa agaaaattaa aaagaccaga ataaagctaa   10380
agatttaaaa tagcctatag gttcctacca gaagttacca gctacctctc tgatagtctt   10440
tccctacaat atcctcctgg attattacat tttagcacct tgacctatct gatgtcctgc   10500
atacacaggc atggtcctgc tcagggtttg ccttctctgc tccctctttc ttggaatgct   10560
cttcccctaa ttgttgcata gtgtgtttct ttacattatt aagctatcct ctagtctcac   10620
ctcagtgaaa cctttcctga ctcccccat gtacatctca cccccacata gatattgaac    10680
tacctgtttc cccttaccct gcttaatttt tctctttaat gcacttattc ccatgtattc   10740
tttaattccg tatcaactgt ctaccacact agaatatgag ctctatgaga gcaggcttta   10800
ttttgtaaac tgctacattt ctatctccta gaatagtact tgaatatagt agtagatact   10860
taataaacac ttgttatatt agtataataa atgaactaat ctcaggaatg ccttggtttt   10920
gtggatagac aggtagggat gggaacttgg gtgatgtatt ttctgaagtt tttatttta   10980
agcttattat tattttgaga tggagtccag ctctgtcgcc caggttggag tacagtggcg  11040
cgatcttggc tcactgcaac gtgcacttcc ccggttcaag cgattctcct gccttagcct  11100
cccaagtagc tgggattaca ggcgcatgcc accatgccca ttagttttg gtattttag    11160
tagagacagc gtttcactgt gttggccagg ctggtctcga aatcctgacc tcatgatccg  11220
```

```
cccgcctcgg cctcccaagt gctgggatta caagcatgag cccccgtgtc tggccttatt   11280 ttctttttt  tgagacagag tcttcctctg tcacctaggc tggagtgcag tggcacgata   11340
ttggctcact ctgcaacctc cacctccagg attcaagtga tccttctacc ttagtctcca   11400
aagtagctga gaccacaggc atgccccacc acgcccggct aatttccgta ttttaagcgt   11460
agacagggtt tcaccatatt gtccaggatg atctggaact cctgagctca ggtgatccac   11520
ccacctcagc ctcccaaagt gctaggatta caggcatgag gcaccatgcc cggccttaag   11580
cttatcattt tctaaatttc ctttagtgag tacttattac actgttttta caaagtaatc   11640
acaaaccaaa catcatgcct cttctgaagt gatctaataa gagtacacag taccatctgt   11700
aaagtgttct tgccagaaag ttgaacctga atgattaagc ctgtaagtct agtttatagg   11760
aaataaggct agaggaacaa gttaaacctc accatagggt tatacaatca gcaaaatcca   11820
gaatggggga aactccacag gtcaaatgac ctaattttaa aaataaatga caagggagaa   11880
aaagtaagag acacctatag atcagaagac acttgggct  gggcatggtg gctcacacct   11940
gtaatcccag cactttggga ggccaaggca ggcggatcac ctgaggtcag gagttcaaga   12000
ccagccggcc aacatggtga accccaactc tactaaaatt acgaaaaatc agccgggcgt   12060
ggtggcgcac gcgtgtagtt ccaactacct gggaggctga ggcaggagaa tcacttgaac   12120
ttgggaggca gaggttgcag tgagccgaga tcgcaccatt gcatgccagt ctgggctaca   12180
aaagcaaaac cccatctcaa aaaaagaag  acacttgggt ttgggtgtgt tggctcatgc   12240
ctgtaaaccc cgtgctggga ggattgcttg agcccaggag ttcaaggctg cagtgaggta   12300
tgtttgcacc actgcactcc agcctaggtg acagagtgtg accttatctt aaaagtaata   12360
ataattaaaa taatctgggg taggggtgga tatgggtgaa acagcttggc catgagttga   12420
tggttgttgg accagggtga tggtccatat agttcatttt attattttat ttacttgaaa   12480
ttttgaaata cttgaaattt tccatattaa gttaaaaagg catttacagt aaacaaaaaa   12540
aagttctagg aaggaattca aaagaaatat aagcagaaaa ttttgtcttt atggagctta   12600
aagatgagat gtgcacccac agtgatagtg cagaaaaata tatcactgga aatgaattcg   12660
tacgaactat tatcaactaa tcttttaaat gctgatgata gtatagagta ttgaagggat   12720
caatataatt ctgttttgat atctgaaagc tcactgaagg taaggatcgt attctctgct   12780
gtattctcag ttcctgacac agcagacatt taataaaat  tgaacgaact tgaggcctta   12840
tgttgactca gtcataacag ctcaaagttg aacttattca ctaagaatag ctttattttt   12900
aaataaatta ttgagcctca tttatttct  ttttctcccc ccctaccctg ctagtctgga   12960
gttgatcaag gaacctgtct ccacaaagtg tgaccacata ttttgcaagt aagtttgaat   13020
gtgttatgtg gctccattat tagctttgt  ttttgtcctt cataacccag gaaacaccta   13080
actttataga agctttactt tcttcaatta agtgagaacg aaaaatccaa ctccatttca   13140
ttctttctca gagagtatat agttatcaaa agttggttgt aatcatagtt cctggtaaag   13200
ttttgacata tattatcttt tttttttttt ttgagacaaa gtctcgctct gtcgcccagg   13260
ctggagtgca gtggcatgat cttggctcac tgcaacctcc gccccccgag ttcaagcgat   13320
tcttctacct cagcctccca ggtagctggg actacaggca cccgccacca tgcttggcta   13380 attttttgtac ttttagtaga gataaggttt caccatattg gccaggctgg tctcgaactc   13440
ctgaccttgt gatccacctg cctcggcctc ccaaagttct gggattacag gcgtgagcca   13500
ccacacccga ctgacatata ttatctatta ggatgtaaca tcattttgaa cagtgttttg   13560
```

```
tatttttgt gtccatcagt gaaagcaaac tgcaagcagt tttgaaataa gcacattgtg    13620
tttgagcctt cccagtttct cctttctgtt catttctgca tatccttatg cattcccct    13680 tctaagggtc agtgtttgcc cgctttgtaa tcattgtgaa gacaggaaag gacctgatac    13740
cagtttctat ttaggccaaa attcatttat agcagtgatt caagttatat ttacgtattt    13800
gatgatcttg tcttttgaaa tgaaaatgtt tgtttcttaa taaagaatt tcagaaaaag    13860 tagagtaggt aatttagtag aacaagtggg ctttctcctt ttctttatgt taagctatgg    13920
ctcacatctt accttaaatg tcaactaatt tgttttttaag tatttatgta cctggtacat    13980
aacctggtac caggtacaaa ctatgtactt ggtaaaaagt ttattagcac aaaaaggtat    14040
atgatgcaaa gtatacttcc ctcttaccct acaacccctg cctccctgtt ccctccccag    14100
acaaccacaa tgatcaattt cttatgtatc ctttgaggaa tttttaaatt ccagagttct    14160
taacttgggg tttatgaata gtctttatga atttcctaga attatattta aattgtattc    14220
aaaactatgg ccatgtacat ttttctggga agatagtcca taattttcat ctgagtgagc    14280
taagatcatg ccactgcact ccagcctggg agacaagagg gagactcaaa aaaaaaaaag    14340
aaaggcccag tatttactac agagagctaa agattaacct ttaaagccct ggggctttca    14400
atttatctgg atgagaatct ttctggaatg aactgtatgt tttatggtca gcttgagtaa    14460
caaatgctga gcatactata ctattattac agggactcag gggcccagtg tggtagctcc    14520
tgcccataac cccagcactt tgggaggcca aggcaggagg atcacttaag gccaggagtt    14580
cgaagctgta gtgagctatg atcacaccac tgcactccag cctagatgac agagtgagac    14640
cctgtctttt ttttttttg agatggtgtt tcactctatt gcccaggctg gagtgcagtg    14700
gtgtgatctc ggctcactgc aacctccacc tcctgggttc aagcgattct cctgcctcag    14760
cctcttgagt agctgggatt acaggcatct gccaccacac ccagctaatt tttgtatttt    14820
tagtcgagac agggttttca ccatgttggc caggctgctc tcaaactcct gacttcagct    14880
accttggcct taaaaagtgt tgggattaca ggtgtaagcc accgcgcctg gctgaccctg    14940
tctcttaaca aaaaagaga gattaagtta tgaatatagt tgctttgaga acttgtggaa    15000
gaaggaaatt ataggcttat aggcagagat aataatacga gcaaatgtac aaataaaaga    15060
aaatagagga cgggcgcggt ggctcacgcc tataatacca gcactttggg aggtcgaggt    15120
gggcggatca cgaggtcagg aaattaagac catcctggcc aaaatggcga acactgtct    15180 ctactaaaac acacaaaaaa ctagcctggc atggtggcac gtacctgtag tcccagctac    15240
ttggtaggct gcggcagggg tatcacttga acctgggagg cagaggttgc cctgagccga    15300
gatcatgcca atgcactcca gcctgacaac agagtgagac tctgtctgaa aaaaagaaa    15360 agaaagaaa atacatccag gaaaaataag ctaacttgc atatgtgtat aggagttgtg    15420
ttagaaaagg aagaagccct caaagatggg aagccatttg caagaaagag aaggtccaag    15480
aggaggcaga agggattgga aatagaaaaa ggatgtaaga aagagttgat tattactcat    15540
aaacagtaat gaaggaaaag gagagtaatt ctacaggaag atgctgaggt gctttgagcc    15600
cagtgaagtt ggaggtaaag acagctgttg aggccgggca cggtggctca cgcctctaat    15660
cctagcactt tggagccca aggcaggtgg atcacctgag gtcaggagct caagaccagc    15720
ctgaccaaca tagagaaacc ccatctctac taaaaataca aaattagacg ggcgtggagg    15780
cgcatgcctg taatcccagc tacttgggag gctgaggcag gagaatcact tgaacctggg    15840
aggcggaggt tgcagtgagc cgagattgcg ccattgcact ccagcctggc cgacaagagt    15900
gaaaactgtc tcaaaaaaa aaacaacaa aaacagctg ttgagattga gaggattaga    15960
```

```
gttggcaact ggagaagagt gagaagcttg gtttcaagct tgtgatagtc aggattgtga   16020
tagtcaggaa agaaccagtc ataaagatat atgtgtgtgt atacatataa atatgttata   16080
tatatgtgtg tgtgtgacac atatatattt ttgtttgttt ctttgagaca gtgtctccct   16140
ctgacaccca ggctggagtt cagtggtgtg atcatagttc acttttacct tgcaatctgg   16200
gttcaagcaa tctctcatct cagcccctca agtagctagg actacaggta catggcattt   16260
gcccagctaa ttttttaagtt tcttgtagag atgggccagc catattttaa attgtgtttt   16320
gaatgttata ttagaattaa aagtccaaag ccgggtgtgg tggctcacgc ctgtaatccc   16380
agcactttgg gaggctgagg tgggcggatc acgaggtcag gagttcgaga ccagcctggc   16440
caatatggta acaccatctc tactaaaaat acaaaaatta gctgggtatg ggggcacatg   16500
cctgtagtcc cagctactca ggaggctgag gcagaggaac ctcttgaacc caggaggcag   16560
aggctgcagt gagttgagat cgtgccactg tactctagcc tgggcgacag agcaagattc   16620
cgtctcaaaa aaaaaaaaag tccagtataa tgcccatgtg atagatcgac tttttcatga   16680
aatctcttct gtaatatcaa tataatctga ataacacttt gatctatatg atgagaaagc   16740
tgggagcctg ggagcgatac ccccatgctt ttgttgtatt aattgtattt tctacggata   16800
aactctaatt gctaaaaata aaacaacttt attgacccaa gcaagcctaa agttctgaaa   16860 tcttttttt attttttgttt gtttgttttgt ttgttttgt ttgtttttgtt ttgagacgga   16920 gtctcgctct gtcgcccagg ctggagtgcg gtggtgcagt ctcggctcac tgcaagctcc   16980
acctcccggg ttcacaccat tctcctgcct cagcctccca agtagctggg actacagacg   17040
cctgccacca cgcccagcta attttttttgt atttttagta gagaaagggt ttcaccgtgt   17100
tagccaggat ggtctcgatc tcctgacctc gtgatctgcc cgccttggcc tcccctaagtt   17160 ctgggattac aagtgtgagc caccacgccc ggctgttttt ttttgttttg ttttgagacg   17220
gagtctcact gtgttcccca gactggagtg cagtggcatg atctcagctc actgccacct   17280
ccatctcctg ggttcaagca aatctcctgc ctcagcctcc cgagtagctg ggactacagg   17340
catgtgccac cacacctggc taattttttgt attttttagta gagacggggt ttcactatgt   17400
tggccaggct ggtccaaaac tcctgacctc aggtgatctg ctcgccttgg cctcccacag   17460
tgccaggatt acaggcatga gccaccttgc ccagccagtt ctgaaatctt ttatgaagcc   17520
tataaaaaaa gataataata ccaatctaga aaatatttct taaggcagtc atgcattagt   17580
ttgaactttc caaacaaaaa aatgcaatgt gtaatacttt tttttttttt tttgagatgg   17640
agtcttgttc tgttgcccag gctggagtgc agtggtacaa tctcggctca ctgcagcctc   17700
tgcctctctg gttcaagtga ttctcctgcc tcagcctccc aagtagctgg gattacaggc   17760
gtgcaccacc atgcatggct aattttttgta tttttagtag agacagggtt tcaccatgtt   17820
gacaaggctg atctcgaact cctgacctca ggtgatccgc ccacctcagc ctcccaaagt   17880
gctgagatta caggcattag ccaccacgcc cagccttttta ttttagtaga ccatgtttt   17940 caccatgttg accaagctgg tcttgagctg acctcaagtg atccgcccac ctccacctcc   18000
caaaatggtg ggattatagg catgagccac cgcacccagc ctgtaatact ttttgaaga   18060 tctagaacca cattgttcaa agagatagaa tgtgagcaat aaatgtaact taaatttttc   18120
aacagctact tttttttttt tttttgaga caggtcttta ctctgttgtc ccagctggag   18180
tacagtggtg cgatcatgag gcttactgtt gccttgacct cctaggctca agcgatccta   18240
tcacctcagt ctcccaagta gctgggactg taagtgcaca ccaccatatc cagctaaatt   18300
```

```
ttgtgttttc tgtagagacg gggtttcgcc atgtttccca ggctggtctt gaactttggg   18360
cttaacccgt ctgcccacct aggcatccca aagtgctagg attacaggtg tgagtcatca   18420
tgcctggcca gtattttagt tagctctgtc ttttcaagtc atatacaagt tcattttctt   18480
ttaagtttag ttaacaacct ttatacatgt attctttttc tagcataaag aaagattcga   18540
ggccgggtgc ggtggctcac gcctgtaatc ccagcacttt gggaggctga gatgggcaca   18600
tcacgaggtc aggagatcga gaccatcctg gctaacatgg tgaaacccccg cctctactaa   18660 aattacaaaa agttagccag gcgtggtagc gggcacctgt agtcccagct actcaggagg   18720
ctgaggcagg agaatggcgt gaacccagga ggcagagctt gcagtgagca gagattgtgc   18780
cactgcactc cagcctgaga cagagcga gactccgtct aaaaaaaaaa aaaaagattc   18840
gaatccttat cttggttgat ttttgcgtat ctagttccac tgaattattt atataattgt   18900
atagactaca gcacgagaca gcttagcttg tcactctact gtactatatt ctgcagtact   18960
atcataaggg aatttcctcc ctaccccctgc tctgaattgt tcaattgtac tatttgctgg   19020
agtaatgctt gatgccttct tgatccatta tactagagta tatgtagtat ttgtagattc   19080
tgaaggagtg ggagcctcta ttctgagttt taaaggtact tatgtacagt ggaggtagct   19140
ttttgacagc ctcatcttcc aaactataga gtcattgttt tgttgagtgc aatatggtac   19200
ttgaagcatc tatatcggcg aagaaggacc caagtctcct tgaccttacc tacctacatt   19260
cactttctct ggtaggaaga ttgtgggtgc ctctctccag acttagtttc catgtcaaaa   19320
aagaaaaaag aagattgtg ggctttgcta caatccaatt ctggatccaa tataaccttc   19380
attgcttaat tactgtgtga tctgggacaa gcctctactc tataaaatg aagataaggc   19440 caggcttgat ggctcatgcc tgtaatccca gcacgttggg atgccaaggc aggaggatca   19500
cttgaggtca ggagttcgag accagactgg gcaatatagt gaaaccacat ctgtacaaaa   19560
ataaagatag aaagtagccc agcgcaatgg ctcacacctg taatcccagc actttgggag   19620
gctgaagcag gcgatcactt gaggtcggga gttcaagact gtagacagat agataggtag   19680
gtagatagat agagatatag atatagttgg ggttttttg ttttgttttg ttttgtttt   19740 gagatggagt ttcgctcttg ttgcccaggc tggagtgcaa tggcgcgatc tcagtttact   19800
gcaacctccg cctccgggt tcaagagatt ctcctgcctc agcctcctga gtagccagga   19860
ttacaggcat atgccaccat gcccggctaa tttttgtatt tttagtagag acagggtttc   19920
tccgtgttgg tcaggctggt cttgaactcc tgacctctcc caaagtgttg ggattacagg   19980
cgtgagccac cgctcctggc cttttttttt tttttttttt tttttttgag acagagtctt   20040
cctctgttgc ccagggtgga gtgcagtggc actcttctca gctcattgca acctctgcca   20100
tcctgggttc cagtgattct catgcctcag cctcccaagt agctgggact caggcgtgtg   20160
cccaccacgc ctggctaatt tgttgtatt tttagtagag acagggtttc accatgttag   20220
ccaggctggt ctcaaactcc aggcctcaag tgatctgcct gcctcagcct cctgggattg   20280
cagacatgag ccactgcacc cggccaagag agggtaataa atgttaaatt acctggctag   20340 taaaaatat tctctaagtg tcttttctca caattcccaa tgccttttt tttttttgg   20400 cacaatctca ctctgttgcc caggctgaa tgcaatggtg caatattggc tcactgtaac   20460
ccccgcctca caggttcaac ttattctcat gcctcagcct cccgagtaac tgggactaca   20520
gtgcaccacc accacaccca gctaattttt gaatattttag tagagacagg gtttcaccat   20580
gttggccagg ctggtcttga actcctggcc tcaagtgatt cacccacccc gcaagtgctg   20640
ggattacagg tgtggaccac cgtgcacagc cctagtgact ttttttttag ccccttaatc   20700
```

```
ttttctttcc tgggtctctt cattgtcagt gtctgctatt tactccctac ctagtcaccc   20760
ccttcaccag tatattatgt cctttatgtt ttattttgca ggatcttatt ttgcttttct   20820
attgaatccc ctccatctag aatagtacta gacatagtaa atattggttg tatgagtgaa   20880
tcgctgcttt taattatcat caccattgct ctctctactt ctggtctatg atccactttg   20940
agttaacttt tgttatttgg tgtgagatag gagtataatt tcattctttt acatgtggtt   21000
atacttttgt ctcaacactg tttgttaaaa acacaaaaag tattattttc ccatttaatc   21060
atctttggcc tgggcacggt ggctcatgcc tgtaatccca gcactctgga aggccaaggc   21120
agatggatca atttgaggcc aggagttcaa gactagccaa catggtgaaa ctaaaaatac   21180
aaaaaattag ctgggtatgg tggtgcatgt ctgtaatccc agctactcgg gaggctgagg   21240
cacgagaatt gcttgagcct aggaggtgga ggttgtagtg agctgagatt gtgtcactac   21300
cctccagcct gggtgataga gtgagtctgt ctcaaaaaaa aaaaaaaaaa attaagaaaa   21360
taaaaatcgt cggccaggca tggtggctca cacctgtaat cccagcactt tgggaggcag   21420
aggcgggcag atcacgaggt caggagatgg agaccatcct ggctaacatg gtgaaacccc   21480
gtctctacta aaaataaaaa aattagccgg gcatggtgct gggcgcctgt agtcccagct   21540
gctcgggagg ctgaggcagg agaatggcgt gaacccagga ggtggagctt gcagtgagcc   21600
gagatcgtgc cactgcactc cagcctggga acagagcga gactccgtct caaaaaaaaa   21660
aaaaaaaaaa attgtcttgg tatttattat tgttgaaaat cgcttgatca cagatgtatg   21720
tatgagttta tttctgtact gtcaattcca tttattgat gtatgtgtct attcttatgc   21780
tattaccaca ctttcttgat tactatagct ttgtggtgag gtgttgagat tttaaactaa   21840
ttataagcat cttacatgaa ctacttaccg tttatatttg attatgcagc atgaaataat   21900
tatgaatata tcattaaata tgccatatta acttttatta agttttatgt gatcataaca   21960
gtaagccata tgcatgtaag ttcagttttc atagatcatt gcttatgtag tttaggtttt   22020
tgcttatgca gcatccaaaa acaattagga aactattgct tgtaattcac ctgccattac   22080
tttttaaatg gctcttaagg gcagttgtga gattatcttt tcatggctat ttgccttttg   22140
agtattcttt ctacaaaagg aagtaaatta aattgttctt tctttcttta taatttatag   22200
attttgcatg ctgaaacttc tcaaccagaa gaaagggcct tcacagtgtc ctttatgtaa   22260
gaatgatata accaaaggt atataaatttg gtaatgatgc taggttggaa gcaaccacag   22320
taggaaaaag tagaaattat ttaataacat agcgttccta taaaaccatt catcagaaaa   22380
atttataaaa gagtttttag cacacagtaa attatttcca aagttatttt cctgaaagtt   22440
ttatgggaca tctgccttat acaggtatta gaaacttact gcctttctct aatgcttcta   22500
gtgtaaaaac ttgcagactt atgtaaagta gggctgtatc gccgtgcccc cattgtctgt   22560
taatcttgtt tttatatttt tgattgtgtt tccttttctt tttttttttt ttttttaagac   22620 agggtcctgc tctgtcactg aggctggagt gcagtggcgt gatctcggct cactgtagcc   22680
tctgtctccc agcctcttcc tgccttagcc tcccaaatag ctgggactac aggcacacgc   22740
taccatgccc ggccaatttt tgtattttt gtagagatga ggttttacca tgttgcccag   22800
gctggtaact cctgagctca ggtgatctgc ccacctcggc ctcccaaagt gctgggttc    22860 acaggtgtgt gtttatttct atctaattat ttacacaaac acaatgtatt tatatattgt   22920
gtatctcttc tgctacaatg taaattctat gagagtagta attttgtctg tctcaacact   22980
gttttcccta agtttggtac atagtaggca ctcagatgct taaggaatg aatgaattgt    23040
```

```
gctttaattc cactttacta aacccaaatc tcccttttgga cattgttatc tatgtgtttt    23100
caaagaagta taatcataat ttgacagaaa tccttgagag cagaactaa gtgagggatt    23160 gggcagggtt cagatgttaa aacagtaag ctcagcaggg tgtgattgct catgcctata    23220
accctagcac tctaggaggc tgaggtggga tgattgcttg aggccaggag tttgaaatca    23280
gcctgggcaa catagtgaga ccccatcact accaacaaaa taaataaata aatgtacatg    23340
gtggcatatg cccatagtcc tagctacttg ggaggctata gtgggaggat agcttgagta    23400
cagaagtctg aggctgcagt gagctatgat tgtggcactg catgctagcc tgggcaatag    23460
agcaagaccc tgtctctaaa ttaaacaaaa aaaaaagtac tctagttttc tatgcaatgc    23520
attatatctg ctgtggattt agggcagtat tatatcagat aattttaggc atttggtagg    23580
cttaaatgaa tgacaaaaag ttactaaatc actgccatca cacgtttat acagatgtca    23640 atgatgtatt gattatagag gttttctact gttgctgcat cttattttta tttgtttaca    23700
tgtcttttct tattttagtg tccttaaaag gttgataatc acttgctgag tgtgtttctc    23760
aaacaattta atttcaggag cctacaagaa agtacgagat ttagtcaact tgttgaagag    23820
ctattgaaaa tcatttgtgc ttttcagctt gacacaggtt tggagtgtaa gtgttgaata    23880
tcccaagaat gcaactcaag tgctgtccat gaaaactcag gaagtttgca caattacttt    23940
ctatgacgtg gtgataagac cttttagtct aggttaattt tagttctgta tctgtaatct    24000 attttttaaaa aattactccc actggtctca cacccttattt tatcaatcgt aaggtgcaca    24060
tttttcacat cttaacatct ctgaaattgg gaacatttta ctattgaggg tgtgtcattt    24120
gtttaatttg tgtgctttct ttcttagtga tacacgaaat aatagtgcca cttacattgt    24180
tggtgtctta gctttagtga aatacagtat tgataggcaa atttcttagt gttaaggtag    24240
aaaacaagga ctcaaataa cttttgatggt ctgtgtattt gttttttgttt cctaggagta    24300 aaatttccag ttgattttt aaaatttgat ttttaaaaaa aatcacaggt aaccttaatg    24360
cattgtctta acacaacaaa gagcatacat agggtttctc ttggtttctt tgattataat    24420
tcatacattt ttctctaact gcaaacataa tgttttccct tgtattttac agatgcaaac    24480
agctataatt ttgcaaaaaa ggaaaataac tctcctgaac atctaaaaga tgaagtttct    24540
atcatccaaa gtatgggcta cagaaaccgt gccaaaagac ttctacagag tgaacccgaa    24600
aatccttcct tggtaaaacc atttgttttc ttcttcttct tcttcttctt ttcttttttt    24660
tttctttttt tttttgaga tggagtcttg ctctgtggcc caggctagaa gcagtcctcc    24720
tgccttagcc ccccttagtag ctgggattac aggcacgcgc caccatgcca ggctaatttt    24780 tgtatttta gtagagacgg ggtttcatca tgttggccag gctggtctcg aactcctaac    24840
ctcaggtgat ccacccacct cggctcccca aattgctggg attacaggtg tgagccactg    24900
tgcccggccg gtaaaaccat tttcatttat tctggcaaca tctctttatt gagcattgtg    24960
aatatgttag tgaatgtgct agatgctcat agatttatat aaaaagttag tgaagaagga    25020
aagatggtat attaagtggt tagacaagtg ttctaatcag ttagagttca gagaaggtca    25080
gggtacctga tataatcaag agagagacct tacagccagg tgaggtgaat gtacctataa    25140
tcccagctac ttaggaggct gaaatgggag gatcacttga gtccaggttt gagaccagcc    25200
caggcaacat agcaagatcc ccatcagata caccaaaaag acagatttct tttttttttt    25260
tttttttgag acagagtctc gctctgtcgc ccaggctgga gcgcagtgac acgatgtcag    25320
ctcactgcaa cctccgcctc ccaggttcaa gtgattctcc tgcctcagcc tcctgagtag    25380
ttgggactac aggggtacga caccagacct ggctaatttt tgtaatttta gtagagtcgg    25440
```

```
ggtttcacca tattggtcag gctggtctcg aactcctgac ctcaggtgat ccaccctcct   25500
tggcctccca gagtgctggg attacaggcg tgagccacca gcccggcca aaaagagag    25560 ctcttatagg cccttccttg ctttggagct ttatctgctc tgtgatgctt atctaaaata   25620
gccataaggt cactgatatt tttaagcatt tggaaattac ttcagctggg tgccatggct   25680
catgcctata atcccaaccc tttgggaggc tgaggtagga ggtcctttga gcccagcttg   25740
ggcaacacag tgagacactg tctctgcaat taaaaaaaaa aaaaagtag ctgggtgccg    25800 tggctcacgc ctgtaattcc agcactagga ggcttgagga ttgcctgagc tcaggagttc   25860
aagaccagtt tgggcaacat agcaagtcct tgtctatatt aaaagttttt ttaaattatc   25920
tgggcatggt ggtgtgtgcc tgtagtccca gctacttggg aagctgagac agaaggatca   25980
cttgagtcca ggagatgtag actacagtga gctatgatca ctccactgca cttcagcgtg   26040
ggcggcaaag caagatctag ttgcaaaaaa aaaaagaact ggctgggtgc ggcggctaac   26100
acctgcaatc ccagcacctt gggaggctga ggccagtgga tcatgaggtc aggagattga   26160
gaccaccctg gccaacatgg tgaaacccgg tctctactaa aaatacaaaa attagctggg   26220
tgtggtggca cgtgcctgta atcccagcta ctccagaggc tgaggatgga gaatcacttg   26280
aacctgagag tcggaggttg cagtgagccg agattgcgcc actgcactcc agcctggcga   26340
cagagcgaga ctccgtctca aaaaaaaaaa aaaaaaagct tcacgcctgt aatcccagca   26400
ctttgggagg ccgagtcaag tggatcacga ggtgtggaga tcaagactat cctggctcac   26460
atggtgaaag cccgtctcta ctaaaaacac agaaaaatta gctgagcgtg atggcggact   26520
cctgtagtcc cagctactcg ggaggctgag gcaggagaat agcatgaacc cgggaggtgg   26580
agcttgcagt gagccgagat cccgccactg cgatccagcc tgggcgacag agtgagactc   26640
tgtctcaaaa aaaaacaaa aaacttagc tgggcgtggt ggtatgcacc tgtggtccta   26700
gctacttggg aggctgaggc tggagcattg ctttaacata gagagtcaag gctgcagttg   26760
agctatgact gtgccactgg actccagcgc aggtgactga gaccctatct tttaaaaaaa   26820
gggaaaatta cttgaactta aaaggtgtaa ttgttaaaga aaatgtagtg atttgctctg   26880
ttgttactta tatgtgcatg aatgatggag atcttaaaaa gtaatcattc tggggctggg   26940
cgtagtagct tgcacctgta atcccagcac ttcgggaggc tgaggcaggc agataatttg   27000
aggtcaggag tttgagacca gcctggccaa catggtgaaa cccatctcta ctaaaaatac   27060
aaaaattagc tgggtgtggt ggcacgtacc tgtaatccca gctactcggg aggcggaggc   27120
acaagaattg cttgaaccta ggacgcggag gttgcagcga gccaagatcg cgccactgca   27180
ctccagcctg ggccgtagag tgagactctg tctcaaaaaa gaaaaaaaag taattgttct   27240
agctgggcgc agtggctctt gcctgtaatc ccagcacttt gggaggccaa ggcgggtgga   27300
tctcgagtcc tagagttcaa gaccagccta ggcaatgtgg tgaaacccca tcgctacaaa   27360
aaatacaaaa attagccagg catggtgcg tgcgcatgta gtcccagctc cttgggaggc   27420
tgaggtggga ggatcacttg aacccaggag acagaggttg cagtgaaccg agatcacgcc   27480
accacgctcc agcctgggca acagaacaag actctgtcta aaaaaataca aataaaataa   27540
aagtagttct cacagtacca gcattcattt ttcaaaagat atagagctaa aaggaagga   27600 aaaaaaagt aatgttgggc ttttaaatac tcgttcctat actaaatgtt cttaggagtg   27660
ctggggtttt attgtcatca tttatccttt ttaaaaatgt tattggccag gcacggtggc   27720
tcatggctgt aatcccagca ctttgggagg ccgaggcagg cagatcacct gaggtcagga   27780
```

```
gtgtgagacc agcctggcca acatggcgaa acctgtctct actaaaaata caaaaattaa    27840
ctaggcgtgg tggtgtacgc ctgtagtccc agctactcgg gaggctgagg caggagaatc    27900
aactgaacca gggaggtgga ggttgcagtg tgccgagatc acgccactgc actctagcct    27960
ggcaacagag caagattctg tctcaaaaaa aaaaaacata tatacacata tatcccaaag    28020
tgctgggatt acatatatat atatatatat atatcatatc tatatatata tatatgtaat    28080
atatatgtta tatatatatt acatatatat atgttatata tatgttatat atatataata    28140
tatatatgtt atatatatgt tatatatata tatacacaca cacacacata tatatgtata    28200
tatatataca cacacacaca catattagcc aggcatagtt gcacacgctt gtagacccag    28260
ctactcagga ggctgaggca ggagaatctc ttgaacttag gaggcggagg ttgcagtgag    28320
ctgagattgc gccactgcac tccagcctgg gtgacagagc aggactctgt accccccca    28380 aaacaaaaaa aaaagttatc agatgtgatt ggaatgtata tcaagtatca gcttcaaaat    28440
atgctatatt aatacttcaa aaattacaca aataatacat aatcaggttt gaaaaattta    28500
agacaacaga aaaaaaaatt caaatcacac atatcccaca cattttatta ttactactac    28560
tattattttg tagagactgg gtctcactct gttgcttatg ctggtcttga actcctggcc    28620
tcaagcagtc ctgctccagc ctcccaaagt gctgggatta taggcatgag ctaccgctcc    28680
cagccccaga cattttagtg tgtaaattcc tgggcatttt ttccaggcat catacatgtt    28740
agctgactga tgatggtcaa tttattttgt ccatggtgtc aagtttctct tcaggaggaa    28800
aagcacagaa ctggccaata attgcttgac tgttctttac catactgttt agcaggaaac    28860
cagtctcagt gtccaactct ctaaccttgg aactgtgaga actctgagga caaagcagcg    28920
gatacaacct caaaagacgt ctgtctacat tgaattgggt aagggtctca ggttttttaa    28980
gtatttaata ataattgctg gattccttat cttatagttt tgccaaaaat cttggtcata    29040 atttgtatt gtggtaggca gctttgggaa gtgaatttta tgagccctat ggtgagttat    29100
aaaaaatgta aaagacgcag ttcccacctt gaagaatctt actttaaaaa gggagcaaaa    29160
gaggccaggc atggtggctc acacctgtaa tcccagcact ttgggaggcc aaagtgggtg    29220
gatcacctga ggtcgggagt tcgagaccag cctagccaac atggagaaac tctgtctgta    29280
ccaaaaaata aaaaattagc caggtgtggt ggcacataac tgtaatccca gctactcggg    29340 aggctgagge aggagaatca cttgaacccg ggaggtggag gttgcggtga accgagatcg    29400
caccattgca ctccagcctg gcaaaaata gcgaaactcc atcaaaaaa aaaaaagaga    29460 gcaaagaaa gaatatctgg ttttaaatat gtgtaaatat gttttggaaa gatggagagt    29520
agcaataagg aaaaacatga tggattgcta cagtatttag ttccaagata aattgtacta    29580
gatgaggaag cctttaaga agagctgaat tgccaggcgc agtgctcacg cctgtaatcc    29640
cagcactttg gaaggccgag gtgggcggat cacctgaggt cgggagttca agaccagcct    29700
gaccaacatg gagaaacccc atctctacta aaaaaaaaa aaaaaaatt agccggggtg    29760 gtggcttatg cctgaaatcc cagctactca ggaggctgag gcaggagaat cgcttgaacc    29820
caggaagcag aggttgcagt gagccaagat cgcaccattg cactccagcc taggcaacaa    29880
gagtgaaact ccatctcaaa aaaaaaaaa aagagctgaa tcttggctgg gcaggatggc    29940
tcgtgcctgt aatcctaacg ctttggaaga ccgaggcaga aggattggtt gagtccacga    30000
gtttaagacc agcctggcca acatagggga accctgtctc tattttaaa ataataatac    30060 attttttggcc ggtgcggtgg ctcatgcctg taatcccaat actttgggag gctgaggcag    30120
gtagatcacc tgaggtcaga gttcgagacc agcctggata acctggtgaa acccctcttt    30180
```

```
actaaaaata caaaaaaaaa aaaaaattag ctgggtgtgg tagcacatgc ttgtaatccc   30240
agctacttgg gaggctgagg caggagaatc gcttgaacca gggaggcgga ggttacaatg   30300
agccaacact acaccactgc actccagcct gggcaataga gtgagactgc atctcaaaaa   30360
aataataatt tttaaaaata ataaatttt ttaagcttat aaaagaaaa gttgaggcca    30420 gcatagtagc tcacatctgt aatctcagca gtggcagagg attgcttgaa gccaggagtt   30480
tgagaccagc ctgggcaaca tagcaagacc tcatctctac aaaaaatttt cttttttaaa   30540
ttagctgggt gtggtggtgt gcatctgtag tcccagctac tcaggaggca gaggtgagtg   30600
gatacattga acccaggagt ttgaggctgt agtgagctat gatcatgcca ctgcactcca   30660
acctgggtga cagagcaaga cctccaaaaa aaaaaaaaa agagctgctg agctcagaat   30720
tcaaactggg ctctcaaatt ggattttctt ttagaatata tttataatta aaaggatag   30780 ccatcttttg agctcccagg caccaccatc tatttatcat aacacttact gttttccccc   30840
cttatgatca taaattccta gacaacaggc attgtaaaaa tagttatagt agttgatatt   30900
taggagcact taactatatt ccaggcacta ttgtgctttt cttgtataac tcattagatg   30960
cttgtcagac ctctgagatt gttcctatta tacttatttt acagatgaga aaattaaggc   31020
acagagaagt tatgaaattt ttccaaggta ttaaacctag taagtggctg agccatgatt   31080
caaacctagg aagttagatg tcagagcctg tgcttttttt ttgttttgt ttttgttttc    31140 agtagaaacg ggggtctcac tttgttggcc aggctggtct tgaactccta acctcaaata   31200
atccacccat ctcggcctcc tcaagtgctg ggattacagg tgagagccac gtgcctggc    31260 gaagcccatg cctttaacca cttctctgta ttacatacta gcttaactag cattgtacct   31320
gccacagtag atgctcagta aatatttcta gttgaatatc tgttttttcaa caagtacatt   31380 tttttaaccc ttttaattaa gaaaacttt attgatttat ttttgggg gaaattttt      31440 aggatctgat tcttctgaag ataccgttaa taaggcaact tattgcaggt gagtcaaaga   31500
gaacctttgt ctatgaagct ggtattttcc tatttagtta atattaagga ttgatgtttc   31560 tctctttta aaaatatttt aactttatt ttaggttcag ggatgtatgt gcagtttgtt    31620 ataggtaa acacacgact tgggatttgg tgtatagatt tttttcatca tccgggtact    31680
aagcataccc cacagttttt tgtttgctt ctttctgaat ttctccctct tcccaccttc   31740
ctccctcaag taggctggtg tttctccaga ctagaatcat ggtattggaa gaaaccttag   31800
agatcatcta gtttagttct ctcatttat agtggaggaa ataccctttt tgtttgttgg    31860
atttagttat tagcactgtc caaaggaatt taggataaca gtagaactct gcacatgctt   31920
gcttctagca gattgttctc taagttcctc atatacagta atattgacac agcagtaatt   31980
gtgactgatg aaaatgttca aggacttcat tttcaactct ttctttcctc tgttccttat   32040
ttccacatat ctctcaagct ttgtctgtat gttatataat aaactacaag caaccccaac   32100
tatgttacct accttcctta ggaattattg cttgacccag gtttttttt ttttttttt    32160 ggagacgggg tcttgccctg ttgccaggat ggagtgtagt ggcgccatct cggctcactg   32220
caatctccaa ctccctggtt caagcgattc tcctgtctca atctcacgag tagctgggac   32280
tacaggtata caccaccacg cccggttaat tgaccattcc atttctttct ttctctcttt   32340
tttttttttt ttttgagac agagtcttgc tctgttgccc aggctggagt acagaggtgt   32400
gatctcacct ctccgcaacg tctgcctccc aggttgaagc catactcctg cctcagcctc   32460
tctagtagct gggactacag gcgcgcgcca ccacacccgg ctaattttg tatttttagt    32520
```

```
agagatgggg tttcaccatg ttggccaggc tggtcttgaa ctcatgacct caagtggtcc    32580
acccgcctca gcctcccaaa gtgctggaat tacaggcttg agccaccgtg cccagcaacc    32640
atttcatttc aactagaagt ttctaaagga gagagcagct ttcactaact aaataagatt    32700
ggtcagcttt ctgtaatcga aagagctaaa atgtttgatc ttggtcattt gacagttctg    32760
catacatgta actagtgttt cttattagga ctctgtcttt tccctatagt gtgggagatc    32820
aagaattgtt acaaatcacc cctcaaggaa ccagggatga aatcagtttg gattctgcaa    32880
aaaagggtaa tggcaaagtt tgccaactta acaggcactg aaaagagagt gggtagatac    32940
agtactgtaa ttagattatt ctgaagacca tttgggacct ttacaaccca caaaatctct    33000
tggcagagtt agagtatcat tctctgtcaa atgtcgtggt atggtctgat agatttaaat    33060
ggtactagac taatgtacct ataataagac cttctgtaac tgattgttgc cctttcgttt    33120
ttttttttgt ttgtttgttt gttttttttt gagatggggt ctcactctgt tgcccaggct    33180
ggagtgcagt gatgcaatct ggctcactg caacctccac ctccaaggct caagctatcc    33240
tcccacttca gcctcctgag tagctgggac tacaggcgca tgccaccaca cccgttaat    33300 tttttgtggt tttatagaga tggggtttca ccatgttacc gaggctggtc tcaaactcct    33360
ggactcaagc agtctgccca cttcagcctc ccaaagtgct gcagttacag gcttgagcca    33420
ctgtgcctgg cctgcccttt acttttaatt ggtgtatttg tgtttcatct tttacctact    33480 ggttttaaa tatagggagt ggtaagtctg tagatagaac agagtattaa gtagacttaa    33540
tggccagtaa tctttagagt acatcagaac cagttttctg atggccaatc tgcttttaat    33600
tcactcttag acgttagaga ataggtgtg gtttctgcat agggaaaatt ctgaaattaa    33660
aaatttaatg gatcctaagt ggaaataatc taggtaaata ggaattaaat gaaagagtat    33720
gagctacatc ttcagtatac ttggtagttt atgaggttag tttctctaat atagccagtt    33780
ggttgatttc cacctccaag gtgtatgaag tatgtatttt tttaatgaca attcagtttt    33840 tgagtaccttt gttattttg tatattttca gctgcttgtg aattttctga gacggatgta    33900
acaaatactg aacatcatca acccagtaat aatgatttga acaccactga gaagcgtgca    33960
gctgagaggc atccagaaaa gtatcagggt agttctgttt caaacttgca tgtggagcca    34020
tgtggcacaa atactcatgc cagctcatta cagcatgaga acagcagttt attactcact    34080
aaagacagaa tgaatgtaga aaaggctgaa ttctgtaata aaagcaaaca gcctggctta    34140
gcaaggagcc aacataacag atgggctgga agtaaggaaa catgtaatga taggcggact    34200
cccagcacag aaaaaaaggt agatctgaat gctgatcccc tgtgtgagag aaaagaatgg    34260
aataagcaga aactgccatg ctcagagaat cctagagata ctgaagatgt tccttggata    34320
acactaaata gcagcattca gaaagttaat gagtggtttt ccagaagtga tgaactgtta    34380
ggttctgatg actcacatga tggggagtct gaatcaaatg ccaaagtagc tgatgtattg    34440
gacgttctaa atgaggtaga tgaatattct ggttcttcag agaaaataga cttactggcc    34500
agtgatcctc atgaggcttt aatatgtaaa agtgaaagag ttcactccaa atcagtagag    34560
agtaatattg aagacaaaat atttgggaaa acctatcgga agaaggcaag cctccccaac    34620
ttaagccatg taactgaaaa tctaattata ggagcatttg ttactgagcc acagataata    34680
caagagcgtc ccctcacaaa taaattaaag cgtaaaagga gacctacatc aggccttcat    34740
cctgaggatt ttatcaagaa agcagatttg gcagttcaaa agactcctga atgataaat    34800 cagggaacta accaaacgga gcagaatggt caagtgatga atattactaa tagtggtcat    34860
gagaataaaa caaaaggtga ttctattcag aatgagaaaa atcctaaccc aatagaatca    34920
```

```
ctcgaaaaag aatctgcttt caaaacgaaa gctgaaccta taagcagcag tataagcaat   34980
atggaactcg aattaaatat ccacaattca aaagcaccta aaaagaatag ctgaggagg    35040
aagtcttcta ccaggcatat tcatgcgctt gaactagtag tcagtagaaa tctaagccca   35100
cctaattgta ctgaattgca aattgatagt tgttctagca gtgaagagat aaagaaaaaa   35160
aagtacaacc aaatgccagt caggcacagc agaaacctac aactcatgga aggtaaagaa   35220
cctgcaactg gagccaagaa gagtaacaag ccaaatgaac agacaagtaa aagacatgac   35280
agcgatactt tcccagagct gaagttaaca aatgcacctg gttcttttac taagtgttca   35340
aataccagtg aacttaaaga atttgtcaat cctagccttc aagagaaga aaaagaaagag  35400
aaactagaaa cagttaaagt gtctaataat gctgaagacc ccaaagatct catgttaagt   35460
ggagaaaggg ttttgcaaac tgaaagatct gtagagagta gcagtatttc attggtacct   35520
ggtactgatt atggcactca ggaaagtatc tcgttactgg aagttagcac tctagggaag   35580
gcaaaaacag aaccaaataa atgtgtgagt cagtgtgcag catttgaaaa ccccaaggga   35640
ctaattcatg gttgttccaa agataataga aatgacacag aaggctttaa gtatccattg   35700
ggacatgaag ttaaccacag tcgggaaaca agcatagaaa tggaagaaag tgaacttgat   35760
gctcagtatt tgcagaatac attcaaggtt tcaaagcgcc agtcatttgc tccgttttca   35820
aatccaggaa atgcagaaga ggaatgtgca acattctctg cccactctgg gtccttaaag   35880
aaacaaagtc caaaagtcac ttttgaatgt gaacaaaagg aagaaaatca aggaaagaat   35940
gagtctaata tcaagcctgt acagacagtt aatatcactg caggctttcc tgtggttggt   36000
cagaaagata agccagttga taatgccaaa tgtagtatca aaggaggctc taggttttgt   36060
ctatcatctc agttcagagg caacgaaact ggactcatta ctccaaataa acatggactt   36120
ttacaaaacc catatcgtat accaccactt tttcccatca agtcatttgt taaaactaaa   36180
tgtaagaaaa atctgctaga ggaaaacttt gaggaacatt caatgtcacc tgaaagagaa   36240
atgggaaatg agaacattcc aagtacagtg agcacaatta gccgtaataa cattagagaa   36300
aatgtttta aagaagccag ctcaagcaat attaatgaag taggttccag tactaatgaa   36360
gtgggctcca gtattaatga aataggttcc agtgatgaaa cattcaagc agaactaggt   36420
agaaacagag ggccaaaatt gaatgctatg cttagattag gggttttgca acctgaggtc   36480
tataaacaaa gtcttcctgg aagtaattgt aagcatcctg aaataaaaaa gcaagaatat   36540
gaagaagtag ttcagactgt taatacagat ttctctccat atctgatttc agataactta   36600
gaacagccta tgggaagtag tcatgcatct caggtttgtt ctgagacacc tgatgacctg   36660
ttagatgatg gtgaaataaa ggaagatact agttttgctg aaaatgacat taaggaaagt   36720
tctgctgttt ttagcaaaag cgtccagaaa ggagagctta gcaggagtcc tagccctttc   36780
acccatacac atttggctca gggttaccga agaggggcca agaaattaga gtcctcagaa   36840
gagaacttat ctagtgagga tgaagagctt ccctgcttcc aacacttgtt atttggtaaa   36900
gtaaacaata taccttctca gtctactagg catagcaccg ttgctaccga gtgtctgtct   36960
aagaacacag aggagaattt attatcattg aagaatagct taaatgactg cagtaaccag   37020
gtaatattgg caaaggcatc tcaggaacat caccttagtg aggaaacaaa atgttctgct   37080
agcttgtttt cttcacagtg cagtgaattg gaagacttga ctgcaaatac aaacacccag   37140
gatccttttc tgattggttc ttccaaacaa atgaggcatc agtctgaaag ccagggagtt   37200
ggtctgagtg acaaggaatt ggtttcagat gatgaagaaa gaggaacggg cttggaagaa   37260
```

```
aataatcaag aagagcaaag catggattca aacttaggta ttggaaccag gttttgtgt    37320
ttgccccagt ctatttatag aagtgagcta aatgtttatg cttttgggga gcacatttta   37380
caaatttcca agtatagtta aaggaactgc ttcttaaact tgaaacatgt tcctcctaag   37440
gtgcttttca tagaaaaaag tccttcacac agctaggacg tcatctttga ctgaatgagc   37500
tttaacatcc taattactgg tggacttact tctggtttca ttttataaaa gcaaatccag   37560
gtgtcccaaa gcaaggaatt taatcatttt gtgtgacatg aaagtaaatc cagtcctgcc   37620
aatgagaaga aaaagacaca gcaagttgca gcgtttatag tctgcttta catctgaacc    37680
tctgttttg ttatttaagg tgaagcagca tctgggtgtg agagtgaaac aagcgtctct    37740
gaagactgct cagggctatc ctctcagagt gacattttaa ccactcaggt aaaaagcgtg   37800
tgtgtgtgtg cacatgcgtg tgtgtggtgt cctttgcatt cagtagtatg tatcccacat   37860
tcttaggttt gctgacatca tctctttgaa ttaatggcac aattgtttgt ggttcattgt   37920
ctccttaaat tagactgtaa gcaccttgat ggaactcata ctacctttta tttcacacac   37980
acgcacacgc gcacacacag cctacacata cactgcctag ctcattgtag catactaaat   38040
actgatttta atgaataagc taaaccttcg aaacccattt gctaatccca gcactttggg   38100
aggccaaggt gggtggatca cctcaggtca gaagtttgag accagcctgg ccaacatggt   38160
gaaaccccac atctactaaa aatacaaaaa ttagctgggc gtggtggcca atgccttgta   38220
atcccagcta ttctggaggc tgagacagga gaatcgcctg aacctgggag gcggaggttg   38280
cactgagctg ggattgtacc actgcactcc agcctgggtg acaaagtgag actccatctc   38340
aaaaacaaac aaacaaaaac acatcatttc ccctatagca aaaacatgac ggcacttact   38400
gtatcaagag aggtgagaaa aaggagccac agcaggatga ttcaagggac tctgcatagc   38460
tccattttaa gaatatgcct actgcaggtc agagaaggta agcaaactgc ctaaggccac   38520
acagccaggt acagaactct caccaatatt attgccagca atcgcaattt tggtgtttat   38580
tcttggtacc aagttggaga ctatagggtt ctcttcctaa tagagaccat ctagcctttc   38640
actgttttgt ggatacttct ttctcttctt ctttttttt ttccctttta aaatctagtt    38700
attttttct ttttggtttc tttgacacag gtctcttac tctgttaccc aggctggaat     38760
ggagtagtgc agtcatggtt cactgtagct ttgacttcct gggctcaagc gatcctccta   38820
cctcagcttc ccgagtagct gggaccacag gcgcccacca acacctccag ctaattttta   38880
agttttact agagacaaca tctcactatg ttgcccaggc tggtctcaaa atcctgggct    38940
caagtgatcc cacctcagcc ttccaaaatg ctgggattac aggtgtgtgc accacgcctg   39000
gcctattttt tttttaattg ctcataaatc atctttttc tttaaaaaa agaaagatgg     39060
gaggctaaag caggagaatc acttgaaccc aggaggcgga ggttgcagtg agctgagatc   39120
atgctgctgc tctccagcct gggcaacaag agtgaaactc catctcaaaa aaaaaaaaa    39180
agaaagtaca caattttact ttctggacct aatggtcaag gccaataatt tggtcaccta   39240
tgaaataaat aaaagcttta ccatatatat gaccatttga taatgtaata tgaaatgttt   39300
atgtactaaa ggcagaatag tctagaaaaa acattctgta tcacaacgtc taaaaatgaa   39360
tatcatcttc atcatagaac caggctcttt ctcctaattt ttttttttga gatggagttt   39420
tgctctgtca cccaggctgg aatgcagtgg cacaattttg gctcactgca accttcagct   39480
cccaggttca ggatcaagtg attttcgtgc ttcagccttc taagtagctg ggattacagg   39540
tgactgccac cacacccagc tcattttttt gtattttttt agtagagaga gggtttcacc   39600
atgttggcca ggctcgtctc gaactcctga cctcaaataa tccacccgtc tcagcctccc   39660
```

```
aaagtgctga gattacaggc gtgagccacc aggcctggcc tcctaatttt tatttgtaga    39720
agtggcacca aaattttcca agttctcatg caaaaattca ggctcatctc agtttatttt    39780
tttcatttat ttatctccca ctaaattgac aacttctaat aattaggttg gttctttgta    39840
ttcccagcac agggttctat gcagaataca cacacagcag ttgctggcaa taatattggt    39900
gagagttctg tactgggcta tgtgatctta gacagtttgc ttatgttctc tgacctgccg    39960
taggcacatt cttaaaatga agctgttcag accccctcga ttcatcctgc tgtggcttct    40020 tttcccacc taaatcttaa atacccttt agctgctagt aagtgaatga tgttttttta     40080
tgaactttct gaagtcagat tagatgaagt tgagaaaagc ctgatattct tataaagtta    40140
tatatgtgca tcatagaaaa cttagaaaat acagataaac aaaaatcatc catggacgaa    40200
ccttgaagac attgtgttaa ctgaaataaa ccggacacca aaggacacat gttatatgct    40260
tccacttata tgagatacct agaatagtta catttggtta ctctgggtac attgcctata    40320
gataagcctt gctccacaag gagcagttaa aaaaaaaaaa aagataaatt cataggatgg    40380
aaggtagaat agtggttact agggacttgg ggaggggaa atggggagtt actgtttgat     40440
gagtgcagat ttcagtttgg gatgatgaaa aagttctgga gatagatagt ggcaatggta    40500
acacaacagt gtgaaaataa tgccactgaa ctgtacactt aaaatgatta aaatgataag    40560
ttaattgtaa tttgtgttat ccagaaatgg ttagcaattt attggtgtat attctttag    40620 tattcctgtg tgtgcacagg ggtgcttgta tatactttat ctttaaaata tatccaggaa   40680
gctaggcaca gtggcttaca cctgtaatcc cagcactttg ggagggtgag gcaggaagat    40740
tgcctgagcc ccggaggtca aggctgcagt gagttgtgat cacgctactg cactctgttc    40800
tgggcaaccc ctgtctggga aaaaaaaaaa aattagtgag gcttagtggt gcacacctgt    40860
agtctcagct acttgagtgg ctgggtagg attgcttgat cccagcaagt tgaggccgtg     40920
gtgagccatg atggtgccac tgcactccat cctgggtgat atggtgagac cctgtctcaa    40980
aaacaagaaa tccagataat tctgtgcatt ataatctagc ttttactgga tcattaaaat    41040
tcttttttct ttttttttt tttttctga gatggagttt cactcttgtt gcccaggctg      41100
gagtgcagtg gtgtgacctt ggctcaccgc atcctctgcc tcccgggttc atgcgattct    41160
cctgcctcag cctcccgagt agctgggatt acaggcatgt gccaccatgc ccagctaact    41220 ttgtatttt agtagagaca gggtttctcc atgttgacca ggctggtctc aaactcctgg    41280
cctcaagtga tccacccacc tcggcctccc aaagtgctgg ggttacaggc gtgagccacc    41340
gcactcagcc tgggtcgtta aaattcttaa gtgacttcat ttttaattac tatatgggat    41400
tctatctttc cagtgtatca tgatttattt gacctattgc tgaatgttgg aggtttcagg    41460
gtaagaggca cagtttgcta ttatgtacat cactatagtg gcatcctgat agctaaatat    41520
ttgcctacat ccctgattat ttccttagtc taaattactg ggactaggat tttggtgttt    41580
gatacatgtt actaaattgt ttttagaaa gattaaacca gttatgctc ttccagcccc      41640 tgtggtatat gatagttccc attttcctgt accttgccaa cactgggtga tatccagttt    41700
taaaatctaa atcttgcatt gctatgagaa ctacaattag agaaggctta tcttctactg    41760
cccattctct gtacagagca aatccctcta gacctgaagc cccttggagt tgtcaagaaa    41820
cctttgagat gactccccac tctgtatctg agctgtcacc agtattctcc acttcttcag    41880
gattgccatg gcaactaaat tgatgaaaag atttaggagg cctttctctt ctttgcaatt    41940
cctatgatcc ttttttgaatg tgggtttggg actctgtcaa tatacccatc atctaattct   42000
```

```
gtccattgtg ttttaaagtt taaggttgca atttctgatt acatctgcct tagccatact    42060
gtattatatt tgacattcaa tatacaatgt ccttgttttt ctgtatttct aatcttattc    42120
ccagagatgt gtctatttgt tcaggattca ttttgcaacg tgttttttact aagcatctac   42180 ccaaaaccgt tgaagtcaga tttcaggctg tcttacgtct aaagtagcac aggcaggaaa    42240
aactattgaa gtgggatttt ttttteectt tttgtactga accgagaaaa agtatataga    42300
tgatagagaa ttcctaatttt ggtatcattg atatctgggt ttttgtttgt ttttacagaa   42360
gactgattaa ctatacttat ttattaattt atcttctcat taataaacac ttgctgagtg    42420
cttactgtct gctaggcatt agggagacaa atatgattaa gggaagcttc ctcctatcaa    42480
ggtcatgtgt tccatttggg tatactaatg cattagcaat gtaaatcaag tagtgagaga    42540
tcatctgttc ccgataggag atggattatt ggtggggact tctgtgtgtg tgtgtgtgtg    42600
tgtgtgtgtg tgtgtgtgtg tatgtatgtg ataaaataaa tataggaaat gttaattata    42660
gattctaagt agtagatata taaacactca ttgcaaagtt gcttcaagtt ttctgtatat    42720
ttgaaaatat tcacaacatg tcgacaaaac tagcatgata aagccactat ttgtgctaag    42780
acttcagctt gtatctggat taggcttatt atgtagtagt aggaacatta gaaatagttt    42840
taactcatta aatacacatg ttttatggga aggttttata tatatattta tatgtaatga    42900
atgtgaacaa acaagggtca gatatacact ctgcttccct ccagaccagt tccggctgct    42960
ctgctgcaca tttcaggagt cttattagaa ttagccacat tctgcccact tgcccttact    43020
tctcatattt cacaactcct cctggtgggg acttaaggag acattcaaac taggccttga    43080
aagatgagaa ttttttccaag tggaaaaaga ggagtggcag caagtaaggt aaaggtacag    43140
agtcatggaa ttcccaggaa acgtaaagtt gtcatgtgtt ataggaaaac aacttgtgtg    43200
aggggtgttg ggagaaatga gagataatac cagggtataa agggccttt gaatgctatg     43260 ttgaggaatt ttatcctaat ggcagtaatg actaacaatt atatagtgtt caaaaagtat    43320
aaatcagcag tggtatacca ctaagggttt ttttctttc ttttttttt tgagacagag     43380 ttttgctctg ttgcccaggc tggagtgccg tggcacgatc tcagctcact gcacttccgc    43440
cacctgggtt caagtgattc ttctgcctca gccagtgttt cactgtgatg gccaggatgg    43500
agcactaagg gtctttatgg aagaaaaaga catgataaac aaggctttta gggaacttct    43560
acagtaatgt agctgtatta aaagtagaga tcagagcagc atagtagaag tagaaggcta    43620
gagctaattg aaggagcact tcagaattag aatcaagaag tcttagaaac ctattggttt    43680
tattctccct aatgtatttg gccacttacc tgctggggaa tttgtctaag ttataaaaaa    43740
taattccttt gggaaaccca aaggaaagtt atctattaat aattacccca ctactttttc    43800
tgatttatgt aatggccacg tagaggttag atgtgatggt tgtgacagta gtgactaata    43860
cagcctgtga agcattttgg tcagatatct atgtgctttc attccaggtt gactgaggca    43920
agactttggc tagggtttga tcagtgatgt aactactcac gagtaccacg tggtggcaat    43980
ggcattgctg cagaccttgg cagcaaagca gtgttagagt agcagtagaa acctttgtga    44040
agctaggaat acattttctg gtcataaaaa cctcctgaaa attgtgaact cagtgtagca    44100
ggagaaagaa gatggcttgt ttttagtaaa gggcaaagtc atttttaagg atcagaagaa    44160
gaaacggaga gtgaaacaat gtgttcctgc cctactcccc cactggactt tttggcaacc    44220
attgctgttc cttctaaaag tgatttttaa acatgtatat tttgaagcca ggcacagtga    44280
ctcacgtctg taatcccagc actttgggag gccgaggcgg gcagatcacc tgaggtcagg    44340
agttcaagac cagcctggcc aacatggtga aaccccgtct ctactaaaaa tacaaaaatt    44400
```

```
aggccaggtg tggtggctca cgcctgtaat cccagcactt tgggaggccg aggcgggagg    44460
atcatgtggt caggagatcc agaccatcct ggctaacacg gtgaaacacc atttctacta    44520
aaaatacaaa aaattagctg gcatggtgg cgggcgcctg taatcccagc tactcaggag    44580
gctgaagcag aagaatggct tgaacctggg aggcggagct tgcagtgaac caagattgcg    44640
ccactgcact ccagcctggg caacaaagtg agactccgtc tcaaaaaaaa aaaaaaaaat    44700
tagtcgggca tggtaacagg tgcctgtaat cccagctact tgagaggctg aggcaggag    44760 aattgcttga accaggtagg cggaggttgc agtgagccaa gatcgcacca ctgcactcca    44820 gcctgggca acagagcaag actgtctcaa aaaaataaa taaataaaat aaattcttaa    44880
gaaggatatt ttggaaaact ccttacatac ctaaattctt tgtttatcaa atacttggac    44940
ttagcacact cttctttgaa atggaccaat aaacaacagg agcccataag caaaagaac    45000 tcattatttt aaaaacagta actatcctta caggctttct cagggctctt tctgttggat    45060
ccttccctct cacaggtcct tgctaatgat ctctaggtgg acacattcta gatgagatgt    45120
ccctgtctag aatggcagca ccatgagggc tatatcctca gtactaggac agcgcctggt    45180
gcttaataga tagtaaatag ttgtctaatt aactgagcaa acagatagat tcatgaatta    45240 gcttttgct ttttctgtta gaaactaaag gttcaggtca ggcacaatgg cgcatgtctc    45300
taatcccagc actttgggag gccgaggcgg gctgatcact tgaggtcagg agttcaagac    45360
cagcctggcc aacatagtaa aaccctgttt ctacaaaaat taccaaaatt agccgggcgt    45420
cttggcaagc acctgtaatg ccagctactt gagaggctga ggtgggagaa tcgcttgaac    45480
ctgggaggaa gaggttgcag tgagccgaga tggtgccaac ctgggtgaca gagggagact    45540 taaaaaaaa aagaaagaaa gaaagaaaag aaactaaagg ttcaagaat cccagaaaag    45600 gaagagtcct cacaagccag taatctaggc aggattactg atagtatttt tatatttgtt    45660
gtatttttat aaaatgccat agatagaggg cttttttcaa cattacatca gtctaaaaat    45720
cacacatttt tatatgaact aacctaaatg tctgatgaat ctcacaacac caagtctttg    45780
aaatgtgccc atataaataa aatgttaaca gattcatgct aatttttaaat atcgatagtg    45840 tttaaatgcc ttaattattt tttcactccc tagctttaaa agaaaataac caacttcaaa    45900
aggacatcac aataacatca agtctatttg ggggaatttg aggatttttt ccctcactaa    45960
catcatttgg aaataatttc atgggcatta attgcatgaa tgtggttaga ttaaaaggtg    46020
ttcagctaga acttgtagtt ccatactagg tgatttcaat tcctgtgcta aaattaattt    46080
gtatgatata ttttcattta atggaaagct tctcaaagta tttcattttc ttggtgccat    46140
ttatcgtttt tgaagcagag ggataccatg caacataacc tgataaagct ccagcaggaa    46200
atggctgaac tagaagctgt gttagaacag catgggagcc agccttctaa cagctaccct    46260
tccatcataa gtgactcttc tgcccttgag gacctgcgaa atccagaaca agcacatca    46320 gaaaaggtg tgtattgttg gccaaacact gatatcttaa gcaaaattct ttccttcccc    46380
tttatctcct tctgaagagt aaggacctag ctccaacatt ttatgatcct tgctcagcac    46440
atgggtaatt atgagccctt ggttcttgtc cctgctcaca actaatatac cagtcagagg    46500
gacccaaggc agtcattcat gttgtcatct gagtacctac aacaagtaga tgctatgggg    46560
agcccatgga agatacatgg tatacaacat agctcttgct ctattggaag ctaagtggaa    46620
tgggagaaat tggtgacagg caaccccata atttcagaaa gctatgaaaa agtactcaga    46680
catattcctt ataacactgg tgtcacatca caaagaccta tttaatgtgc ttctgattta    46740
```

```
tagggagaga catcctatac ttcaggaact gcactttgat ccacagaaag cctagtgatg    46800
tagagctcct gttagttcaa aaggaaaaga aaagaacaac acagaaagcc taattatgca    46860
atagagtcaa gtgctttata gcaatgttac agttatcaaa aaaaatccag atggacctct    46920
gagaggatgc cattggagta accaggcaga tgcagttgat cagagctgac ttcctataag    46980
aagtgagcac tgagctgagg aataatggca taaatgaagg aaagtgagat ggaaatttga    47040 gttttttaatt ggaaagacaa tacatcaggc agattttttaa ataggggcaa acaaacagac    47100
acataggaga tgctaggcat ggggtcccca ctaggatgct gcttagaaac atgcaggggt    47160
ggtgagtact cccaaagtac acttcattcc tagctcagtg attcttatct gagtgttaaa    47220
gttccttctt cagcaccccg ttccacagtc caactgggaa ctttaagacc tttcttggag    47280
tctttctagg aactcaagtc tgctactat acagaacagt ggctttggtc cccagttgtg    47340
ccttgcagta ttttttgtgtt caggaagaaa cagtagctct tggataaaga agctagctag    47400
aaactctgtt gctatggcag tgcttcaaaa tgtatttcct taaatgcttt ctttgtaact    47460
atcttcattt agttcatctc tcagataatg agagatcaga gtcccatccc cagtataata    47520
ctcttcttta gggtactttc accatcttca gtctaaacac agactagact ttcaattata    47580
atgtgtaaga tttaaaatgt tattattgtg tgactttgaa tatctgtgta aatctactat    47640
ctcctctttg gtatatacgt gtgtttattt ttttctggag atctgtaact gaaatgctta    47700
atttctgaat tgttttggat atcacaactt aataccaaca taagttttga gccttttttct    47760 ccctaaatct ggtgtgagtc taactgaaac tcaaatgaac ttttttaaaaa taattttttc    47820 ttttctttaa tttttttttt aagtagagac agggacgcac tgttaactag gctggtcttg    47880
aactcctgat cttgagccat cctccccgac ctgagcctca ccttatagag agggtcttgc    47940
tctgttgccc aagctggagg gcagtggcat aatcacagct cactgcagcc tctcgacctc    48000
ctcaagcgat cctcctgcct tagcctccca gtagctggg actataggcg tccaccacca    48060
tacccagcta attttttttt ttattttttg tagagacaag gtctccctat gttgcccaag    48120
ttggtctcaa actcctggac tcaagcagtc ctctcacctc agggtcccaa agtgctgggg    48180
ttacaggtgt gagccatggc acctggccag aacttctagt aaaaagaata ttgttgccgg    48240
gtacggtggc tcacgcctgt aacccccagca ctttgggagg ccaaggcagg cgaatcacct    48300
gaggtcggga gctcgagacc agcctgacca acatggagaa accacatctc tactaaaact    48360
acaaaaaatt agccgggcgt ggtggcacat gcctgtaatc ccagctactt gggagctacg    48420
gtgcctggcc tagtttatta tttcttaata tctgttgtct tccagtgtct tccttaattc    48480
ttcacaatac cctgtacaat gcttagcaca cagtgggcag tctgtaagtt tattaaatgt    48540
ttggtgtggc ccatacttcc tatccacaaa gaatgtaaca tgttaagaca tctagatgag    48600
ggaatgattt aagaggaact acaataatat tctgaaactt ggactctgga tctctgcatt    48660
tagactttcc taaccagcc agcaagtaga tcatcatgtc acaaggctta ggttgggctt    48720
gctgttcaga gaatgaatta aggattaagg agaaaaaaaa gcagaaaggt tttgctctgt    48780
ttttcaggtt ctattgagtt gttaacttct aacaagttat cttatttgct tcattgcatg    48840
aggcccattg tagtaagaag aggaatttat atgctaaatg ttctggtgat agaatgactt    48900
ttcttttttt ttacagtcca aaggtctttt tttttttttt ttaacaccta ttatgccatg    48960
aattcatagg gaataggttc cagctgctca ggctccttcc cattggttct cacaaagtgt    49020
gcttctctgg gtggagcagg ctggtgcttc agttgaaccc acgtaccttt ctctttggct    49080
tctttctttt tctgatcatt ttccttcacg cgtttcagga agctgtcttg gctcttagag    49140
```

```
tgtttaatgt gctcaatacg cacattaatt ctcttggcaa gaatcttgcc cttaacttgt    49200
ttacagcgat gccaacagca tgctgggtca cgttgtagac ttttccagtt ttgccatggt    49260
aacacttgtg gggcattcct ttttgaacag tacccgttcc cttgatgtct acaatttcac    49320
ctttcttaca gattcgcata tacatggcca aaggaacaac tccatgtttt ctaaaaggcc    49380
tagagaacat atatcaggtg cctctcctct ttccctttgt gttcgtcatt ttggcaaatt    49440
actgaaagat ggtggttctg gccaaaagga ggaatgactt tttaatagct gtgtttgtat    49500
ctgagccttc cctctgcctt tcattttttt tgttttgttt tgttttgttt tgtttgaga    49560
tgaagtttca cttttgttgc ccaggctgga gtgcaatggt gtgatttcgg ctcattacaa    49620
tgtccgcctc agcctcctgg gtagctggga ttacaggcac ccgccaccac gcccagctaa    49680
tttttgtatt tttagtagag acagggtttc accatgttgg ccgggctggt ctcaaactcc    49740
tgacctcagg tgatctgtcc acctcggcct ctcaaagtgc tgggattgta ggcgtgagcc    49800
acatcacctg gccactttt taactctttc caatggttaa ttccgtttga tatggttcct    49860
tggaacttgc acattaccct ttatcaatta tcaccctgta ttggggtgg ggaggatgat    49920
acctctcttc atagttagat cctacttact ttcaacagag ttcttaacaa tcctagaaac    49980
tcacaggtcc agaaaagaca agcataaagg aaactataaa taatgcattt gaagactaac    50040
tcaggaaatc aatgattatt tccccccagg ctacccagtg tcttaaaaaa acagtttaat    50100
taatacaatc ttttgtttca attttctacc tatatttatg gcttttagct tttctaataa    50160
aagctcaaaa tgaattacag tcatcagtga cttttaatg aatagaagac ttttgcaatt    50220
tttaactatt tgttttact tattaaatat ttccgccttg gccaggcatg gtggctcacg    50280
cctataatcc cagcactgtg agatgccaag gcaggaggat cacttgagtt taagagttct    50340
agaccaggct gggtatggtg gctcatgcct ataatcccag cactttgtga ggccaaggtt    50400
ggcggatcac ctgaggtcag gagtttaaga ccagcctggc caacatggta aaaccccatc    50460
tctacaaaaa atacaaaaat tagccaaggg gtggtggtgg gcacctataa tcccatcttc    50520
ttgggaggct aaggcaggag aatcgcttga acctggaggc agaggttgca gtgagccgag    50580
atcatgccac tgtattccag cctgggtaac agagcaagac tctgtctcaa aaaaaaaaa    50640
aagtttgaaa ccagcctggt caacacagca agacacccat ctcgttgaaa ataacggtc    50700
gggcgcagtg gctcacgcct gtaatcccat cactttggga ggccgaggca ggcagatcac    50760
ctgaggtcgg gagttcgaga ccagcgtgac caacatggag aaaccccatc tctactaaaa    50820
atacaaaatt agttgggcga ggtggtgcat acctgtaatc ccaactactt gggaggctga    50880
ggcaggagaa cagcttgaac ctgggaggca gagaggttgt ggtgagccaa gatcatgcca    50940
ttgcactgca gcctgggcaa caagagcaaa actccatctc aaaaaaaata aataaataaa    51000
aataaataaa taagtacttc tgcctttaag ccacttccta gaaggcagtg gcacaaagtg    51060
atacatttgg aggagtaaat atattacaaa atgaattagg ctgggcgcag tggctcatgt    51120
ctgtaatccc cgcactttgg gaggccaagg cgggtggatc acttgaggtc aggagttcga    51180
gactagcctg atcaacaggg taaaatccca tctctactaa aaataccaaa aaaactagct    51240
gggcgtggtg gcaggcacct gtaatgtcag ctactaggaa ggctgaggca ggagaatcgc    51300
ttgaacccag gaggtggagg ttgcagtgag ccaagattgc accattgcac ttcagcttgg    51360
gcaacagagt gagactccgt ctcaaaaaaa aaaaagaac taacatgcca gaactttgcc    51420
ttcagtatgt tttgtgattt ttcccttctt gtgccatttc atcattagtt ccatgtatta    51480
```

```
tttaagattt cttatcaacc agcaccttgg gattttttg tgtatgtgtt ggtttagggg    51540
gtttatttgt tttttctttt tttttcggta attgaaaatg tgaagcaaaa tgtcacctgt    51600
tttttctttc atgtctgaca ctcatgtctt gtttacccc gacatgcaga agctgaaatc    51660
cccatttcat acagtcttca atgtggaggc agtagggatg gagaaaataa tgtactttgt    51720
gctctccggt actctttctt tcctattgtc tgaggggatt tgggcataat ttattttgct    51780
gcagagataa aaatttgtta tatatatttt ttatcattca gggccaagga atatagattt    51840 ttttttttcag ccttgtctca gctgggtgtc tttatttact ctgtcttaaa gtgttccttt    51900
tattatcatt attatttttt aatcattgaa ttccatttgg tgctagcatc tgtctgttgc    51960
attgcttgtg tttataaaat tctgcctgat atacttgttt aaaaaccaat ttgtgtatca    52020
tagattgatg cttttgaaaa aaatcagtat tctaacctga attatcacta tcagaacaaa    52080
gcagtaaagt agatttgttt tctcattcca tttaaagcag tattaacttc acagaaaagt    52140
agtgaatacc ctataagcca gaatccagaa ggcctttctg ctgacaagtt tgaggtgtct    52200
gcagatagtt ctaccagtaa aaataaagaa ccaggagtgg aaaggtaaga aacatcaatg    52260
taaagatgct gtggtatctg acatctttat ttatattgaa ctctgattgt taattttttt    52320
caccatactt tctccagttt tttgcataca ggcatttata cactttttatt gctctaggat    52380 acttcttttg tttaatccta tataggtttt ttgaacctat aacataagct acaacatgag    52440
aaatgtgcgg ttagatagat atgtcccttc tgaaggtcag aaaaaaatat aatggaggta    52500
aaacctgaac aagcttggaa actgatggta gacttcttca aggcagccct tgccctaatt    52560
aaaattcttg tctttctaga aaaagtctag ctgttgattt accacagaaa ataataataa    52620
taattactat tattattatt ttttgagaca gggtcgccct gtgtcaccta gattgcagtg    52680
gtgcagtcat ggctcactgc atcctccgtt tttcaggctc aagcaatcct cccacccttag    52740 cctcctgagt agctgggtcc acaagcatgc gccacccaca cccactaagt ttttgtatttt    52800 ttggtagaga tggagttttta ccttgttgcc caggctggtc tcaaattcct ggactcaagt    52860
agtccgcccg ccttgccctc ccaaagccag aaaacattta gaatatcttt cagagatgtg    52920
tatttacacc actattaaca cagggctgta tagcagtcca gtactggact atgtagtcca    52980
gtactattct tttccttact ggagggccag gcgtggtggc aggtgcctgt aatcccagct    53040
actcaggagg ctgaggcagg agaattgctt gaacctggga ggcagaggtt gcagtgagct    53100
gggaccgtgc cattgcactc cagcctgggc gacagagcaa gactccgtct caaaacaaaa    53160 aaaaaagag agagagagca gtaattcagg tctcacccat cttcaatcca gggggcctag    53220
ccttagtatt tgacccatag taagcaccca ataattgttt aaattaatta acctctgagg    53280
ccctttaaat ctgttgataa gtatcttatt ttgcaaagtc ctaagcactt ggaagagcag    53340
aggaactatt tactgggtgt gtatgctttt ctaacaatat tttatagctg cttttgttt    53400 ttagaatgaa tttgaacatt gaaaaggcag gcaatagga tgattctgtg aattctgcta    53460
aaactgagta gaaagaatga gtgtagagat gtcgacattg atcaactttc tatcttcata    53520
agagatctga ttctaacata tccatttaga ctcaagtaga atattgtgta tagagtgagt    53580
ggcagtgagt aatttggtaa aaatttgctg acctgctttt attctttcct cctttctttc    53640
ttcctttcct tccttccttc cttccgtcct ttcctttcct ttcctcccct tccttccttc    53700 tttcctttctt tctttccttt cttttccttt tccttccttct tccttcctcc cttccttttc    53760
ttttctttct ttccttttcct tttctttcct ttctttcctt tccttttcttt cttgacagag    53820 tcttgctctg tcactcaggc tggagtgcag tggcgtgatc tcggctcact gcaacctctg    53880
```

```
tctcccaggt tcaagcaatt ttcctgcctc agcctcccga gtagctgaga ttacaggcgc    53940
cagccaccac acccagctac tgacctgctt ttaaacagct gggagatatg gtgcctcaga    54000
ccaacccaac cccatgttat atgtcaaccc tgacatattg gcaggcaaca tgaatccaga    54060
cttctaggct gtcttgcggg ctctttttg ccagtcattt ctgatctctc tgacatgagc     54120
tgtttcattt atgctttggc tgcccagcaa gtatgatttg tcctttcaca attggtggcg    54180
atggttttct ccttccatttt atctttctag gtcatcccct tctaaatgcc catcattaga   54240
tgataggtgg tacatgcaca gttgctctgg gagtcttcag aatagaaact acccatctca    54300
agaggagctc attaaggttg ttgatgtgga ggagcaacag ctggaagagt ctgggccaca    54360
cgatttgacg gaaacatctt acttgccaag gcaagatcta ggtaatattt catctgctgt    54420
attggaacaa acactttgat tttactctga atcctacata agatattct ggttaaccaa     54480 cttttagatg tactagtcta tcatggacac ttttgttata cttaattaag cccactttag    54540
aaaaatagct caagtgttaa tcaaggttta cttgaaaatt attgaaactg ttaatccatc    54600
tatattttaa ttaatggttt aactaatgat tttgaggatg agggagtctt ggtgtactct    54660
aaatgtatta tttcaggcca ggcatagtgg ctcacgcctg taatcccagt actccaggag    54720
gccgaggcag gtggatcagc tgaggtcagg agttcaagac ctgtctggcc aacatggtga    54780
aaccctgtct ctactaaaaa tacaaaaaaa ttaactgggt gtgctagtgc atgcccgtaa    54840
tcctagctac tctggaggct gaggcagcag aatcacttga acccgggagg cggaggttgc    54900
ggtgagccaa gatcacacca ctgcactcca gtctgggtga cagagcaaga ctccatctca    54960
aaaaatatat atatatatat atacacacat atattttatt tcaactgtta gacaagagtc    55020
caaaggccaa agaataaagt tttaggccag tcctttatta gaaatgagt caaatcccaa     55080 agcaagtttt tttatgagtt aatgaatata atgactaca tatttatgc cttaaaaatc      55140 acttttaatg aatggtgttt tatggcttgt aaatcagagt tttaatcagt aaagaaagtt    55200
tttaatcctc aaaaacacgt tatcataaaa gacactgttt ggcatcaaat gtggtatttg    55260
gccatgttca ttagggtcat tttaggaatc tcatacattc tacttagcta tgcttaattc    55320
ctgataccat ggcatttct gaaatgtttc aaggatgaca tctctgctgt ttttaatttg     55380
gtaatgatat ctgctgattt attaagtgaa aaaagtaatg gtgtcattac cttggatgaa    55440
gaaacaaaaa taaagcattt gccacatttt tcaactttgt tttcctttct tacaaaattg    55500
ctataagctc attgcccca aattggacaa tatagggaat aaaaaagata atttggggtg     55560
gggttagaca cgggtcttgt tatgttgccg aggctggtct ctaactcctg gcctcatgca    55620
atcttcctac cttggcctcc caaagtgctg ggattatagg tgtgagccac ttcaccaagc    55680
tgagatgcca cctcttaaaa gagagaataa ggacagatta cagccactgc tcatgcctgt    55740
aatgtcagta ctttgggagg ccaaggtggg agaattgctc gaggccaaga gttcaagacc    55800
agcctgggca atgtagcgag acctgatctc tatgaaaagg gggtggggg ggaaaactag     55860 ctggggccag gcgtggtggg tggcttacgc ctgtaatccc agcactttgg gaggccgagg    55920
cgggcagatc acctgagggc aggagttcag gaccaacctg accaatatgg agaaaccctg    55980
tctctactaa aaatacaaaa ttagccaggc ttggtggctt atgcctgtag tcccagctac    56040
tcgggaggct gaggcaggag aatcgcttga acctgggagg cagaggtttc agtgagctga    56100
gatcgcgcca ttgcactcta gcctgggcaa caagaatgaa actccatctc aaaaaaaaaa    56160
aaaatcagct ggaaggtggc aaacacctgt ggtcccagct actcaggagg ctgagacagg    56220
```

```
aagatcactt gagtccagga ggtcaaggct gcaggtgagc catgtttgtg ccactgcact    56280
gcagcctgga tgacagaccg agacccttct caaaaaaaaa attttteccg gtatttttt     56340 ttggggggg  gtttaattct tgttgcccag gctggggtga attggggaat tttgggttaa   56400
gggaaccttc ggcttcctgg gttgggggt ttttcctgtt taggcttccc cagtagctgg    56460
gattacaggc atgcaccacc acgcccggct aatttttgt attttagta gagacaggt     56520 ttctccatgt tggtcagact ggtctcgacc tcttgacctc aggtgatccg cccaccttgg    56580
cctcccaaag tgttgggatt acaggcctga gccaccgcac ccggcctgta ctcttattct    56640
ttaataataa aatatttctg tgtttcttta gtcattttac ataaactttt atttatttat    56700
ttatttttat ttatttattt ttttgagacg gagtctcgtt ctgttgccca ggctggaatg    56760
caatggctca atctcagctc actgcaagct ctgcctcccg ggtacacgcc attcccctgc    56820
ctcagcctcc ctagtagccg ggactacagg cgcccgccac cacgcccagc taatttttt     56880 ttttgtattt tcagtagaga cagggttca ctgtgttagc caggatggtc ttgatctcct    56940
gacctcgtga tccaccgtc tcggcctccc aaagtgctgg gattacaggt gtgagccacc    57000
gtgctcggcc cataaacttt tatttttaaa ataatgtcat gataataat attgcttagg    57060 tgtctttaat atattagtaa catttctgtt ttattgtaca tcaacattta tattcaaatt    57120
aatgggtgaa gagtactcca ttggactagg tatatcgtaa tttaatctcc tattattgga    57180
caactacatt gttctaaaa ttatactatt cctatgacta aacctttgca tatatcttt     57240 atctccctag gatatattc taaaactagc attgttgact gaaagtgtaa atacgtgtta    57300
aggtgtttgc tacataatgc catatttcct ttttaggaaa ctaagctact ttggatttcc    57360
accaacactg tattcatgta cccattttc tcttaaccta acttattgg tctttttaat    57420 tcttaacaga gaccagaact tgtaattca acattcatcg ttgtgtaaat taaacttctc    57480
ccattccttt cagagggaac cccttacctg gaatctggaa tcagcctctt ctctgatgac    57540
cctgaatctg atccttctga agacagagcc ccagagtcag ctcgtgttgg caacatacca    57600
tcttcaacct ctgcattgaa agttccccaa ttgaaagttg cagaatctgc ccagagtcca    57660
gctgctgctc atactactga tactgctggg tataatgcaa tggaagaaag tgtgagcagg    57720
gagaagccag aattgacagc ttcaacagaa agggtcaaca aaagaatgtc catggtggtg    57780
tctggcctga ccccagaaga atttgtgagt gtatccatat gtatctccct aatgactaag    57840
acttaacaac attctggaaa gagttttatg taggtattgt caattaataa cctagaggaa    57900
gaaatctaga aaacaatcac agttctgtgt aatttaattt cgattactaa tttctgaaaa    57960
tttagatcta gataaagcta tagtgtggat tattttatgt atatttactt gagaaaataa    58020
ttattaaata ttagtggaaa agctatactt tgggtatgat ataggacttt cgaattggaa    58080
ttttcctttc tatctgtaaa agcaagtagg tatagtttta ttccccagaa ggcatctttt    58140
tctccccctt gtctcacatg ggtgaattta ccagcatatt taactaaatt cagactggtt    58200
ccaaatgtac tgccagatag tagcatttct ctagtgtttg ttttcatcct ggcttgtaag    58260
aatgccctgc cacttctgcc ctgcaatatc ccttgctatt aggattttgg catcaccttg    58320
ggtccttaat gccagaaatg ggaattgctt catactgtgg aaaaataccc attaaaatat    58380
taagaccagt aaaacctcgt ttctgcttgg gctatttgtg gatttcagac atcctgagaa    58440
gtttaccacc cctgtaatta attgtcattg tcatcactc ataataaaaa taattgcatg    58500
gccgggcatg gtggctcaag cctgtaatcc cagcactttg ggaggctgag gtggtcagat    58560
cacctaaggt caggagatca agaccagcct gaccaacatg aagaaacccc atctttacta    58620
```

```
aaaatacaca attagccggg cgtggtggcg catgcctata atcccagcta ctcaggaggc    58680
tgaggcagga gaattgcttg aacccggag gcggaggttg cggtgagccg agattgcacc    58740
attgcactcc agcctgggca acaagagcga aactctgtct caataataag aagaagaatt    58800
gcgtgaatat ttctttaaaa ctatgatgag ataacatacc agattatcaa atggattcag    58860
tagtgggtgt gccatttatt gcacactgag agatgaccaa gtcattctga aatatcttta    58920
ttaatatatc cttcctagga tttttcatcc taacttctcc ataggtagtt acttagcata    58980
acatctctgt ggccagatgt atcccactac taaaagggca agtaagctg tggctgccct     59040 ggtagataca atgagtaagt gcacagtgat ggctataaat gttttcatct cataatccca    59100
tgtccagacc agcaatttgc tctgaaagct cttacctgtg tctgtttcaa tggctcttga    59160
tcacttgcct gcacgtccag aattccttat ttattcattg aaaattagcg ttctttatcc    59220
ctttgttttg caagttcagc ttttagaga tggctaaaat ggtctaatct ttcttggcaa     59280
aggcaattct gagctgcaga ttagactaca agtggcttgg gtacatgttg tctttaaaca    59340
agcgaagagg aaaactttga gctctattca gacttggtga agtgtggtaa atttatgatg    59400
aaagctactg actgtattac acatgattaa ttctgaagcc catattaaga tgatcttttc    59460
agcagttcag cattgctctt ctaactgaac agtttcaagg ctgggatttc agcaattaat    59520
cagttcagaa ttgctaatga tctggcggag ggtggtagca aaaggggag gatgtcatta    59580 gcttctctag cctgcctttt ttcagtgccc tgtggcagta tggagtgagg caacatgaaa    59640
gaaagatggc ctgaccttca tggcagtatt gtgcaacacg taaatactgg tgtgagtggc    59700
tgtggctatg gctagtaaat gatggcccctt ggtaaacaaa gttatttatc agacaatacc   59760
taccagctag gtcaactgtg cccataattg atctggttaa tttcttttgc tgcctattga    59820
tttttatttg gttgatagat aatagctaga ggactctaaa tttctttggg gaagaacatg    59880
aaccccttct aagccttctt acgagagaat tgatcgcttt gcactgacc tttagtaaca     59940 tcctgatttc agtgttttgt aactatcaga gggttgagtc ttggttttaa gccatgtata    60000
tctgtagcat aactttctgt gtaggctagt tacctctcag cttataaagt gtaggctgat    60060
aaatttatag tacagtagag tgtcactatg caaagaaacg atcttaggga atcgaatgat    60120
atctgctatt aaagcaaaat taatatatat tttttctttt tactttttt tttttttaaa     60180 gacatgaaat ctcactgtat tgcccaggct ggtcttggtc tcagactctt gagctcaagc    60240
agtcctccca cctcagcttc ccaaagtgct gggattatag gcatgagctg ccgtgtctgg    60300
cccagtatat atttttaag ttttaagttt tgtggtacgt agtaggttta taatattatt     60360
ttgaatcctt agttgtaatt ttatgtctgc tgatgtgtac ataatttta ttaaactatt     60420 tatttgagac ttcaggtatc tttttttttt ttttgagacg gagtctcgca ctctcgccca    60480
ggctagagtg cagtggcgcc atctcggctt actgcaagct ctgcttcctg ggttcacgcc    60540
attctcctgc ctcagcctcc tgagtagctg agactacagg tgcccgccac cacgcctggc    60600
taattttttg tatttttagt agagacaggg tttcaccgtg ttagccagga tggtctcgat    60660
ctcctgacct tgtgatctgc ccgcctcagc ctcccaaagt gctgagatta caggcgtgag    60720
ccaccgcgcc cagccgagac ttcaggtgtc ttagaatttt ttaaatgtac cctttctgag    60780
aaaaacagag acttaaagct aggataactg gtattctatt tttttttttt tttttttttt    60840
ttacctccag cctgggtgac agagcaagac tctgtctaaa aaaaaaaaaa aaaaaattca    60900 cttaaatag ttccaggaca cgtgtagaac gtgcaggatt gctacatagg taaacatatg     60960
```

```
ccatggtgga ataactagta ttctgagctg tgtgctagag gtaactcatg ataatggaat   61020
atttgattta atttcagatg ctcgtgtaca agtttgccag aaaacaccac atcactttaa   61080
ctaatctaat tactgaagag actactcatg ttgttatgaa acaggtata ccaagaacct    61140 ttacagaata ccttgcatct gctgcataaa accacatgag gcgaggcacg gtggcgcatg   61200
cctgtaatcg cagcactttg ggaggccgag gcgggcagat cacgagatta ggagatcgag   61260
accatcctgg ccagcatggt gaaacccegt ctctactaaa aaataaaaaa attagctggg   61320
tgtggtcgcg tgcgcctgta gtcccagcta ctcgtgaggc tgaggcagga gaatcacttg   61380
aaccggggag atggaggttg cagtgagccg agatcatgcc actgcattcc agcctggcga   61440
cagagcaagg ctccgtctca aaaaaaaaa aaaaaacgt gaaaaataa gaatatttgt      61500 tgagcatagc atggatgata gtcttctaat agtcaatcaa ttactttatg aaagacaaat   61560
aatagttttg ctgcttcctt acctccttt gttttgggtt aagatttgga gtgtgggcca    61620
ggcacggtgg ctcacacctg taatctcagc actttgggag gccgaggcgg gtggatcacc   61680
tgaggtcagg agttcgagac cagcctggcc aacgtgttga aacccegtct ctactaaaaa   61740 tataaaaatt aggtgggcgt ggtggcaggc acctgtaatc ccagctactc aggaggctga   61800
ggcagcagaa tcgcttgaac ccaggaggtg gaggttgcag tgacccaaga tcgcaccatt   61860
gcactccagc ctgggacaa gagcgagatt cttgtctcaa aaaaaaaaa aaaaaaaaa     61920 ggtttggagg gtggtgagct gagatagtca actattaact cctatctacc tgctgggact   61980
acactggtga ggtggagcct aagtcctaaa acaacaagtg aggcagctgg acgcggtggc   62040
tcgcatcagt aatcccagca ctttgggagc ctgaggcggg cagatcacaa ggtcaggagt   62100
tcgagaccag cctggccaat atggtaaaac ccagtctcta ctaaaaatac ataaattggc   62160
tgggcgtggt ggtgtgcacc tgtaatccca gctactggg aggctgacac agaagaattg    62220
cttgaactct ggaggctgag gttgcagtca gctgagatcc tgccactgca ctccagcctg   62280
gcgacagagt gagactctgt ctcaacaaca acaaaagaaa gaacaagtga ggcaaaacct   62340
ggagacccca gcttcatgta acacctagtt tgagtattgt tgagagtttt tcaggaaaaa   62400
agtctgataa cagctccgag atagtcttaa catatgaaaa agcaaaaaag ggaggagaca   62460
gatcatttgt cctataccct tctctttaa ggttttaatt ataacttgtg taatacagga   62520
gacctctggg tgttttagt tgactataaa ctaaatctga gtacacattt cagggctgct    62580
aaaaatgctt atttgaaact gggccgtatt aacacaagca gaggctctgg agcaagtgaa   62640
gtacagatcc agagcccac tgtattctcc aatggagtga ttgcctgaaa gatgatgtca    62700
gttttaagca ccgtgcttgg ttttttaacat ggtcactgac aaattggaga gtgtttatcc   62760
agaggtagat ggtaaagata cataaaagta acttgaaata ctgtcttttg aagaagaaat   62820
gagaagattt aaggaaataa gacactgtct tcaagtatct gaagaaccgt tacccggaag   62880
agaactgtta tctggaacag gattaagact cactcatggg gctccagaaa gcagacgagt   62940
gcatggagga cgcagaagat gcagattgtg tggctcaact ctaaaatctt tctaacaaaa   63000
ttagttctct ggatgtgttc cagttcactt gatgatgatt cttttgtttt tgttttgtt    63060 tttgaggtgt agttttteac tcttgttgcc caggctgctg gagtgcaatg gcacgatctt   63120
ggcttgctgc aacctccccc tcccgggttc aagcgattct cctgcctcag cctcccgagt   63180
agctgggatt acaggaatgc accaccatac ctaattttgt attttttagta gagacagggt   63240 ttttccatgt cagtcaggct ggtcttgac tcccgacctc aggtgatcca cctacctcgg    63300
cctcccaaag tgctgggatt acaggtgtga gccatcgcgc ctagcctatg atgattcttt   63360
```

```
tcacagagat acaggcactt aaggagagga tctaaacccc ttggacacat tgccgttgaa    63420
cttctaagat cttaggtttc cacttactca tgaaaattat accacagggt cagagggtag    63480
tgttcattgg agccaggtgc cagaacaagt tattacaaac tactatttta gagaaaaatg    63540
tcattaaagt ttaagatacc ttaagctata ggtttgcatc aaagttaatg aaaggtaaaa    63600
agatgccaag cgtggtggct caggcctgta atcccagcgc tttgggggc caaggcgggc     63660 agatcacgag gtcaggagat cgagaccatc ctggctaaca cggtgaaacc ccatctctag    63720
taaaaataca aaaaattagc cgggcatggt ggcgggcatc tgtagtccca gctactcagg    63780
aggctgaggc aggagaatgg catgaaccca ggaggcagag cttgccgtga gctgagatcc    63840
agccactgca ctccagcctg gctgacagag caagactgca tctcaaaaaa aaaaaaaaa     63900 aaaaatgcaa atcaaatcta aagtagttca gtctttaaac tcaaagccaa tacatttgct    63960
ttgaactaca aatgaactga agttttaag tgtaataaat gttactaaat cggcttttgt     64020
agcagttaaa caaaaaactt caaaaattgt aaggattctg tgagggagca tggctgctgc    64080
tgctgctgct gcttgcagat agcctgctgt gtttaggatt tagttaaata catttctcct    64140
gtttaaaact aaatggtctt tccttagttt gcttagttct tcagaagggc ctttgaaaca    64200
ctgggaaata aacaagtgat tctttagcta ctgctttctg aaatacttat ataaaagctc    64260
tgcactgtat tctcccatcc ctctcagggg aatattagag ggttaggact ccccaggtag    64320
acattctagg ggtgaaaatt tgtcattaca ttgacatttc agatttaggt tttcaacaat    64380
actgttttct tctttcacat attgccatct agtaatatag atgttctccg tccacattaa    64440
tcaaaactat tgacatggat aattcctaat tccttgaaca ctataatgga gatctatagc    64500
tagccttggc gtctagaaga tgggtgttga gaagagggag tggacagata tttcctctgg    64560
tcttaacttc atatcagcct cccctagact tccaaatatc catacctgct ggttataatt    64620
agtggtgttt tcagcctctg attctgtcac caggggtttt agaatcataa atccagattg    64680
atcttgggag tgtaaaaaac tgaggctctt tagcttctta ggacagcact tcctgatttt    64740
gttttcaact tctaatcctt tgagtgtttt tcattctgca gatgctgagt ttgtgtgtga    64800
acggacactg aaatattttc taggaattgc gggaggaaaa tgggtagtta gctatttctg    64860
taagtataat actatttctc ccctcctccc tttaacacct cagaattgca tttttacacc    64920
taacgtttaa cacctaaggt ttttgctgat gctgagtctg agttaccaaa aggtctttaa    64980
ttgtaatact aaactacttt tatctttaat atcactttgt tcagataagc tggtgatgct    65040
gggaaaatgg gtctctttta taactaatag gacctaatct gctcctagca atgttagcat    65100
atgagctagg gatttattta atagtcggca ggaatccatg tgcagcaggc aaacttataa    65160
tgtttaaatt aaacatcaac tctgtctcca gaaggaaact gctgctacaa gccttattaa    65220
agggctgtgg ctttagaggg aaggacctct cctctgtcat tcttcctgtg ctcttttgtg    65280
aatcgctgac ctctctatct ccgtgaaaag agcacgttct tctgctgtat gtaacctgtc    65340
ttttctatga tctctttagg ggtgacccag tctattaaag aaagaaaaat gctgaatgag    65400
gtaagtactt gatgttacaa actaaccaga gatattcatt cagtcatata gttaaaaatg    65460
tatttgcttc cttccatcaa tgcaccactt tccttaacaa tgcacaaatt ttccatgata    65520
atgaggatca tcaagaatta tgcaggcctg cactgtggct cataccata atcccagcgc    65580 tttgggaggc tgaggcgctt ggatcacctg atgtcgggag ttcaagacca gcctgaccaa    65640
catggagaaa ccccgtttct actaaaaata caaaattagc cgggcttggt ggcacttgcc    65700
```

```
tgtaattcca gctactcggg aggctgaggc aggagaatca cttgaacctg ggaggcgggg    65760
gttgcagtga gctgagatcg catcattgca ctctaacctg gcaacaaga gcaaaactcc    65820 atcaaaagaa aaaaaaaatc gggtgcagtg gctcatgcct gtaatcctaa cactgtggga    65880
ggccaagaca ggcagattgc ctgagctcag gagttcgaga tcagcctggg caacatggtg    65940
aaaccctgtc tctactaaaa tacaaaaaat tactcagcgt ggtggcatgc gcctttagtt    66000
ccagctactc aggaggctga ggcaggagaa tctcttgaac ccgggaggtg gaggttgcaa    66060
tgagccaaga tcgtgccact gcactccaac ctggcaacag agcgagactc cgtcttaaaa    66120
aaaaaaaaaa ttttgcagcg caaaccagga tatcctctgt tctcatttgt tctagatttc    66180
aaaagaaaca gtccttcctt tggggaaaag agaaggaaa aggagtttta taaaaggaaa     66240
gaaaagattc ataagaacaa gaagtgggcc cacttgcata tacctttgta gaaaactgtt    66300
cactgttgtt gaagaaaagc tcttcatatt aatatgcagt ccagatgcag tggctcacac    66360
ttataatctc agccctttgg gaggctgaga caggaagatt acttgaggcc aggagtttga    66420
aaccagcctg ggcaacatag tgagactctg tctccacaaa attttttttt aattagccgg    66480
gcatggcagt gtgcttctgt agtcttagct actgaggaag ctaagccaga gaatcactt     66540 gagcccagga gttcaaggct gcagtgagct atgatcatac cattgcactc ttgcacttgc    66600
acagagcaag accctgtctc ttaaaaaaaa aaaagtgtgt gtgtgcatat gcatatatac    66660
atatatatac atgcaaatgt atctgtttat aattcagatt gcttcaaaaa gatgttgcac    66720
tttatgatac tgagaacagt gagaagtaaa taagatagag tgtaggagga ggaataattt    66780
cagaacagcc atctgagaac ttctgtgaca acagatcagg caaaatgaaa tgtgaaagta    66840
attttatagg ccaggcgtgg tggctcatgc ctataatccc agcactttga gtggccaagg    66900
caggtggatc acttgaggtc aggagttcga gaccagcctg gtcaacatgg tgaaaccttg    66960
tctctactaa aaacacaaaa aaattagtcg agcgtggtgg catgtgcctg taatcctagc    67020
tgctggggag gctgaggcag gagaatcact tgaacccggg aggcggaggt tgcagtgagc    67080
ctagattgca ccactgcact ccagcctgtg agacagaatg agaccctgtc ttaaaaaaaa    67140
aaaaaaagta attttataaa ctattgtgca caattcgatg tattcataat taattaaatg    67200
attatttttg ttggttttaa cttttattca gtggctattt attgggagcc tactgtgttc    67260
tgggcactag gaatgcaaca gtaaataaga ctaactaagt ccctggtagg attcaggttc    67320
tgtcgagggg agatacacaa taaagatgaa tttaagataa caataaatgc tatggagaaa    67380
tatacagaac agtggaatag tattagctgt caaaggttgt tgattacttt cgtttaagga    67440
ggccagggaa agcctttctg aaaaaattga gctgagacct aaataacaag aaataattgt    67500
ccttgaaaaa tgaagggaat gcatcttata ggcagaggaa tagcaaacat aaaggtcttg    67560
aggtaataat gagtgtggtt ttttgatttc tgtattttgg ttttttttgag atggtgtctc    67620 cctctatccc ccaggctgga gtgcagtggc acaatcttgg ctcactgcaa actctgtctc    67680
ctgggttcaa gcaattctcc tgccttggcc tcctgagtag ctggtattac aggcacgcgt    67740
gctaccacac ccgactagtt tttatttta gtagagatgg ggttttacca cgttggtcag    67800
gctggtctca aactcctgaa ctcaagtgat ccaccacct caacctccca aagtgctggg    67860
atcacaggcg tgagccacca tgcccggcca gagcttggtt tattttttaa aagataggcc    67920
aatgttggtc gtgtgtggtg gctcgtgcct ataatcccag cactttggga agccaaggca    67980
ggcaaatcac ttgaggtcag gagttcgaga ccagcctggc caacatggtg aaaccccatc    68040
tctactaaaa atacaaaaaa ctagcatggt gtggtggtgt gtgcctgtaa tcccagtgcc    68100
```

```
tgtaatccca gctactccag aggctgaggc aggagaatca cttgaaccga aaggtaggag    68160
ttacagtgag ccaagatcgc atcactgcac tccagcctga cgacagagc aagactcctg     68220 tctcaagaaa taataatgat aaaaggttcg ggcacagtgg ctcacacctg taattccagc    68280
actctaggag gccgaggcag gcagatcccc tgaggtcagg agtttgagac cagcctggcc    68340
aacgtggcaa aaccccatct ctactaaaaa atgcaaaaat tagctgggca cggctgggtg    68400
tggtggctca ttcctgtaat cccagcactt tgggaggtca aggcggacag atcactgagg    68460
tagaaaccct gtctctacta aaaatacaaa aatttgccca gcgtggtggc gcgtgcctct    68520
aatcccagct acacgggagg ctgagacaag agaatcactt catcaaccg ggaggtggag     68580 gttgtggtga gctgagatcg caccattgca ctccagcctg gcaacaaga gtgaaactcc     68640 atctcaaaaa caaaaaaaaa ttagctggga atggtggcat gtgcctgtaa tcacagctac    68700
ttgggaggct ggggcaggag aatcgcttga acccaggagg cggagattgc agtgagctga    68760
gattgcgcca ctgcactcca ggctgggcga aagagcaaga ctccgtctca aaataataa     68820 taataataat aataggccag tgtagctgga gtaatttgca aattatgtgt ggaggcagag    68880
attacacaag gaatgggaga aggtcataga tgagggccag atcacatagt atttggtggt    68940
aaggaattca gattttatcc ttgtggtaat tggtggtgtg gagatggtta aaaacaaggt    69000
tggtttggga tgggtttgaa gagaggactt gctaatggat taaatttgga ggataaggta    69060
aagagaaatt gaaggagtga cacttgggtt ttggcttgaa caatagatct tgttagtaat    69120
attaaattag atgaagaagg catggtaggg aatatggggg agtgggaaag gcaggaagca    69180
ggaatggaac caggaactct gttttagatg tgagaatttg ttgttgttgt tgttgttgtt    69240
gttgttgttg ttgttgttgt tgtgacagca tctcgttctg ttgcccaggc tagagtgcat    69300
ggagtgcggt agcacgatct cagctcactc caacctccgc ctcccggttc aagtgatttt    69360
cctgcctcag cctcccgagt agctgggatt acaggcacct gccacaatgc ctggctaata    69420
cttgtatttt tagtagagat ggggttttac catgttggcc aggctggtct taaactcctg    69480
acctcaggta atccacccac ctcggcctcc caaagtgctg ggattgcagg tgtgagccac    69540
tgtgcccggc cagatgcatg aattttgaga tgtatactag acttctggat agagaagtta    69600
agtaggcagt tggacacatt gtatgaagct caggggtaca aggaggacta tgaacatggg    69660
agtcttctga caaatttatc actagactcc tcattcaagt aactaggaaa tgtcagatat    69720
tcttccccta gtaatagcca gtggttatac tcttgccttt agttttcttc acaatactct    69780
tggcaacaca taaggccttc cctacaatct gagtttcagt cagaattgtt tctgagcgtt    69840
cttcctcaaa tttctcccca gtctcattat tctttattct catgtccatg accagtcata    69900
atagtaatta tgaaaaacct ctaactttct ttagtgcatt gaatgtatat tttatcattt    69960
tggttgtgtt aactgtaaat ctctcagtgg aaatctgaaa agcctttatt tccttagatg    70020
ataatataca attgatttag gagataggga attttcagt tacctttata acagcacagt     70080
attagcagtc taatctaaat gctaagtgaa tgttttgaga ggagatagat gttgaaaatt    70140
aaaatacatt aagtcccagt gaggtgaaaa gccgattgtt aagttctgca cacaaaagat    70200
ttgcttcagt gaattgattt caacagctga gatcctagta atttcacctg gtctaccaaa    70260
aagaatgatt ttacttgctt ttggtcaaat ctctgcccag caattctttt tctttctttc    70320 tttttttgt tttatgtgtg tgtgtgtgtg tgttttttt tagcagagtc tcactttgtc       70380
acccaggcgg gagtgtggtg gtatgatcac agttcactgc agcctccaac tcctgggctc    70440
```

```
aagtgatcct ccagcttcag cttttcaaga aattgggact gcaggcacat gcaactatgc    70500
ctggctgagg ttttatgtat ctttttttcta gagaagggt ctcactgtgt tgcccagctg    70560
ggtctccagc tcctggtctc aagctgtcct cctgcctcag cctcccaaag tgccaaagtg    70620
ctagggttat aggtgtgagc cattggtgcc cagctactgc ctgcctggca attctgaatg    70680
ccttaaattt tttttttttt tttttttttt tttgagacag agtttcactc tgtcacccag    70740
gctggagtgc agtggcatga tcgtggctca cagcaacctc tgcctcctgg attccagcaa    70800
ttctcatgcc tcagcttccc gagtagctgg gactacaggt gcatgccacc acgcccagct    70860 aattttggt ttttttgttt gtttgtttgt ttgttttgag acggagtctc gctcagttgc    70920
ccaggctgga gtgcagtggc gtgatctccg ctcactgcaa gctccgcctc ccgggttcac    70980
gccattctcc tgcctcagcc tcccgagtag ctgggactac aggcgcctgc cactacaccc    71040
ggctaatttt tttgtatttt aagtagagac ggggtttcac cgtgttagcc aggatggtct    71100
cgatctcctg acctcgtgat ccgcctgtct cggcctccca aagtcctggg attacaggcg    71160
tgagccacca cacccggcct aattttttt ttttaattt tatttttaat tttttgagat    71220
gcgagatgga gtctcgctct gttacccagg ctggagtgca gtggcaccat ctcagctcac    71280
tgcaacctcc acctcctgca ttcaaaagat tctcctgcct cagcctccca agtagctggg    71340
attacaggtg cctgccacca cgcccaacta atttttgta ttttttagtag agatgaggtt    71400 tcaccatgtt ggtcagactg gtgtcgaact cctgacctca agtgatctgc ctgcctcagt    71460
ctcccaaagt gctaggatta caggggtgag ccactgcgcc tggcctgaat gccttaaata    71520
tgacgtgtct gctccacttc cattgaagga agcttctctt tctcttatcc tgatgggttg    71580
tgtttggttt ctttcagcat gattttgaag tcagaggaga tgtggtcaat ggaagaaacc    71640
accaaggtcc aaagcgagca agagaatccc aggacagaaa ggtaaagctc cctccctcaa    71700
gttgacaaaa atctcacccc accactctgt attccactcc cctttgcaga gatgggccgc    71760
ttcattttgt aagacttatt acatacatac acagtgctag atactttcac acaggttctt    71820
ttttcactct tccatcccaa ccacataaat aagtattgtc tctactttat gaatgataaa    71880
actaagagat ttagagaggc tgtgtaattt ggattcccgt ctcgggttca gatcttagct    71940
gataagtgga agagctggga ctttaagcag atgagaatct aaagactttg ctcttttcac    72000
ttcactgggg tgtcttttctc tctctctctc ttgctctctc tctctctttt ttttttttccc    72060 aagacggagt ctcactccat tgcccaggcc agagtgcagt ggtgcgatct cagctcactg    72120
aaaactcatc ttgcccaggc tggtcttgaa cccctgacct tgtgatcctc ccgccttggc    72180
ctccccaagt gctgggatag cgtgagcca ccgtgcccag ccaataatag ctaaaattta    72240
tataatgttc actgggccag gcacagcggc tcgttcctgt tatcccagca ctttgggaag    72300
ctgaggcagg cagatcgctt gagccaagga gttcgatacc agcctgggca acatggcaaa    72360
accccatctc taccaaaaaa aatatacaaa aattagccag gcgtggtggc atgtacttgt    72420
agttccagct actcggaagg ctgagttgag agtatctctt gagcccaaga agagggact    72480 acagtgaacg gagattgcgc cactgcactc cagcctagac gacagacaga agatctcaaa    72540 agaaaaaaa aaaaaaaga tcactttatg ctggactgc tctaaaggcc caaccatgtt    72600
ttaactaatt aacaatttta tgacaactct atgagctatg tactgtaatt atgcctatat    72660
tacagatgtg aaaattgagg ctcagagagg ttgaataagt tgctcaaagt cacacaggta    72720
ataagtgatg gaactagaag ttgaactcag gaagtctagc tccaagtcta aattctttgt    72780
taatttattt ttcggggccag agtcttactc tgtcacccag gctggagtgc agtgccacta    72840
```

```
tctctgctca ctgcaacctt cacctcccaa gttcaaacct tgttcaattc ttgtgccttg    72900
gcctcccaag tggctaggat tacaggcatg tgccacaaca actagctaat tttttgtctg    72960
attctgttgg ccagtctgga gtgcagtggc gcaatctcag ctcactgcag tctccagctc    73020
ccaggttcaa gtgattctcg tgccttagcc tcccaaatag ctgggattac aggcacgtgc    73080
caccacaccg atagtttttt ttgtattttt aatagaaaca aggtttcaac atgttggcca    73140
ggctggtctc aaattccaga cctcagatca tctgcccgcc tcaggctccc aaagtgctgg    73200
gattacaggc atgagccact gcacccggcc ttaatttta tatttttatt agagatgggg    73260
ttttgccatg ttggccaggc tggccttgat ctcctggcct ccagtgatcc acccgccttg    73320
gcttcccaaa gtgctgggat tacaagcatg agccactgca cccggcctcc aattctaaac    73380
tcttaacaac aatactatag tttcttgaaa agttgttgaa ggcttcacgg agggaaaaaa    73440
aatggagcat tctaacaact ttgcagatga acccaagaa gactcaatga ctttctcctg    73500
atcatattgt agcagatgac ttagccagaa ctctgacttc ctcacaggga gaaagtctgc    73560
aagatttcac acttacctgt caggcctgag ctggctgctt tctcagctcc ctaagtgcta    73620
tgttcccagt ctgcttttct tccttttca agtgtgcact accaggcatt tcagaacatc    73680
ccaggctggt cgcggtggct cacacctgtg atcccagcac tttgggagcc caaggcgggt    73740
ggatcacctg aggtcaggag ttcgagacca gcctggccaa catggtgaaa ccccatctct    73800
actaaaaata caaaagttaa ctgggcgtgg tggtaggcac ctgtaatcct agctcaggat    73860
tactcgggag gctgaggcta gagaatcggt tgaacccagg aggcggaggt tgcagtgagc    73920
caagattgcg ccactgcact ctagcctggg acaagaggg agacttcatc tcaaaaaaaa    73980
aaaaaaaatc ccagctgggc acagcggctc acttctgtaa tcccagcact ttaggaggcc    74040
aaggcaggag gatcacttga gcccaggagt tcaagactag cctgggcaac atagtaagac    74100
cctgtctcta caaaaaaatt taaaaattaa ttgggtgtcg tagcacactc ttgtattccc    74160
agctactcag gaggctgagg tgagaagaat gcttgagtct gggaggtcga ggctgcagtg    74220
agccatgatg gtgctactgc actccagcct ggcaacatt gtgagacctt gtctcaaaac    74280
aaaacaaaac atccttctac tgagcacttt ctgtcccttt atagaaactt aagagggaac    74340
cagtagaggt aatttcctaa ggaaaactgc tttgggacat gatcacaaat gaagcctgga    74400
gttttgaact gctgaggtca gcctgttttt accttctgag cctatcaagt aattgttcca    74460
gatgccaaga aaagctgctg gccttatttc tgcttctgcc tttaccacag gggagcgcca    74520
tgtgagccag tcctctgttt ttcctccact gtatgctagg cagtattagc accagattct    74580
tcccctcttt aaaaagaaat tctagtgctt tggatttttt cctccatgca gaatagcaat    74640
gatgaaagt atgtggtcaa agtaatgaca ttctgaaaat actaaatgtc accatagtat    74700
ttttctctgg aagagaaatg tatatgtaga ggtgaaactt caaatttctt ttttttttt    74760
tttaagacga agctttgctc ttcttgccca ggctgaagta caatggcgtg atcttggctc    74820
accgcaatct ctgcctccag ggttcaagtg attctcctgc ctcagcctcc taagtagcta    74880
ggattacagg catgtgccac cacgcccagc tgattttgta ttttagtag atgggggtt    74940
tctccatgtt ggtcacgctg gtcttgaact cccgacccca agtgatccac ccacctcggc    75000
ctcccaaagt gctaggatta caggccaccg cgcccggcct gaaacttcaa atttcttttt    75060
tttttgaga cagagtctcg ctatgtcacc caggctggag tgcagtggcg ccgtctcggc    75120
tcactaccag ctccactcca cctcctgggt tcacaccatt ctcctgcctc agcctcccaa    75180
```

```
gtagctggga ctacaggtgc ccgccaccat gcccagctaa ttttttgtat ttttagtaga   75240
gacgggtttt cactgtgtta gacgggatgg tctccatctc ttgacctcgt gatccgcctg   75300
cctcagcctc ccaaagtgct gggattacag gcgtgagcca ctacgccaag cccgaaactt   75360
caaatttctt atctcataac taggcatcct tatcactgag tgttagcctg gatataaaca   75420
ttcctaatct tttgtacttt tcatgtcagc atttggctcc acttggctgc ctggggagaa   75480
cttctagcat tatgagcatg caggtcctat caacaggttg ggggtgcggt ttattcatac   75540
aggtagtgag agtggcacag atggatgctg tcccttaaaa caaacagact tgtctttggg   75600
agcctgaggc gggtggatca tgaggtcagg agttcaagac cagcctggcc aacatagtga   75660
aaccccgttt ctactaaaaa tacaaaaaat tagccgggtg tggtggtgtg cacctgtaat   75720
cccagctact agggaggctg aggcaggaga atcacttgaa cccaggaggt ggaggttgca   75780
gtgagccgag atggcaccat tgcactccag cccaggcgac agtgcaagac tgcgtctcaa   75840
aaaaaaaaaa aaaacacaca gacttgtcct actgccattt cttttcactc tggcggtaaa   75900
gtaagagtgt gtgtgtgtgt gtgtgtgtgt gtgtgtgtgt gtgtgtgtgt gtgtgtttct   75960
gtccgtctgt ctgtcaaggg ggagggtgac cactttctaa aaggccatcc gtgtattttt   76020
agcttcctga tttttttctc tatcgcagtc tctttgaagc caggtgaatt ttaggccttg   76080
gcaattttct ttttattgca atgggaaggt caagacactg agagtcaccc aaaacatatc   76140
catccaaaat gatacaattt tagggtttat ttttaagtga tacccaagtt atttgctaag   76200
aacctatgcc agtgtgttta tgagaatttg cactgtccca cactgttgcc accagccaca   76260
tgggactgtt taaatttaaa ttttacaaat tagccagtca tggtggtgtg cacttgtagt   76320
cccagctact taggaggctg aggcaagagg attgcttgag cccagaagtt caatactgca   76380
gcaagctatg atcgtgccac tgtactccag cctgagtgac agaatgagac ctcatctctt   76440
caaaaaaaaa gaaaaaaatt aaaatatgaa gtttagttct tcattcaccc taaccacatc   76500
tccagtgctc aataactata tgtgactcat ggctacctta ttagcataga tatagaaacat   76560 tgtgactatc acagaaagtt gttttgaaca gtgttgccaa gccctgtaag tggaagaggc   76620
agtgcagtgt gatctgtgtc ttcaggaaac caggtagtca gactagttca atgaggagag   76680
gcagaacctg gcttcacttc tagattaaaa actgcttagg tggcctaaag atacaatggc   76740
cattctcaga gtagtgagaa ggaaggaaca gatgtttagg gggctagaag aaagtcagag   76800
agggccgggc gcagtggctt atgcctgtaa tcccagcact ttggaaggcc aagacaggca   76860
gatcacgagg tcaggagttc gagaccagcc tgaccaacat ggtgaaaccc tgtctctact   76920
aaaaatacaa aaattagccg ggcgtggtgg tgcgcgcctg taatcccagc tactcaggag   76980
gctaaggcag gagaatcgct tgaaccctgg aggcagaggt tgcagtgagc ccagatcgca   77040
ccactacgct ccagcctagg tgacagagag agactccgtc tcaaaaaaaa aaaaaaagt    77100 cagaggagac aaggagcatg tacacctaaa atcaacatag acccctctgt tgatggggtc   77160
atagtgagta cttgaggtac caagtctgga taaacatcaa acttcagcca ataactttga   77220
gtttctagcc atccaagcct cttattaaac atacagaagg acctttttc ccttgcatct    77280 aacaagttaa agcacctgca gagatcatta gggaggagcc ttggcctgat tggtgacaaa   77340
agtgagatgc tcagtccttg aatgacaaag aatgcctgta gagtgcaggt caactacata   77400
tgcacttcaa gaagatcttc tgaaatccag tagtgttctg acattggac tgcttgtccc     77460 tgggaagtag cagcagaaat catcaggtgg tgaacagaag aaaaagaaaa gctcttcctt   77520
tttgaaagtc tgttttttga ataaaagcca atattctttt ataactagat tttccttctc   77580
```

```
tccattcccc tgtccctctc tcttcctctc ttcttccaga tcttcagggg gctagaaatc    77640
tgttgctatg ggcccttcac caacatgccc acaggtaaga gctgggaga accccagagt    77700 tccagcacca gcctttgtct tacatagtgg agtattataa gcaagatccc acgatggggg    77760
ttcctcagat tgctgaaatg ttctagaggc tattctattt ctctaccact ctccaaacaa    77820
aacagcacct aaatgttatc ctatggcaaa aaaaaactat accttgtccc ccttctcaag    77880
agcatgaagg tggttaatag ttaggattca gtatgttatg tgttcagatg gcgttgagct    77940
gctgttagtg ccaacatgtt agtgagaaaa tatctttgga taggtaaaaa tcaaggagga    78000
gttctcctct tcctaaacca tcttaattta cttacataga agaaagcaca gcagctggcc    78060
caccacggac gggcccagag caggggaaga ttctcggtga acatttcttt ttttttttct    78120
ttttttttga ggtcgagtct ctgttgccca ggccagagtg caatggcgcg atctcggctc    78180
actgcaacct ccacctcccg ggttcaagtg attctcctgc ctcagcctcc caaatagctg    78240
agactacagg cgtgtgccac cacgcccgac taatttttg tatttttttt ttagtagaga    78300
cggggtttca ccgtgttagc caatatggtc ccgatctcct gacctcgtga tccacccgcc    78360
tcagcctccc aaagtgctag gattacaggc atgagccact gtgcccagcc ctctccatga    78420
acattttcta attaaacttg acacttaata caatgttatg cttaggactg ctataaagct    78480
tacctctgga gttgcgcagc acaaaggcct tggtgtgtgt ataaatttgg tttgttcttt    78540
tcacagcaaa agctacccac cttttgcctcc tgtgcctgct tctgcccagg gacttaggtc    78600
ctcttacacc ttagagaaag gccttagcat ctggtcacag gcagatgagt gacagcaaga    78660
aaacctggct gcaatgtaat tttgtttcca tcctctttat tagttatcaa ttggatttt    78720 atgaaatttc caagttccac tcaaggattt ctcagtgttt ttttactttg gtatagtgga    78780
aaccagggtt gccagaaagt attattttgg gggtgagtta gtcaaccttc gttcagtcag    78840
acagacagga gcacctcagc aattcccaga aacgggctga tgggaaagag caacatacat    78900
gaatgtcttg aagaacacag ccaacagagc ccattgggca gttctgatt tccaggtaca    78960 cagcatctcc acagtctctt ctgattttta ttccctgag tatatggatt ccagctcagc    79020
atgtagcctt tccctgctga gtctctaacc aggataacat gtatttttt gactggatga    79080 attatcttcc catctcttga catttacagt aattaccacc aagtatggta ttttcagtgg    79140
ccgtgattat cagttaccaa cacagaatta ggatgaaggg aggaagggag ggaaggaagg    79200
tgggtgtttt ttcacacagt gtcttagcca gcaatttagc aaattaatgg aaattagatc    79260
tttgattttt ttttctttca agcatttat ttgagagact atcaacctt ataccaagtg    79320 gccttatgga gactgataac cagagtacat ggcatatcag tggcaaattg acttaaaatc    79380 catacccta ctatttaag accattgtcc tttggagcag agacacagac tctcccattg    79440
agaggtcttg ctataagcct tcatccggag agtgtagggt agagggcctg ggttaagtat    79500
gcagattact gcagtgattt tacatctaaa tgtccatttt agatcaactg gaatggatgg    79560
tacagctgtg tggtgcttct gtggtgaagg agctttcatc attcaccctt ggcacagtaa    79620
gtattgggtg ccctgtcaga gagggaggac acaatattct ctcctgtgag caagactggc    79680
acctgtcagt cccatatggat gcccctactg tagcctcaga agtcttctct gcccacatac    79740
ctgtgccaaa agactccatc tgtaagggat gggtaaggat ttgagaactg cacatattaa    79800
atatactgag ggaagacttt ttccctctaa ctctttttcc catatgtccc tcccctcct    79860 ctctgtgact gccccagcat actgtgtttc aacaaatcat caagaaatga tgggctggag    79920
```

```
gctgggcatg gtggctcatg tctgtaatcc cagcactttg ggaggccgag gcaggtggat   79980
cacttgtcag gagtttgaga ccagcctggc caacatggtg aaaccccatc tgtactaaaa   80040
aaaaaaaaac aaaaagtagc caggcctggt ggagcatgcc tgtaatgcca gctatttggg   80100
aagttgaggt gtgagcatcg cttgaacgtg ggaggcagag gttgcagtga gccaagattg   80160
caccactgca ctccagactg ggtgacagag tgagactttg tctaaaaaaa aaaaaaaga   80220 gagagagaga aaagctaggt gcggtggctc acgcctgtaa tcccagcact ttgggaggct   80280
gaggtgggca gatcacgagg tcaagagatc gagaccatcc tggccaacca acatggcgaa   80340
accccgtctc tactaaaaat acaaaaatta gctgggcgta ggggcgcacg cctgtagtcc   80400
cagctacttg aggggctggg gcaggagaat cgcttgaacc ccggaggcgg aggttgcagt   80460
tagccaagat cgcgccactg cactccagcc cgggcgacag agcgagactc cgtctcaaaa   80520 aaaagagag agagagaaat gatgggctgg gccagtgccc cacccctgta atcacaacac   80580
tgggaggcca aggtgggaga atcgcttgag cctgggagct gaagaccagc ctgggcaata   80640
cagtaggacc tcatgtctac aaaaaaatta ttaaaaatta gccaaggctg ggtgcggtgg   80700
ctcatgccta taatcccggg ggtgaagttg agcccaggag tttgagacca gcctgggcaa   80760
catggcaaaa ccctgtctct accaaaaata caaaaaatt agccagggt ggtggtacgt    80820 gtctgtagtt ccagctactt aggaggctga gatggaagga ttgcttgagc ccaggaggca   80880
gaggtggcag tgagctgaga tcacaccact gcactccagc ctgggtgaca gagcaagacc   80940
ctgtctcaaa acaaacaaa aaaatgatg aagtgacagt tccagtagtc ctactttgac     81000
actttgaatg ctctttcctt cctggggatc cagggtgtcc acccaattgt ggttgtgcag   81060
ccagatgcct ggacagagga caatggcttc catggtaagg tgcctgcatg tacctgtgct   81120
atatggggtc cttttgcatg ggtttggttt atcactcatt acctggtgct tgagtagcac   81180
agttcttggc acattttaaa tatttgttga atgaatggct aaaatgtctt tttgatgttt   81240
ttattgttat ttgtttttata ttgtaaaagt aatacatgaa ctgtttccat ggggtgggag   81300
taagatatga atgttcatca caaaaacata aatcaaggcc gggcatggtg gctcatgcct   81360
ataattccag cactttggga ggtcaagatg gaggtcaagg tgggagccta gaagttcgag   81420
accagcctgg gcaacataag gagacttcat ctgtacaaca aatttaaaaa gtagctgggt   81480
gtggtggcag atgcctgtag tcgcagctac ttgggaagct gaggtgggag gatcacttga   81540
gctcaggagg ttgatgcttc agtgagccac gatcacacca ctgtactcca gcctgggcga   81600
cagagcgaga ccgtgtctca aaagaaaaa agaaagtata aatttacaca aaacaataa     81660 aataatccca gtaattccac cacttggaga tgatcaccat aaaactccac caggcatatg   81720
tgcgtatata tacacgtgta ttttataaaa tgtgatcata attacactgt tttgcttttt    81780
tccttaagat attacataca ttttttccaca tcgttaaatt acagtgctgt tttcctggtg   81840
gctttccttt aacagattga agttcatgtt aatacagttg ccagaggctg tgggctttca   81900
ctgtcaccag gagtcactcc tagggcctct tcagagcaag gccttatgtc ctgaagcatt   81960 gcctttttt tttttttttg aggtggagtc tcactctgtc acttagcagg ctggagtgca   82020 gtgcccagt cttggctcac tgcaacctcc gcctcctggg tttaaatgat tctcctgcct   82080
cagcctcagg gcggatcacc tgacatcagg agtttgagac cagcctggcc aatatggcga   82140
aaccccatct ctactaaaaa tactaaaaaa aattagccag gcatggtggc acgcacttgt   82200
agtcccagct acttgggaga ctgaggcagg agaatcgctt gaacccagga tgttgaggtt   82260
gcagtgagct gagatcacac catcacaatc cagcctgagt gacagagtga gactccatct   82320
```

```
gaaaaaaaag aaaaaacaat tagcctggca tggtggcagg cacctgtaat ccctgctact   82380
tgggaggctg aggcaggaga attgcttgaa cccgggaggt ggaggttgca gtgagctgag   82440
atcgtgccat tgcattccag gctgagcaac aagagcaaga ctccgtctca aaaaaaaaaa   82500
aaaaaaaaaa aaaaggccag gtgcagtggc tcacgcctgt aatcccagca ctttgggagg   82560
ccaaggtggg tggatcacct gaggtcagga gttccagagc agcctggcca acattgtgaa   82620 accccgtct ctactaaaaa tacaaaaatt agctgggtgt gatggcatgt gcctgtaatt    82680
ccagctactc aggaggcaga gacaggagaa ttgcttgaac ccaggaggcg gaggttgaat   82740
gagccgagat tgcgccatca cactctagcc tcggcgacag agcaagactc cgtctcaaaa   82800 aaaaaaaaa aaaattagc ttctacctca ttaatcctaa gaactcatac aaccaggacc     82860
ctggagtcga ttgattagag cctagtccag gagaatgaat tgacactaat ctctgcttgt   82920
gttctctgtc tccagcaatt gggcagatgt gtgaggcacc tgtggtgacc cgagagtggg   82980
tgttggacag tgtagcactc taccagtgcc aggagctgga cacctacctg ataccccaga   83040
tcccccacag ccactactga ctgcagccag ccacaggtac agagccacag gaccccaaga   83100
atgagcttac aaagtggcct ttccaggccc tgggagctcc tctcactctt cagtccttct   83160
actgtcctgg ctactaaata ttttatgtac atcagcctga aaaggacttc tggctatgca   83220
agggtccctt aaagattttc tgcttgaagt ctcccttgga aatctgccat gagcacaaaa   83280
ttatggtaat ttttcacctg agaagatttt aaaaccattt aaacgccacc aattgagcaa   83340
gatgctgatt cattatttat cagccctatt ctttctattc aggctgttgt tggcttaggg   83400
ctggaagcac agagtggctt ggcctcaaga gaatagctgg tttccctaag tttacttctc   83460
taaaaccctg tgttcacaaa ggcagagagt cagaccctcc aatggaagga gagtgcttgg   83520
gatcgattat gtgacttaaa gtcagaatag tccttgggca gttctcaaat gttggagtgg   83580
aacattgggg aggaaattct gaggcaggta ttagaaatga aaggaaact tgaaacctgg    83640 gcatggtggc tcacgcctgt aatcccagca ctttgggagg ccaaggtggg cagatcactg   83700
gaggtcagga gttcgaaacc agcctggcca acatggtgaa accccatctc tactaaaaat   83760
acagaaatta gccggtcatg gtggtggaca cctgtaatcc cagctactca ggtggctaag   83820
gcaggagaat cacttcagcc cgggaggtgg aggttgcagt gagccaagat cataccacgg   83880
cactccagcc tgggtgacag tgagactgtg gctcaaaaaa aaaaaaaaaa aaggaaaatg   83940
aaactaggaa aggtttctta aagtctgaga tatatttgct agatttctaa agaatgtgtt   84000
ctaaaacagc agaagatttt caagaaccgg tttccaaaga cagtcttcta attcctcatt   84060
agtaataagt aaaatgttta ttgttgtagc tctggtatat aatccattcc tcttaaaata   84120
taagacctct ggcatgaata tttcatatct ataaaatgac agatcccacc aggaaggaag   84180
ctgttgcttt cttttgaggtg atttttttcc tttgctccct gttgctgaaa ccatacagct   84240
tcataaataa ttttgcttgc tgaaggaaga aaaagtgttt ttcataaacc cattatccag   84300
gactgtttat agctgttgga aggactaggt cttccctagc cccccagtg tgcaagggca    84360 gtgaagactt gattgtacaa aatacgtttt gtaaatgttg tgctgttaac actgcaaata   84420
aacttggtag caaacacttc caccatgaat gactgttctt gagacttagg ccagccgact   84480
ttctcagagc cttttcactg tgcttcagtc tcccactctg taaaatgggg gtaatgatag   84540
tatctacctc ctaggattta ttgaggcagc ttaaatacct tttgtatttc ctgttgctgc   84600
caaaacaaat tgttgcaagg tcagaagtct gaggtggctc aactgtttct ttgtttcagg   84660
```

```
tttcatgagg ccaaaataaa ggtgttcgca gggcgtgttc ccttctagag gctctgggtc    84720
cttgcagttc taggactaag atccctgttt cccactggct gttggctggg catcattctc    84780
agcttcttga ggctccccac attcctaggc tcctggcctg tctgcctcca tcttcaaaac    84840
cagcaatggg tggtcaagtt tttctcacac tgaatcttgc tgactactgt atctttctaa    84900
ctcctgccag agacatttct ctgtttctaa gggctcaagt gattagattg cacccacttg    84960
gtaatccaaa gtgatcttca tatcttaagg cccatagcct taattatagc tgcaaagtcc    85020
cttcgcagca gtacctagat tactgttgga atgaataacc agaagacagc aatcaaggga    85080
ggacatcttt agaattctgc ctaccacttg tatttaacat gcttaatcca cagatgacac    85140
tctctaccat tatttcctgg tcctcacact gctcagagat tggaatcctt tttaagcaaa    85200
gagaatgaag tcatcacata gttcagtcct gctgtatttg ctggaaacag tgaaggaaga    85260
tagagaaaat ggagctaact gccaatatta ccattttata atcagtcctc aatcatagcc    85320
ctatgaagtg ggtatttgtt acctcattgg aaaaatggga gttgaatctc aagttccttg    85380
tttgtaagat tttactcaga tttgcacagc taaaaatgac tacatggaga cccaaagcca    85440
cctttctgtt cccatcatca gctttccatc tgcctctgtc actgaccccg ggacagaagg    85500
ttcaagcctt aagggaattt ggagagagaa ctagattttg aggggaactc acactcactt    85560
ccctttgggg ccacagtagg agacagtaaa agcagcccca tgtcaggcaa agggtcttac    85620
aggagtggat catggctgct gttccactt ctctctggct tcccagctta tgactgtgta    85680
tcttagttgt caaagccttc cagttcatcc tcacctacag cttgacttcc caagggccca    85740
tgccagctcc ctgtctacct gccagtgagt tgatgagtct cggtgttagt agtaaaggca    85800
ggcgggaagc aagcagaagt gctactgggc cttgagggta agccaggcct cagccttctg    85860
accccatcac taatgggtta ataggaaaag cagtatccat ctagtacagc ctgccttttc    85920
aggaatagtg agtaaaagca aagatgacta aaatacatta aagttttctg taattgtctc    85980
taaggtctcc caacaaacat atacccccatc tgtttcaagc tctgcataac cttccccaga    86040
agtcaagttc aggccctggc ctcatggtgc ctggcccagg ttaagagtgc tacctgatga    86100
tggagttaat acacgttgct ttgacctctg acttttaagat gtcctcccac ttttccaccc    86160
cgcaatctct agccctctct gggcacagca gcaattggga actagttcct gtactgcctt    86220
tatctcattt tacaaaacaa acttctacaa agaagctgga aaggaaggag gagaaaggat    86280
tatcatgcag gcacagggag ggggcctaga gaagagctct ggcagattat gtccctctta    86340
aaaaatgcaa ccagaatcat caacaaagta tcacctcaaa aatatgcagg agaaaaagaa    86400
aggaatcaat gttggggtgg ttggagcaga aggagccaaa ctgcccagaa ggtgtcctct    86460
gaaggctgcg aggagcagac taggtcagcc ccagaggcag atggcacaca cagaatggca    86520
ggattaccgg tagctgcaga tttattgaca gaagccctag agactgggcc tgctgcccag    86580
ggaatgtggg ggctcactta tcaaagacta ctggaaaatg gctgagccgg caacccttc     86640 cactacagtg atgcctggtt ttcttgcaca gcctgtaact ctgcctgtaa caaggagaaa    86700
attaaagcaa cgaatctggc caaatagaaa attaaggaaa actagaaaca gctcctatgg    86760
agagcaggga ttgggggaggt gtagaggggc tgatcctgaa tgtctggagg atcaggaaaa    86820
tgtaagcaat tgtttaaggg actggtagga atcaagatct ggagagagat cctcccgact    86880
ctggtggctg gggaatatga actgtggaga catggtttca aggactcaaa atgatatgac    86940
agcttaacat ttacagttca gtgcagaggc tctcaaagca tgatcccctg ataggagtgt    87000 gaggggggcaa caccatcacc taggaatttg ttagatatgc aaattcccag acccactgaa    87060
```

```
tcccagacag gtggggccag caacctgtga atctacaaca ggctcaagtt tgagaacaaa    87120
tgacttagtg taaggggctg ctaattgata taaaatgtta cctgtggtct attattttgt    87180
ctgtagtgaa tatttgggctt gttaaggata aataaggttt gtgggctggt aagtggttct   87240
tctctacaag gttgcaacag ctggcttcag ttaacttcaa aaaggccctt taagcaaaga    87300
cagtagtccc cccactcatc catggttttg atttcagtta cttatggtca accatggtcc    87360
aaaaatatta aaaggaaaat tccggaaacc agtcactcgt tttaaattgt acaccattct    87420
aagtattgtt tgacttgttc tattttatta ttagttattg ttgttaatct cttactgtgc    87480
ccaatttata aattaaattt tatcataggt atgtatgtat agggaaaaac ataatatata    87540
tagggtttgg tactatccga gggttcaggc atctacttgt ggtcttggaa catatgcccc    87600
gcagataagg ggggactgct gtacaatgca aaggacaaag attaaattat attagcaatc    87660
taggagcaga agggcaagac tgcttttta aaaaacagct aaaggtttag gaggttttat     87720
taatatttaa attgtattga aaccacagct gcagcctttg actccagcat agagatatgc    87780
aaatatggct ttcaaaagaa aggcaatttc agacagccct caaagtaaca ggaacaaata    87840
aaacaaatga ttttgtaatt tatctttatt gactgatgtt gcacaaggca caggccatac    87900
cctgtgagag tcagcaacag ccgagctctc tgaggagaga agagaaagcc aggctggagg    87960
gagaggcagg ccgacccata gacaggtgac aggaaagaca cagagcaggc agatgggaga    88020
agaagacaac taaattaaaa gggaaggaaa ataaaaaccc agccctgggt cctgtagacc    88080
atctgatctt gctggctctc agcagcaaca acaataatca ttaatgacta tcatttgcca    88140
cactactact aagtgccatg cactattcct cacatacaaa tgaggaaaat gaagctttga    88200
gaggtcaagc aacttaccca aggtcacaca acaaaaggaa ggggcagagc ccagattcaa    88260
agatttgtgt gaggctgaag ccctgtgctc tttccagtgc attatgctgg gaaccagtcc    88320
tgggaggcag tgaataacaa taaggttaat gggccgggcg cagtggctca tgcctgtaat    88380
cccagcactt tgggaggcgg aggcgggcaa atcacgaggt caggagatcg agaccatcct    88440
ggctaacatg gtgaaaccct gtctctacta aaaatacaaa aaattagccg ggcgtggtgt    88500
cgggcacctg tagtcccagc tactcaggag gctgaggcag gagaatggca tgaacctggg    88560
aggcagagct tgcggtgagc cacgatcgcg ccactgcact ccaacctggg tgacacagtg    88620
agactccgtc tcaaaagaaa aaacaaaaca aaacaataag gttaatgatt gagggacac    88680 tttgtgccca gttctgtggt attctgtatg ggcatgcgtg tgtctgtgtg tgtgtatatg    88740
tatgtaactg tggaaaagag ggtgaaaacc tccatttctg accttcaaat tggttactat    88800
ccaatgagta aggcaagaaa agaaagccaa agaaacttg cagaattctg gtgtaaaagt     88860
tcttttgggg ccgtgtggtg gggccagctc tgcctgttgt ggaagacttc tggtggaggc    88920
atctcagctg gccttggcct tgagtaaaat ttagccagat gaaaaggaaa gctggagatt    88980
acacaggccc aggtgagagc ctccagctgc tagaattgga ggaaggagca cctgattcag    89040
agagatgaga aaaggcaaga gaatcctgaa aggatacata tctctgaccc tttgtcccca    89100
tccaatctcc ccagaccttc catcccaagc ccaaacacaa ccttacctgc tgctcctttt    89160
caggcaccct ggccaccaaa tataggaacc cataaatttt gctcatactc tatgttctac    89220
taggcaagtc ctgatctgtc atctctacag gccccaatcc ttcccgctca cccctacaga    89280
gccttctcca ggttttctag gccagaatct ctccccactt agaatactcc agaagttttg    89340
ctttatttgt gagactttat tcaattgaag ttacttgtgt gcatatgtta tcctctctat    89400
```

```
ttgactagaa ggtccttata atcccttatg accataatta ttttatcttt gatataaccc    89460
agctctgtaa ctagcagata ctttgttagg catccagtgg gtttttccta aatgaatgaa    89520
gtaaaggatg aatgaatgga ctcagtgcat tgaagggctt atccaactat tggttccact    89580
ctcaagacct ttggaaaact agccatgttc tggaatgcta attcccttca atgcctttcg    89640 cccattttc tatgaccctg atttactcca aaaacaatat aagggatcta agtgtccaag     89700
aatgactcct tctaaaccca cacctaagga ttttctctct ttttgtgtgt gtgtgtgtga    89760
gacagagttt cactcttatt gcccaggctg gagtgcaatg gtgcgatctc agctcactgc    89820
aacctccgcc tccagggttc aagtgattct ccctgtctca ccctcccgag tagctgagat    89880
tacaggcgcc tgccatcaca cccagctaat ttttgtattt ttagtagaga cagggttcac    89940
cacgttggcc aggctggtct cgaactcctg tcctcaggtg atccaccac cttggcctcc     90000 caaagtgctg ggattacaag catgagccac cacacccggc ctctttgatt ctcttttgcc    90060
tatcatgaag tctacccctt tgtaattaat tagaccaatg tccacccaga cagaataaca    90120 ttttcccta tccatcagcg aggtcttctc cgtgatggac attcaaggca gacagagaga     90180
ctgctgctgc aataactggg gaaataatta tggtgttcat gatgatttct ttgcaggttc    90240
aaagcactag cccagccatt atctctccca cttcactagg ataaaattgc taaccccact    90300
ttataggtgc taaaacaggt ccagggcctt gtcaaaggtc actcagtgag ctggtggcag    90360
acctggaaat aactagccta ggagtctcga tattcattag gccacagatg gaaatgccct    90420
cattatgctg tctgggctat gtctgagaga gagtcaacta actggactcc agttaaatgg    90480
agatatgcac tggaagataa gtttgtgact acagagtgtt tttctctgca atgctgcagc    90540
agttggcact ggttaattcc agagggtgtg tgtgtgtgtt tgtgtgtgtg tgtgtgtgtg    90600
tgtgtgtgtg tttaaagcat tatcacgcgt cctagatgag ggaagagagg gtgaatccaa    90660
ggtaacacag acacacaggt aagcagatgt ttgccatctt ctcttgaaag tcatataaaa    90720
ccaaatgaca gtgtatatta gcaggagaaa ctcaggaggc tcttcccagc tgttaggcta    90780
tacgactctg gaataagcta gtacaaatta ggtagaaagt ctaggattgt tcctagagcc    90840
tggtggcggg aggtctttcc tggaggcaaa ggactgtggg gctgtctcag ggccttctgc    90900
agctgctaaa gtgagaagcc tgccgacggg atcatcccca agcccacaga agctctgaaa    90960
gctatggaaa ccaagatctg tacaggagcc acttctggtt tctaatgcct gagagattaa    91020
aatggaaaaa aaaattccca tggaaattca agaatgcaag aatgttctgg ggccaggcac    91080
ggtggctcat gcctgtaatc ccagcacttt tggaaggccg atcacctaag atcagaagtt    91140
caagaccagc ctggtcaaca tggtgaaacc ccgtctctat aaaaatagaa aaattagctg    91200
ggcgtggtgg tgtgcacctg taatcccagc tactcaggag gctgaggcca gagaatcact    91260
tgaaccctgg agccagaggt tgcagcgagc tgagatcatg ccattgcact ccagcccagg    91320
caacaagagc aaaactccat ctcaaaaaaa aaaaaaaag ttctacaacg tggcacagg     91380 tccgttctgg ctaaggcagt gatgtccccc tcccaccaaa gcccaaacct tctaacatca    91440
tcctaaagtg tgggaatcac ctcttcacct caggccagct ctgggctttt ctcagcctat    91500
tcatcagcct ccattagtcc tcagctctgc tgaggcctca gcagcttccc agtcccactg    91560
aaggctgtgg ggcatagaat gggcagaggg caggccgggc gtggtggctc aagcctgtaa    91620
tcccagcact ttgggaggcc gaggcgggca gatcacgagg tcaggagatc gagaccatcc    91680
tggctaacac ggtgaacccc atctctacta aaaatacaaa aaattagcca ggcgtggtgg    91740
caggtgcctg tagtcccagc tacttggtag gctgaggcag gagaatggca tgaacccggg    91800
```

```
aggcggagct tgcagtgagc caagatcctg ccactgcact ccagcctggg cgacagagca    91860
aaactccgtc tcaaaaaaaa aaaaaaaaag aaagaatggg cagagggcat aaaacctgag    91920
tccagaggtg gtggttgcac aacattgtga atgcactaaa tgcccctgaa ttgtacattt    91980
taaaatggct aattgtatgt tatgtgaatt tcaatcgatt tttaaaaaaa ataaaactga    92040
gccacctttg gggtggggag aggagctggg ccaggctctg aggatttgag ggttgaaact    92100
ccttgcaggg agtgaaatga acgacaatgg ggaggccagt ctggccctcc caactcctcc    92160
tccaggacca gatgggaact ggggctaggg agaaaggccc aactgggcg gcgccgggct    92220 ctgggcagaa gagaagcact cagtgaatgt gaggaggctg cagccgtcgg ctcatttgca    92280
tcataagtga ttggttttcc ctgctcgtcc ctcatcagga cacaatggac agttgtttgc    92340
tggcgcagca gatccattta ccaagggaga gaggagacag agcacaagtg accgatgggg    92400
aatagtgttg aagggtgggc agccgcctcc cctcccctgt gctcccaggc cactgggact    92460
cttgttctca cacaatgaga agggacctta gagagcaaat caccgcttca ctttatagaa    92520
gaagagactg aggtgctgag aggaggtgag ccttgctgtg gtcaaacagc aagaacatag    92580
caaaactaag cattttaaac tctaacctct ggatcctttt tctttgagac aaggtctcgc    92640
tctgtcaccc aggctggagt agtacagtgg cacaatctca gctcactgca acctctacct    92700
cccaggctca agtgatcccc ccacctcaac tttctgtggg ccacgacacc tggctaattt    92760
tttgtagaga caaggtctca ctgtgttgcc cacatttttc tcgaactcct gggctcaagt    92820
gatcctccag ccttggcctc ccaaagtgct aggattacag gtgtgagcca cagcactggg    92880 cctgttggt ttttgttttg ttttgttttt ttgagatagg gttccactct gtcatccagg    92940
ctagagtgca gtggtatgat cactgctcac tacagcctca cactcctggt tcaagtgatc    93000
ctcccacctc agcctcctga gtagctagga ctataagtat gtgccaccac gcttagctaa    93060
tttttatttc ttttattttt tctagaaaca gtgtttccct atgttgccca ggctggtctc    93120
acctgggttc aagtgatcct cccacctcag cctcctgaat agctgggatt acaagtgtga    93180
gccactgcac caggcctgga ttctaaactg tcatttgagg gttcacttcg tttccccata    93240
ataccttctc tgtgcccttc ttcccatctc tgtggtctcc tgttcccggg gccttcgttt    93300
ccatcattct gtctcctggg tctatttctt tttctctgtt tctgttcctc tctgtatctt    93360
ttcctcttgg tttccaggca gctaggataa ttactagact tttaattaac ccctgcccta    93420
acaaaggtgg gtctggcatg aggcagcaat ttagcaagtg tcttggtttg ttttggggat    93480
aggtggggag agaaaaatat gtgttgggggc ctattataaa ccaggcacta agacagacac    93540
ataatgcact ttatctcatt tcatcctttc aatcttgcaa ggtaggtgtt cttagagaca    93600 aaagggtga ggctcagaga ggttaagtaa cttgtgcaag ggcacccagc tagcaaattg    93660
tagttacctg actccaaaac ctctgttctt ccatctcaca ccctggcaca gggtctaact    93720
cagggtaagg ggctcattga tttcaggcgc aaggaggca caaagtcact gaaggagacc    93780
actgttttgt tgctgtcctc taggcagcga ctgcgtcccc ccagagcccc ctccttctct    93840
gagccccttc tgcagcgtgg cgaaatctca caaatgcaag cttttgcccc cagggaggtg    93900
gggaggcagt gatcaagaaa gaaacctgac aaacccagac caaccatggg ggtctccctc    93960
ctgttaacac ccctccctaa cagccctcct ggtggttccc tgtctgcccc tcccctttat    94020
gggtcaagcc tgctggcgtc tgtttcattg tgctgtgggg gaaggggaga gtcagggggtg    94080 agtgggtgtc tgtgtgcatg aacataaggc ctccgggttc attctgacac tgaatgaaaa    94140
```

```
actcaccaat tattcgtcca gtctcattaa tatgcagaca gacatctgtt atttaggagt    94200
caacagcaga ggcattttct tgtcgggagg ggcactagtg tacagggctc tcttgtctct    94260
ccgctgctag cgggtagcta ctcaggaatc atcccacacc tcccgacctg agcctcccc    94320 tctctctgac cctcactcac agctttgagg acagcaagta agggattgac cagacagaga    94380
tggagggaga tctgggaacc tggctggaag gaaggaagca ggagaggagc tgccttgtgt    94440
agaacaaact gagaacaaaa cgctaaaccc tttcctgggg aagagaatgt ggagttgggg    94500
gagagagctg tgccaagagt gcctgcccca ctgggaatct cagggacatg acccctcccc    94560
ccacaccttc ctcagcctgc aggacaagtc tgagtgcatc tgaagcaggg agagggtcac    94620
tatggcaaca tgaagtcctc acccagagac tgcagaaaac gtaataagag gagttcagaa    94680
aaatggagac caagggacct caatcttttt tttttttttt caatttattt attttttttt    94740
attgatcatt cttgggtgtt tctcgcagag ggggatttgg cagggaggga cctcaatctt    94800
tggaggagtc actaaagctc tcttcaggcc ccaagatagg ggtgggaaca agacataacc    94860
acctcctgct ttctgtcttc tgtcttcctc cagcctttaa gtcccagcac aaaatacccc    94920
tccaagaagc cttccccaac tccctcaggc ccagcttaga agcacttaag ccttggtgtc    94980
ttggttgtaa agaataaaag ttgacatcag ctgagcaaca caatgaggta gatgtggtga    95040 tcagcccct tttctaggtg caaaaactga ggttcagaga ggtgctgggc ctcaccaaag    95100
attccccagg gaagaagcag cagagctcaa cccaggccct gggacttctg cctctgaacc    95160
tgaagctctt cccacgacta cccctggga gggccagagt cacaagggga ggacccttgt    95220
cagctgaagt gtttcaggag tttgattgag tcctctcttc ccatccaccc tgtccttccc    95280
cctcctccct cctaggcagg cggattgcct aggttaagaa acactagtct gggcgaggtg    95340
gctcacgcct gtaatcccag cactttggga ggccaaggca ggtggatcac taggtcagga    95400
aattgagacc atcctggcta acacggtgaa acctcgtctc tactaaaaaa tacaaaaaat    95460
taggccgggc gcggtggctt atgcctgtaa tcccagcact ttgggaggcc aagacaggcg    95520
gatcacgagg tcaggagatc aagaccatcc tgactaacac ggtgaaaccc cgtctctact    95580
aaaaatacaa aaaatgagcc ggacgtggtg gcaggtgcct gtagtcccag ctactcggga    95640
ggctgaggca ggagaatggc gtgaacccag gaggcagagc ttgcagtgag ccgagattgc    95700
gccactgcac tccagcctgg gcgacagagc gagactccgt ctcaaaaaaa aaaaaaaaa    95760 aattagccag gcgtggtggc gggtgcctgt ggtcccagtt actgggcgg ctgaggcagg    95820 agaatggcgt gaacctgtga ggtggagctt gcagtgagcc aagattgggc cactgcactc    95880
cagcctgggc aagaaagcga gactctcaaa aaaaaaacca ctagtctggg cgcggtggct    95940
cctgcctgta atcccaacac tttgggaggc caaggtgggt ggatcacctg aggtcaggag    96000
ttcgagacca gcctggccaa catggtgaaa ccccatctct actaaaaata caaaaattag    96060
gtcaggcatg gtggctcacg cctgtaatcc cagcactttg ggagactgaa gcaggcggat    96120
catgaggtca agagatggag accatcctgg ccaacatggt gaaaccctgt ctctactaaa    96180
aatacaaaaa tggctgggca cggtggctca tgcctgtaat cccagcactt tgggaggccg    96240
aggtgggtgg atcacgttag gtcgggagtt caagactagc ctgaccaaca tggagaaacc    96300
ccatctctac taaaaataca aaattagctg ggcatggtgg cacatggctg taatcccagc    96360
tacttcagga agctgaggca ggagaatcac ttgaacccag gaggtgaggt tgccgtgagc    96420
cgagatcgcg ccagtgcact ccagcctggg caataagagt gaaactccgt ctcaaaaaa    96480 aaaaaaacac taaaattagc tgtgcatggt ggcgcgcgcc tgtagtccca gctactcagg    96540
```

| | |
|---|---|
| agactgaggc aggagaatcg cttgaaccca ggaggcagag gttgcagtga gccgagatgg | 96600 |
| tgccactgca ctccagcctg aatgacagag tgaaactccg tctcaaaaaa aaaaaaaaaa | 96660 |
| aaaaaaaaaa aacacagaaa ctctggcagc catcacagtg tgattatttg tttatttcat | 96720 |
| taaatgttta acgaggctac attgtttccc aaaccaatgt ctaatttgtg aaggaaacag | 96780 |
| cgcagagaag gaagctgggt gactcctgca tctggggtgg ggaagggagt aaggtcccct | 96840 |
| ccctccatcc tacagaggcc tttgaggatc agcaacagtc ccattccctc ctcccaccca | 96900 |
| ctgagctcct cagcccagag ccctcctccc cagaaataaa acgtctggca acccagacct | 96960 |
| gcagaaaggg accaaaaatc cattcctggt ggtattgaaa atgtattaaa ctttggggg | 97020 |
| tcctccagct gattgatttt tctaattatg tttgctttag atggatattt aaatgcattt | 97080 |
| gcattccctg agctcacatg gcaggatatg gaggttggag gaaagagggg gcacaaacac | 97140 |
| tccacactct gcactttggt ggttgcaggc ttgaacctgc tatacactga gaagtccaaa | 97200 |
| gtggaaaaga gaagccactc agctaaaaat cgcaagtcga ttttatggc aggtccttgt | 97260 |
| ggggaagggg tcagtcctca gagacagatg gagatccacc tagctgggcc tggagcccct | 97320 |
| gccctctcct gtaccttag ccgaggactc agggtctttg agtcagtccc taaccaggtc | 97380 |
| tcagtttgag ggggtggtta ccaagcaca cttagataat ttcaaatgcc attgaagtta | 97440 |
| tcctagaatc tttgagactg gctgagatga actagtccca taggagaggt tgggataggg | 97500 |
| atatctgatg atccagggag tggtgggtag ggattccttt cctctcaaga ctggaacctg | 97560 |
| gcataaggga aaggagaagc tattttttat tttttatttt ttaatttttt ttagagacag | 97620 |
| ggtctcactc tgacactcag gctggaagac aatggcatga tcatagctca ctgcagtctc | 97680 |
| taactcctgg cctcaagcga tcctcccagc ttggcctccc aaaggaggaa tcttggctgg | 97740 |
| gattataggt gtgagccact gccgagaagc tattatttta aatgacacac ctcagagcca | 97800 |
| aatctcccag ctccaacacc acatccagat aaccatctat ccaaaaaaca actctgatca | 97860 |
| cttcactctc tgcctgaaat tcctggtggc ttcatcctct gaggatgatt tcattcatcc | 97920 |
| tcagaatgaa attctgattc ctctgtggac cctgcagtag cctcagtgta ccttcctagc | 97980 |
| cttgtcttct attctccctg ccatgggagc cccaacagtg ctatgctcat tctcatctcc | 98040 |
| acgtgtttac acatgctgta ccctctgccc agagtgcctt tcctacccct tccctgcccg | 98100 |
| gaaaactcct cttcaaccct caggacctgg ctcacaggac tggcttctca ggctgcaagg | 98160 |
| agctcccata gcatcccata catgtacaaa tatccctcag ccatggcacc ctcacacctg | 98220 |
| aggtacctct cttccacact gggctggcct ccaaaagctt agagactggt ccttgcaatc | 98280 |
| tcccaagcca gtgtatgcca cacagttggt gttcagtaca tacttgctga atgaatgaat | 98340 |
| gagggaggaa tgggctataa atttgggtgg gatcccagca gatagttggg taaggtcagt | 98400 |
| gttctcttcc agtgtgtctg ggagaactgg ctagggctgg gggagggaag ggccagggat | 98460 |
| ggttcctggg ggagaatgtc accgaaaaga ggccagtggg accagagcca ggaagggaat | 98520 |
| acaggacaat ctgaaaccag actcccgaga aaacagacca gtactgtctt tcctgacaac | 98580 |
| aggcgctcag ccgtcctctc caccgtcttt cctttaaggg acagggtagg ggtgactcta | 98640 |
| acagctgatg ctcccctgaa agccatcatg aaactcagca tgggaggaga gaaaggtccc | 98700 |
| tggcctgagc ctctaaggag accccagaat caaactactg acctcttagg aaacttcacg | 98760 |
| ctgtacaggg gtagcttctg tgatgtggag gcttttgatg ccttcttttt ttttttttt | 98820 |
| ttttttttg gagacagagt cttgctctgt catccaggct agaatgcagt ggcgcaatct | 98880 |

```
cggctcactg caagctccgc ctcccaggtt cacccgggtt cacaccattc tcctgcctca    98940
gcctcccgag cagctgggac tacaggcact gccaccgcgc ctggctaatt ttttgtattt    99000
ttagtagaga tgggtttca ccgtgttagc caggatggtc tcgatctcct gaacttgtga    99060
tccgcccacc tcggcctccc aaagtgctgg gattacaggc gtgagccagc gcgcccggcc    99120
tgatgcctcc ttatccccac aaccccagg gtaccagcag gctccaagcc aggggtacag    99180
atggtgagca ggacccctcc cacactagca gcaggcctgg ctgggctgag aaatgctgac    99240
taattatatg tcggtctgct ctaaaacccc ctaatggcct gagaattgcc cacttcatta    99300
actaggatga acagtcccag gatgtctcct tctcccaact ctgactccta aaaggacact    99360
tctgatccaa cctatggctt tgtcctctgc tctatctgtg acatggaca ggaaagttcc     99420
ccagctgagg tctaactttc cctcttactg ctaaagattg gtagattgat ttttttaaaa    99480
agcaacaaaa ctaaagccac agccgttttc catggaggtg ggctttatta ggtgactgtt    99540
gaggcaaggg aggttctagg gctggtggac tgatgggggg caagggcttc tccttgcttt    99600
tgaatttagt gcatgttgcc tagaggttag atgtgtgaga atagctgcag aagtgagagg    99660
agaggaaaag agaaggtcat agaatggaca ttttccttgg gccagaacca ggatatgggg    99720
actgggggtg gagaggagg gtactcttca cataggagac tccaccaagg tcaccatttg     99780
ataccagctt ccctaacgcc cacctgcccc atcccagttc atgccccaga tgccagccct    99840
gttagctccc tcaacatcca ctggagaaga ggagggagga ggagatgaga aacgatgata    99900
cccttctgcc ctccagctcc cctgcccaga attgctcgct ctgcctgccc taacttccca    99960
gccaggatca ggaggtcagg aagcctgggc gcaggcaggg gaacaattgt gtccctcacc   100020
accccctcttc acactctgcc ctctcctagc ccctcacatg aggttgcagc ttttggctcg  100080
atccttgtgt atctcgccct cattccccg gtctggccgt cctgacagct gagcggatcg    100140
ctgcattccc cggcgtgagt cagttcggcg cagctgccta tggccacggc caagggaggc   100200
cactgtagcc acatggaaga catccctgac gctgcgctca gaggaccggg aggagcactc   100260
aacataggac acagccccca cctgcttggc cagcacagtg ccctggaaaa ggaaggagtg   100320
catgggagaa agttataggt cttagcctgc agcttagaaa ggggcatgga ggctgtgggc   100380
tggggttgaa tgtcaaggct gggggcagtc aagggatcag gtcagaggtc acagaccaga   100440
acaaaggatg agccaggtaa ggtgttttca aatcagagac tgaaggggca gaggtgcacag  100500
gtctaggctg ggatgaggtc agacgtcaag ggtcccacct gctcatgtgt aacagggata   100560
agcctctgct tggacagctc cctcagtgtg gccaggtcag tccgcatgtc cagtttacag   100620
ccaaccagca caaccttggc attggggcag aactcttgag tctctccttg ccactatgta   100680
ggagaagaaa agaaattgt ggagggtgg agggaggcac agcgtgagcc tttgtgccat    100740
gccagcagtg tgccctctct tcctcaagca cgcagaaacc atgtatccct caggactctc   100800
ccacatgagg aaggaggtga gaatgctagg cttggtttga gagcaggatg gggtgagaga   100860
gaagcagcgg ggaggagagg gctggcgtgg gcctgtggac tcttctccct cagtggctat   100920
gaagggtctg ccagcctgga aacttcccat tcccactcgc ctttcccata ctctctcctg   100980
ggaacaaatt tatcccaccc tcccctcccc cacctgggaa ctggggctgc ctagctgac   101040
ttctgtccat tcacccctgg cttttgtcat ggaaactggg gctggagag gaggccacag    101100
ggctttcctg agctccagga tcaggcttcc catcccatcc cctccatctg ggactcccac   101160
tgccaaggag ttggaagagc agagaaggaa tcctgtgagt gcttctccct tcactccccc   101220
acctccccta gctgctgtat ccagctctga ggactttcag gaaaggggtg gctgggaggg   101280
```

```
atgggggctg gaggcagggg tggcagggat gagagcttca ctcgctaacc agctgatggc    101340
cataccccag ccatcactcc ctcctcctgg cccatgttat gtcaggacca tggtggtctg    101400 gtcccccctca gtctagctgc cctatttccc caggctccca ccttcttgag aacactgtcc    101460
agtgtttctg gtcggctaat gtcgaagcag atgagcacag catcagaatc aggataggcc    101520
agaggccgga cattatcata gtaagaggaa cctgaaggaa gacagggcat gaggggcctg    101580
agtggatggg aggcctggaa gggaatggga gaccttacag atcctggtca agggatgctg    101640
ggagcagaga atggaaaaga gcaaccatta atacccatca ttaatacccca tcatggagtc    101700 tgggtttccc aagtggggga gcgggcagaa gggaggtcac atggtgggaa acggctctct    101760
gcttccctag tggtttaaaa agtaataatt tttattcttg actgaggttt ggaccccttt    101820
gagaagctca taaaatctat agacattctc ataaaatgtt gcatgtgctt tctgggcttt    101880
ggcagtctaa agccctgaag ggaactcttg taaaaataaa aaccctcctt atgttgggag    101940
gaggaaaaga gcagtggcag ggagagcact ctcccattct cctgggactt gacctcagat    102000
ttatctagtt caatggagag aaacagcctc ctgaccaccc ctcactcaag acattctaaa    102060
tgtcttttct gcttttttat tttttgagat ggagtctcgc tctatcgctc aggctggagt    102120
gcagcggcat gatctcggct cactgcagcc tccgcctccc aggttccagc gattctcttg    102180
cctcagcctc ctggtagctg agattacagg cacgtgccac acgccgatt aattttgta    102240 tttttagtag acacggagtt tcaaccatgt tggccaggct ggtctcaaac tcctgacctc    102300
aggtgatccc cccacccccag cctcccaaag tgctaggatt acaggcgtga gccaccgtgc    102360
ctggcctcta aatgtctttt ctaaacccag tcttatctct gaaggaacat gttccaaatt    102420
aaaagccatt ccttcccaac tttcccaggt aggcaggacc cagctgaggg gctcagatcc    102480
taggctttct ccttcaggac atggtttctg tcaggctctg caagttctac ctcagtttcc    102540 ctggattttta gcagaatatt gattttccc ttcctgttgg aattggatgg atgggctggg    102600
cttacctgga acctaagggt ctaaccaagg gaggggacag agtgggccgc cttggaagtc    102660
agggtgaccc ccaggggactt ggctacctga agtgtcccac atgttgagct caatgcggcg    102720
cttgtcgatc tcaaagctcg cagtgtagtt ctcaaacacg gtggggacat aactctgcag    102780
acacggatgg atccagatga gatcatctct ccaagtcctc accccagata aatgccctcc    102840
tcactcccac accccgtcca gcccagcccc tggacacaag ttggtctggg attgggcaaa    102900
ggggagatcc cgggagctcc tgccccccc cccccccccc cggagaatct ctgctaagct    102960
ccaagacctc ctcctgttcc cttctggtcc cttcagcccc ctagttcttc ccctctccat    103020
tgcccaggac ctccgacatt cccctcgccc tccctcccgg atgctctggt tctcccaaac    103080
cccatctatc tcaccctgct ccctaattcc tcccacccca atcctctgca gtccttcctg    103140
agccctcaag gcctcccgc gtcctccgac cccctgtctc ttgtccctgg ttacccgagt    103200
acccattccc atccgtcgcc agggcccctg tcacccaccc ccagcagcc ttagcgtccc    103260 cctcccaaga cgcaggtccc tcaccccggg ataggcgtcc ttggcgaaca cctgcagcag    103320
cgccgtcttg ccgcactctg cgtctcccac caccacgatc ttgcagcggc cgctctgccc    103380
ctccatggtc ccggctacga gccggtcccc cacgccaccc ctctcccggt ccctccttc    103440 gcctctcccg ccctgcaac tgcagccgct cgggccgcca acaccggcat ctcccgggcc    103500
cgcgccgagc cccgccccg gtccgcggc ccccctccg cccgccccc agccagcgcc    103560 gcgcccccg gcctcctcc cacccccgca gccggggtcg gggccagaag atctggcgga    103620
```

```
gccctgggaa cagaggcctc agagccgggg tccagcccgc cggtgtggtc tgaggggccc   103680
ctgccggttt gggacaggcc gaactgggct tatttgactt tctcggatat aagggcaggt   103740
cagagttcaa gcgaagttct taggggtaga atatgagcgg cacaagcgcg aagctcgggc   103800
ctgctgtgta cccacgcgtg cacgcaggtg taccagtgcg acaagagct ggggcagcca    103860 tccacttcct gaacacggcg ggagagagat gctaagggga aggagggagc ctctttggtt   103920
ttctctcccg cgtccgccta tgtcctggca ggggtcttg gggaaatggg agggtgaacc    103980
ccagcacacc cacccggacg gtggtgacat catagctttc cgtccccatg gcaacgggca   104040
gccgggtctc cggttacatt gacttaaccg ccggcctaga ctagcagaga agcgtggact   104100
gagttcctcc agccaagcac tgggtggaaa gttttggggg agctgcgtcc tctggtggat   104160
gcttggggac aaggagataa ggaagagaaa gaaccaaccg ccagagttgc tctgctggag   104220
ccagagctaa acccaaaagt caggcttgat taagagtctg acaataggcc gggcgcggtg   104280
gctcacgcct gtaataccag cactttggga ggccgaggcg ggcggatcaa gaggtcagga   104340
gatcgagact atcatcctgg ctaacacggt gaaacccgca cggtgggcgc ctgtaatccc   104400
agctactcag gaggctgagg caggagaatg gcgtgaaccc gggaggcgga gcttgcagtg   104460
agccgagatt gcctcactgc actccagctt gtgcaataga gtttcgaaaa aaaaaaagtg   104520
cttttttata tcgaggcaat tcgagtcaat aatatatgct gcaaataatt ctgtaaagat   104580
aactagaagc tgggcgcggt ggctcacgcc tgtaaactca gcactttggg aggccaaggc   104640
ttgcttgcgt gcaggagttt gaggccatcc tgggcaacat tagcgagacc ctctctctag   104700
aaaaaaaaat caaaacttag ctaggtttgg ccactctagg cacgctgcct atggggtagc   104760
cctgctctgc aaagagcagt aaaacataaa gttagccggg cgtggtgaca catgcctgtg   104820
gtcccagcta ttcaggaggc tgaggtggga ggattgcttg aagccgggag tttgaggctg   104880
tagggagctg tgatcgcccc acctcgctca gcctgggtga cagagtgaga ccctgtatca   104940
aaaaaataaa aatataaata taactagagc acgcagcatc atcactatgt tacagaaggg   105000
aaaatgagga acagaacgtt aacaccaaag tcagaaagtt ttaaaggctt ggtctccatg   105060
cttctacttt gccactgcaa gaccacagtg aattaagtct catccctgcc tgggttagat   105120
gtcagagcct gagacacaat gtagttggac tccagtccac aggtggctga ctccaaatct   105180
gatatgagtt aactccaaat ctgatgtaag ttcaagtttt gggactgttc cttaactttt   105240
tttttttttt tttgagacgg agtctcgctc tgtagcccag gctggagtgc agtggcgcga   105300
tctcgactca ctgcaagctc tgcctcctgg gttcatgcca ttctcctgcc tcagcctccc   105360
aggtagctgg gactacaggc gcctgccacc acgcctggct aatttttgt attttttagt    105420 agagacgggg tttcaccgtg ttagccaggt gaatctcctg acctcgtaat ctgcccgcct   105480
cggcctccca agtgctggg attacaggcg tgagacaccg cgcccggcct ttttttttt     105540 cgagatggag tctccctctg tagcccaggc tggagtgcag cggcatgatc ttggctaact   105600
gcaacctccg cctcctgggt tcaagcaatt ctccagcctc cgcctcccta gtagctggga   105660
ctataggcac ctgccaccat gcctggctaa ttttttgtagt tttagtagag ctggggtttc    105720
accatactgg tcaggctggt ctcgaattcc tgacctcagg tgatccaccc acccgcctcg   105780
gcctcccaaa gtgttgggat tacaggcgtg agcacggcgc ccggcccttt tttttttttt   105840
ttttaacagg gtctcactct gttgcccaga ctggagtgta gtggcgcgat ctcggctcac   105900
ctccgcctcc caggctcaag cgattcctct gcctcagcct cccaagtagc tgagattaca   105960
ggcgcgcgcc actaccgccc ggctaacttt tttattttta gtaaagacgg ggtttcacca   106020
```

```
tgttggccag gctggtcttg aactcctgac ctcaaatgat ccaccagcct cggcctccca  106080
aagtgctggg attacaggcg tgagccaccg cgccaggcct atcccttaaa atagttttta  106140
atttgaataa ggtttactat gaataaataa atcacagtcg gcttgatccc aagagcacag  106200
acgttcctgg tgccccttt cgtgctctcc cagcttgcgc cactatggcc ctggcccttt   106260
aaggctgagc gcgaggcccc gcctcgcccg gcgccccgcc cctcccgctg atcccgcag   106320 ccgcggctct tcccgacgcg ttccgacttc cccagctgtg cactctccat ccagctgtgc  106380
gctctcgtcg ggagtcccag ccatgtccga cgagagagag gtagccgagg cagcgaccgg  106440
ggaagacgcc tcttcgccgc ctccgaaaac cgaggcagcg agcgacccc agcatcccgc   106500 ggcctccgaa ggggccgccg ccgccgccgc ctcgccgcca ctgctgcgct gcctagtgct  106560
caccggcttt ggaggctacg acaaggtgaa gctgcagagc cggccggcag cggcccggc   106620 ccctgggccc ggccagctga cgctgcgtct gcgggcctgc gggctcaact cgcagacct   106680 catggctagg caggggctgt acgaccgtct cccgcctctg cctgtcactc cgggcatgga  106740
gggcgcgggt gttgtgatcg cagtgggcga gggagtcagc gaccgcaagg tgagcgggtt  106800
gcgtagggca gggcagggct gcgcaggcca ctgggcagtg gggcacgagt gggcgagcgc  106860
cgggggtgtg gcagggcggg agaaactggc gcggacctgg gtgcacgagc gtggaaagcg  106920
tagccaagga acttgtgttt gggggctcct ggagagcggc atttatgtgg ggaggggaga  106980
cgaaattatc gcccccttcc caaccatttt aagttgtggc cgccgcccag aagctgtgct  107040
ggtggggggg aaaacaataa ggtgcccatg cgcatgcgca caaccacact accgtcccca  107100 cccaccccc ccccccccat taaaaccaca cctgtacccc tacccaccaa acactctctg   107160
ggtaattgtg gtctgtgact atgagtgacg gttagtgccc cctttccccg aggggagcttg 107220 aggggctatg tcgtcggggt tgggcggggg cacagcggcc gtgccagagt cctggtcaca  107280 tgcagcccccg tggtctgtgg gggtgtgagg cggcccctcc caaagcaagg ccaaagagac  107340
gagacacgcc catcacggag gagagagagc ctttgctacc ccaccgccac cagccttaca   107400
ccgccgatct gattttgggg tggggaggc gggattgggt catccgatct ttgtcttggg   107460
ctctgtgtct cccgtgactg cagtatctcc tcctcctgtg actcagccct cagccttcgg  107520
gccacgaccc ggggctgccc ttgggaatgc ctggggcggg gagtggaagg ggggacccac  107580
ctctgccttc ctcctgcaga ggaccccac ttcagaaacc ccagtgccag gggtttggac   107640
tggaacggag aggtgcggcg ccttgaactg gttggccaag tctgcaggcc tgtttctcct   107700
tctcatttat cattaatctt ggccacaacc ctggacacca gagagctcaa aatgatcagc   107760 ttttgagag acctgggatg aggcctcagc acgccatttg tttagaggtt ctttttttt    107820 ttcttttttct ttttttttt tttttttttt agacggagtt tcgctcttgt tgcccaggct  107880
ggagtgcaat ggcgcgatct cggctcaccg caacctctgc ctcccgggtt caagcgattc   107940
tcctgcctca gcctctcgag tagctgggat tacaggcatg cgccaccatg cctggctaat  108000
tttcgtattt tttagtagag acaaggtttc accattttgg gcaggctggt ctcgaactcc  108060
cgacctcagg tgatctgccc acctcggcct ccctaagtgc tggggttaca gacataagcc   108120
actgcgcttg gccaggagtt tccttttaa atcagacccc tcaatgagag gcccacaga   108180 tgcagcctct tgcagacctg ccagcccaat tctggagcca gtttgttgg attcatcctg   108240 tatgcaaaca gcttctcctt aaggcttcc tctgaattca gctctggccc caccctcaaa   108300
ctgacttcta aatgatccca ctcttgagca ggcgtctaag aggaatattt tcgggaggta  108360
```

-continued

```
gttgtagttc atgttactgc tgaaggccac ccacctcacc tccctccat acactttccg  108420
cctggtaaat acaggatatc ctgtccaggg caagaatctg atgtaagagc ctggattctg  108480
cggggagggc ccttccctct ctctccctcc tcctccctcc tggtgtctgg gttggggagg  108540
ggtcatggcc ctgatttgga tggcctgagg gttagcatga gccagggtaa gtgagacttg  108600
ttctgggtca aatctgggac tggccatgac cctaaatgac caatgcactc ctcgcagctc  108660
tcctgggttg ttctgtatct gctagtcctg agtccctggg tggagggctt ccgttccttgt 108720
tctccagacc tcatctcagg ccagaacttg aaggaaaga ccccagcatg ccctcagttc   108780
tcgtattcag tggagtgtgg gggcttgagg acatgaaaaa gggcgtaagt ggcagtccca  108840
tccccttcc ccatggaccc taactcttgt taatatacag aattcccatc attcctggca   108900
gggatcaaga cagacccaga ttgtcccaga acagcaccca cacctccctc ttcatgctct  108960
tcagagagcg cagagaagtc tttctcctg acgctccctc cttttccctg cccttcccttc  109020
gacccactt gctaagctgg agagaaaggt tctgttatct ttgtccccttt tcctcctgc   109080
acagaggctc tcgtgggggt gggggggaag ccttttactg ctgcgtaggc ctctgtagcc  109140
cttcttgtct gttgcccctc ctgcaccatc tctgagtgaa atgtttttct gggctcccag  109200
tgctggctca aacacacttc tccgaggtg accacaccct gctgtaagcg ctcagagaac   109260
tttgtctgca ctttggtatg gccctgacca cacagtgccg tcttcttttg gttgtgtgac  109320
ttccttgctg ctattatatt attattatta ttattgttag ctaacattat taagtgctta  109380
ttatgtgcca gacattgtgc taaaatttt tttttccatt tggaaaaact gccctaattg   109440
acagataaga aaactggagc tggaaaagtg gagctcaaaa agattaagta attttatgc   109500
atccgaagtc acacagtcag taaacagttg agaccgcttt tgtaaccaca gcagtttgat  109560
cttttccaca atacttcatg ctgccctaac tgtaagcttc ttgcattcag ggatcttaca  109620
caatagtgac atgtaagatc tgtaagaaga tgataaggat agtatctgcc tcaaagaact  109680
gatgtaaggg ttaattaagc attatatata aagcacttga aatcgggctc ggccctcagt  109740
cagcactcag taaaggtgag ttgttattgt tgttgatgat gatgttatta ttattattac  109800
catgactatt gctgcttctc ctgctacttc atttggaaga aggtggcctt gtacctaggg   109860
ggaaatcagt aaatagcctg tgggtgaatg aatgagtgac tgaatgatac tcttctgttc  109920
ttcaaggcag gagaccgggt gatggtgttg aaccggtcag ggatgtggca ggaagaggtg  109980
actgtgccct cggtccagac cttcctgatt cctgaggcca tgacctttga ggaagctgct  110040
gccttgctcg tcaattacat tacagcctac atggtcctct ttgacttcgg caacctacag  110100
cctggccaca gcgtcttggt acacatggct gcaggtgaca ggtcccctca ctttatcacc  110160
ccttaccccca cccagatttc cttccaggcc ccttccctgc agcctgtctg ggttgttgtc  110220
atggcaacac caggctgcct tggcctgtgg ctcccagagg cctctgctgt gtagttgccg  110280
tggtaacatt caggcaccag gtctagtctg gtgtgctatc cttagcaacg tgccctcacc  110340
ccacaccccc acctctctag ctaccttccc caccacttct cagtcatgga aattagacac  110400
ggccctaaaa tgagcgtagg caaaatgaag gtgacaggct gagtccctgg gaggctagaa  110460
tggagtggtt ggtggccagg gcaactccat atcccctgct tatgggtgtc ttgctgcagg  110520
gggtgtgggt atggctgccg tgcagctgtg ccgtacagtg gagaatgtga cagtgttcgg  110580
aacggcctcg gccagcaagc acgaggcact gaaggagaat ggggtcacac atcccatcga  110640
ctatcacacg actgactacg tggatgagat caagaagatt tccccctaaag gtgggggca  110700
taatatggga gggggtaggg aggcacagga cagggagggg agctccagat ctgtggatcc  110760
```

```
taatgttgtt cttgggttcc cctactctat gacaggagtg gacattgtca tggaccctct  110820
gggtgggtca gatactgcca agggctacaa cctcctgaaa cccatgggca aagtcgtcac  110880
ctatggtgag ttagtgggcc agggatggag agagcatgtg agggcaggag ggagggtcta  110940
aggggtggga tatagaggcc agggcttttg aatgaagaag gggtagggac tcaggtgctc  111000
tgtagacgat cagggttagg aatggtcctg tatgctgcat tcagattgct gactcttggg  111060
taccagctct tttcattctc tgtcacaact tttcatatga gtgatagtaa attctacatt  111120
cttttttttg gttttttttt tgagatggag tttcgctctt gtcgcccagg ctggagtgca  111180
atggcatgat ctcggtcagt gcaacctctg cctcctgggt tcaagcgatt ctcctgcctc  111240
accctcccga gtagctggaa ttacaggtgt ctgccaccac gcccaactaa ttttgtatt  111300
tttagtagag gcggtgtttc accatgttgg ccaggctggt cttgaactcc tgatctcagg  111360
tgatccagcc gcctcagcct cccaaagtgc tgggattata gccgtgagcc accacgcctg  111420
gccaaattct acattcttgt ttggggatta ttcttgaaca accagcctgc cttctttctg  111480
tcctacctcc ctgagcatct taggcagggt gcattttcat ttaaaaaagt atttcataca  111540
acaaaataag ccaggcatgg tggctcatgc ctgtaatccc agcactttgg aaggccaggg  111600
caggcagatg gcttgagcct agaaattcga gaccagcctg gtcaacatgg tgtaccttat  111660
ctccacaaaa aatacaaaaa ttagccaggt gtggtggcac tgtactccag cctgggcaac  111720
agagcgagac cctgactcaa acaaatgaac aaacaagcaa atacataaag attagagcaa  111780
tttttttttt tttgagacag aatatcactc tgttacccat cctggagtgc agtggcgcaa  111840
cctcggctct ctgcagcatc cacctccctg gttcaagcag ttctgcctca ggctcctgag  111900
tagctggaat tacaggtgcc catctccacg cctggctttt tttttttttct ttttcttgag  111960
acagagtctg gctgtcaccc aggctggagt gcagtgacac gatctcggct cactgcaacc  112020
tccacctccc ggattcaagc aattcttctg cctcagcctc ccaagtagct gggactgcgg  112080
gcgcacgcca ccatacctgg ctaattttg tattgttgtg ggttttttg tttgttttgt  112140
tttgttttt tttttgaga cggagtttcg ctcttttgc ccaggctgaa gtgcagtggc  112200
gcgatctcgg ctcactgcaa cctccgcctc ccgggttcaa gcgattctcc tgcctcagac  112260
ttcctgagta gctgggatta caggcatgta ccaccatgcc cagctaattt tgtattttca  112320
gtagagacgg ggtttctcca tgttggtcac gctggtctcg aactcctgac gtccagtgat  112380
ccgcccacct cggcctccca aagtgctggg attataggcg tgagccacca tacccggcca  112440
acacctggct aattttcgta tttttagta gagacaaggt ttcaccattt tgggcaggct  112500
ggtctcgaac tcctgacctc aagtgatccc ccaccttgg cttcccagag tgctgggatt  112560
atggatgtga gccatagcac ccagccccta gagcaattta aagtcagcca gggttggttt  112620
gggcctggta accagcagtt tgagaattat ccaatcactc cctggcactg gtgtggagaa  112680
ttgcaagggg atcacaggga acagagagca cagatgcaga cacacaggga tgtgcctggg  112740
ggggttcaca ggctatgtca ccttgtcctt caggaatggc caacctgctg acgggcccca  112800
aacggaacct gatggccctg gcccggacat ggtggaatca gttcagcgtg acagctctgc  112860
agctgctgca ggccaaccgg gctgtgtgtg gcttccacct gggctacctg gatggtgagg  112920
tggagctggt cagtggtgtg gtggcccgcc tcctggctct gtacaaccag gccacatca  112980
agccccacat tgactcagtc tggccccttcg agaaggtgaa tgtgaggact ttgcaggag  113040
ggcttgggta ggactcatga aggctggggt cccaaggggc agattcctgg ggaagaggag  113100
```

```
ggctgcctgc atcacactgg ccectgttgg atgagggttg gatagcactg ggagccgcat    113160
ctttccttcc tccccaggtg gctgatgcca tgaaacagat gcaggagaag aagaatgtgg    113220
gcaaggtcct cctggttcca gggccagaga agcagaacta gggcaagtgg ctgtgagacc    113280
ctagagacca gcgaagggag aagttgggaa gctacgttct gttggccacc agacttgcat    113340
ttcagcctct gtcataatgc tctgccctcc ctccecegaa gttctctgtg gtgatgaccg    113400 ctctccectg ccectccccg cttcctgacc tctgaagagg ttgggaagtg accatttgga    113460
tgtctgggcc ctgccaaggc gacagggagg gtcagaggga ggccggctgc ttcctgcccc    113520 cacccttttcc ccgggcctgc tgtgctgctt ttgtgccaag gttagccagt ccccectgtt    113580 gtgttccatg tgctttcacc tctgcctcat ctttcctccc gtccctgccc cgccacctcc    113640
ccaaagaatt gaaacgtcag ctcaggatat ggggccaatc tctgtgagtc cagcatgtac    113700
ctgtctctcc ctagtgtccc ttcagcctgg gctgaccagt gcccgcctct gggcttgacc    113760
agttcccaat ctcgtcctct gtccccaact tcttaagcac aattgggctt cttccatctc    113820
caggttttct gccattctta accaaggctg cctcttccaa cagggcggga atcagaccta    113880 ctccectagg tcacaactct gggaaggata cagagccecc acccttcact gagttctctg    113940
gatttgttct cagtgcctta gcaacgaaaa cctgtgcttg tgtgtgtgtg gcggcgggga    114000
gggaggatcc tgtttcccac ctccttctcc tccctgtac tccccagtgc cttccttgtt     114060
ctggtggagc tgggggtttct ctcctcccca gtcccacaac actgccaaaa atctgtgtat    114120
gtgccattgg gtggggcagc cccaagcctc ctggggaggc agggcaaaaa caggtgccct    114180
catcgtggtc tgtgccatgt cccgtctcta tggtggttga ggagaaaggc ggggaagctt    114240
cctcagcctt gcagatatgt gtggcattta ctagccagag ctctgaaagg cagtgctgtc    114300
tgtttcttgt actgggacca aagtaaaaat ccaagcacat tccccttgca gttaggggag    114360
gccctactgc cttctcaaag cagagaggca gcttatcaaa ctcagcccaa aactctgttt    114420
acatgggtgg ggagatggag cagggaagta cagagtggga tggtcaggac ctgggccatt    114480
gcaaccaaaa tggggacttc ctgggtaggg aggtcactcc ctctactcac tgagctagga    114540
ttagggaggg ttattgcccc aaccattgca atggaggtg gagggacagg ctcagcctcc    114600
tcattgtcta aatgaggcct aaatgtgtga agtgcgattt ctgcttttgt gtaccccacc    114660
accccattac cacagctgcc tttgtgtgtt tgtgtcaata aaaagccaaa ccctgggtcc    114720
tgcttgttgc ctctgagagt ggagggaagg tgagctcctg gaaggctagt gctgccagca    114780
gaagatctgg gctgcttcct gccecctgcc tcttccatg cccaaatcac gtttcctttc    114840
atgagtgaaa tgaggaagaa catcatggca tgcaggctct ttttactgtt ctgggcagtg    114900
ttttgcaatg tgtgacccct ccgcactgtt ggtgaacata cagacctcct atatgggcac    114960
ccaagcccag gccagtgtga gaaccttggc gggggggtgg ggaggatgag aagggaggc    115020 ccctagcctg actcagaggt gaagactgct aggccctgct gtccttgggg tacgactgtc    115080
agggcctcta cctccecgcc ccgcgggtg ggcttctgga agtggatctc caggacgtca    115140
tgcagctccg ggccatccaa gatatcagga atgttgagca ccagtaccga gcggggaact    115200
ggctgcgacc tgatctggaa aaggagccag gagatggcaa aggctcatgg gagagggct     115260 gggggctggg ggtagggcag gcagtgcccc atgggggtat gaggtcggga ggcctggaga    115320
ggctgatggt gggtaggtag gtcagtgggg tttggggcct ctgatccttc attgggcaag    115380
ttcctggcag gcagacaggt tacccagccc agcccctgtt cttcacccct cctgcttacc    115440
tcagccttct ggatctcccc attcacatac ggagagactc tcagagggac ttgctgccca    115500
```

```
cccagtggca ctgtgaactg gccgatttgg cacagacgct gagccactgt ggggagcaag   115560
gaggggtggg cctttagcat caagccctct cctctccctg caccataatc ttgcacaccc   115620
tataccctct cccctgcagg aggcctgcat agccctcacc tccatcccta gcaaacccca   115680
gcatgacact ccctggcagt agctcccgaa cgtccacatc gccacctccg ttcctagtct   115740
tgccaaagaa gatctctagc ttgtccagca gctcctcctc actcagcctg aggctggcag   115800
gaaatccagt gaccaacacc ctccggccac tcaactggct ggacacctag ggggagacag   115860 caagggtgg tcccagacac agctccactt ccccatgccc aggtgcatgg catgctttgc   115920 atgcccagg attctgtcat accatcacct ggatggtggt gaccatgggc agctccaagg   115980
gctggacctg cacccgcagc cggcactcct ccatgttgat cgtgtgctcc ttttgttgca   116040
gcacctgctc agccactggg tggtgggaaa cagggtcagt actgggaacc ctccccacct   116100
ccctcctgag gctccccatg agcttacctt tggggtcatc aaaggtgatc agagcagagc   116160
ccgcaagcag agggcagtgg atccgcaaat tggaaactaa agacttaggc acttccgggt   116220
cctgctgggt gtgtcctcgg aataccaggg ggatcttggg cactgaaaat gggacctgga   116280
agtaggggag gggagtagga gtgttcctca ctcccaccta ggaggaaggc atctccgatt   116340
ccattccatt gatgctgagt gccggagata aatacattta ctgaaagaaa agctggataa   116400
atgagtggat gaatgcaggt ctggtccata caggcaatt tacatacaac atcttaattt   116460
gtcctgggag gtgggtagct ctactttaca gatgttcaag taacataatg gaggtcacac   116520
agcaaggaag tagcagagcc aggaataaaa ccgagaactc cccagctctt ttttgtgttt   116580
ctttgtttta aagggagtct tgctctgtca cccagctgga gtgtagtggc atgatcttgg   116640
ctcactgcaa cctccacttc ccaggttcaa gcaattcgga ctcagcctcc caagtagctg   116700
ggattacagg catgtgccac caaacccagc taattttgt attttagta gagacgggt    116760 ttcaccctgt tggccaggct ggtctcaaac tgacctcagg tgatccacca gcctcggcct   116820
cccaaagtgc tgggattaca ggcgtgagcc actgcgcccg gcctaatttt tgtatttta   116880 gtagagatgg gatttcactg tgttggccag gctggtctca aactcctgac ctgaggtgat   116940 caggcccct tggcctacca aagtgctggg tttacaggtg tgagccaccg cacccggcct   117000
cgccagctcg tttttaccaa acaacaccag atcctttagg gggggttatt gcgggcggat   117060
ttttgaaacg gagggctggt gataggcttt ttataggtat gcatgtatat ggttctagcg   117120
tagtggattt tgggaattgc ggt                                           117143
```

<210> SEQ ID NO 4
<211> LENGTH: 86101
<212> TYPE: DNA
<213> ORGANISM: Homo sapiens

<400> SEQUENCE: 4

```
aggcctcctt ctacaactaa ggagatctga ttatcaaact aaaatggtcc ctaaggaacc     60
aagcggagcc cacccttttt ctaatccaag gttgcttctg tttactgctc aagcaccttc    120
tggaagcagc aaggccccca tgggagcaac tctcactgaa tccatttgaa ggttttgtag    180
gtcttacaac aaaccctatt cagccttgta ttaggcatgt tacagaacca acgaattcgg    240
agatgaagtc aggtcttcca gttcagcctg cgaggaagac aggtgatccg aatcctaaga    300
atgcaaaaga tgggccgggt gtggtggctc atgcctgtaa tcccagcgct ttgggaggcc    360
gaggcaggca gatcacctga ggtcgggagg ttgagaccag actgaccaac aacggagaaa    420
```

-continued

```
ccccgtctct acttaaaaat gcaaagttag ccgtgcgtgg tggcccatgc ctgtattccc      480
agctactcgg gaggctgagg caggagaacc acttgatccc tggaggcgga agttgcggtg      540
agcggagatt gcgccattgc acaccagccc gggccacaag agcgaaactc cgtctcaaaa      600
aaaaaagcaa aagatactac caagccctgc ggagcaaggt acctcacact tcatgagcga      660
gttaagatgg gttttcacaat ttttcaagca aggaaacggg ctcggaggtc ttgaacacct      720
gctacccaat agcagaacag ctactggaac taaaatcctc tgatttcaaa taacagcccc      780
gcccactacc actaagtgaa gtcatccaca accacacacc gaccactcta agcttttgta      840
agatcggctc gctttgggga acaggtcttg agagaacatc cctttaagg tcagaacaaa       900 ggtatttcat aggtcccagg tcgtgtcccg agggcgccca cccaaacatg agctggagca      960
aaaagaaagg gatgggggac ttggagtagg catagggggcg gcccctccaa gcagggtggc     1020
ctgggactct aagggtcag cgagaagaga acacacactc cagctcccgc tttattcggt       1080
cagatactga cggttgggat gcctgacaag gaatttcctt tcgccacact gagaaatacc      1140
cgcagcggcc cacccaggcc tgacttccgg gtggtgcgtg tgctgcgtgt cgcgtcacgg      1200
cgtcacgtgg ccagcgcggg cttgtggcgc gagcttctga aactaggcgg cagaggcgga      1260
gccgctgtgg cactgctgcg cctctgctgc gcctcgggtg tcttttgcgg cggtgggtcg      1320
ccgccgggag aagcgtgagg ggacagattt gtgaccggcg cggttttgt cagcttactc       1380 cggccaaaaa agaactgcac ctctggagcg ggttagtggt ggtggtagtg ggttgggacg      1440
agcgcgtctt ccgcagtccc agtccagcgt ggcgggggag cgcctcacgc cccgggtcgc      1500
tgccgcggct tcttgcccctt ttgtctctgc caaccccac ccatgcctga gagaaaggtc      1560
cttgcccgaa ggcaaatttt cgccaagcaa attcgagccc cgccccttcc ctgggtctcc      1620
atttcccgcc tccggcccgg cctttgggct ccgccttcag ctcaagactt aacttccctc      1680
ccagctgtcc cagatgacgc catctgaaat tcttggaaa cacgatcact ttaacggaat       1740
attgctgttt tggggaagtg ttttacagct gctgggcacg ctgtatttgc cttacttaag     1800
cccctggtaa ttgctgtatt ccgaagacat gctgatggga attaccaggc ggcgttggtc      1860
tctaactgga gccctctgtc cccactagcc acgcgtcact ggttagcgtg attgaaacta     1920
aatcgtatga aaatcctctt ctctagtcgc actagccacg tttcgagtgc ttaatgtggc      1980
tagtggcacc ggtttggaca gcacagctgt aaaatgttcc catcctcaca gtaagctgtt      2040
accgttccag gagatgggac tgaattagaa ttcaaacaaa ttttccagcg cttctgagtt      2100
ttacctcagt cacataataa ggaatgcatc cctgtgtaag tgcattttgg tcttctgttt      2160
tgcagactta tttaccaagc attggaggaa tatcgtaggt aaaaatgcct attggatcca      2220
aagagaggcc aacatttttt gaaatttta agacacgctg caacaaagca ggtattgaca      2280 aatttatat aactttataa attacaccga gaaagtgttt tctaaaaaat gcttgctaaa       2340
aacccagtac gtcacagtgt tgcttagaac cataaactgt tccttatgtg tgtataaatc      2400
cagttaacaa cataatcatc gtttgcaggt taaccacatg ataaatatag aacgtctagt      2460
ggataaagag gaaactggcc ccttgactag cagtaggaac aattactaac aaatcagaag      2520
cattaatgtt actttatggc agaagttgtc caacttttttg gtttcagtac tccttatact      2580
cttaaaaatg atctaggacc cccggagtgc ttttgtttat gtagcttacc atattagaaa      2640
tttaaaacta agaatttaag gctgggcgtg gtggctcacg cctgtaatcc cagcactttg      2700
ggaggccgag gtgggcggat cacttgaggc cagaagtttg agaccagcct ggccaacatg      2760
gtgaaaccct atctctacta aaaatacaaa aaatgtgctg cgtgtggtgg tgcgtgcctg      2820
```

```
taatcccagc tacacgggag gtggaggcag gagaatcgct tgaaccctgg aggcagaggt   2880
tgcagtgagc caagatcatg ccactgcact ctagcctggg ccacatagca tgactctgtc   2940
tcaaaacaaa caaacaaaca aaaaactaag aatttaaagt taatttactt aaaaataatg   3000
aaagctaacc cattgcatat tatcacaaca ttcttaggaa aaataacttt ttgaaaacaa   3060
gtgagtggaa tagttttac attttgcag ttctctttaa tgtctggcta aatagagata   3120
gctggattca cttatctgtg tctaatctgt tattttggta gaagtatgtg aaaaaaaatt   3180
aacctcacgt tgaaaaaagg aatatttaa tagttttcag ttactttttg gtattttcc    3240
ttgtactttg catagatttt tcaaagatct aatagatata ccataggtct ttcccatgtc   3300
gcaacatcat gcagtgatta tttggaagat agtggtgttc tgaattatac aaagtttcca   3360
aatattgata aattgcatta aactatttta aaaatctcat tcattaatac caccatggat   3420
gtcagaaaag tcttttaaga ttgggtagaa atgagccact ggaaattcta attttcattt   3480
gaaagttcac attttgtcat tgacaacaaa ctgttttcct tgcagcaaca agatcacttc   3540
attgatttgt gagaaaatgt ctaccaaatt atttaagttg aaataacttt gtcagctgtt   3600
cttcaagta aaaatgactt ttcattgaaa aaattgcttg ttcagatcac agctcaacat    3660
gagtgctttt ctaggcagta ttgtacttca gtatgcagaa gtgctttatg tatgcttcct   3720
attttgtcag agattattaa agaagtgct aaagcattga gcttcgaaat taatttttac    3780
tgcttcatta ggacattctt acattaaact ggcattatta ttattattat tttttaacaag  3840
gacactcagt ggtaaggaat ataatggcta ctagtattag tttggtgcca ctgccataac   3900
tcatgcaaat gtgccagcag ttttacccag catcatcttt gcactgttga tacaaatgtc   3960
aacatcatga aaagggaaaa tgattccata gcgttattat gaaagtagtt ttgaactgta   4020
atggtagagg atgaatagct cacaatacaa attgtcatt tcccttttaag agagaattcc    4080
catttatgt gagagtccac atgttcctca tacccatagt ttgccacatc ttgagtactc    4140
ttcagaatta tttgaatttt ttgaattta tctgtggaat gtattttttt tttttctttt    4200
tttgagacac agtcttgctc tgttgcccag gctggaatgc agtggcgtga tctcggctca   4260
ctgcaaccac cgcctcctgg gttcaagtga ttctcctgtg gcagcctccg gagtagctgg   4320
gactacaggc gtgtgccacc acgcttggct aattttttgt gtttttagta agatggggt    4380
ttcaacgtgt tagcaaggtt ggtctcgatc tgacctcgtg atctgctcgc ctcagcctcc   4440
caaagtgttg ggattacagg cgtgagcccc cgcacctggc cgaattttat cgtggaatgt   4500
attcttaatg tgaatagttt ttgattccga accatgaata ataagaaaat aaataaaatt   4560
taaatgaaaa taaaagctaa tatatacagc ttttaataat atagttaaat gccatcttgt   4620
aactttgtg aactcttgtt cacctttct atagattcgc aagagaatgg attaatgatc     4680
ttgtttaatt aatatgcctt aacaaaagta atccatagtc aagatcttaa gcattttttt   4740
ccttatgatc tttaactgtt ctgggtcaca aatttgtctg tcactggtta aaactaaggt   4800
gggatttttt ttttaaatag atttaggacc aataagtctt aattggtttg aagaactttc   4860
ttcagaagct ccaccctata attctgaacc tgcagaagaa tctgaacata aaaacaacaa   4920
ttacgaacca aacctatta aaactccaca aaggaaacca tcttataatc agctggcttc    4980
aactccaata atattcaaag agcaagggct gactctgccg ctgtaccaat ctcctgtaaa   5040
agaattagat aaattcaaat tagacttagg taagtaatgc aatatggtag actggggaga   5100
actacaaact aggaatttag gcaaacctgt gttaaaatct tagctcattc attaattgtg   5160
```

```
tcatgctggg caaatcagtc tctctggcct cttttttcctc actcgaaaaa tggagacgat    5220
gaaaataatg tctcataggt ttggattaaa ttaaataatg taggtactta gtaaatgttc    5280
tctttcatcc ctcctttgat aaatttgcca actgagattt gctgaattac gtctttctta    5340
tgccaaaaaa acctaggact tgttttgatg ttaattaaac taaactatat ttctgcaggc    5400
tatcacagag gacagagatt attttaccga tatactataa gtatcatgat ttggaaggag    5460
tttccctggc gtaggtgccg catgttccta agcaattatg taataagatt atatattcag    5520
tcattcaaat aattattacc tacttgacat aagtaatgaa cttcccttt tcttcagagt    5580
gttaatctct agtaagggga ataaagagta cacagataaa gtagtgta aggttgaatg    5640
tagtatgtgc taagagaaaa atataaaaaa gtaataatgag agttgagaag aaagagcaaa    5700
tagtattggg caaagttagg caattattcc tttgagctaa accttgaagg ataggtgaga    5760
gattaagaaa tttgaagatg tggtagagtg ataatgttct aggcagaggg aacaacatga    5820
ggaagaatat gtagtgtgtt caggaaatag caagtaattc aggttggctt tggttgtttt    5880
gtgtctgaaa gggaccaata gacaaggcaa aaaggcagac taaaggcagg cattgaatgc    5940
caagctaaag aaattgaatt tgtttggttg gttggtgagc agagaaatca catgcaaatt    6000
tcatcatgct acttattgtg tcaaacccta gatcacctcc ctttgtcctt atagcaaaat    6060
ctaaacttga tatggctttc aagttccttt gtgatcaggc ccctgattta cactcttggc    6120
tcagcttgcc atattcatcc tctcacctat cttcatttgc cattcattcc tactgaattt    6180
cttttcgtta ccaaaaccac aatgctctct ggctctttat taaacatatt gttacctcta    6240
cccacaacct acttttcc tactttttgt ctagctaatt tgcgtgctcg tctttcagat    6300
cttggcttat ttctgcttct gagaaatact tcctgtctgc cctcgttgag cttctagtga    6360
aggagacata cataagcaat tatagtgtga tacatgcttt gaaagaaatt catggctata    6420
gggagtgcat atacaaaggg aatataggta atgggcaaat atttacatgt atgttattgg    6480
ataccaaatg gtatacatag gattcagtaa atatttgtag agtgagtatt agtattattt    6540
gcttttagaaa gcctaatgat caaacagcag tctttggaga taacgttttt caaaatgtca    6600
tgtctgtgcc attagaatct tctagactgc tcattgaaag gacagattcc aggccccact    6660
ctgaatctct taatttataa ttttttggaaa tgatgcccat gagtctacat tttaaactac    6720
ctgaatgatc cctatagaaa gagaaaactg gaggtaggaa gatcagttag gggatgtgta    6780
atggtctagg tgatagagac aagtgcctga attacagtaa taacagtgaa agtaaatatg    6840
gaacataaaa ctataggacc ttgcagtagt ctagatatgg aggattcaaa aaaaggaaca    6900
aatgacaggg caaagcatat gcagaacaca gtagtaacag tcatagaaat ggataaggga    6960
gtcatccatt ctgcaaatac ttactgctta cttgtgtctg gcaacctgct cggcattaag    7020
gatacaaata tgaataagat gtcctttgac ctctaagtac tcagtctcgt aagcacgtct    7080
tgtaagcaca tcttggttgc ttccataaaa ataaatacac tagtgtgata tgttataaga    7140
gcatgtacca agtgcatgaa aagtgagcag ccatctctgg ttggtcagaa aaagctccat    7200
aaagcagttt tgctgaatc ttgaaagata tacctaaggt caaatggtta attctttaat    7260
cataacctgc tagaattgat ctataaccaa ggaaggatag taaggaatta ataaggccac    7320
tctcaactca ctgcaaagga gttaactttt tgaaggctgt aatacataaa tctgctgact    7380
agtctcttga gaccttttgc ttttacgttt acttttagatt cagtattgaa aagtaagagt    7440
aatggactta agctgtgttt ttcaacctgt tttgttcagt tctaacatgt aatatttttt    7500
aaaaaattat tcctaaagtt ctatgaggaa ttgtgctgtt tctgcctctc agcagtcctt    7560
```

```
ccttttgcat taaatcatag gcatttctgt taccattctt cagcttatta atgagatcct    7620
caggttattt gggaaatgtt tatttggtaa ttaactcttt ttcacctagt tcattttttt    7680 aactttttt  tttaaatagc cgagtttctt ttcattgctg aactaaaatg gatgtgttat    7740
tattagctga actccttagt ttactttaga gttcacccct tgtatggttc tatggatttt    7800
gacaaattgt ataatgtcgt atatctgcca ttatggcatt atacagaata attttgctgc    7860
cctaaaaatc tcccgagttc cacctgctca cccatccctc ctcctgagcc cctggcagcc    7920
actgatcttt ttactgtctg tatagttttg ccttttccag aatgtcatgt agttggaatc    7980
atacagaata tagcattttc agactggctt ctttcactta gcaatatgcc gagaccagct    8040
cgattgtaga gaccctaacc cagcggcact agaggaatta aaggcacaca gaaatatagc    8100
ggtgtggagt gggaaatcag gggtctcaca gccttttgac agcaagccag tgataagcat    8160
tgtttctata gattatagat taactgaaag tattccttag gggaaataaa gggctgggcc    8220
gaagtaaagg gatgggtctg gctagttatc tgcagcagga gaatgtcctt aaggcacagg    8280
tcgctcatga tagtttgtgg tttaagaacg cctttaagcg gttttctgcc ccgggtgggc    8340
caggtgttcc ttgccctcat tccggtaaac ccacaagctt ccagcgtggg tgtcatggcc    8400
atcacgaaca tgtcacagtg ctgcagagat tttgtttatg gccagttttg gggccagttc    8460
ccaacagcaa tatgtgttta aggttcttcc atgtcttttta atgatttcat gctgaataat    8520
attccatcgt attgatgtac cacagcttgt ttatccattc atctattgaa ggacatcttg    8580
attgcttcca aattttggca attatgaata aagctggtat aaatattcac atacaggttt    8640
gtgtgtgaat atattttcaa ctcattttgg ttcacaccaa agagcacgat tgtgggatca    8700
tatagtaaga gtatgtttag ttttatgaga aactacaagc tttcttccaa agtagctgtt    8760
gcattttgta ttcccaccag cagtgaatga gagttcttgt tgctcacatc ctcaccagca    8820
tttggtgtgt cagtgttttg aattctagcc attctaacaa gtgtgtagtg gtacctcatt    8880
gtttgtttta tttaattttt ttttttttttt tttggagatg aaatctcgct tgtcgccca     8940 ggctggagtg cagtggcgtg atcttggctc actgcaagct ccgcctccca ggttcacgcc    9000
attctcctgc cttagcctcc tgagtagctg ggactacagg caccgccac  cacacctggc    9060 tgatttttttt gtatttttag tagagacggg gtttcactgt gttagccagg atggtcttga    9120
tctcctgacc tcgtgatccg ctcgcctcgg cctcccaaag tgctgggatt acaggcgtga    9180
gccatcatgc ccggcctgtt ttattttta aagtcaattt tctttcaaga attagctact    9240
ttttagtatc tttaattaaa aatctcatta gagaaggagg ttggatattt tgttgaagtg    9300 gggttttaa gttacacatc catttgcttt attagtgatt atgtctagtc catgttaact    9360
tgaaaaatga gactataatg agacattta ttaggctgc tacaaacagt tttaaatttg     9420
gtcttcactt tattttagta acattgatag agcttatttt tcccaaaagc taagttagag    9480
attataggac caaccgaagc aactattttc taagagtaat aataagtgac tcaggtgcca    9540
aatttgtagt taccatcaac tattggaacc atatgagtac ttaatgccct ggagagtcaa    9600
atataatcta ctctaataca gaaaatagaa atattgaaaa actgtaaatt ggatttcata    9660
ttgttaaagc cacctatagc tttagaaact ctgaacatta ttttcttaga aaatggatgt    9720
gttcaataag aatagaaatt atgtattact gtctgcaact cactttgtct aattatatcc    9780
aatttattca tccagtcaat atttcaggag tgactaatat accagacatt tttgtagttg    9840
ctagggatac agtgacaaat aagacaaaat ctctacctca gattgctcac agcctagtag    9900
```

```
ggggaaaaag aacagtgtat gatcaaactc ttcagggaac acatagggggg gcaaacactt    9960 aatcttacct tagggatcac tacagttttc tggaggaggt agtttctaaa tggaagcctg   10020
aaagagttgt tccaggtcaa gaaaagcaaa gaaggggaaa cagcttgtac aaagtcctag   10080
aggttaaaga aaacattctt tcaggatatg caaatggttg ggtatgggta aaaagtagac   10140
tgtaaaagaa tggcatcata aaaattaagt aaattgtcac ataaatatat atatttctta   10200
tgtacccaca aaaattaaaa atgaagaaat taagtaaatt gtgaaaggcc ttcatactat   10260
ggagtttgac ttgatcttga aaagtaagat cttgaaaggt ttttagcaca agtgatattg   10320
tcagatctgg tacattggta ggttttcagt aaatgtcttc ccttactcct tttttctctt   10380
tccttctgct tttgtttaaa gcgacaagat gttgctcttt tcccaggctg aatacagtg    10440 gcatgatcat agctcaagct cctgggctca agtgatcctc ccgcctcagc ctctcaagta   10500
gctaggacta caggcatatc accacaccag cgttttcttt gtagaggcag agtctcactc   10560
tgttgctcag gcaggtgttg aactcctgcc tcaagcaatc ctcccacctc agcctcccag   10620
agccctcaaa ttataagcca ctgtgctcgg ggcatccttt ttgggggta atcagcaaac    10680 tgaaaaacct cttcttacaa ctccctatac attctcattc ccagtataga ggagactttt   10740 tgttttaaa cacttccaaa gaatgcaaat ttataatcca gagtatatac attctcactg    10800
aattattgta ctgtttcagg aaggaatgtt cccaatagta gacataaaag tcttcgcaca   10860
gtgaaaacta aaatggatca agcagatgat gtttcctgtc cacttctaaa ttcttgtctt   10920
agtgaaaggt atgatgaagc tattatatta aaatatttaa atgaaacatt ttcctacata   10980
tatttgttct ataagatga atctgatttt tatgctaata ttttggctaa gagcctggta    11040
gaagatctta catttttaaa taatctttta ggttgagtcc tttaatagaa tagttttac    11100 attagaaaca tgtaagttgt tgttcttgtg atgttgaatt ggctggtttt ctgtatattc   11160
tgtgattttt taagtaacaa aaataacagt ggtgaaaagc agtaagtcag tccttgaatt   11220
atcaatttaa aataaattgt gtacttttca tctttggaga gaatatgatt tactttacaa   11280 atttttttt tggtttttttt ttttttttgag atggagtctc tgtcacccag gctgtagtgc   11340
agtggtgcga tctcagctca ctgcaagctc cgcctcccgg gttcacgcca ttctcctgcc   11400
tcagcctccc aagtagctgg gactacaggc gcccgccacc atgcccggct aatttttttgt   11460 atttttagta gagacggggt ttcactgtgt tagctaggat ggtctcgatt tcctgacctc   11520
gtgatccgcc cgcctcagcc tcccagactg ctgggattac aggcgtgaac cactgtgccc   11580
ggcctacttt acaaaatttt tgagtttaaa atacacggtt tccagcagct gaaatttgtg   11640
agtacatatg tgttggcatt taaacatca cttgatgatt atttaatgct tcatgagaga    11700 tttactttt aaaatgtaat ataaaatatc taaaagtagt attccaacaa tttatatgaa    11760
tgagaatctt cttttaaaaa taagataaac tagttttgc cagttttta aaataaccta     11820 agggatttgc tttgttttat tttagtcctg ttgttctaca atgtacacat gtaacaccac    11880
aaagagataa gtcaggtatg attaaaaaca atgcttttta ttcttagaat actagaaatg   11940
ttaataaaaa taaaacttaa caattttccc cttttttac ccccagtggt atgtgggagt    12000
ttgtttcata caccaaagtt tgtgaaggta aatattctac ctggtttatt tttatgactt   12060
agtaattgag aatttgacaa tagcgttata cctttgccct gagatttaca aatctgtacc   12120
tagcattctg cctcatacag gcaattcagt aaacgttaag tgaaataaag agtgaatgaa   12180 aaataatat cctaatgat cagggcattt ctataaaaa taaactattt tctttcctcc       12240
cagggtcgtc agacaccaaa acatatttct gaaagtctag gagctgaggt ggatcctgat   12300
```

```
atgtcttggt caagttcttt agctacacca cccacccctta gttctactgt gctcataggt    12360
aataatagca aatgtgtatt tacaagaaag agcagatgag gttgataatt gtcatctcta    12420
atacttctgt taaaaggaaa tatgaaaaga aaatattaga taatgtcttt gataagtgtg    12480
ttagtaactg acaataattt tattctatta agtgtagatt ggaataaata caaatacatt    12540
tagtggtagt ccagtggtgt caagcattat gttttagtac gatgtgatta acgtagaata    12600
gcttacaaat attcctttac tggcctatat aagcgtttaa gaggcagtat ttggtgtgac    12660
tgaattcttt ttacaaatga ttgtggtaat tgggcatta aagcagcatt aaataagctt    12720
ttgttttctc tacttaaatg tgttctaagg tctgtattgc cagtagtact gaattgaggt    12780
cttaaattcc acaagtgtaa ttacacaact atgtgataaa ctgcaatatt tatccattca    12840
ttaaactgta aactctttgc agtctcacca cagtttctct tactaggatc tagaaatatt    12900
tcctattgta ggctggttgc agtggctcac gcctgtaatc ccaacacttt gggaggctga    12960
gaagggtgga tcacgtgagg ccaggagttt gagagcagcc tgtacaacgt ggtgaaaccc    13020
tgtctctact aaaaataaaa aaattggcca ggtgtggtaa cacacacctg taatcccagc    13080
tacctggggg ctgaggcatg ggaattgctt gaacctggga ggcagagggt gcagtgagcc    13140
gagattgtgc cactgcactc cagcctgggt gacagggagg ctgaggtggg aggatcacga    13200
ggtcaggaga tcgagaccat cctggctaac gtggtgaaac cctgtctcta ttaaaataga    13260
aaaaattagc tgggcgtggt ggcagacacc tgtagtccca gctactcagg aggctgaggc    13320
aggagaatgg catgaacccg ggaggcggat cttgtagtga tctgagatca tcacgccact    13380
gcactccagc ctgggcaaca gagcaagact ctgtctcaaa aaaaaaaaa aatcctgtta    13440
taaaactact taaaaatctc tgagtagctg agatttggct aatcatgact tagtatttga    13500
aaagttgtga ctatttttt tttttttaat tgagacaagg ttcttctctg ttgcccaggc    13560
tggagtgcag tggcaccgtc gcagttcact gcagcctcaa cctcccaggc tcaattaatc    13620
tttcttcctc ttagccttcc aagtatctgg gactacaggt accatgccac cagtatacta    13680
ccagtcctgg ctaatttttt ttgtattttt tgtagagatg ggtcccgcca tgttgcccac    13740
acttgtctca aattcctgag ctcaagcagc caccacaccc acctgtgacc attcttttt    13800
atttttatga gataataaac atacaagttt aaagaaatgt ctgtacataa atgtgattat    13860
agtacaaaca agtatttgga agttcatcta aacaaatgca tcacagttta taggcaaaac    13920
atgaaagatt ggataataat gggaaaaaaa gtaaatattc accaacattc tttctctttt    13980
ttcttttcg tttttttttt ttttgaggcg gagtcttgcc cttttgccca ggctggagta    14040
cagtggcacc atctcggctc acagcaacct ctgccttctg ggttcaggcg attctcctgc    14100
cttagactcc cgagtagctg ggattacagg caccaccac cacgcctgac taattttgt    14160
attttttagtg gagaggaggt ttcactgggt tggccagggt ggtcttgaac tcctgacctc    14220
aagtgattcg tttgtctcag ccacattttt tttgtctaag aagatactgg gccagatcat    14280
tgtttctcaa attgcagatt atgacctgtt catagttgtg aaacttattt tgtgagtcgt    14340
atatgctctt tttaaatgaa atgaaaattc tgagtacatc acatgtagtt agggtttaga    14400
aaataaaaaa tacaatatat ctagttaaat ttggacttca ggtaaacagc gaataatttt    14460
gagatatact taacactaaa aaattattca ttgtttatct gaaattcaaa tttaatgagg    14520
tgtcctgtat tttatccaga agtcctacac acagtaaagt ttgttttgta aaacttttt    14580
acttaacctt tgtgtgccca tgtgtgtgtg cagtcataaa gtgtgtgtgt gtgtgtgtgt    14640
```

```
atttaaaaaa ctaggttgta ctcaaagcct gagcttaatt tattcccaaa ccagtattac   14700
attttgttta ttctagcaaa atagcattct gttttgattc ctctttagct gggagtaagt   14760
taaccctatt ctgttgctta gatgaaataa tatggataaa atcattttga aaatatgtat   14820
ttaatatata gtatgccttt aggctgtagt gttgtctaaa tgaatgctaa agtctccaag   14880
ctttagcttt taagtcataa cctcacagca tcatctgact ttccaactca ttgtggacag   14940
tattaccata aagtaatgat caccaagcca tatcttacca ccttgtgagt agtactaagg   15000
aagtaagtat agtttattca ctgtgttgat tgaccttcct aattactata cttaagtact   15060
tgaatcaatt cattttgttt caaatgtgtc atgtaatcaa atagtagatg tgcttttga    15120 tgtctgacaa aaaataagtt tttgcattct agtgataata tacaatacac ataaatttt    15180 atcttacagt cagaaatgaa gaagcatctg aaactgtatt tcctcatgat actactgctg   15240
taagtaaata tgacattgat tagactgttg aaattgctaa cattttgga atgccttgtt    15300 aaattattta tcttacattt ttaatttcct aatctgtaat ttatctaagc ctttgagaaa   15360
gtctctaaac ctggtcctat atgtgatttt aacttcctgt gaaactctgc tgtctctctg   15420
ttaaagttgc atatatacaa tatataccgt agtccctat tcatgggta tacattccaa     15480 tatccccag tgaatgcttg aaaccttaga tagtaccgaa ccctatatat atatattaaa    15540
aatgtgtagt atttatatat atatatacct ataatctttt tttctataag cacatacct    15600 gtgataaagt ttaattcata aattaggcac agtaagagat taacaagaac taataataaa   15660
ataggacaat tataacaaaa taccgtaata aaagttatgt gaatgttgtc tctctgtctc   15720
aaaatatctt attgttctgt actcatgtgg cagcagcttc atcagcagat gtggcctctc   15780 cagtaattt tatatttttc agtccaaacc tattcttgaa tctgtgtaac caaccatccc    15840
ttacttgcag taaatggctt ggtgtcattc atttcagggg atcccttact gaagttttcg   15900
tttaggctct atgctttctg gcgtaatatg tagctgtcaa tcaaaacaac ctgttcatgt    15960
tttctaccca caaatgtaat accttttcta cttctatggt gcactgtgtg ccacaacat    16020 ttgcagtttg aggtgtgaca gcaaaaccag ctcatatgtc tttctcctc acaatctcac    16080 agatagattt gttcttacca tagatgtcgc agtacaattt ttttcctttc cttaagtcga   16140
gaactttcac tgtttcaatt aaaggaagca ctttatggct tcttttggc atatttgaat    16200 tgccagcatc attatacttg tgctttgggg ccattgttaa gtaaaataag ggtgacttga   16260
acacaagcac tgtggtacca caatagccga tctgataacc aagacaacta ctaagtgact   16320
aataggtggg taccatatac agcctggata cgctggacaa agggatgatt catgtcccaa   16380
gtgggatgga gcaagatggt gcaagttttt ttttctccat ttccattttc ctttcctaag   16440
atttccacat cctagtggtg caagatttca tcacactact caggatgaca cacaatttaa   16500
aacttactaa ttgcttactt ctggaatttt ccattaaaaa ttttttggacc taggttgatt    16560 gcagataact gaaatcacca aaagtgaaac catggataag gggggactac tactatatgt   16620
gcattgagag tttttatact agtgatttta aactataatt tttgcagaat gtgaaaagct   16680
atttttccaa tcatgatgaa agtctgaaga aaaatgatag atttatcgct tctgtgacag   16740
acagtgaaaa cacaaatcaa agagaagctg caagtcatgg taagtcctct gtttagttga   16800
actacaggtt tttttgttgt tgttgttttg attttttttt tttgaggtgg agtcttgctc   16860
tgtcacccgt gatctcagtt taccgcaacc tctgcctccc gtgctcaagc gatcctgcct   16920
cagcttgcca agtagctgag attacaagca tgcaccacca tgcccaacta ttgtatttt    16980 agtagagatg gcatttcacc atgttggcca ggctggtctc aaatggtcgt gagccaccat   17040
```

```
gcccagcctg aactactctt tttaattggc accattgaag gattgctcct ctttctttaa    17100
agagaaaata tattaccttt cctttcttga ctactgaagt agtattttat ctcaaagtat    17160
tgagagtaga aactaacttg gtgtgcctgt gatcccagct actcaggagg ctgaggtggg    17220
aggatcgctt aagcccaggc ggtcaaggtt gcagtgagct gtgtgtgtgc cactgcactc    17280
ccacctgggc aacagagtga gaccgtgtct caatggaaaa aaagagaaac taatttgatt    17340
tcgatgacag tatttaaata ctgtgtaaga cagtactatt taatatgtgg ttgtgacaca    17400
aaaacaaagc ctattgaaaa ttttcagaga caataagata tataattaac aaaatctgag    17460
cttttttttt ttctaattag aaagtaaatg tggtttagat ataccatagt ttacctaatc    17520
aggtcatgga atattgcatt tttcttagta tgtgtgtatg tctgtataac tgtgtaggat    17580
ttgatatctg tttttgtctg tgtggtatca tgtacgtatg tatatgcata tgtaaaatca    17640
gatttaccct tgttataggg ccacagaatt gatttggaac atctgtttg ataggtctta     17700
gaatatttaa ttgtatatat agtaagatta ggtgagtttt aattgtgtag aactgctaaa    17760
gaaaggtttt tagggattgt tgtatgaata aaaggcttta ggttcattgg aatcagggga    17820
atcaggcttt actagaagaa caggagaagg ggtgactgac cgaaaaataa aatgccaagt    17880
actcagaata acccctttaaa tactgatatg taatatttag cacattctac ataaactgtt   17940
tctatgagaa aggttgtgag aataatataa attatatggc ttataaaata ttaatgtgct    18000
tctgttttat actttaacag gatttggaaa aacatcaggg aattcattta aagtaaatag    18060
ctgcaaagac cacattggaa agtcaatgcc aaatgtccta aagatgaag tatatgaaac     18120
agttgtagat acctctgaag aagatagttt ttcattatgt ttttctaaat gtagaacaaa    18180
aaatctacaa aaagtaagaa ctagcaagac taggaaaaaa attttccatg aagcaaacgc    18240
tgatgaatgt gaaaaatcta aaaaccaagt gaaagaaaaa tactcatttg tatctgaagt    18300
ggaaccaaat gatactgatc cattagattc aaatgtagca aatcagaagc cctttgagag    18360
tggaagtgac aaaatctcca aggaagttgt accgtctttg gcctgtgaat ggtctcaact    18420
aacccctttca ggtctaaatg gagcccagat ggagaaaata cccctattgc atatttcttc    18480
atgtgaccaa aatatttcag aaaaagacct attagacaca gagaacaaaa gaaagaaaga   18540
ttttcttact tcagagaatt ctttgccacg tatttctagc ctaccaaaat cagagaagcc    18600
attaaatgag gaaacagtgg taaataagag agatgaagag cagcatcttg aatctctac    18660
agactgcatt cttgcagtaa agcaggcaat atctggaact tctccagtgg cttcttcatt    18720
tcagggtatc aaaaagtcta tattcagaat aagagaatca cctaaagaga ctttcaatgc    18780
aagttttttca ggtcatatga ctgatccaaa ctttaaaaaa gaaactgaag cctctgaaag   18840
tggactggaa atacatactg tttgctcaca gaaggaggac tccttatgtc caaatttaat    18900
tgataatgga agctggccag ccaccaccac acagaattct gtagctttga agaatgcagg    18960
tttaatatcc actttgaaaa agaaaacaaa taagtttatt tatgctatac atgatgaaac    19020
atcttataaa ggaaaaaaa taccgaaaga ccaaaaatca gaactaatta actgttcagc     19080
ccagtttgaa gcaaatgctt ttgaagcacc acttacattt gcaaatgctg attcaggtac    19140
ctctgtcttt tttttttgt aaatagtaca tatagtttta tagatgacga ttccttctgt     19200
gtttttttct gcttttttaaa atcttcatat cttatattta atcttaggca tcatctgtat   19260
acatgattgt ttaggtcttt aattaccagt gtttagaatc aggtcactca aacatggtag    19320
ataagtttgc atagtttgtg tatatccatc actcttgaga cagttttatt ttaagttccg    19380
```

```
gggtacatgt gcaggatgtg caggtttgtt acataagtaa acgtatgcca tgttggtttg    19440
ctgcacctgt caacccttca cctgagtatt aagcccagca tgcattagct attttttcctg   19500 gtgctctcct tcccccccaca caccccacc tcctgacaga ccctagtgtg tgttgttccc    19560
ctccctgtgt ccgtgtgttc tcattgttca gctcccactt atgagtgaga acatgtgatg    19620
tttagttttc tgttcctgca ttagtttgct taggataatg gcttccagct ccatctgtgt   19680
ccctgcaaag gacgtgatct tgttcctttt tatggctgca tggtattcca tggtgtatag   19740
ttccacattt tatttatcca gtctatcatt gatgggcatt tgggttgatt ccatgtctgt   19800
gctattgtga atagtgctgc agtgaatgta caggtggatg tatctttata atacaatgat   19860
ttatcttcct ttgggtatat accccgtaat gggattgctg agtcagatgg tattttttggt  19920 tctaggtctt tgaggaattg ccacactgtc ttccacaacg gttgaactaa tttacattcc   19980
agccaacaac ttgagacagt ttttgactca taaacattca gagcttggct agctaattcc   20040
tgctttaatt taaaaagtgt ttattatatg caaattggac aactcatata aatatgtggt   20100
gctacttact atgtatttc tctaaagcat gttaaaaaaa taggctagat atagtggctc    20160
atgcctgtaa tcttagcact ttgggaggct aaggcaggag gatcacttat ggtcaggagt   20220
ttaagaacac cctgggcaac atagcgagac cccatctcta caaaaaattt aaaataccca   20280
ggcatggtgg catgcttctg atgttgtagc tactcaggat gctcagacag gaggatcact   20340
tgagcccaag tgactgaggc tgcagtgaac caaaattgta ccagtgcact ccagcctggg   20400
ccacaaaatg agaccttgtc cctgaaaaaa aaaaagaaa aaaaaattt aatagagga     20460 aatactagct aagtttaatg taggccagtt ctaaataat gatttattgc tgctgttgtt    20520
acataatttt cttaaatatt ttaaagattg catactgtta ctgctctatt tctgcatctc   20580
cgtggtgtaa ctctgtcctc tttgttgttg caacagttca cttagcaact aaactgtatg   20640
tttacaaagt gattttatct ccctatgaga agactttagt gaatagctca gtgaatagta   20700
gagttggtga gaccacagta cagaactgtt tgaagtttgg gttaaatttt tagaggaaaa   20760
tgtttgatac tatgcatatc atagttaaag ccaatgaaaa agctaatata ggccaggcgc   20820
agtggctcac gcctataatc ccagcacttt gggaggccaa ggcaggcaga tcacttaagg   20880
tcaagagttc aagaccagcc tggccaacat ggtaaaaccc catctctatg aaaaaaaaca   20940
aaaattatcc agatgtggtg gcatgtgcct gtaatcccag ctactcggga cgctaaggca   21000
ggagaatcac ttgaacctgg gagatggagg ttgcaatgag ctgagatcac gccactgcac   21060
tccagcctgg gtgacagaac gagactccat ctcaaaaaaa aaaaaaaaaa aagctaatac   21120
atgtgatcac tgatgaaatg caattaagaa ctggttagta gaaaattcag agggtcaaga   21180
aatttaacag agcagttgaa ctcatttgcc tttatcgttg agattagatc atctttcagg   21240
ctgttagtat atggaccctg ttttttaaaa ttgtggtttt gttttttttca atgtgaaaga  21300 attaagaaaa ttgttacttt tctaattcct tttctgtgcc ttgcttttct gttcacacca   21360
gtattaacag caatgaaatt ttttcaattt tattttccaa taaaaattac tttgagttttt  21420 ttttatggta gctagctact tccttgacct agatactaat tttgattgag ttggtaacta   21480
ttattaaaaa aacaacttag gtctaattta tcttgagcta aaaaatgtaa taactgaaaa   21540
atagagcata tttaggattc tttctgcttt aaatttgaca ttcagttatt ttcatgtaat   21600
ttgtgttttg agcactacct tttaattaat ttatttattt ttatttttta gagactgtct   21660
cattctgtta cctagtctgg agtgcactag tgtgatctca gctcaccgta gcctcaccct   21720
cctgggctca agcagtcctt gcacctcacc ctcctgagta actggcacca caggcataca   21780
```

```
ccaccacacc cagctaattt ttattttca tagagtcatg gtctcactat gttgcccagg    21840
ctagtctcga actcctgggc tcaagcagtc ttcctgcctc agcctcccaa aagtgctgag    21900
attacaggca tgagccactg tgcccaaaca ctacctttt aacttagtga aaatatttta    21960
gtgaatgtga ttgatggtac tttaattttg tcactttgtg tttttatgtt taggtttatt    22020
gcattcttct gtgaaaagaa gctgttcaca gaatgattct gaagaaccaa ctttgtcctt    22080
aactagctct tttgggacaa ttctgaggaa atgttctaga aatgaaacat gttctaataa    22140
tacagtaatc tctcaggatc ttgattataa agaagcaaaa tgtaataagg aaaaactaca    22200
gttatttatt accccagaag ctgattctct gtcatgcctg caggaaggac agtgtgaaaa    22260
tgatccaaaa agcaaaaaag tttcagatat aaaagaagag gtcttggctg cagcatgtca    22320
cccagtacaa cattcaaaag tggaatacag tgatactgac tttcaatccc agaaaagtct    22380
tttatatgat catgaaaatg ccagcactct tattttaact cctacttcca aggatgttct    22440
gtcaaaccta gtcatgattt ctagaggcaa agaatcatac aaaatgtcag acaagctcaa    22500
aggtaacaat tatgaatctg atgttgaatt aaccaaaaat attcccatgg aaaagaatca    22560
agatgtatgt gctttaaatg aaaattataa aaacgttgag ctgttgccac ctgaaaaata    22620
catgagagta gcatcacctt caagaaaggt acaattcaac caaaacacaa atctaagagt    22680
aatccaaaaa aatcaagaag aaactacttc aatttcaaaa ataactgtca atccagactc    22740
tgaagaactt ttctcagaca atgagaataa ttttgtcttc caagtagcta atgaaaggaa    22800
taatcttgct ttaggaaata ctaaggaact tcatgaaaca gacttgactt gtgtaaacga    22860
acccattttc aagaactcta ccatggtttt atatggagac acaggtgata acaagcaac     22920
ccaagtgtca attaaaaaag atttggttta tgttcttgca gaggagaaca aaaatagtgt    22980
aaagcagcat ataaaaatga ctctaggtca agatttaaaa tcggacatct ccttgaatat    23040
agataaaata ccagaaaaaa ataatgatta catgaacaaa tgggcaggac tcttaggtcc    23100
aatttcaaat cacagttttg gaggtagctt cagaacagct tcaaataagg aaatcaagct    23160
ctctgaacat aacattaaga agagcaaaat gttcttcaaa gatattgaag aacaatatcc    23220
tactagttta gcttgtgttg aaattgtaaa taccttggca ttagataatc aaaagaaact    23280
gagcaagcct cagtcaatta atactgtatc tgcacattta cagagtagtg tagttgtttc    23340
tgattgtaaa aatagtcata tacccctca gatgttattt tccaagcagg atttaattc     23400
aaaccataat ttaacaccta gccaaaaggc agaaattaca gaactttcta ctatattaga    23460
agaatcagga agtcagtttg aatttactca gtttagaaaa ccaagctaca tattgcagaa    23520
gagtacattt gaagtgcctg aaaaccagat gactatctta aagaccactt ctgaggaatg    23580
cagagatgct gatcttcatg tcataatgaa tgccccatcg attggtcagg tagacagcag    23640
caagcaattt gaaggtacag ttgaaattaa acggaagttt gctggcctgt tgaaaaatga    23700
ctgtaacaaa agtgcttctg gttatttaac agatgaaaat gaagtggggt ttagggctt     23760
ttattctgct catggcacaa aactgaatgt ttctactgaa gctctgcaaa aagctgtgaa    23820
actgttagt gatattgaga atattagtga ggaaacttct gcagaggtac atccaataag    23880
tttatcttca agtaaatgtc atgattctgt tgtttcaatg tttaagatag aaaatcataa    23940
tgataaaact gtaagtgaaa aaaataataa atgccaactg atattacaaa ataatattga    24000
aatgactact ggcactttg ttgaagaaat tactgaaaat tacaagagaa atactgaaaa    24060
tgaagataac aaatatactg ctgccagtag aaattctcat aacttagaat tgatggcag     24120
```

```
tgattcaagt aaaaatgata ctgtttgtat tcataaagat gaaacggact tgctatttac   24180
tgatcagcac aacatatgtc ttaaattatc tggccagttt atgaaggagg gaaacactca   24240
gattaaagaa gatttgtcag atttaacttt tttggaagtt gcgaaagctc aagaagcatg   24300
tcatggtaat acttcaaata aagaacagtt aactgctact aaaacggagc aaaatataaa   24360
agattttgag acttctgata cattttttca gactgcaagt gggaaaaata ttagtgtcgc   24420
caaagagtca tttaataaaa ttgtaaattt ctttgatcag aaaccagaag aattgcataa   24480
cttttcctta aattctgaat tacattctga cataagaaag aacaaaatgg acattctaag   24540
ttatgaggaa acagacatag ttaaacacaa aatactgaaa gaaagtgtcc cagttggtac   24600
tggaaatcaa ctagtgacct tccagggaca acccgaacgt gatgaaaaga tcaaagaacc   24660
tactctgttg ggttttcata cagctagcgg gaaaaaagtt aaaattgcaa aggaatcttt   24720
ggacaaagtg aaaaaccttt ttgatgaaaa agagcaaggt actagtgaaa tcaccagttt   24780
tagccatcaa tgggcaaaga ccctaaagta cagagaggcc tgtaaagacc ttgaattagc   24840
atgtgagacc attgagatca cagctgcccc aaagtgtaaa gaaatgcaga attctctcaa   24900
taatgataaa aaccttgttt ctattgagac tgtggtgcca cctaagctct taagtgataa   24960
tttatgtaga caaactgaaa atctcaaaac atcaaaaagt atcttttga aagttaaagt   25020 acatgaaaat gtagaaaaag aaacagcaaa aagtcctgca acttgttaca caatcagtc   25080 cccttattca gtcattgaaa attcagcctt agctttttac acaagttgta gtagaaaaac   25140
ttctgtgagt cagacttcat tacttgaagc aaaaaaatgg cttagagaag gaatatttga   25200
tggtcaacca gaaagaataa atactgcaga ttatgtagga aattatttgt atgaaaataa   25260
ttcaaacagt actatagctg aaaatgacaa aaatcatctc tccgaaaaac aagatactta   25320
tttaagtaac agtagcatgt ctaacagcta ttcctaccat tctgatgagg tatataatga   25380
ttcaggatat ctctcaaaaa ataaacttga ttctggtatt gagccagtat tgaagaatgt   25440
tgaagatcaa aaaaacacta gttttttccaa agtaatatcc aatgtaaaag atgcaaatgc   25500
atacccacaa actgtaaatg aagatatttg cgttgaggaa cttgtgacta gctcttcacc   25560
ctgcaaaaat aaaaatgcag ccattaaatt gtccatatct aatagtaata atttgaggt   25620 agggccacct gcatttagga tagccagtgg taaaatcgtt tgtgtttcac atgaaacaat   25680 taaaaagtg aaagacatat ttacagacag tttcagtaaa gtaattaagg aaaacaacga   25740
gaataaatca aaaatttgcc aaacgaaaat tatggcaggt tgttacgagg cattggatga   25800
ttcagaggat attcttcata actctctaga taatgatgaa tgtagcacgc attcacataa   25860 ggttttgct gacattcaga gtgaagaaat tttacaacat aaccaaaata tgtctggatt   25920
ggagaaagtt tctaaaatat caccttgtga tgttagtttg gaaacttcag atatatgtaa   25980
atgtagtata gggaagcttc ataagtcagt ctcatctgca aatacttgtg ggatttttag   26040
cacagcaagt ggaaaatctg tccaggtatc agatgcttca ttacaaaacg caagacaagt   26100
gttttctgaa atagaagata gtaccaagca agtcttttcc aaagtattgt ttaaaagtaa   26160
cgaacattca gaccagctca aagagaaga aaatactgct atacgtactc cagaacattt   26220
aatatcccaa aaaggctttt catataatgt ggtaaattca tctgctttct ctggatttag   26280
tacagcaagt ggaaagcaag tttccatttt agaaagttcc ttacacaaag ttaagggagt   26340
gttagaggaa tttgatttaa tcagaactga gcatagtctt cactattcac ctacgtctag   26400
acaaaatgta tcaaaatac ttcctcgtgt tgataagaga aacccagagc actgtgtaaa   26460
ctcagaaatg gaaaaaacct gcagtaaaga atttaaatta tcaaataact taaatgttga   26520
```

```
aggtggttct tcagaaaata atcactctat taaagtttct ccatatctct ctcaatttca  26580
acaagacaaa caacagttgg tattaggaac caaagtctca cttgttgaga acattcatgt  26640
tttgggaaaa gaacaggctt cacctaaaaa cgtaaaaatg gaaattggta aaactgaaac  26700
tttttctgat gttcctgtga aaacaaatat agaagtttgt tctacttact ccaaagattc  26760
agaaaactac tttgaaacag aagcagtaga aattgctaaa gcttttatgg aagatgatga  26820
actgacagat tctaaactgc caagtcatgc cacacattct cttttacat gtcccgaaaa  26880 tgaggaaatg gttttgtcaa attcaagaat tggaaaaaga agaggagagc cccttatctt  26940
agtgggtaag tgttcatttt tacctttcgt gttgccaatc actattttta aagtgtttat  27000
tcagtagact tggtatgcta acaattaaga gtgttataaa ctatgtcttt tcagccattt  27060
ttgtgtagtc agtttggggg agtatggttt gatatacaga tacacagatt cagtattcgt  27120
atacagattt gatatcttgg tatacagatt cgatatctct gaatctgtat accaagaaat  27180
catgttttaa gggtctcaat atattttcaa aaagattatt agtataataa ttgagaaatt  27240
actgttaaaa agttttgagt ttctctagaa aatttgaaac tcttaacaaa acctgcataa  27300
tactaactta actgttttca tatacatagc aagttcagac tctgacttat atgaacttta  27360
aaagttggtt tccgggaggc cgaggcgggc ggatcacgag gtcaggagat cgagaccatc  27420
ccggctaaaa cggtgaaacc ccgtctctac taaaaaata caaaaaatta gccgggcgta  27480
gtggcgggcg cctgtagtcc cagctacttg ggaggctgag gcaggagaat ggcgtgaacc  27540
tgggaggcgg agcttgcagt gagccgagat cccgccactg cactccagcc tgggcgacag  27600
agcgagactc cgtctcaaaa aaaaaaaaaa agttggtttc cgattatacc atttactggg  27660
taatatatac tacttagtta cactacttac atagcttcag tttccttatc tataaaatgc  27720
aaataacacc tcccatgagg gctgggcgtg gcgctcatgc ctgtaatccc agcactttgg  27780
gaggccgagg tgggtggatc acctgaggtc aggagtttga ccagcctg accaacatgg  27840 tgaaacccca tctttactaa aaatacaaaa aattagccaa gcgtggtggc gcgcacctat  27900
aatcccaact actccagaag ctgaggcagg agaatcacct gaacctggga ggtggagggt  27960
gcagtgagct gacatcacac cactgctctc cagcctgggc aacagagcga gactgtctca  28020
aaaaaaaaaa aaaaaaagtg tatttaaagc acttagcagt gaacttgaca tatagtaggc  28080
agagagcatt cagtaagtgt tggcttgctc ccttttttc atttaggaag tgatctaaaa  28140
acagtattgt tagtaaatgg tatcttgatc ttaatgttat gtggactatt ttaacttccc  28200
ttttaaatgt atatatatct aacaacttag ttcaactaca gtcatgtgtc atttgacagg  28260
gatatatgtt ctgagaaata gattgttaga tttcatcatt gtgggaacat catagagtat  28320
acttacacaa acctaggtgg tatagcctac tatataccta ggctgtatgg tatagcttat  28380
tgctcctagg ctgcaaacct atacagcatg ttactgtcct gaatactcta ggcagtttta  28440
acacagtggc aagcatttgt gtatgtgaac atagaaaagg tacagtaaaa atacggtatt  28500
aaaatcttat ggggctgggc tcagtggctc atgcctgtaa tcccagcact tgggaggct  28560 gaggcaggcg gatcacctga ggtcaggagt ttgagaccag cctggccaac atggtaaaac  28620
cttgtctcta ctaaaaatat aaaaattagc tgggcatggt ggtggcacac gcctgtaatc  28680
ccagctacta gggaagttga agcaggagaa tcacttgaac cctggaggca gagatttcag  28740
tgagccaaga tcgcaccact gcactcctgc ctgggcgaca gagcaagact ccatctgaaa  28800 aaaaaaaaa atcttatggg accactatta aagtcttata ggatgaccat tgcatatgtg  28860
```

```
gtctattgtt gaccaaaatg tcattatgtg gcaaatgact gcattaggtt aaccttatac   28920
atacctatat taggtatgta tttggttttg ttttttttgtg tgtgtttttt tctattagtg   28980
tatctgactg gtaataatct taaataattg aatctgtttg ttagttgcaa ttaaagcaaa   29040
tgccaaaact ccaacatttc agtggataat cttaaataac tagttccttt ttaaaaaacc   29100
tataaactca taaaaatatt ttagttatta gaactcttcc tgtctagacc ccatgtatta   29160
cagagagaca ccgaagttag tctcctcatt caaaaagtgc cttttgcccc taagtcattc   29220
tggtggatac agatttactt aatcaagtgt tgtccaggtc acattcaata taggatttac   29280
tttatggaca aagtagtacg tttatagtac ttaaactatt tgctgtcctt tagtgtgaaa   29340
ttctgaggta tatatgctta aagatatttg taattctttt gtggaaaata atggctttat   29400
ttatagcaac ccattctgtt cttgtgcata ctgaagtata ttgactttcc acctagggaa   29460
aaaaaaaaca ataactcaga cttgtaaatg ctttcaacgg tgttactact taatttccct   29520
catttctgta acatataagt gtaaactta gtcagcttct ggttactgga acagtacagg   29580
tcactgttaa acaattaaac cacttttata ataatctaac acctcctaaa gccttgcatg   29640 gacatttta cttattaaat tatacaaatt tattccctgt aataaagcat caaaaagcaa   29700
agtacctgtt atatattatc tcagcatgac atggaaatgc ctaccttgaa ttatggttta   29760
atcttaccct cttagcctct gtagaatttt taaataagaa ttgtttctat tactagtact   29820
ttaatgtaat ttgataattg taaaaagcct cttaactcta attcaggac ctacataata   29880 aattactcct tcagttaatg gctgcccccg tgctgaaaaa aaaaaaaaaaa aagagagaaa   29940 aagtttattt gaagaaattt tgttaggcct tattgccagt aaacctagag ttatatttag   30000
tgtcagtttt tcaaaaagta gcttatctgt ggtatctggt agcatctgtt tatcctatt   30060 aggatttatc ctgtttagac cctgttaaat agtggtgttt taaagtggtc aaaacagaac   30120
aaaaatgtaa ttgacattga agactgactt tactctttca aacattaggt cactatttgt   30180
tgtaagtatt tttgttttaac atttaaagag tcaatacttt agctttaaaa aaatggtcta   30240
tagacttttg agaaataaaa ctgatattat ttgccttaaa aacatatatg aaatatttct   30300
ttttaggaga acccctcaatc aaaagaaact tattaaatga atttgacagg ataatagaaa   30360
atcaagaaaa atccttaaag gcttcaaaaa gcactccaga tggtaaaatt agcttttat   30420 ttatatctgt tctccctcta taggtatggt atataatatt ctgacctcag gtgatccacc   30480
tgcctctcaa agtgctggga ttacagacat gagccactgt gcctaatcaa ggacctcttt   30540
atactcttaa aaattactga ggacctaaaa gagcatttgt ttatgtggaa tatatctatt   30600
gatatttacc atattagaaa tgtaaattga ttaatgttaa aattagtaat attatgcgtt   30660
ggtcatttgg aagatatgag ttcactgagt tatgcggatc ttccgaaagt tgacagtttt   30720
attatgcagt attaaacaat cactttcatt gatgccatta ccgatcagaa aagtttaagt   30780
agtagaaagc tgtcaagctt acagagccag atacaagctt cccaaaaatt ctgattttca   30840
tctaaaagct tgaattttc cccggcaata agtattgtca cttattttc ttgtaggtga   30900 caagcttatt ttcattcatt tttgaaaaga tgtctgccga atacccaagt ctgaataact   30960
atagtttgtt ggttattctt tcaagtaaaa ggtatttcat gaaaaaatag ctagtatagc   31020
tcacaactca atcatttaag tgtgtttct tgagaaacgc actgaagtat gcaagcataa   31080
tataccaaca gtacaaatat caacagtgaa aaggacatac ataacatttt actaataaga   31140
cagttttgac agcttggatt ccctaaaatg gttgtagata cctaacagga ttccactgat   31200
catttcttga gaatcattgt cctataatat atacataata atctaaatttt acaatatcag   31260
```

```
tattaactac tgacaataaa actactaagg aaaatgtaag aattgtttgc agttttttgtc   31320 cttagagtat ataggttgag tatccctatc tgaaatgctt gggaccagga ctatttcaga   31380
tttcagattt tttcagattt tgaaatgctt gcatatacaa tacataatga gatatctggg   31440
gataggactc aagtctaaac acgaaattta tttaagtttc ataaacacct tatacatata   31500
acttaaatgt aattttatac aatattttaa ataattttg cataagacaa tttaaattgt   31560
gatccatcac atgaggtcag atgtggaatt ttctactggc ctcatgttgg cactcaaaaa   31620
gtttcagatt tgtgaccatt ttggatttttc agattaggga tactcaaccc atatattatt   31680
aagaatgttt agtcaaaata ctgtgttcaa atgtcactca aaataattct tccggatgtg   31740
gttaccaatt tgataattag gttacattcc tttttttcca tttgttttca atttaggat   31800 ttgtcttttc ttatttaatt ttacatttga ataaataaaa cattacatag ttcattcatc   31860
agaactacaa aaggtatac ttagagtttt tattcaccca cctcttgctt actataggta   31920
atctttttta gtgttttttt ttcaggattc tgtttaataa aaataagcaa atacatgtat   31980
atactcatta cccttcttta ctcaaaagat acagtatata caccattttg caccttgttt   32040
attggttgtt gtttacttaa gaattatttg gagatgactc cttaatgagt atatagagat   32100
cgtcctcatt cttttttgtg gttacatagt agttgatcat ctggctgtgt cagtgtttcc   32160
tagtttattt aaccaatttc caactagtgg acttattgaa gatttaatta ggttccagtt   32220
acatactgag aatgaacaat atctaaagct tagcttttaa accttcataa gactaaattt   32280
taaatttggt atttgcatca gaaattagct aacacccttg agttatgatg gttaacatca   32340
actgactaaa tttatgctga tttctgttgt atgcttgtac tgtgagttat ttggtgcata   32400
gtcattatca atttgtgaat caatttattt tcatagttaa catttattga gcatccgtta   32460
cattcactga aaattgtaaa gcctataatt gtctcaaatt ttttgtgtat ttacagtaac   32520
atggatattc tcttagattt taactaatat gtaatataaa ataattgttt cctaggcaca   32580
ataaaagatc gaagattgtt tatgcatcat gtttctttag agccgattac ctgtgtaccc   32640
tttcggtaag acatgtttaa attttttctaa attctaatac agtatgagaa aagtctcgtt   32700
tttataaatg aacatttcta aaaataatga cactaacgtt aagaagttaa cacttcccgt   32760
tttataaaat ttataaaatt tataaaatac tttggtagta ttttatagtg ctgttcatat   32820
cattatttta tttttttaatt ttatgacagc tttgtaaagt agacagattt tattctaatt   32880
ttatggatga agtactaagg ttgagaggaa ttaaggaaat tgctccgaat cagttaacaa   32940
aaagattgca gatattaaaa atatccttt atctctcctc tctaaacctt taaaaagta    33000 ctaagatagt ttttttaatg tataattccc aaggacaatg atgagaagaa acaacaaaag   33060
tttggaagcc aaaaacataa aggatttagt aagcatgaga aagctaaaac ctgacactag   33120
agcaaacaga gatgctttcc cctaaaaaac ctgaaaaaga ttcaaattgg cagcaacagg   33180
tacttctgaa ggtgaagtag aaaataggaa gattagttga aattcttttt aagaaacatc   33240
tatatttcct ccccccactgc aaataggcgg ttatccttct tctgccagga aatcagaagg   33300
ttgttcttga aaaagatgaa ttgagaggat tctgaattga aggtgggctg gagggagggg   33360
acaccaggca caattgaggg aaagatacta aaatgaaaga tcagatacaa atctgtatgt   33420
caagcagtga gacctagctc cttcccacac ttggttccca aatgcaggcc ctctaggcat   33480
gagactggaa gattttttttt tcctagggaa tatgcctgac ccaatagaaa agaccaaaaa   33540
atactgacag ttgaggatac tcagatgaaa cagtatagcc agtcaccaga ccaggaagtt   33600
```

```
aactgttgac atgcacagag cttccaggaa gctacttagt gcttcacttt taaataagaa    33660
aagatagtca aagataacta gtcattggaa gaaagctact atgaaacata gtcaccaaag    33720
tacaaaatcc atagcagaaa ggaacctaga ggaaatcgac tatgaaaact tcataaaaac    33780
ctactaatat tctcaggtaa gaaaagaaaa aatggccgta aaataagaac aagttgctat    33840
aaaaagctct tagaaattaa aaatatgata gcacaaataa attaactcag tagaaataat    33900
ggaagaatca tgaaagttcc cagaatacag aataaaatga aaaaaggtat gaaaagtcaa    33960
ttctgtggat ctatcatctg aaaatacaga gtttgagaag gaaggcacag aagagaaatg    34020
aagaaagaaa tttttaaaata aatacataat tttaaaagtt ctactagtac tgaaggacat    34080
gagtttcctt aattaaaagg gcccactgag tgagcacaca agtaaaaatg acccacagta    34140
aggcacatcc ttgtgaattt ttagaataat agaggcagac aggaacctta aattcattag    34200
aggaccaaga agttaggttt caaattgttt caagccataa tagtatgaat tctcttatta    34260
tcaacaatgg aatctagaag actgtagatc ttatataata cagagaagtg ccttcaaaat    34320
actgagagaa aatgatttcc aacctagaat ctgaattaag tgtgagggta gacattttc    34380 agatgtgaag tactaaaaga tctcttgtgc gcttttctca ggaaactaac caaaacaaat    34440
gcatacacca agaaggagga aggtatagga cttaagaaat aagaattcaa catagaagag    34500
aggcaaaggg agctttcagg atgatattga agggagatcc cagagtagct gtgttgctaa    34560
gtctagaaag gcagctagac tactttggaa ctgaagaaga taagagactt tggaagagtt    34620
tgccttcaag ataaaaataa agcagtacct gcatgtttta atgtattagg aaacttctta    34680
gtaaagatgg tgaattgagg ccaggcacag tggcttacac ctgtaatcca gcacattggg    34740
aggctgaggt gggtagatca cttgaggcca ggagttcgag actagcctgg ccaacatggt    34800
aaaatcccat ctctactgaa aatacaaaaa ttagccaggc gtggtggcac acgcctgtaa    34860
tcccagctac tccagaggct gaggcacaag aaccgcttga acctttgagg tggaggttgt    34920
ggtaaaattg caccactgca cttcagcctg ggtgacagag tgagactctg tctcaaaaaa    34980
aaaaaaaaaa aaaaaagat ggtgaattga acatactcat atcctttctt tgccttccaa    35040
acttttacca aaacatcatt gaagaaactt acacacacac aaaaaaaaaa caaggaaaat    35100
aggaaataac aaagtaacta aatttctcaa agcatgcaga aggaaactga atgaaagctg    35160
gtggtgggga cagcagagaa ccaacgattt tacactcagg tctcaaaaga ctaggaattg    35220
gtggcttcat ttcttatctt tagaattggg tggtgcagaa ggagggagcc aaaatggaat    35280
aagttgaaat tatgtttaag aagcaatact cgccgggtac ggtggctcac atggaggctg    35340
aggcgggtga atcacctgag gtcaggaatt cgagaccagc ctggctaaca tggtgaaacc    35400
ccatctctgt taaaaatgca aaaattagct cggcatggta gcatgcccct gtaatccagc    35460
tactcaggag gctgaggtgg gagaactgct tgaacccagg aggtggaggc tgcagtgagc    35520
caagattgcg ccactgcact ccagcctgga cgacagagca agaccccaca tcaaaaaaaa    35580
aaaaaaaaaa gcagcagcag caatactcat gaagctgggc aactgtctcc tgcccgctct    35640
atgaaaagaa ccagaggctt attctccaga gaggatacag tagaaggtga acacactagg    35700
cacagttgaa ggcagaagca actacttgaa agcaagaaga agttaatata tgcatattga    35760
atgttgggat ctcccctcac caagcccttt tccaccactc agcttccaga acatagacag    35820
ctaagttttc actagtggaa gtttccattt aatcaagcta ctgtgtagct tgcagtcaac    35880
aagttctatc tttgtaccaa gtgcttcaaa acagcctttt ggtccctcac tcttaactat    35940
aaacagacat ccaaagatta tgagacatca gaaaaagcaa aaataaaata accaaaaaac    36000
```

```
acattaatga aaacaactta agaagaaacat tattcaagga gaagaaaaaa tgttttttta   36060
aaaactataa tttgtgaaca gaatgaaaag aggtttatat atatagctaa gagtttagat   36120
gtgaataaac agtaagtaca tagaaaataa gcagatttta aaaattaact caagagaaag   36180
caaaagttgt aaaggaagta cactatttat atactaccca ttaatggccg ggtgtggtgg   36240
ttcacgcctg taatcccagc actttgggag gccgaggcgg gtggatcaca aggtcaggag   36300
atcgagacca tcctggctaa catggtgaaa ccccatctct actaaaaata acaaaacaaa   36360
attagccaga cgtagtggtg ggcgcctgta gtcccagcta cttgggaggc tgaggcagga   36420
gaatggcatc aacccaggag gcggagcttt cagtgagccg agattgcacc actgcactcc   36480
agcctgggcg agagagcgag actccgtctc aaaaaaaaaa caacaaaata aaaaaataaa   36540
ataaaatata ctgcctatta atactacata tactttatac tgacttagcc gtaatgtaaa   36600
tgttgaacat tgatagtgag aggtgaagct ggctgggctt ctgggtcgtg tggggacttg   36660
gagaactttt ctgtccggct aaaggattgt aaacacacca atcagcgctc tgtgtctagc   36720 taaggtttg taaacgcacc ggtcagcact ctgtgtctag ctaaaggttt gtaaatgcac   36780
caatcagcac tctgtaaaat agaccaatca gcaggacgtg ggcggggcca aataagggaa   36840
taaaagctgg ccacctgagc cagccccagc agccgctcgg ctccacttcc atgccatgga   36900
atctttgttt tttcactctt tgcaatgaat cttgctgctg ctcactcttt agtgagcact   36960
acctttatga gctgtaacac tcaccacgaa ggtctgcggc ttcactcctg aagtcagcaa   37020
gaccacgaac ccaccaggaa gaagaaacaa ccctgtacgt gccatctttg agagctgtaa   37080
cactcactgg gaaggtctgc ggcttcactc ctgaagtcag caagaccaca aacccaccag   37140
aaagaagaaa ctctggacac atctgaacat caggaagaac aaactcggga cacactatct   37200
ttaagaactg taacaccatg agggtccaca gcttcattct tgaagtcagc aagaccaaga   37260
acccaccaga aggaaccaat tccggacaca gtagaattaa atacgtaatt taggaagatg   37320
aaaggcaaga gtgtgtgtgt agtaaggtag aagctgtgtt gacagagctg aattttcatt   37380
ttctgtaggg gtacttcaag agaaaaagtc aagaagaaac atgtcactta gacatataaa   37440
tatgataaaa tcatctaaaa ctgtttaaag tagttgcaaa atcttttcta gctgataaat   37500
ttttaagcct aaaaatatca ttgaaattat tttaatgtta cattttatt tattttattt    37560 tatttattta tttattttga tacagagtct cactctgtcg cccaggctgg agtacagtgg   37620
cacgatcttg gctcactgca acctctgcct cctaggttca gcgactctc ctgcttcagc    37680 ctcccaagta gccgggatta caggcgcgtg ccaccatgcc cggctaattt tttgtatttt   37740
tactagagaa gggtttcac cgtgttagcc aggatggtct ggatctcctg acctcgtgat    37800
ccgcccacct tggcctccca agtgctggg attacagacg tgagccactg taccaggcct    37860
aatgttacct tttcaaaaac acctgattgt ggaattgttg aagtcactga gttgtatttc   37920
tggaatgtgt ttttagcag gctgcacata cacatatgta gaaagccagg tgatttttt    37980 ttcatttctt ttttttttat caaaaacagt tgtattaaat aagaaaggaa atacgtattt   38040
acccgtgtat taccttaatt tatgtgtaaa atgggagaat agtttaatgt atttaacaaa   38100
caaacatttg ttaaagtacc tgctcaaact acctaatata tactatagtg aaagatataa   38160
ggataaataa gtctaactca gattgctagc ctgggaacca gacatgaaaa caagaattat   38220
aatgtaatat aaaattctaga atagatgtaa aaagtgatct aagaacatag aaaaattatc   38280
agctaatcac atgactgctc aatgggaaaa gtacttcaga cagaatgtaa agaatgcttg   38340
```

```
gttaaagatg gcattccaaa tcttggaatt tggttggggg acagagggaa acaaaaagaa    38400
atggggaggt taggaccaaa taggaagctt cctgtatgtc atttctgata agttgaaacc    38460
taggtaggtg ataggctgtc tttggaagtt tctaacaaga ggaacaaaat aagattggtg    38520
ttttagaagt ataccaaagc aaaactgttg caaggagatt agtaaataca ggtcttaacc    38580
tagcagagga ggtagagggt agagaatgat tgagatagaa attcagtaga tttggccaga    38640
tagtgataag ttgagactgg caaattattt ccacttagat ttaaatatag atatcttgag    38700
cataacctac aaggcaaact ccttatacta aaaatattct gaatatttaa aaagaaagga    38760
ttaaaagatc aatcaataga agtttgggga cagaaggttt attcattctt gtgcattaga    38820
tctcatctag atcacctgtt tgaagaaatc attccagcaa ttatcttgtc tctctcctgc    38880 atggatttt ttcctaatag attgttctca tcaccctaag cagttgttgt acatctctca    38940
tcttaaaaag aacagccttt cttaagtaat ctcaacagtc cattttcttc tcttaaagcc    39000
caactcatta gaattgtccc tcctcttttc acttatctct ttgagtactc tcctgaaccc    39060
agtctagtca gtcctttcag tagaactggt cccctgctt acctccctac tcctcaatac    39120
acagtgaatt ctcaacaaag aagccggggg atccttttaa acataagaca gattatgtca    39180
tttctttact cagaactatt ccgtggtgtg ccatctcaga gtagagacta aaagccactt    39240
gtcatggtgt acagattctt catgatctgg ctgctttgct attttttccag tctgaccttc    39300 taatgttccc cttgctctcc ttgctccagg cacacttgtg tctaggccaa tcgacatatt    39360
tgtttgtctg tttccttcca ctgaaatata catgcaaaaa caaaattttg ttaccgtgtt    39420
ccccagcaaa acaatgtctg gcacctggta ggaattcatt aaatagttga tggatgggcg    39480
aacggataac taaaggaaca acttcaagtt ccaggtatcc agggtttggt aaaaggaaat    39540
ctggggtttt caacaagata tcaagtatta ggaagaccac gtatgctgag aaagatgatc    39600
acttttggac atgttgagtt tgaaatgagt gtgaaacatc aaggtacaga tgtctgatgc    39660
tatatgtagt gtaaaatgta ggaacaaccc taggagaaaa atcgggcatg aggataaagg    39720 atatttcat tgttaggtga taatttaagc aatggaaatg actcacatta gcaagggaaa    39780
gtgtctaagg aagacatcca gttttggaga cttttttga ggaatcagga agaggtaaaa    39840
ccagtaaaag atgaaagagg tacagtgatg gtgagaattt taaagaagg aaaatgtaaa    39900 ctgtcatagc tattaggaaa gttgagtaga atgagtttgc gcgcatccca catgcatctg    39960
ggaggtcatt aacaactta ttgagaacag tttctgtaga gtagtgggag aaatgagagt    40020
ttattgagta gaaattgagg aagtgaaaat agctacatta cctattgaag aaggttgact    40080
gtggagtgta acagtgagta ttagcttgag gcagagataa aggtgagtga gaaaataaga    40140
gtttcaaagg taggcaagat ttttgggcta aataaaaagg gcactttaaa aaaggtataa    40200
ataggtagaa gagagaaaag ggagcgaggt gggataattg aaagagggga tctcctgtgg    40260
agactgaggt attaggcgga gtagagagtt caggtgaaga tgtgaaggtg agagaagagg    40320
atgggtagac atttccctgg tgaaggaggt aaggagtact atgatggaat tagaggggac    40380
acactgagag ggtccacact tgacagactc tcttctatta tgtgttatgt gaggtagatt    40440
gtaaagtcaa aggctagcct tgaaaaatgt gatattgttt tggaatggca accatggtga    40500
atacaaaaca gttaccagaa tagtatcacc atgtagcaaa tgagggtctg caacaaaggc    40560
atattcctaa atatttatat gtgtactagt caataaactt atatatttc tccccattgc    40620 agcacaacta aggaacgtca agagatacag aatccaaatt ttaccgcacc tggtcaagaa    40680
tttctgtcta aatctcattt gtatgaacat ctgactttgg aaaaatcttc aagcaattta    40740
```

```
gcagtttcag gacatccatt ttatcaagtt tctgctacaa gaaatgaaaa aatgagacac   40800
ttgattacta caggcagacc aaccaaagtc tttgttccac cttttaaaac taaatcacat   40860
tttcacagag ttgaacagtg tgttaggaat attaacttgg aggaaaacag acaaaagcaa   40920
aacattgatg gacatggctc tgatgatagt aaaaataaga ttaatgacaa tgagattcat   40980
cagtttaaca aaaacaactc caatcaagca gcagctgtaa cttcacaaa gtgtgaagaa    41040 gaacctttag gtattgtatg acaatttgtg tgatgaattt ttgcctttca gttagatatt   41100
tccgttgtta aataatgtcc tgatggtttt ccccctttgg tggtggtaat tttaaagccc   41160
tttttaatgt tttagatttt ctaaatccaa agattaggtt taaattattc taatgtttct   41220
ttcaaagata acttcttgtg gacttgttaa aaaaaattag acacacaatc taggactgct   41280
gttactggaa tatattttct atcatgctac taattttctt tttaaaatgt gataaaaata   41340
gggccgggcg tggtggctca tgcctgtaat cccagaactt gggagacta aggcgggcgg   41400 atcacctgag gtcaggagtt caagaccagc ctggccaaca tagtgaaacc ctgtctctac   41460
taaaaataca aataaataa ataaataaat aaatagctga gcgtggtggc aggcacctgt    41520
aatcccagct gcttgggagg ctgaggcagg agaatcgttt gaacccggga ggcagaggtt   41580
gcagtgagcc gagatcgcgc cattgcactc cagcctgggc aacaagagtg aaaaactctg   41640
tctcaaaaag agataaaaat agtaaagata ttcatattta tacagcttta caagttgaaa   41700
catcctttca tttatgaaga attaaagggg gtacccttt tagagaaaag gagagcatgt    41760
aaacttcgag gaaattgata tgtataattt tataaaacag ggcttgcgct tttttttttt   41820
tgagacagag tttcgctctt gttgcccagg ctggagtgca atggtgcaac ctcggctcac   41880
cgcaacctcc tcctcccgag ttcaagtgat tctcctgcct cagcctgctg aatagctggg   41940
attacaggca tgtgccacca cacctggcta cttttgtgtt tttttttactt ttatatattt   42000 ttttttttgtt tagtagagac agggtttctc cattttggtc aggctggtct tgaactcccg   42060
acctcagatg atctgcccgc ctcagcctcc caaagtgctg ggattacagg cgtgagccac   42120
tgtgcctggc caggggttgt gcttttaaa ttttcaatttt atttttgcta agtatttatt    42180
ctttgataga tttaattaca agtcttcaga atgccagaga tatacaggat atgcgaatta   42240
agaagaaaca aaggcaacgc gtcttttccac agccaggcag tctgtatctt gcaaaaacat   42300
ccactctgcc tcgaatctct ctgaaagcag cagtaggagg ccaagttccc tctgcgtgtt   42360
ctcataaaca ggtatgtgtt tgtctacaat actgatggct tttatgacag agtgtaattt   42420
tatttcatta actagtatct acaaatggct ttgtttaaag aatgaacaca ttagtgcagg   42480
aatggatgaa tgaaatcatc atattttcta attagcctgc agtggcagcc tctggcccct   42540
tgctaggcct gcctcatcct actaaagtga tctgtgcttc caaattacta cttcttttcc   42600
cccttcaaat cttcttatt ttgtcattgt aaatgctctc agctaggtgt taaagtagtc    42660
ttactgatat tcaaatgtga ataactgata gccctgaacc ttctatgagc tatttatatt   42720
ttccaaagag gattctcctt aagccaatat tatctaggta gaattttagg caatggagag   42780
gtgaaaataa tattgatgac attaatagct aactttgagc attttctagg tgtaagatgc   42840
tcttctaagc acttcacatg cattaggtat atccttgctta atcctcacag tcaccttgaa   42900
agaaaggcac tgttactttg tttccatttt gcaaatgaga gaactgaagc atagagaggg   42960
ttaagtaact gccccaaagt cacttaacta gtaagtggaa gtgctatgat tccaaagcaa   43020
agagtctgac tccagagtca aactctgaac aaacaaaaag acactttggg ttagatatcc   43080
```

```
tgggtgaaa gcaagcactt tgaaagtaag ccaagcctgt gtacagatct gaccacctga      43140
ggtcacattc cctaaaatac ttaaacttct cccttttgtt tcccatctaa gtttttgaac      43200
ttaagagatt ttgtaaaaca tcacatttt ttatcctcac agtaccttcc tatggcagat       43260
ttagcaggag gcgtataaac ggggtggaaa aggtacagca gactgtggaa tgtatggatc      43320
atttatatta cattaaaatt tttagtttct agtaaataac ttaaatgttt ttgtagtgaa      43380
gattctagta gttaatgaaa attttttggta aattcagttt tggtttgtta taattgtttt    43440
tattgtgtga tacatgttta ctttaaattg tttttctttt ttgtgtgtgt ttattttgtg      43500
tagctgtata cgtatggcgt ttctaaacat tgcataaaaa ttaacagcaa aaatgcagag      43560
tcttttcagt ttcacactga agattatttt ggtaaggaaa gtttatggac tggaaaagga     43620
atacagttgg ctgatggtgg atggctcata ccctccaatg atggaaaggc tggaaaagaa     43680
gaattttata ggtactctat gcaaaaagat tgtgtgttaa cttttatgta ttccctcatc     43740
cctctttctt ctcttaactg tctctcgaac taaaaagttg gctagaaatc aaattttat     43800 gcatttaatt gttttaagtg cattatggtt aagcattctg tagaagtctt ttgaaaagtg    43860
ctgtttgtcc tggggtttaa tgaactggat tttcttgatt tgggacatt ttcttaggca     43920 tttataaata tagcccaatt tataaagtta aatttggccg ggtacagtgg ctcatgcctg   43980
taatcccagc actttgggag gccgaggcgg gtagatcacc tgaggtcagg agttcgagac     44040
cagcctggcc aacgtggcga acccccatct ctactaaaag tacaagaact atctgggcgt    44100
ggtggcaggc acctgtaatc ccggctactc tggaggctga ggcaggagaa tcgcttgaac     44160
ctgggaggca gaggttgcag tgagccaaga ttgagccact gcactccagg ctgggcgata    44220
agagtgagac tccatctcaa aaaaaaaaaa aagaaaaaag ttaaatttga gggccagaca    44280
tggtggctca tgcctgtaat cccagcactt tgggaggctg aggtgggcag atctcttgag    44340
cacaggagtt tgagaccagc ctgggcaaca tggtgaaaac ccatctctac aaacaaatta    44400
aaaaattagc ccagccaggc gcggtggctc acgcctgtag tcccaacact tcggaaggcc    44460
aagatgggcc aattacctga gggtcaggag ttcgagacca gcctggccaa catggtgaaa    44520
ccccagctct actaaaaata caaaaattag ccaggtatgg tgatgcatgc ccgtaatccc    44580
agctactcgg gaggctgagg caggagaatc atttgagccc agtaggtgga ggttgcagtg    44640
agccaagatc acgccactgc actccagcct gggcaacaga gcaagaccct atttcaaaaa    44700
aggccaggtg cggtggctca cacctataat cccagcactt tgggaggttg aggtgggcag    44760
atcacctgag gtcaggaatt tgaaccagc ctggccaaca tggcaaaacc ccatctctac     44820
taaaaataca aaaattagct ggacgtggtg gcacgcgcct gcaatcccac ttacttggga    44880
ggccgaggca ggaaaatcgt ttgaacccgg gaggcggagg ttgcagtgag ccaaaattgc    44940
accactgcac tgcagcctgg gcaacagtga gactccatct caagaaaaaa aaaaaaaaaa   45000 aaaagaaag ttaaatttga atggccttaa tggtagattc ctcccccgac acacacttac      45060
ttcatgtttt ctttcattat atattttaat ggatacaaaa tataaataaa cactaaaagt    45120
taaacagaaa tatttgaata tcaataatgc caaataacta gaaaatctca gagctctaaa    45180
acagcaacaa tttagaaact atataacctc tttttattgt agtttttaca gaaacataat    45240
ttaaagcttt ttgttatcag agatatatta cattatgcca gtggcaaaag atgggattta    45300
tttcctcagc atccttatct ttaaatttct gtacatcttt ccaaaattta tagctttgga    45360
aaagtgataa aactttttt cctgaatttt gttttaactt ttaaaaacag aaatattgtt     45420
tacatcttgc gtatcttata taacaaacat ctgcttatag attccagtaa gaaaagttgg    45480
```

```
ttaaacggtt gtattatttt ctcgtactaa atagactgca taaggtagaa gttaagaatg    45540
attgccctgt agtctaagtg ggaatgtgga ggctttcgtt agtttttct gataattcag     45600 caaatctcta ttgagcactt gctatgtgcc aggtactatt ctgggtacta gggataataa    45660
aggaaaacaa aaaagtccct gccctgatga gtcatacatt ctatgtggaa ggcatagaaa    45720
atattgaaat ataagtgaat tgtgtagtat gttagaagaa gatacatact ataaagatag    45780
ataaagttgg aaaggtggca gagaaagttg ggcaaggaga tgcgattttt aatctaataa    45840
gtagttagga aggcttcact gagtcagcta catttgataa atgacctaaa gtaaaaggag    45900
ggagcatagg actatcctag caaaagaccc ccagcctcta agaggggagc atgcttgaag    45960
tatttgagga acaggaagtt agtgcaactg gagtagagtg ggcaggagaa gagtagtagt    46020
agatgagata caaaaggaag acctcataga ccttcgtaag accccttacct tttactctgc   46080 acgatttta ctgaataaac cactggaagg cttaaagggt aacatgatct gacttttttt     46140
tgagacagtc tcactctatt gctcaggctg gagtgcagtg gtgcaatctc ggctcactgc    46200
agcctccacc tcccaggttc aagcgattct cctgcctcag cctcccgtgt agctgggact    46260
acaggcgcgc accaccgtgc ccggctgatt tttgtgtttt tagtagagac agggtttcac    46320
catgttggcc aggttggtct caaactcctg acctcaggat ccaccctcct cggcctccca    46380
aagtgctgga attacaggtg tgagccactg tgtccagcct gatctgactt attttgaaa    46440 aaataattct ggctgtttgt tgaggagagg ggcaaagatg gacacacaga gaccacttaa    46500
gctattgcag aaatacatgt gagaggtggt tggttggacc agggaagtgg cagtggaatt    46560
ggtggaaagc agttggactc tggggtattt tgaaagtggc actattagga gttgctcaag    46620
gattagatat aaaacgtgag agaggaggag aataagaatg gctgtgaaga ttttggcctt    46680
agcagctgga aggatagagt tgtatgtaac tactagaatt gagaagacca aagatggagg    46740
gaaatggaga gtttggtttt ggacatttga agcttgagat gtaatagtag acagccaagt    46800
ggagatgtta ggtaggcagt tggatatgga agtctataca caggtaaagt ataggccaaa    46860
taaatcaatt cacaagtcat cggcatatag atggacttga aggccatgaa aaagagactg    46920
agaaagagca gccagaaagt taggaataaa tgcagaatgg ggtgttgcat tccaaatgaa    46980
gatggaattt tagggaatag aaaatgacca gctgtggaag ctgcttctaa taggtaaagt    47040
aagatgagga ctgagattgg ccgctggatt tagcactgca gaagacatta ctaatgttat    47100
taaaaatagc tcaatagatt ggtggagtga tatcctgatt agaatgcaat taaagagcag    47160
ttgaagagga ggaattggag acacagaata cagtcgattc tttttgggagt tgccaaaaag   47220 aagcagagag agggacattg cttggagagg aagtaggatc aaagagtctt agttttggct    47280
tgttttaagg tagaaaaaaa ccgtttctta tgctgattca cattgttcag tagagaggga   47340
aaaaattgat gatgcaggag agagaggagg catttcctga tcgttggcct tgtaggcagc    47400 aagggggtagg agctagtgca caaatggtag aagagggcaa agtgtaagga tgcagatgct   47460
tggaagaggg caaagtgtag ggatacagat gctgtgagtg gatagatatg agggtgggag    47520
cttatggaag ttctcttttg attacttctg ttgtcttagt gctaagagta tgaatgagaa    47580
aggaggagtt agagatttga gaacagaggg gacaggatca aagagagcac caagactaag    47640
aaaggcagtt ctcaggcgtg atttctaaaa aaatctcttt cataagaaaa ataatctaaa    47700
atataattat ttaaaatcaa ggatctcatt tttcaggaac aaatatgagt tgaaatcatt    47760
ctgttgactg ttaagtggaa ttttttgtttt tgttttatata ttttgagata gggtctcact   47820
```

```
cttgtccagg ctggagtgca gtggcactat catggctcac tgcagcctca acctcctggg   47880
ctcaagcaat cctcccacca cagcctccta agtagctggg accacagatg tgagctacca   47940
ctcttggctg atttttttta ttatttttg tagagatgtg ggggtctcac tatgttgcct   48000
aggctggtct caaacttctg gcctcaagca atcctcctgc ctcagcttcc caaaatgctg   48060
ggagtatagg catgagccac catgctcagc aatgaagttt ttatcagtat gatactttga   48120
tacatgtcaa ataattttct gaaattatat tgtagatcat atgaactcat aaaaacttaa   48180
tgatcttgaa caatgtagtt tttgtacaga gaatagttgt agttgttgaa ttcagtatca   48240
tcctatgtgg tttttatgat aatattctac ctttatttgt tcagggctct gtgtgacact   48300
ccaggtgtgg atccaaagct tatttctaga atttgggttt ataatcacta tagatggatc   48360
atatggaaac tggcagctat ggaatgtgcc tttcctaagg aatttgctaa tagatgccta   48420
agcccagaaa gggtgcttct tcaactaaaa tacaggcaag tttaaagcat tacattacgt   48480
aatcatatac ggcagtatgg ttaaggtttc tgtgtagtct gtgacttcca tgtcaaaatg   48540
ttgcacaagc cagttgtcag tgacagttgc catcccacac tgctgttctc ctgtcatccc   48600
tagcccccat ttaagagaga tcacacattc atgcattgct tgcttccctc tttccccacc   48660
ccctccttaa cctcttgatg tatgagaaga atatgagtta ctaatttgat ccactatttg   48720
gggattgcta ataaagcatt tttgcatttt attttttgct ttttaaaaat aattgatatt   48780
ttaacaatat gaaacaatat attcctagct acaaaatttt taattctcag tatttcttag   48840
ataaattcag tttttattct cagttattca gtgacttgtt taaacagtgg aattctagag   48900
tcacacttcc taaaatatgc attttgtttt tcacttttag atatgatacg gaaattgata   48960
gaagcagaag atcggctata aaaaagataa tggaaaggga tgacacagct gcaaaaacac   49020
ttgttctctg tgtttctgac ataatttcat tgagcgcaaa tatatctgaa acttctagca   49080
ataaaactag tagtgcagat acccaaaaag tggccattat tgaacttaca gatgggtggt   49140
atgctgttaa ggcccagtta gatcctcccc tcttagctgt cttaaagaat ggcagactga   49200
cagttggtca gaagattatt cttcatggag cagaactggt gggctctcct gatgcctgta   49260
cacctcttga agccccagaa tctcttatgt taaaggtaaa ttaatttgca ctcttggtaa   49320
aaatcagtca ttgattcagt taaattctag aagttttaca tttaaatttt aaatgcttac   49380
taaggatgct caatttctta gatgtactga taatttagt ataaaagca tattcttcag   49440
acagttaaag ttttttgtgca gttttgggga ggtccagaga tctttcttga gcttaaataa   49500
tgcatttcca attaaaaagc aaaataaatt tgcaccattt gattttggta tctgtagctt   49560
gctgccctct tgttctcata gctttgcttt gatcagatcc ctattccact ctggattaga   49620
gaattacatt ttagtacttt tcaaatatgt aatagataca cttttttatct ctatgtagat   49680
tttaaactac ataacaggac tctttgtcat attgaatggt ctgcagtatt gctatctgaa   49740
attaccgata atattgtaca ttcagattca cttaagaggt aaccttgcag agaatttact   49800
tctgtggtat tctggatcac tctaaagaga atgttttata aattaaacat ttttaaggta   49860
aagatatatt ttgtttggca ttagttccat gttggattga ttgcttttta ctgaaagcat   49920
tccatcaagc tgaaacagtc ttttgtttta tgttgcttag aacatcaagc ttgcagtggc   49980
tttcattttc ttgttttgt tttttttaa atcaaatcaa tgcatgtgca taatttggaa   50040
actcaagtaa tataagacat ataaccaaaa aaaagcagtt gctagcacaa ccctccccat   50100
cctcattcat ggtcccaaga ggcaatcgtt tccagtctgt ttgactattt tttagcttgt   50160
actgctgtct tctttctctc ttcagtttag acagcaaccg ttaacttcct gctatggaaa   50220
```

```
atgaggattt cattgtctta ctccaacact gctacatatt tctctaccct cttccccatc    50280
ttccctctac taatacagca tgatttttag tgaaatctgt attcagtgta tacattataa    50340
tgactgaaaa atattttttg caatttaata cctaatcgac ttgtgatcac atttcctttc    50400
tttacagctt actgctttcc atgaagttat taactgtcct tttcatttct cttaattttc    50460
tgtgtcctta cacaggagct ataaaaatcc tgcccaatat gttaaaattt ctccattggt    50520
tccatttctg tttcttggag aacccctgga cctcttcata tgcttactcc attctgaagt    50580
gctcattttc tatgtgtgcc atacagctct cattctgtaa attattctta cctcttttct    50640
gtgttagaaa ccccatttcc tggtttccat gtcatctttc tagagttttt ccccaatttt    50700
taagggccca caactctcag aggcttgttg ggaaaaggag catgcaagct ttttgatatc    50760
ttagggtaag gttggctgga tatagaattc taggttgaaa taatttcttc agaatttta    50820 agacatttca tttatcttct ttagcatagc tcctgctaat tgcagtgcat tctttttttt    50880
tttttttttt tttttttttt gagacaacgt ctcactgtgt tacataggct ggagtgtttc    50940
attttgtaca gatgaggtct ccctgtgttg cctaggctgg tcttgaactt ctgggctcaa    51000
acggtcctca cgctttagcc tccgagagtg ctgggattac agacatgaac cactgtacct    51060
ggcctgcggt gctgttttta tcttcagtca ttcattatgt gctctggttt taagaagtta    51120
agattgtttt gtctttattt ttatttattt atttattttt gagacaaagt ctcgctcttg    51180
ttgcccaggc tggagtgcaa tggcgtgacc tctgctcact gcaacctccg cctctcgggt    51240
tcaagtgatt ctcctgtctc agcctcccga gtagctggga ttacaggtac ctgccaccac    51300
acccagccaa attttgtatt tttagtagag acagggtttc accatattgg ccaggctggt    51360
ctcatcctga cctcaggtga tccacctgcc tcagcctccc aaagtgttgg gattacgggc    51420
atgagccacc acgcccagcc tgttttgttg ttatttaaat ttcacagtaa tgtactttgg    51480 tgtcttttt tttttttttt tttttaactt tttttttttcc tttaattctt ggcccagatg    51540
cttactggca cttactctag aaacacatag tccttcattg agttctggaa aatttctttt    51600
aagtggttct tttataattt ccctccattt ttttctctag ttttttttctg gaactcctga    51660 tgtttggaca ctaggcctcc tatattgttc ctataatttt cttgtctttt ctcctacttt    51720
ctatttgatt gtctttttt attctaactt ctgggatggt tttaatttt tttcttctaa    51780 ttctttatta atatgccatg ttttatagat ttgtctttaa atattttac ataatttgt    51840 aacaaaatac aaaaaaagca attcctaaaa atttagaaag tcaaatgaaa gcaaagaact    51900
taagtgtgtt ttcaattaga gcataatcat accaagaaag tatttcaagt aacttaaaaa    51960
atgttttatg tccctagtgg tatataccc aagaacaaca atagcaacaa caactataaa    52020
atgaaacaaa atcttaagct attgttagta atcatattgc tggtggtagt gttggtattc    52080
ctattctgaa gttatagtgg atgtgaagta tgttgtatgt gtatactctt ttacgtatat    52140
ttgttgtatg tgagtaatta tatgattata gagaacaggg atctttttat cagagaaagg    52200
tgcagatgtg agattgaagt aaaagaaaac ttgtggttct gcatttgtat tggaaatatc    52260
attatgaact cgagatctat attatctttta aaaatacat gctggctggg cacagtggct    52320
cacacctata atcccagcac tttgagaggc caaggtgaat ggatcacttg aggtcaggag    52380
ttcaagacca gcctggccaa catggtgaaa ccccgtctct actaaaaata taaaacttag    52440
ccaggcatga tggcatgctc ctgtagtccc agctactgtg gaggctgagg tgggagaatc    52500
acttgaacct gggacgtaga ggtaggttgc agtgagccaa ggtcgcacca ctgcactcca    52560
```

```
gcctgggcga caaagtgaga ccctgtctca agaaaaaaaa aaaatatgct tattggtttc    52620
atctatcaaa aagaacaaaa aaaaaaaaaa aaggaataat ccagtagtag tgagtaaccc    52680
tagctctcag actgttttct aagtactgtt ttctcttaaa aggatgcaag gtgtcttgaa    52740
gaaatggctg attccagatt cagaggagga aatatatgaa tctggaaagt cttgacatac    52800
cagaaaaaaa ctaagcatca aacactacta gtgtcatgtc aaaaggactt aggagtgtaa    52860
tagaatagat tcttactgat cacagataaa ataatttgag catcagaaag gataataaca    52920
ggctgggcac actggcccac acctgtaatc ccaagatttt gggaggccga ggcaggcaga    52980
tcacttgggg tcaggagttt gagaccagcc tggccaacat ggtgaaaccc cttctctact    53040
aaaaatacaa aaattaggt aggcctgggg gcgggtgtct gtaatcccag ctatttggga    53100
ggctgaggca gggagaattg cttgaaccca ggaagcggag gttgcagtga gccgagattg    53160
tgccactgca ttctagcctg ggtgacagag cgagactcca tctcaaagaa aaaaaaaagg    53220
ataataacag caaaaaattg aaattcataa caaatgataa cttctattct cattgtttta    53280
aaaactaaag cccaggcaca gtgtctcacg cgtgtaattg cagtactttg ggaggctgag    53340
gtgggcatac tcaggagtat gagaccagcc tgggcaacat gacaaaaccc catctctaca    53400
aaaaatacaa aaattaacca ggtgtggtgg catgtgccta tagtcccagc tacttgagag    53460
gccgtggtgg gaggatgacc tgagcccagg aggcagaggt tgcagcgagt tgagatcgtg    53520
ctactgcact tcagcctggg tgacagagcc agagccagac ccagcctcag aaaaacaaca    53580
aaaactaggt aaaaggagaa aaaatcaag catttatctt tcttctctta tatgatctat    53640
attttgggac cctcaagtag atgaggggaa gtttctgttt ataaaaatgt ttcaacaaat    53700
aaggaataat agaattaaaa tataaccatt tcgcaaccct caaattaggg ttgtcttttc    53760
ttctaattct tttttttttt tttttttttt tttttttttt ttttgagat ggagtctcgc    53820
actgtcgccc aggctggagt gcagtggcac gatcttggct cactgcaacc tctgcctcct    53880
ggattcaagc gattctcctg cctcagcctc taagtagct gggattatag gcacccacca    53940
ccacacctgg ctaattttttt tgtatttta gtagagacag gcttcacta tgttggctac    54000
gctggtgttg aactcctgac ctcgtgatct gcccgcttg cctcccaaa gtgctgggat    54060
tacaggcttg agcctgtaaa tccagaaaag gattacagcc ctttttcttct agttcttaaa    54120
gtgaatttgt gtctaccaac ataatttttca agagacctttt attattccct aaatgttttt    54180
cttttttttg tgacattcag ttcttgtttc atagatacag tatcttctca tctttctaaa    54240
gctaatgatt aatgttttat tttcattttc gttttttctg ctccctgcat tttttttttt    54300
taatgaaaac ctttgtctat ttgagtctct ctggttagag actttcctca atggtgatca    54360
ttcactgatc cagaagttgt atgtgaggtg aggcttgtca gctcatgggg tagtaatgta    54420
gtgatttagt ttttaactag gagaccctca aatatcagtg actgttctga gagctgagca    54480
gagtaaggaa attaataggg agactcattg tcagtgtaag aatttttattt cagtttgttg    54540
tttgttgttt gttttttgtt ttttttgttt ttttttggtt ttttttgttt ttttttaga    54600
tggagtcttg ctctgttgcc caggctagag tgcagtggtg cgatctcggc tcactgcaac    54660
ctccacctcc caggttcgag gaattctcct gcctcagcct cccgagtagc tgggactaca    54720
ggcgcctgcc accaccctg ctaatttttt tattttttagt agagacgggg tttcaccatc    54780
ttggccaggc tggtctccaa ctcctgacct tgtgatccac ccgccttggc ctcccaaagt    54840
gttgggatta caggcgtgag ccacagcgcc cggcccagtt ttgttttcaa taatagcatc    54900
tcaccccac cctggctgcg tctgctcagt attccagagt ccacgatatg tatggttcag    54960
```

```
ccctccagaa aataaagtct cctgcatttt ttttttaat  gctgcagcaa gaatagggtc   55020
ctgggttctt tttagtatg  agggagagac agccacctgg ctactggga  taggaaagaa   55080 aatctggtgt ttcaactacg tttgtacaaa atgtcaacca tttcttccta ttttcagccc   55140
caccatatgc tcctgccttc acaggtacct gttgcctcca atttctgagt gttttccttt   55200
aattattttg tttcatgtta actccttaca acaagtttgg tggctgaata accttgggca   55260
agttgtgtag tttctcatat actttagttt tatcgttgtc tgtaaaatgg agatgagtct   55320
tcagattatt gtgaagataa tttgtttgtt tgttttttgg agacggaggc acgctctgtc   55380
ccccaggctg gagtgcagtg gcacaatctc ggctcactgc accctctgcc tcccaggttc   55440
aagcagttct cctgcctcag cctcccgagt agctgggatt acaggcgccc accacctcac   55500
ctggctactt ttttggtttt tagtagagac ggggtttcac catgttggcc cgggtggtct   55560
cgaactcctg acctcaggtg atacgcctgc ctcggcctcc caaagtgttg ggattacagg   55620
catgagccac cttgcctggc caaagattaa ttgttaatat acataaagcg cttaacacca   55680
tgccaggtac cttagtaagt gttcgatgaa atttgctttt tgtattagc  cataatcatt   55740 ctcaggctgc tttgtcattt acttgttcca caaattctta gcttccaaaa ttttggtgat   55800
acctcatttc ctattctctc tagttgcctt tgtccatgta gattttttga ggaagcttgg   55860
gtaaataagt gtattttaaa ctattatgtt taaatcgaag ttccttttat ctgttttcta   55920
atagaaacat ttaaatagca ttaagaactt gtagcagtat aaacaatatg tttgagaagt   55980
actatattgt gaaaatattt tcacttttat acagttttttt acttatttac tgtcttacta   56040
atcttcctaa gactttttaa agtgaatatt tttaaggcag ttctagaaga atgaaaactc   56100
ttatgatatc tgtaatagaa ttgaatacat atttaactac taaatcaata tatttattaa   56160
tttgtccaga tttctgctaa cagtactcgg cctgctcgct ggtataccaa acttggattc   56220
tttcctgacc ctagaccttt tcctctgccc ttatcatcgc ttttcagtga tggaggaaat   56280
gttggttgtg ttgatgtaat tattcaaaga gcatacccta tacaggtatg atgtattctt   56340
gaaacttacc atatatttct ttcttttgat acaattaatt tgtttgtttg tttgagatgg   56400
agtttcggtc tcttgcccag gctggagtgc aatggcgtga tcttggttca ctgcagcctc   56460
cacctcccgg gttcaagtga ttctcctgcc tcagcctctc aagtagctga gccaccacac   56520
ctggctaatt ttgtattttt ggtagagaag gggtttcatc atgttggtca ggctgatctc   56580
gaactcctga cctcaggtga tccactaatc tcagcctccc aaagttctgg gattacagat   56640
gtgagccact gtgcctggcc tgatacaatt aacttgaatg ttatatatgt gacttttttg   56700
gtgtgtgtaa cacattatta cagtggatgg agaagacatc atctggatta tacatatttc   56760
gcaatgaaag agaggaagaa aaggaagcag caaaatatgt ggaggcccaa caaaagagac   56820
tagaagcctt attcactaaa attcaggagg aatttgaaga acatgaaggt aaaattagtt   56880
atatggtaca cattgttatt tctaatatga gaacaaagtc ttagagactt tgaatttaac   56940 attttaatg  agtaaattgt ttttatttg  agtagtaaat tgactttatt ttttagtatc   57000
tagggtattc tttttttggtg ttagacaaag aatagcaaca agggacagaa atatcaggtc   57060
taagccattt gtaatatttt tcctgaattc ttacctatat gatgtggctt ttgcattttt   57120
gtcatggtag ttattagctt tcatgtgtta ttatgcctgg aactaggacc tattgtggtg   57180
tcaattttaa tattaaaaat catggtgttt tgatgtttat atgacataaa ttttattttt   57240
tcgtatctcc cttttgttgt tgctgaagat tttatgtttt tctgcatttc ctcatgattt   57300
```

```
atatagatgt aacatgttct ataggacatg taatttacat gtcctataga actataagtt    57360
acatgtccta tagaacttac agttctatag ttatctgcag aaatattgct ccttatgctt    57420
tatttgctta aaattatcac tagatcatac tattttcata aataaatgaa tatgaaatca    57480
ttcacaggca tacctcagag atactgtgga tttgattcta gaccaccgca ataaagcaaa    57540
tattacagta gagcaaatca cacgaatatt ttggtttccc agagcataca aaagtaatgt    57600
ttacactata gcataatctc ttaaatgtgt agtagcattg tgtctaaaaa aaacaatgca    57660
cataccttaa tacactttat tgctaaaaaa tgccaatgat catctgagcc ttcagtgagt    57720
tgtaatattt ttgctggtgg aggatctttc ctcaatgttg atgcctgctg agtgatcaga    57780
gtggtagttg gtgaaggttg gggcagttgt ggcaatttct taaaataaga caatggcatt    57840
tgcaacattg attggctttt cctttcatga aagatttctc tgtagcatgc aatgctgttt    57900
gatagcattt tatccatggt agaactgctt tcataattgg agtcaattct atcaaactct    57960
gctttatcag aatattatgt aatattctaa atcctttgtt gtcatttcaa caatattcac    58020
agcaccttcg ccaggactag attccctctc aagaaactac tttctttgct tatccataag    58080
aagcagctct gtattaatct gttcccacac tgctataaag aatacctgag actgggtaat    58140
ttctaaagga aagaagctta attgacttac agttccacat ggctgaggag gcctcaggaa    58200
acttacaatc atggcggaag gcaaaggcaa agcaagtacc cttttcataa ggtggcagaa    58260
gagagagtgc aggggaaact gccacttgta agccatcaga tctcataaga actccctcac    58320
tagcacaaga atagcatggg ggaaaccacc cccatgatcc aatcacctcc caccaggtct    58380
ctccctcaac acatggggat tacaatttga gatgagattt gggtagggac acagagccaa    58440
accatatcat tctgccctgg accctcccaa atctcgtgtc cttttcacat ttcaaaacca    58500
atcatgcctt cctaacagtc tccgaaagtc ttaactaatt ccagcattaa ctcaaaagtt    58560
caagtccaaa gtcttcatct gagacaagac aaatctcttc cacctatgag cctgtaaaat    58620
caaaagcaaa ttctttactt ccaagataca atggggtac aggcatttggg taaatgttcc    58680 catctcaagt gggagaaatt ggccaaaaca aaggggccac agtccccatg caagtccgaa    58740
acctagccag gcaatcaatg aatcttttt ttttttttga gacagggtct tgctctgttg    58800
tccaggctag agtgcagtgg agagatactg gctcactgca acctccgcct cctgtttcaa    58860
gcaattctca tgcctcagcc tcccaagtag ctgggattac aggtgtgcac caccatgccc    58920
agctaatttt tgtatttta gtagagatgg ggtttcacca tgttggccag gctagtctta    58980
aaactcctag cctcgctggg tggggtgtct cattcctgta atcccagcac tttgggaggc    59040
tgaagtgggc agatcacaag gtcaggagtt gaagaccagc ctggccaaca tggtgaaacc    59100
ctgtttctat gaaaaattca aaaattagct gggcgtggtg gcacgcgtct gtaatcccag    59160
ctattccaga ggctgaggca ggagaattgc ttgaatccag gaggcagaga ttgcagtaag    59220
ccaaaatcac accactgcac tctagcctgg gcaacaaagc aagactctgt ctcaaaaaaa    59280
taaataaaaa aaataataa aaataactcc tagcctcaag tgagccactg cacccaggcc    59340
agtcattaaa gctctaaaat ctcctttgac tccatgtctc acatccaggg catgctgata    59400
taaggggtgg gctcccacgg ccttgggcag ctctgccctt tggctcttca gtctacagcc    59460
cctgcagctg ctttcatggg ctgccattga gtgacagctg cacagtgcag gctgtcagtg    59520
ggggatgatg gccctcttct cacagctcca ctaggcagtt ccccactgag gactgtggga    59580
ggtggctcca acccgtgtatt tccctcacag tttcctcccc ggtttccctc ctgtactgca    59640
ctaacagagg ttctctatga gggctctgcc cccacagcag acttgtgtgt ggacatcctg    59700
```

```
gcacttccat acatcctctg aaatctaggc agaggctccc acagctgaac tcttgtcttc    59760
tacataccca caggcccagc atcacatgga ggccaccaag gcttagggct tgcaccctct    59820
caagcaatgg cctgatctgt accttggccc tttttatcaa tggctggagc tggagcaagt    59880
gggacacagg ttgccatgtc ccatggctgc acagagcagt ggggccttgg gcccagccca    59940
caaaaccatt tttccctcct aggcctcaag gcctgtgata aagggtcta ctgtggagat     60000 ctctgacatg ccttggagac actgtctcca ttgccttggc tattaacgtt tgtttccttg    60060
ttacttatgc aaacttctgc agctggcttg aattctttcc cgggaaatgg attttctttt    60120
tctacttcat ggttaggctg cagattttcc aaacttgcat gctctgcttc ccttttaaat    60180
ataggttcca atttcaaacc atctctttgt gaacatgtat gactgtgttt ctagaaaaag    60240
ccacatcaca ccttgaacac tctgctgctt agaaatttct tccacaggat accctaaatc    60300
atctctctga agttcaacat tccacggatc tctagcgcag gggcaaaatg ccactagtct    60360
ctttgctcta aagcatagca agagtgacct ttgctccagt tcccaataag atcctcatct    60420
ccatctgaga ccacctcagg ctggacttca ctggccacat cactgtcaga attttggtca    60480
aaaccattca acaagtctct agggagttcc agactttccc acatcttcct gtcttcttct    60540
gagccctcca aactcttcca atctctgcct gttgtctagt tccaaagtca cttccacatt    60600
ttcaggttat cggtatagca gtcccccact cctggtaaca attatctgta ttagttcatc    60660
ctcatactgc tataaaaaat acctgagact gggtaatttg taaggaaaa aggtttaatt     60720 gattcacagt tccacatggc tggggaggcc tcaggaaact acaatcata gtggaagatg     60780 aaggagaagc aagtaccttc ttcacaaggt ggcaggaaag agagtacagg gagaactctc    60840
acttttaagc catcagatct tgtgagaact ccctcactat catggaacag catgggagaa    60900
actgcccccg tgatccagtt acctcccacc aggtccgtcc ctcgacacgt gaggattacc    60960
gttcaagatg agatttgggt gaggacacag agccaaatcg tatgaagctc cttatcattt    61020 aagtttatt gtgacattgc agtaattcag tcacatcttc aggctttact tctaattcta    61080
gttctcttgc tattttcacc atatatgcag ttacttcctc cactgaagtc ttgaaccccc    61140
caaagtcatc catgagggtt ggaatcaact tctggtaaac ttgttaatgt tgatattttg    61200
acttcccatg aaacactagt gttcttaatg gtatttagaa tggtgaatcc tttctggaag    61260
gttttcaatt cactttaccc atatctatca gagaaatcac tatggcagct attctttata    61320
agacatgttt ctttttttt tttttgagat ggagtttcgc acttgttgcc caggctggag    61380
tgcaatggcg tgatcttggc tcacagcaac ctctgcctcc caggttcaag caattctcct    61440
gcctcagcct ccggagtagc taggattaca ggcatgtgcc accacgcccg gctaattttg    61500
tatttttagt agagacgggg tttcaccatg ttggtcaggc tggtcacgaa ctccggacct    61560
caggtgatcc acccgcctcg gcctcccaaa gtgctgggat tacaggtgta agccaccgta    61620
cccggcaaga catgtttctt aaataataag acttgaaagt tgaaatgact ccatgatcca    61680
tgggccacaa aatggatatt gtgttaggag tcatgaaaat aacattaatc actctataca    61740
tctctgtcag agctctgtga cagagacatg aagtgagcac atactgttgc gaaaatggcg    61800
ccagtaggct tgctcaacat agtttccaca aaccttcaat ttgtgttttt aaaaaaatgc    61860
agtatctatg aaactcagtg aagtgaaata cattaaaaca aatatacta tgttaactca     61920 catattactg taattaaact ctgtatgact tttttttttt ttaaacatga gtacactggt    61980
ttcaaaattt cctggaaaac ttatagcagg ccaggtgtca tgggtcacat ctgtaatccc    62040
```

```
aacagtttgg gagtccaagg tggtggatca cttgaggtca ggagtttgag accagcctgg    62100
ccaatatggt gaaactccgt ctctaccaaa aatgcaaaaa ttaaccgggc atgttggatg    62160
tgcctctaat cccagctact cgggaggctg aggcaggaga accacttgaa cccaggagac    62220
agaggttgca atgagccgag atcacaccac tgcactccca gattgggtga cagagtgaga    62280
ccctgtctca aaaaaaaaa aagaaaaaa cttttagcag ttatatagtt tcttatcttt    62340
aaatctccct tctttgggtg ttttatgctt ggttctttag ttttagttgc ttttgaattt    62400
acagtttagt gaattaataa tccttttgtt ttcttagaaa acacaacaaa accatattta    62460
ccatcacgtg cactaacaag acagcaagtt cgtgctttgc aagatggtgc agagctttat    62520
gaagcagtga agaatgcagc agacccagct taccttgagg tgagagagta agaggacata    62580
taatgaggct tgatgattat tcaaggtgag aagctgtttt agactctctg gccatcacag    62640
gaaggagtat gttgaaatgc tgcatttctc aaaagggatg tgtacatttc tgggattttc    62700
agtgatgtgc cagacgagtg tggtggtatg ttttcaacta tataccgagt agaggatggg    62760
agggttctag aattttatat attaattaaa tttggtttaa aatgcaggca aaacttgttt    62820 tattttttgtc cctcctgtac tctgaagcaa aaaaacttt ttattttta gataaaacaa    62880 atatcttcaa agtaatggct tagttttccat gttcttagct gtttctcaag tccttcctgg    62940
agtgtacttg ataatcctct accctaaggg tacttgggta gaaatgtttc cgaagcacta    63000
aactgttaga agtagcatag gctttagaat cgtggcactc tcattttatt agcaaagtaa    63060
atgacaataa aatagctggc caggcgcggt ggctcacgcc tataatccca gcactttggg    63120
agaccgaggc agaaggatca cctgaggtcg ggagttcgtg accagcctgg ccaacgtggt    63180
gaaaccccgt ccctattaaa aatacaaaat tagccaggcg tggtgcacat gcctgtaatc    63240
ccagctgttc gggaggctca ggcaggagaa tcgcttgaat ccaggaggca gaggttgcag    63300
tgagccaagg tcatgccatt gcactccagc ctaggcaaca agagcaaaac tccgtctcaa    63360
aaaaaaaaaa aaaagctat taaatgggcg taaaatgttg ttttaggatc aaataaataa    63420
tctatataaa agttccatat aaatgttagt tactattatt agaacataat tttatatatt    63480
aaactacctc ctaaatttt agacaggtag atagctaaaa aaaaattcaa attctaagat    63540
tagtttgtta gggaggaagg agcaaatatt ttaccaaaac tacttgtttt taattgatta    63600
atttcattca cttgatgact tagtaaatct tgtgaatata gccttaaatt tcttaaatag    63660
tgggactaca aaataaacaa tatttcatca gtaatgtaag cagtgctata ctgagtagaa    63720
ttccctcctg ttccgaaatg ttacaattg ggttctccct gtgagaagtg agtccggttt    63780
taaaacctgt gagtatactt gctgcaggtc tgaaaatgaa ggctttatga ttctttcttg    63840
aaaaattatt tgcctctatc ttttataata ttatttgttg aagcttgtgc attctatgaa    63900
tcatcatgaa gatagcttta atttcatcca caaaatttaa caatattttt ttgtctggac    63960 ataaggggc agaataagag ttggagtagg gccttgccca gccactctgt aactggacaa    64020
gtgatgtatt tatttcttag gacctcattt ccaccttcta tcaagggaaa acctaagagt    64080
aggttatctt tagggttcta agtgcctatg agtctatgag atttgacttt attaaagtta    64140
tctttgtaat tctttgagga gaacgtaggc atccattttt aaaacagtcc tgttagaatt    64200
tgttttcagt aacaatgttg aatgatggcc ttttgaaatc aggttttaca acaaaattgt    64260
ttaaacactg cctgcatatt tagaatctct ataccatat taagatacag agattggata    64320
gtctcccttt tcagtataga taatctccct tcccggtaga gattaggata ttaagatgta    64380
taatatccta aagtgtagca gcagtctggt atgttacatg tctaaattcc atttcctatt    64440
```

-continued

```
ttatttgttt attgatttat ctgtttattt ttgttacact gggtaagatt cccaagaggt   64500
acaagtagaa atttgctaaa gtgagtagga cagaagtgta gaggcaaaca taaaagtatg   64560
tttagtacat atctgtttta aattgtatct actatttcaa agttaatgga attatactcc   64620
tggggctaag aatgagggtt ctagggccaa cctctactac ctatgtggct tgtgcaaatt   64680
agttgtcccc tttgtgcctc agttttacct acaacacaga aacaatgata ttacctaccc   64740 catgactgt  tgtgaagatt aaatgaatta gtacatttac tacacataga tctatttctc   64800
aaaataatga gcattcagat attagccatc tgtaatgtag ttggtgatga ttatgattat   64860
tagagtacat ttataattgg aggatcattt ttgccgtagg gaaatagaat tattaatagt   64920
ttgaggcacc tgagaatatt atgtgagaaa ctgattacat taaccacacc cttaagatga   64980
gctctaattt tgttgtattt gtcctgttta aagccatcta gttacaatag atggaacttt   65040
tttgttctga ttgcttttta ttccaatatc ttaaatggtc acagggttat ttcagtgaag   65100
agcagttaag agccttgaat aatcacaggc aaatgttgaa tgataagaaa caagctcaga   65160
tccagttgga aattaggaag gccatggaat ctgctgaaca aaaggaacaa ggtttatcaa   65220
gggatgtcac aaccgtgtgg aagttgcgta ttgtaagcta ttcaaaaaaa gaaaaagatt   65280
caggtaagta tgtaaatgct ttgtttttat cagttttatt aacttaaaaa atgaccttac   65340
taacaaaatg attataaatc cagataaagt ataaagttag tttatatcag agaagcaaaa   65400
tccactacta atgcccacaa agagataata taaaagagga tctgtattta ttttgaaaca   65460
aacatttaaa tgataatcac ttcttccatt gcatctttct catctttctc caaacagtta   65520
tactgagtat ttggcgtcca tcatcagatt tatattctct gttaacagaa ggaaagagat   65580
acagaattta tcatcttgca acttcaaaat ctaaaagtaa atctgaaaga gctaacatac   65640
agttagcagc gacaaaaaaa actcagtatc aacaactacc ggtacaaacc tttcattgta   65700 attttttcagt tttgataagt gcttgttagt ttatggaatc tccatatgtt gaattttgt   65760 tttgttttct gtaggtttca gatgaaattt tatttcagat ttaccagcca cgggagcccc   65820
ttcacttcag caaattttta gatccagact ttcagccatc ttgttctgag gtggacctaa   65880
taggatttgt cgtttctgtt gtgaaaaaaa caggtaatgc acaatatagt taatttttt    65940 tattgattct tttaaaaaac attgtctttt aaaatctctt atgattagtt ggagctacca   66000
gttggcaaat ttgctagcta actagtgatc tgaaagtaag cctctttgaa cctctgattt   66060
ttcatgaaaa gcaattctct caattctata ttatttcaag ggtaacaagt tacatcctag   66120
tctgtgtact taattttata gaaattgtcc ttaattttat tttctgcaat ttatgttttc   66180
ttactatttc tggtgtatgt gtttatccca ttgtgatgtt atattggtgt cctcaattta   66240
tttccttagc catacactct acttttcatt gtacagggct atttattatc tcagagtcaa   66300 gcttttttt  tttttttttt ttccccgaga tggagtctca ctctgttgcc caggctggag   66360
tgcagtggcg caatctcagc ccactgcaag ttctgcctcc caggttcaca ccattctcct   66420
gcctcagcct cccgagtagc tgggactaca tatacccgcc accgagcctg gccaattttt   66480
tgtattttta gtagagtcgg ggtttcaccg tgttaaccag gatagtctaa atctcctgac   66540
ctcgtgatct accagcctcg gcctcccaaa gtgctgggat tacaggcgtg agccaccgtg   66600
cctggccaga gtcaagcttt tattttattg aatatatggt cttactaagt tcaatagcat   66660
gaatctgttg tgaagaattc aagaattttc ttctatttgt tgagttttgt tttcttagga   66720
gttttgctct ttctcttttg ctgtgttttc tccttatttt ttaaatgtgt ttgtgtttgg   66780
```

```
tgagttatgt tttagtgctt cgtaggtttt tctttgacta tattatatta gtaagccaca    66840
ttgttcccat gccattttat ttcatcttgg tcatatttgg atgactcttt tcacacattt    66900
tattgttatt atagaaggtg gataaacttttt gttcatttaa ttcatcaata tttatttaat   66960
gactgttatg tgctagacag tgttttaagt gctgggtaca tagcgattaa caaaacagat    67020
aagaatccct accctcatag agcttacatt atgaggttgg gggagggaga ttacaaacaa    67080
agaaataagt aatatacatg tgtatagttt ttttagtgct cagaaaaaaa attaagtggg    67140
taagggggta atgtcagaga agagagaggg atgtaatttt agattgagag gtgaggagag    67200
agacctccct ggaaagctga catttgagtg aagcttgaag gaattgaggg agtgaggtga    67260
ggcatgtggc catctgggga aagctttcca ggcaattaca aaggccgcag tacagcagga    67320
tcatgcctag tgtgccgtga agcattggca gagaccagag agtgagaagt aacatccagg    67380
gacagaggca gtgaagagcc aggtcgtgtg ggggtccttg tgtggactgt aacttcctgt    67440
gatgacagga agtcacagga aaattccagg tagagggaca ctgtctgaca ggttttcaca    67500
gaatcattca ggccactgtg ttgagaatag gctgtagggg gcacaagagt acaaacaagc    67560
catttggagg ctcttttcaag cacttaggca aaagatgatg aaccaaacaa aagcaatgga    67620
agtggtgaga agcagtcaga ttcttgttgt attttgaagg taggggggacg gtgcaggatg    67680 gtctgaacat tgggaaaaat ggaattgcca cttagaagga aagactgcaa gaaaagcaag    67740
tatgtgggga agttcaggag ctcagttttta gacagttaag ttttagatgc ttattaggca    67800
tctaagtaga aatgtctact tgatggttac ataggaatct gttcagagga atggctggat    67860
atgaatttgg gagtctttac tacaaatttt tttgtatttt tagtagagac ggggtttcac    67920
cgtgttagcc agaatggtct cgatctcctg acctcgtgat ccacccacct tggcctccca    67980
aagtgctggg attacaggca tgagccactg cacccggcca gtcatacagg ggacatttaa    68040
agccgtgaga ctggatgagg tcactgtggg catgggagta gatagagacg ggaagagatc    68100
caagacctga ttgaagcctt ttatacttag aagcagggaa atataaatgt aaatatagga    68160
atcagtaaaa gaaacagagg aatggccaga gaggttggag gaatactgga gtgaggtatg    68220
ctgaaagcca agagaaaaaa agaattgtcg agtagtgaga gtgattaagt ctgccaaatg    68280
ctatttcata gaattgataa tgaagtgagg accaagaatt gatcattggc tttaacaccg    68340
tggaggagca ctttcagtgg actgaaggtg gggcaaagga aatggaggga aaggaggaat    68400
gatagtgaat ataggcattt caaggatttt tgctttaaga gaagaagaga aatgaatcag    68460
tagccagaag gggaatcagg atcaagagaa catttgcttt ttcagttgaa agtgctaata    68520
gcatactgat gagatactgt atgctgatga gaaagatcca ataaagaagg taaaatgcaa    68580
gatgaaagca aaacaggaac agctgtgggg cactgttctc agatactgtg tggtatggta    68640
tctagaggct ctgttgaaat tggccttagc tagcaggaga gactgttcat ctgtaatcac    68700
aggaaaaaag taagtacgt aggtatagat accaatggaa gagttgatat acaagaggaa    68760
acttgtggca gacctctttt gattgctcta tttcctcgct gaaacagggc acaaaatcat    68820
cagctgagag tcagaatgaa gaaaaggggg ccaggcgcgg tggctaacgc ctgtaatcca    68880
gcactttggg aggccaaggt gggtgtaatc cagcactttg ggaggccaag gtgggtggat    68940
cacgaggtca ggagatggag acaatcctgg ataacacggt gaaaccccgt ctctactaaa    69000
aatacaaaaa attagccggg tgtggtggcg gcgcctgca gtctcagcta ctcgggaggc    69060
agaggcagga gaatggcgtg aacctggag gtggagcttg cagtgagctg agatcacacc    69120
actgcactcc agactgggag attccgtctc aaaaaagaaa aagagaaaga aagggtgtt    69180
```

```
gaaggtttga gagaagagga aaggcatgaa atcattatct aagaaagtgg tagagtaaat    69240
ggactaagta aacacatcat gactgccagg gcccactgga ggtttaatgt tcatgaatat    69300
attgttgttg tgtgatattt tttcaaccgt gttcagctct gatggtgtgg gcatgaagta    69360
gttggaaagt agaatttaac caggtctgta gtttagctgg gtaagtaatg caaagcaaga    69420
agggcaaaga atttgggggt atatgcaaaa ggaggattta ataattgac cttggacaca     69480 atgcagagca aagaagagac attagaagac gtggatcaat gaacaggaga taagaaaagc    69540
tgattgtagg tcacggtggg tttgagttag ggttttagag ggagtgaact gggcagatca    69600
aaggtaggtg gttgaagaag gaggtacttc aaattgagat tctgggggaa atggagttat    69660
tggaaataaa agtcttgggt atgtccattg cagtgagtta ccagtggaaa atagaggaca    69720
tgatcattta ggaagaaaac aaggaacttg ggagcaacag agtattggaa ggattgcctg    69780
tgaggatact gaaatttcca ggaaacatga ccatcgtgat gacagaatga cagtgagtta    69840
tgagttaaaa tcttcaagga atgaaaggca atgagtgagc cagggtcaat ggatgcctgt    69900
agcaaggaac agtaatgaat gacagtctga taacacgagg ttcaaaactg agtgtttta    69960 gagtgggagg agcagcaatg aagcatgagg aagacatctg cctcatctca gcctccagta    70020
gcacaaggtc tgcaggggca actgtacagg cagacaagaa ccaggtttgt tgcaacaaga    70080
tggcaatgag agcacctgca ggaaagggtg acggtagtgg agatcttact gagttccaga    70140
ggccccattg aaaggattcg aggagatgaa gaggtaggag gagatggtgc ccagaaaggc    70200
cacatccaaa gcctggaagc ggaatccagg gaatttggca tgactgagag cctgtgctgc    70260
cttttttaaa tgttttaatt tttgtgtgtt tatagcaggt gtatatattt atgggggagc    70320
ctgtgcttgt tatggggact gacacagatc agctcttggc cccaaggcaa ggtgtgtggg    70380
agaagaaaaa gtgaggaggc ctagatgtca gaggagtccg gctaaaccac tgcagaactg    70440
ctgcctaatt cacagcaacc atgagtaaaa atgctgatga tcatcaggtc aaggatagtc    70500
tggagcagtt aagatgttac tttacatggg aggtatcaat taaagatgat gaaatgcctg    70560
atttggaaaa cagagtcttg gaccagattg ggtttctaga ctaaatacag tgtgggaata    70620
cacaatacac aacctactag cctatgtgaa acacccgaaa ggccagaatg aggaagtgct    70680
ggagaacttg aaagaagctg aagacttaat ccagaaagaa gatgccaatc agatttgaga    70740
agcctggtaa cctggggcaa cttttgcctg gtgtattacc acatgggcag actggcagaa    70800
acccagactt acctggacaa ggtagagaac atttgcaaga agttttcaag tcctttctgt    70860
cacagaatgg aatgtccaga gatggactgt gaggaagaac gggccttgct ggaatgtgga    70920
gggaagaatt atgaacaggc caaggcctgc tttgaaaagg atctggcagt ggctgctgaa    70980
aaccctgaac tcaacactgg gtatgaaatc accgcctgtc gcctggatgg ctttaaatta    71040
gcaacggggg atcacaagtc atttctttg cctaccctaa ggcaggctgt caggctaaat     71100
gtagatgata gatatagtaa ggttcttctt gccctgaagc tttgggatga aggacaggaa    71160
gctgaaggag aaaagtactt tgaaggagct ctggccaata cgtccatgca gacctttgtc    71220
tttggatatg tctttggata tgtcttctct tcttactgaa gagaagactt tgtggatgaa    71280
gctcttgagc tcttaaaaac ctccttgcag gcaactccca cttctgcctt cctgcatcac    71340
catatagggc tttgtgacag gacacaaaag atccaaatga aggaagctac caacaagcag    71400 cctgagggc agaacagaga aaaggtgaca aaaatgataa gatcacctgt atttcatctt      71460
caatctgctg tggaacaaaa gcccacattt gaggttgcct atatagaact ggcaggaaag    71520
```

-continued

```
tatatagaag caggcaatca cagaaaagct gaagacactt ttcaaaaagt gttgtgcatg    71580
aaaccagtgg tagaagaaat aatgcaagac atatatttgc actatggtag atttcaggaa    71640
tttcaaaaga aatctgatgt cagtgcaatt atccgttatt taaaagcaat aaaaatagaa    71700
aaaggcataa ttttcaaggg ataaaagtgt caattctttg gagaaactgg ttttaaggaa    71760
acttcagaga aatgcgttag acctggaaag cttaagcctc cttaggtttc tgtacaaatt    71820
gaaaggaaac atgaatgaag ctctagagta ctgtgagtgg gccctgagac tggctgctga    71880
gttttagaac tctgtgggac agggtcctta ggcactcaaa tattgaccac tttcatattt    71940
catttgattt tctgttaacg tgctaatcaa ggctgaggtg agtggatcac ctgaggtcag    72000
gagttcaaaa ccagtctggc caaagttgcg aaaccgcttc tctactaaaa atacaaaaat    72060
tagccagggg tggtggcaca cacctgtaat cccagctact caggaggctg aggcaggaga    72120
attgcttgaa cctgggaagc ggaggttgca gtgaaatgag atcgcaccac tgcactccag    72180
cctgggccac agaacgagac tgcatctcaa aataaagaaa aaatgataat catcttttct    72240
gcttgctgtt ttcagaaaca tattatgtaa ttcactgtaa tgatgtaatt attgaacagt    72300
tactcaaatc tgataaaata ttagttgcat tcaataatta atgaatcaat gtgtgtgtgc    72360
atgtaagaaa aaccatttgt atgaagcaga aaaaaaatgt taggtagatt tgtaggaaac    72420
aaaatactgg acttacacta aaataaagtg agaaggtcgg tgccatgacc cagtgtaatt    72480
cttgactctc tatttatcca agattaattt ctccccccct tagttacagt gtgagggctg    72540
gatatttgag tttctattca tgatacagta tgtatccctg gaagatgtct ctggttctag    72600
atcatttttc ccagttcagt gagtaacgcc gtgtatttat ttgctataac aaagaaccat    72660
agactggggg cttaaacaac agaaatttgt tttctcacag ttctggaggc tggaaatcca    72720
agatcaaagt gttggcaggg ttaattcctt ctgaggctgt gagaatctgt tcattgcctc    72780
tctctttgct tctggtgatt tgctggcatt ttttggcatt cttttggcttg tagatgtctc    72840 acctccacct ttgcttcatt gtaaggtggt ggtctcccaa tgtacatgtc tgtgtctaaa    72900
tttccccata tattaggaca ccagtcatta tattagagcc tgcccatatg tgtgggtgga    72960
ggattaccca ggtgccgagg caagagactg aaggcacaaa ctatttcagt ataataaaga    73020
aaatagttag attaaggata gtcataatac aaattagata tagagatgat catggacaat    73080
tagcaatcat tataaaccttt aatcattagc ttttagtatt attctttgct gcattactaa    73140
tataacctag gaataactgg cgggtatagg gtgaggtgct gaagggacat tgtgagaagt    73200
gacctagaag gcaagaggtg agccttctgt cacgcccgca taagggccac ttgagggctc    73260
cttggtcaag cggtaacggc agtgtctggg aagacacccg ttacttagca gaccgcaaaa    73320
gggagtctca tttccttgga ggagtcaggg aacactctgc tccaccagct tcttgtggaa    73380
gcctggatat tacgcaggcc tgcccgcagt catccggagg cctaaatccc ctccctgtgg    73440
tgctgtgctt cagtggtcac actccttgtc cacttttatg cttctcccgt actcttggtt    73500
cctctttgaa gttcgtagta gatagcggta gaaggaatag tgaaagtctt gaagtctttg    73560
atctttctta taagtgcaga gaagaaaacg ctgacgtatg ctgccttccc tctctgtttc    73620
ggctacctaa aaggaaaggg cccccctatcc tgtaatcacg tgaattgctt cacctttcca    73680
atcacttaga agattcaccc tccttaccat gccccttgt cttgtatgca ataaatatca    73740
gcaagcccag ccgttcgggc cgctaccggt ctcccgcgtc ttgatggtag tggtcccctg    73800
ggtccagctg ttttctcttt atctctttgt cttgtgtctt tatttcttac aatctcttgt    73860
ctccgcacac gagaacaccc gctaagccgc atagggctgg accctacaca tatgacctca    73920
```

```
tctttttttt ttttttttgag ttagggtctc actctgttgc ccaggctgga gtgcagtggt    73980
gtgatctcag ctcactgcag cctctgcctc cccagctcaa gcaattattg tgccttagcc    74040
tcccgagtag ctgggacgac aggcacgtgc caccacacac ggctaatttt ttgtatttta    74100
atagagctgg ggtttcacca tgttgccagg ggtggtcttg aactcctgag ctcaggcatt    74160
ctgcttgcct cagcatcaca aagtgctggg attataggct tgagccacta tgcccagcgt    74220
gtcttaggat ttttcaactt tataatggtc tgaaaacaaa acatgagtac cttacaacta    74280 ttcttttttca cttccagtac agtatgcaat aaattacatg agatattcaa cacttttttt    74340
tttaaaaaca ggccttgcgt tagatgattt tgctcaactg taggctaata taagtgttct    74400
gaacacattt aagataggct aggctaacct ctatgctcag taggttaaat gtattaaatg    74460
catttctttt tttttttttt gagattgaaa gtcacattta ttgccacgtg aaggaaagcc    74520
aattaagtca aattgattaa tgtttgcaga gtatatctgt ttcgatcctt ttgttttttaa   74580 tctacctttg tcgaatttaa agtgagtttc ctataaggaa caaatagtcg ggttataaat    74640
ttttatccac tctttcaatc tctgtccatt gattggatat ttacatcact tacaatgaag    74700
gtaattattg atatgccagc attcaacttt gtcattttat tatttgtttt ctatttgttt    74760
ctcctgcttt tcattcctcc atttctcttt tcttgccttc ctgaaggtta cttaaatata    74820
ttttaggatt ccatcttgat ttatttttag tgttttcagg cattttttgta ttattttgt    74880 agttgtttct ctaggtgtta caacatacat gtatgactta cagcagtcta ctagtatcaa    74940
tattctacca ctctaagtga agtgtgagaa ttttgctttc attttgattt tggagggaaa    75000
gggattggat agtgaccata tacagacctt tttcttccct acttttaaat actattttct    75060
tggatatcat agtattatta ttttttgtttt agtcatcaaa cataatttat aaactgcatg    75120
aggaaatgat agcttatcgt atatgtccat ttctcaaact ctttccattg tttcttcctc    75180
catcctattg tcctcagtcc tgatgctctg agagtcttcc tttaatcttc tcttttctgt    75240
ttaaacaatt tcttttaggc aattttttgag ttagagaaaa ttcttttagt tttctctcat    75300
ctcagaatat tttatttctc ctttattcct tgagaattgt ttcaggatat agaatttgta    75360
gttgataatt ctttctttca gtacttgaaa aatattgtgc cacttccctc tggcctctgg    75420
ttttagatga gaaatctgtc atcattccaa ttgatgtgtc cctatttaaa tgcattttca    75480
actaacaacg ggtttattgt gacataaccc catcataagt tgtcctcgac tgtgtttcca    75540
gataaggctg cattcacagg tactgggaat tagtcacaat gtatcctgta acatcctgga    75600 accttttcctt atgtcagtca gtcctggtca cctgtttggt ccctggcagt ttttttctcat   75660 ttctgttcag aagaagaaaa aggtaaagat tcttcagatt taggaataac agaattctca    75720
aaaatgtcat tttaccagtt tagttgggga aggagattag actctgagcc ttcctgtgct    75780
tagttctatc cataatcttc tgttttcttaa tcaccagatt ttaaatttta tatcatgata    75840
ttccacgttt gtagattttg ggtgaatgtt tcctttttaa aatttaattt gttttttaagt   75900 gttaaagttc tattagaaag tttcaaggag ccaccttaaa ccagaagtct ttaacaccca    75960
gatctagtca tgatgcctcc cagcttaaaa tcttcagtgg tcccctgtcc cttagaaaat    76020
gaaacccaga ctcttttgta tacccccaaa accattcaac ttcctgcctt aaaccaccac    76080
catacacacg tcagctaaac tctaattttta ggctgggcgc agtagctaat gcttgtaatc    76140
ccaggacttt gggaggctga ggcggctcgc aaggctagga gtttgggaca agtctgggca    76200
acagtgagat tctgtctcta taaacataaa aactaaattt aaaaaaaaaa ctactttaaa    76260
```

```
acataataat aaaacaaact gtacaagttc atattcctga tgcatgataa catttaatgc    76320
ttcctacctt taaaaatctt cttttgttttg catagatgct cttttgttct ccccctcttg   76380
atgaatttgt cctattcatt attcagctca agtattacct ccctagtcag atgcttacag   76440
tctgggttag atcctccttc ctccagcttt tgaagcattt tgttggtttg gctgtttcag   76500
cacttgtcac atggtccatg atcctacctg tacacttctg aataagccac ctactagcct   76560
cagtaataca atgatctctt caaggacagg gactctgttt ggatttctac ttccacttct   76620
gacataatgg gttgaagcag gggtcagttg ttgaaaactc caggtatgca gcatctcata   76680
cggtcctcat agtcacactg ttcatttgct attatcatcc cactttacag atggggaaac   76740
tggagctcag agaggttaag tagcctgctc agggtcacaa tgctataaat tgatttgaac   76800
ttatactttc aggccctaaa gctcttaggt tctttcttat acttcatgct gacaaaacaa   76860
aagcaaactc aacatttgag agttgggctt aaaacaggga catctgtatt tttaatctaa   76920
tgctttgtta ctgtattaca gaaacactgt gatatataat gagttaatta aacgagaacc   76980
tttcttaggt tgggaaagat tgttttggg gaaagcctgt ttccctggga aacagactta    77040
cagatttcat gtaggagatt agaaaatgcc cttaggaaca gcacttgtga ggaagcaaat   77100
gcagcaggat tgggcagaag aagaagaaag gttcagttag tcccacaggg acttctggag   77160
ctgggtggcc cttcagagtc ttgctagcct gaggcaagag ccagtccttg catactggct   77220
cctccaggga gggcatagc cttaagcaag acaatgcctt tcgacagagg gcaagtccag    77280
gagggaactc agaggtgagt tgtcaatagc tagccctccc cagaagctgg aggatcacat   77340
gccttggtcc tgaaggggat ctgcacccgc accatggcat ccactccagg tggaatcggt   77400
gacagtggtt ttataaattg ctaagtcctt tattgtttca gtgacatttt ctaaaaggaa   77460
ttaaaagctt tgaagaattc tatgcaagtt cagagtaggc cagaccacaa agctgcaaaa   77520
taagtttctt cttttccttt tgtcttgtga agatttacct agtgtaggat tctaaaagtg   77580
ttacactaaa aattcttcca gttgttatca gttgtatgat aattaaagaa ataaggcttc   77640
catttctttt gatggaattt gatccagaca tggaaacctc cacttacgta aaagtgcaat   77700
gaggaaacta cactgtttac ttttattttt tctgtattct aaatgttttt caataaacat   77760
gtattttata tttgggaaa acaagatata tttaaaagg acatttggga aaggacagt     77820 actatcatca agttttgaat ataattagag gcaagttcca aaattagaaa atggaacatg   77880
cttgagaaac ttataatttc tttaaaagca gtgtttaaaa ttaagatcca ttaaataaat   77940
ttgaaatgaa aagaaagaaa agatgaacca tcatttgcaa tagaataaac aaatccttat   78000
ctgagaatga catttccatt ccctgttatt tacaacggat acataattct cagagtaaca   78060
aaaacaataa agtataaaga gtagaattaa atgcttagtg cctcttccaa ctccagcttt   78120
cctagcctca gttctatcct ggtttatccc aggatagaat ggatagcacc tacccatctt   78180
tcactttaga attttataac tcttggctag gcacagtggc tcatgcctgt aatcccagca   78240
ctttgggagg ccaaagcagg cagatcactt gaggccagga gttcaagacc agcctggcca   78300
acatggcttg aacccgggag gcggggctg cggtgaccca agattgcacc actgcaccct    78360
agcctaggcc acagagtgag actgcgtctc aaaaaaaaaa aaaaaaaatt ataactcttt   78420
attttgaact aatttcagac cttttaaacaa gttgcaaaaa tcgtggaatt tccaaatatt   78480
cctcacctag cttcccctaa tgttaacatc ttgcataacc gtagtacaat tagaatcaga   78540
aagttaatag tggtataatt attacccata ctgtagatgt atttgaaaaa ttgtttgagt   78600
ttaaggtatt ttaccctgtt tccccttttt tgttctggga tcccaaattg catttagtca   78660
```

```
tttttcccct gtattttcta ccagtctttta atacttcctg tcttcttttt catgatcatt   78720
atgcttttga atagactgat aatgatcatt atgttttga atagactgat caattatttt   78780
gtagcattcc cctcaatttg agttcgtctg atgttttctc atgactagga tgaagttatg   78840
catttctggc aagactacca ctgaagtgat gatgtgtctt tctcagtaca tcatatcaag   78900
gggttaatga tactgatctt aatcacttga ttaaggtgat aatctgctgg gtttctcctc   78960
tgtacaataa cttcctttt ctttgtagtt aataaatatc ttgagggaga ttctttgaga   79020
ctgaatccta tttcacatca aactagcatt catcagttga ttttgtttgc aacaatgatt   79080
actgtggtat ttgcctaatt atgattttc tccctttctt tccttctaca ttaattggaa   79140
ttctataagg aaaagctgtg ccctttccac caatgtattt atttggttat ttatatcagt   79200
atggactcaa gaacatttat tttattctgc aggttaaaat ttggtacctt cattatttta   79260
ttgtttaact tttttttttt agctttgacc attaggagct ttctcatatg gactcgtgtg   79320
ttctttcaac cagcttctt cacttttga acacttcctt attttttgac atcacaagat   79380
gttccaagtt catcttatat gttccctgcc ctagtcttgg aatcagccat ttctcttggc   79440 ttctttttt tagtagaaaa tggtgtttag atccaagatc tggttgctag ataggctcat   79500
tactttactg tggaggcatc agtactgcca ggccctctca gcagacagag gtgggaaatg   79560
tttgtcttcc attttggatt ccctcatgtc tagttggatt tgtttgttgg ttggtttatt   79620
gggtatgtga agtatcactg tggttctagg gagtcagacc tgtacaaaaa gatatacttc   79680
atgtcacttc ctccttatcc ttgcagtccc aatcctaatc ctccttttc ccccactcac   79740 accctgttcc tttagtttct gagtttatcc ttcctgattt cttttgctca atgaacaga   79800 tacatgtgta ttttcttata ttcccttctt ccttataaga aggggaacat actctagcct   79860
ttcttttatg ctttctttt ttaactcaac actgtcctgg agatcagttc atagaaatcg   79920
tcctcactct ttttttacag ctacgtggta caccattgtt tggatgtacc acagtttatc   79980
caactctatc ctgtatatga gctaataaaa gttgcttcca atattttata attataatgt   80040
ttcagtgagt aaccttgttc ataggtgttt tcatgaactt tatgttcatg tgtattttac   80100
tattattaga ggtctatctt cagagaggag tacaagaaat gggattactg ggtgcaaagg   80160
taaatggata tgtgtctttg ctaggtattg ccaaatttat ctccagaaat cttgcacaaa   80220
tctgtactcc tgttagcaat gtgtgcgtat acctgcttcc acatgacctc agtaaaagaa   80280
tgtgttgtca tattggtatt gaaattttag cactgtaagc aacaggtcat tttggaaaac   80340
ctgagctttc gccaaattca gctatttga tttgctttta ttattagcat ataccaaaat   80400
aaataggcat attagagttt cctttcttgc atcttaaaat tcatctaaca catctataat   80460
aacattcttt tctttttttt ccattctagg acttgccct ttcgtctatt tgtcagacga   80520
atgttacaat ttactggcaa taaagttttg gatagacctt aatgaggaca ttattaagcc   80580
tcatatgtta attgctgcaa gcaacctcca gtggcgacca gaatccaaat caggccttct   80640
tactttattt gctggagatt tttctgtgtt ttctgctagt ccaaaagagg gccactttca   80700
agagacattc aacaaaatga aaaatactgt tgaggtaagg ttacttttca gcatcaccac   80760
acattttggt attttctat tttgacagtc cagtatcaag gaaatagctt ttatacaaat   80820
tggatagttg aggtagtatg tgaggtaaag tttaatcata tattaattgc ccatgaacct   80880
caggagatgg gggaatgggg aaatgacagc aactagaaag agaagaatga cttgaaggga   80940
aatgagttag gagaaattgt gagaaggatg ttcagaaatg cagactttgt aagcaaactg   81000
```

```
gaaattggtt acaagaataa tatgagttat ctgtggtttg cagcagtcag cagtgtgatt    81060
agttaataat atagagacta caggtttaca tttaaactcc atatctagtg ttttatacag    81120
attatatttc tttgacttga tttaatccca gataagagac actgatatta ttttccctag    81180
atcatgtatg cattttctgc ttaaatctat atatacatta tataatatta gctggtgttt    81240
attgagtgtt tactatgtgt cagaccttgt tctaagcttc tcatttaatt ctcccacaac    81300
cttatgaggt agggaactgt ttttctattt tatcagtgag aaacaggtta aatggcttgc    81360
cttaggtcaa atgccaagtt agtaaaacta ggattcatac ttaggccatc gaatgcagaa    81420
cccagactag gaactgctat gcaatgctgc ttcccagtaa aatttgagat ttcatgagtt    81480
ggtaactagt gaagaataca caaaaaataa gcctcttaat tctgtagttt aatatttgaa    81540
atgtgtgtta ttcagaattt atataaaaat atattttaaa agcattagag tagctgtata    81600
aagaaagctg tgttgacatt ttacctagag actctatgca taatgaataa cactctgcta    81660
tatctagttt ctaaattagg ggtgggagtt gtattcatta tttagttccc atacagcata    81720
tctactgttt acaccccaca ttttcttttt ttctttcttt cttttttttt ttttttttt     81780 tttttttta gagacagagt cttgctttgt cacccccagg ctggagtaca atagcacaat     81840
ctcggatcac tgcagtgtct gcctcctggg ctcaagcgat tctcgtgcct tagcctccca    81900
agtagctggg actacaggtg cgtgccacca cgcccagcta attttgtat ttttagtaga     81960 gacatggttt caccatgttg ggcagtctgg tctcgaactc ttggcctcaa gtgatctgcc    82020
caccttggcc tccccaagta ctgggtttac aggcatgagc caccgagccc gcattttctc    82080
tgagacgtct tcaaaggcag tttactaatc ctgctgaaga dacaactgtc atttacacag    82140
cattttaaag ttttacaaaa tactgtcatg aattaggtta aaccatatga aattgctgat    82200
atttgaccag ttgtgatttc tcaagcaaca gtttcatgta gtttaaccta taatcatttt    82260
caattaattc ttggaacaga cgtgaggtag gtgaggcaat tctttctttt ctctaaccaa    82320
agaagtacct ttatagatgt gagatgattc ccagctatta agtagtaaat agagctagga    82380
cttgagcccc aatcttccag cttcaatcca gatcatatga cagcttgctg attaaactag    82440
atgacagaga agatctcttt ccttcagata cacatacttt ttctctgttc ccctctccct    82500
atcagctaga ttcccctaaa tcactgatac tggttttgta attttgcatc ggcatgtttg    82560
acaattggta tcacatttag ggttttttcat tctttttttgg tccaaacttt tcatttctgc    82620
ttttaaagga aatactttg gaaacataaa tatgtgggtt tgcaatttat aaagcagctt     82680
ttccacttat tttcttagaa tattgacata ctttgcaatg aagcagaaaa caagcttatg    82740
catatactgc atgcaaatga tcccaagtgg tccacccca ctaaagactg tacttcaggg     82800
ccgtacactg ctcaaatcat tcctggtaca ggaaacaagc ttctggtaag ttaatgtaaa    82860
ctcaaggaat attataagaa gtatatatgg aggccatcgt atattctgtt gtatacctag    82920
taaacatggt aaaatgtaat taaacttaat tagaaaatgt ggttgttatg tggctcctgt    82980
aagtatagtt atttagaaat tttatttatt gaagcaagat atgaaactct gggtgcacac    83040
tttccaaaca ggtgctttca tttacatgtg attgaaaagt gttttttgcc atttatttca    83100
ctgttccata caattagggt tgtttctaag ctgtttgtaa gctgtttcta agctatttaa    83160
gtggttaaat cacagtagat gcaaatcaag ctaaagtctt taacattggc taatggctga    83220
ttcttaaata gctaatactt gctaagggta tctatattaa ctcatttaat cctcataaca    83280
accctatgag ataaaaccta agtcctcact taacattgtc aataggtttt tggaaactga    83340
ttttaaggga agtgatgtat aacaaaacca ttttttttc tcatcactgt tctaacaaaa     83400
```

```
tgatgttgaa gatttaaatg acattgctca aagacctgct atacattgtt tgacttaaag    83460
tcacagtttc cgagaaccta tcaattatgt taagtgagga cttgactcta ttatcctgat    83520
tttgtagatg aggagactgt ggcatagaga gaggttaagc aattgcctaa taaggtcaca    83580
aagctagaaa agtaggtatt agaacccaga tagtgtgtgt tctcaagatg gctttaaaat    83640
atttatcttt gtttaatctg ttaataataa aaaacaaaag attaaagcat aagtgacgtc    83700
ccctacctcc ttttttatct tttactgtga ttattcttca tcttccttcc ttttcatgtc    83760
attttatatg ttcttatgta aaattacttt catctagaat aggaataatg tgaactgaaa    83820
tcacctaacc tattaggagt taggggaggg agactgtgtg taatatttgc gtgcttaaat    83880
attttcaatg aaaagttact ttgatttagt tttttatgtt actacataat tatgataggc    83940
tacgttttca ttttttttatc agatgtcttc tcctaattgt gagatatatt atcaaagtcc    84000
tttatcactt tgtatggcca aaaggaagtc tgtttccaca cctgtctcag cccagatgac    84060
ttcaaagtct tgtaaagggg agaaagagat tgatgaccaa aagaactgca aaagagaag    84120 agccttggat ttcttgagta gactgccttt acctccacct gttagtccca tttgtacatt    84180
tgtttctccg gctgcacaga aggcatttca gccaccaagg agttgtggca ccaaatacga    84240
aacacccata agaaaaaag aactgaattc tcctcagatg actccattta aaaaattcaa    84300
tgaaatttct cttttggaaa gtaattcaat agctgacgaa gaacttgcat tgataaatac    84360
ccaagctctt ttgtctggtt caacaggaga aaaacaattt atatctgtca gtgaatccac    84420
taggactgct cccaccagtt cagaagatta tctcagactg aaacgacgtt gtactacatc    84480
tctgatcaaa gaacaggaga gttcccaggc cagtacggaa gaatgtgaga aaaataagca    84540
ggacacaatt acaactaaaa aatatatctta agcatttgca aaggcgacaa taaattattg    84600
acgcttaacc tttccagttt ataagactgg aatataattt caaaccacac attagtactt    84660
atgttgcaca atgagaaaag aaattagttt caaatttacc tcagcgtttg tgtatcgggc    84720
aaaaatcgtt ttgcccgatt ccgtattggt atacttttgc ttcagttgca tatcttaaaa    84780
ctaaatgtaa tttattaact aatcaagaaa aacatcttg gctgagctcg gtggctcatg    84840
cctgtaatcc caacactttg agaagctgag gtgggaggag tgcttgaggc caggagttca    84900
agaccagcct gggcaacata gggagacccc catctttaca agaaaaaaa aaaggggaaa    84960 agaaaatctt ttaaatcttt ggatttgatc actacaagta ttattttaca agtgaaataa    85020
acataccatt ttcttttaga ttgtgtcatt aaatggaatg aggtctctta gtacagttat    85080
tttgatgcag ataattcctt ttagtttagc tactatttta ggggatttt tttagaggta    85140 actcactatg aaatagttct ccttaatgca aatatgttgg ttctgctata gttccatcct    85200
gttcaaaagt caggatgaat atgaagagtg gtgtttcctt tgagcaatt cttcatcctt    85260 aagtcagcat gattataaga aaaatagaac cctcagtgta actctaattc cttttttacta    85320 ttccagtgtg atctctgaaa ttaaattact tcaactaaaa attcaaatac tttaaatcag    85380
aagatttcat agttaattta ttttttttttt caacaaaatg gtcatccaaa ctcaaacttg    85440
agaaaatatc ttgctttcaa attggcactg attctgcctg ctttatttt agcgctatca    85500 caggacccag agcctatgcc ttttaaact taccacaaaa gcagaagatt aattcaattt    85560
aagatgatac tctcatttgt tacgtccttt tttttttttt ttggagatgg agtcttgctt    85620
tgtcgcccat gctggagtgc agtggcatga tcctggctca ctgcagcctc cacttcccgg    85680
gttcaagtaa ttctcccacc tcaagcctcc ctagtagctg ggattacagg gacgcaccac    85740
```

```
catgcccagc taatttttgc attttttagta gagactgggt tttaccatgt tggccaagct    85800
ggtctcaaac tcctgatgtc aggtgatcca tctgcctcag cctcccaaag tgctgggatt    85860
ataggcgtga gccactgtgc ccggccaata tttgttactt tcttaggttt aatagagaaa    85920
agggataaaa catttctaac tgggagttaa tagcatggag aaggtcttaa atcagatgtt    85980
ttaatgcctt aaatgtctgt ataatatcat gttttcaaat ctaattataa atacgtttaa    86040
agccaagaat aaatctttta aaaaattgac ttgtttcctt ccataactct gagccatgat    86100
t                                                                    86101

<210> SEQ ID NO 5
<211> LENGTH: 166188
<212> TYPE: DNA
<213> ORGANISM: Homo sapiens

<400> SEQUENCE: 5
accagtctta acatggtgaa accctgtctc ttctaaaaat ataaaaatta gtggggcgtg      60
gtggcctgca cctgtagatg caattacttg ggaggctgag gtaaagagt cacctgagcc     120 tggggaagtg gaggcttcag tgagctctga tcataccact gcaatccagc ctgggcgaca    180
gttagaccct gtctcaaaaa aaaaaaaaaa aaattaaaa aagaattta tcatgaacag     240 ttaatacacg cacatggttg gaaacaaagg atactgttaa aacagtttca gctgggcgca    300
gtggctcaca cctgtaatcc cagcactttg ggaggccgag ttgggtggat catgaggtca    360
ggagatcgag accatcctgg ctaacacggt gaaaccccgt ctctactaaa aatacagaaa    420
aattagccgg gagtggtggc aggcgcctgg gaaggctgag gcagtagaat gggagtgaacc   480 caggaggcgg agcttgcagt gagccgagat cacaccactg gagtccagcc tgggcgaccg    540
agcgagactc cgtctcaaaa aacaaacaaa caaacaaaca aaaaagttt cttagacaaa    600 ttgattacaa ttgcatatca aattttaatt tcaagcttat ttccttttcca agcaggctaa    660 atattcctct tagacatttt gtaaaaaaga agcatattag aatcatcagt attagcctgg    720
agaaagcaaa caatgtctgg aattattagc tatcttctaa gtctagttaa aggtaactgt    780
cttgtgccaa gactgacagt gagctaaatg aactgttttt ttttgagaca ggatcttgct    840
ctgctgccca ggctggagtg cagtggtgct atcatagctc aatgcagcct taaacacctg    900
gacttaagga atttttccac ctcggcctcc caaggattac aggtacatgc ctggctggtt    960
ttttaaactt ttttttttt ttttgagaca gaatcttgct ctgttgcccc cactggagtg    1020
aagtagtgtg atcttggctc actgcaaccc ccacctcccg ggctgaagct atcctcctgc    1080
ctcagcctcc caagcaaata gaactacagg catgtgccac caagcctgac taatttttgc    1140 attttttagta gagacaaggt ttcaccatgt tgctcaggct ggtcttgaac tcctgagctt    1200
aagcgatcct cccacctcag cctaccaaag tgctggtatt acaggcatga gtcgctgtgc    1260
ctgccttaca gttttttgta gagatgagat cttgctatgt tgccaggctg gtctccaact    1320
cctgggctca agtgctcctc tggcttcaag tcttctaaaa tgttgggact acaggcatga    1380
ggtaccatgc ctggccagct cattaaagtg tatcagaaat ggtagtagct tctctaaagg    1440
gatagcacat gacatcagac tataatactc aggtttgagg ctgggtgtgg tggctcacac    1500
ctgtaatccc agcactttgg gaggccgagg tgggcggatc acttgagatc aggagttcca    1560
gaccagcctg gccaacgttg taaaactcat ctccacaaaa attacaaaaa ttagccaggt    1620
gtgatggtgt gcacttgtag tcccagctat ttggaggct gaggcaggag aatcacttga    1680
aaccagggcg ggtggaggtt gcagtcagcc gagattgtgc cactgtactc cagcctggga    1740
```

```
gacagagcga gactctgaaa aaaataaaaa tataaatata aaataaataa aactcaggtc   1800
agaaacacat cttctttctc agtatacagt cttgctgcag attctgtaag cacacagacg   1860
gttaagcata cagaatctgg aagaagactg gattctagat ctatcactta ctagctctgt   1920
gatctggcgc aaggccaggc aattgaattt taatctgtag gcccgagatt tctttctttt   1980 ttttttttcta tggagacgga gtctcgctct gtcgcccagg ctggagtgta atggcgtggt   2040
ctcggctcac tgcaacctct gcctcccgga ttcaagcgat tctcctgtct cagcctcctg   2100
agtagctggg attacaggtg cctgccacca tgccaggta  attttttgtat ttttagtaga   2160 gacgggtttc accatgttg  gccaggctga tcttgacccg ctgacctcgg cctcccaaag   2220
tgctgggatt acaggcgtga gccactgtgc ccaccagaga tttctaaatt gagctgattg   2280
tcaggaacat ccagggagct ttcaaaaatg attccaggct gaggctgggc ggggtggctc   2340
atgcctgtaa tctcagcact ggggaggcc  gaggtgggtg gatcaccgga ggttgggagt   2400
ttgagaccag cctgaccaac ttggagagac cctatctcta ctaaaaatac aaaaattagc   2460
tgggcgtggt ggcgcatgcc tgtaatccca gctactcaga aggctgaggc aggagaattg   2520
cttgaaccca ggaagtggag gttgcagtga gctgagattg tgccattgca ctccagcctg   2580
ggcaacaaga gcgaaactcc atctcaaaaa acaaacaaac aaacaaacaa aaacaaaac    2640 caaaaaaaaa aaaatgatt  ccaagctggg catggtggct cacacctgta atcccagcac   2700
tttgggaggc cgaggcgggc agaacaggag gtcaagagat cgagaccaga ccatcctggc   2760
caacacagtg aaaccccgtc tctcctaaaa ataccaaaat tagctggggg tggtggtgca   2820
cacctgtagt catagctact tgggaagctg aggcaggagg atcgcctgaa cccgggaggc   2880
agtgagccga gattgcgcca ctgcactcca gtgtggtgac agagccagac ttcctctcaa   2940
aaaaacaaac aaaggttcca aggctctact ccagaaatta agacccatta tgtgtgggct   3000
gggcacagga atatgtttaa atccccccc  acctccccag ggtgattctg ctgctgaatt   3060
aggttttgga accacttcca tggggaaagg gtaaactaaa ctggagaatg caaaaacctt   3120
tttttttttt tttttttttt ttgagacaga gtctcaccct gttgcccagg ctggagtgca   3180
atggcgcgac ctcggctcac tgcaacctcc acctcccagg ttcaagggat tctcctgcct   3240
cagcctccca gtagctggga ttacaggtg  cccaccacta cacccggcta attttgtgtg    3300 tgttttagt  agagacggag gttcaccatg ttagtcaggc tggtctcgaa ctcctgacct   3360
caggtgatct gcccgcctcg gcctcccaaa gtgctgggat tacaggcgtg agccaccgcg   3420
cccggccagc aaaaaccttt tctaagagtt aattttgcag gatggatcct gagctccttc   3480
aggtgtttga taacatttta tttattttt  gagacagagt ctcgctctgt caccgaggct   3540
ggagtgtagt ggcgcgatct cgctcactg  ccccctccac ctcccaggtt caagagattc   3600
tcctgcctca gcctctcgag tagctgtgat tacaggcgcc caccactatg cccggtaatt   3660
tttgtatttt tagtagagac ggggtttcgc catgttggcc aggctggtct caaactccgg   3720
acctcaggtg atccacccgc gttggcctcc caatacgctg ggattacagg cgtgagccac   3780
tgcgcctggc tgtttgctaa cattttaaaa ttttcaacctt cctcttcctt aactggtctt   3840
cccctacccc ccctcaagac ggggtctctc gctctgtcgc cccagctgcg gtgcagtggc   3900
gtgaacatag ctgacggcag aagacctcct gggctcaaac gatcctcctg gctcgtgctc   3960
ccaaagtact gggattatgg cgtgtgacac cacgcctggc gtcaaacgtt tgtctttta    4020 tttatttat  tttgtatttt ttgagacagg gtttcaatc  tgtcgcccac gctggagtgc   4080
```

```
agtggcacaa tttacggctc accgcagcct cgacctcccg ggctcaggtg atcctttcgc    4140
ctcagccctg ctaatatctg ggatcacaga cgtgggtttt accatgttgc ccaggatggt    4200
gtcaatctcc tgggctcaag tgatccgccc acctcggcct cccaaattgc tgggattaca    4260
ggcgtgagct accgcgccct gccacaaacg catatcttct aacgtaccat ttcatttact    4320
tgctatattc attatctgaa ttttctcata ttagaatgta agcagaataa aggcagtgat    4380
ttttcttttt actggcgatc ctcagagcca agaagagtct gggacatagc aggccatata    4440
aatgttttcg aatgagtgaa tcatcaacga gtggatgaaa cgataatgtg gctaacaggc    4500
agcagtaagg aggctgtgta gaataaaccc gtaatcccga tgttggcagt ttgcttagaa    4560
agaaaaaggg aggcagtcgg agaggggcac acgttttaac aaaatactgg gaggaggagg    4620
aaggctagtt ttttttttgt tttcaagttt ccttctgatg ttactcccat gcttccgggc    4680
acattacgag ctcagtgcct gccggaaatc tcccacctgg tggcaaccta cccttgcata    4740
caccccaccc aggggcttca agccttgcag ctgagtaaac acagaaagga gctctactaa    4800
ggatgcgcgt ctgcgggttt ccgcgcgacc taggcgcagg catgcgcagt agctaaagtc    4860
accagcgtgc gcgggaagct gggccgcgtc tgcttatgat tggttgccgc ggcagactcc    4920
cacccaccga aacgcagccc tggaagctga ttgggtgtgg tcgccgtggc cggacgccgc    4980
tcggggacg tgggagggga ggcgggaaac agcttagtgg gtgtggggtc gcgcattttc    5040
ttcaaccagg aggtgaggag gtttcgacat ggcggtgcag ccgaaggaga cgctgcagtt    5100
ggagagcgcg gccgaggtcg gcttcgtgcg cttctttcag ggcatgccgg agaagccgac    5160
caccacagtg cgccttttcg accggggcga cttctatacg gcgcacggcg aggacgcgct    5220
gctggccgcc cggaggtgt tcaagaccca gggggtgatc aagtacatgg gccggcagg    5280
tgagggccgg gacggcgcgt gctggggagg gacccggggc cttgtggcgc ggctcctttc    5340
ccgcctcaga gagtgggcgg tgagcagcct tccagtgcg gaggcacggg ggcggaacgt    5400
tggtgcttgt gcggattccg ccgtccccag gttctgcttg gctccggagg gacgccccc    5460
tcagccctga aacccgtgcc tctccagccg ccccggatct gaacttgtga tcacggagtg    5520
tttacgtcgt gccaggcatt ttaatgcatt gttctagttc attttccagc agtcgcattc    5580
ctcgccttgg ccctacatgt agcgctcatt acaaacacgg ccagaatctc ttattaacaa    5640
acagcagcca ggagtgagat ttaaaataga ctggggtttt aggagaccct tttatgacac    5700
gtaattctgc tcccacgacg ctcccattta taccgccggt ccagctaagg gtctggtaat    5760
ggagcgccgt tgaagagcag tatgatgaag tggtcaggac caacggactc tggagctggg    5820
ctgcttggga tcaagtcgct gcccctctgc ttattaacgt gtgaccttgg gccagtcatg    5880
gacgctatct gcttcagctc agcattcagt gctctccgtc acccgacccc atctatccag    5940
gattatctct ccctggaaag ctacaaacgt ctcaccctat gtgggccaaa tgttctggat    6000
aggcctagtt aacctcttct ctccctgttt tctttgcgct tcttgcagc tatgtagtta    6060
tgctaatgaa aagagcatcc tagggggagc agagttgtgg attctagtcc tgactagagg    6120
actagtgcaa atgcgatact cctgatgaaa atgtttcat tcgttagata taaatgtgtt    6180
aggcagggtt atggacacta gatgaaaaaa gaaatacctc tactttcata gagatcacta    6240
ttggacagca aggcagaaat aattacaatt caagttggag gctatggag gtgagcttgt    6300
aagaggttac aagaggcgcc aaggcaggat cgccaaagac ggaagacttt ggaagagtct    6360
catacaacgg aagaggcgtt atatgagaca ccaaagtcca cgttgagtct tggtggacta    6420
gaagtttgct agggagaggg cttgaaacga ggtagattgg cgttgctggt gtagaaaagg    6480
```

```
aaggagactg gcccaggtgg gtggggttag atgaccaaag gcttttagtg tggtgttgag    6540
ctgttgaaat tttatgctgt agccaatgaa aagtctgaaa tgtttttttt tttttttttt    6600
ctgagacgga gtcttactgt gtcgcccagg ttggagttca gtggtgtaat cctggctcac    6660
tgcaacctcc acctcctggg ttcaagcgat tctcctgcct cagccaccgg agtagctggg    6720
attacaggca cgtgccacca cgcctagcta attttttgtat ttttagtaga gatggggttt    6780
caccatgttg gccaggctgg tctcaaactc ctgacctcaa gtgatccacc caccttggcc    6840
tcccgatgtg ctgggattac aggtattagc cactgcacct gacctacata gattttacat    6900
aagactttaa aacagggcgg gcgcagtgac tcacgcttgt aatcccagca ctttgggagg    6960
ctgaggtggg cggatcacaa ggtcaggaga tcaagaccat cctggctaac atggtgaaac    7020
cctgtctaca ctaaaaatac aaaaatccca gcactttggg aggctgaggt gggcggatca    7080
cgaggtcagg agatccagac catcctggtt aacactgtga acccctgtct ctactaaaaa    7140
tacaaaaaat tagctgggtg cggtggcagg tgtctgtagt cccagctact tgggaggctg    7200
aggcaggaga atggtgtgaa cccggaaggc agagcttgca gtgagccgag attgtgccac    7260
tgcactccag cctgggcaac agagcgagac tccatctcaa aaaaaaaaaa aaaaaaaaa    7320 aagactttaa aaaaaattat aagaaaggac agaccaagtg cagtggttcg ttccagcact    7380
tagggatgcc aaggtgggag gattgcttga tgctaggagt tgaagactag cctgtgtaac    7440
atagcgagac ccatctctac aaaaaaatta aaaagttacc tttagaactt acgattttta    7500
tgtgtagact ccatataagc agagggtcta tgcttattca ctatttatta ccttccatag    7560
tccctgcaca tataataggt gcttcataaa caatttaatg aatgaataaa ttactgagaa    7620
aacactggaa gttttgggt tagcattgtg ttaggtgctt gatatggtct ggctgtgttc    7680
ccacccttat ctcatcttga attcccatgt tttgtgggag gtacctggtg ggacataatt    7740
gaatcatgtg ggcaggtttt tcctgtgctg ttctcctggt agtgaataag cctcacaaga    7800
tctgatggtt ttaaaaatgg gagtttccct gcacaggctc tctctctttg cctgccgcca    7860
tccatgtaag atgtaacttg ctcctccttg ccttcctcaa tgattgtgag gcctcctcag    7920
ccatgtggaa ctggctgcag agtcattaaa cttcgttctt ttgtaaattg cccagtctca    7980
ggtatgtctt tttttatttt tttttgagac agagtctggc tctgtggcta ggctggagtg    8040
cagtggtgcg atctcgactc actgcagcct ccgcctcccg ggttcaagcg attctcctgc    8100
ctcagcctcc caagtagctg ggactatagg tgcacgccac catgcccagc taattttttgt    8160 atttttaata gagacggagt ttcactgtgt tggccaggt ggtcttgatc tcttgacctc    8220
gtgatcttcc cgcctccgcc ttccaaagag ctgggattac ctacccagct gggtatgtct    8280
ttattagcag cgtgaaaaca gactaaaaca gtaaactgat accaatagag tgggatgcag    8340
ctgaaaagat acccgaaaat atggaagcaa ctttggagct gggtaacagg cagaggtcag    8400
agcagtttag agggctcaga agaagaccag aaaatgtggg aaagtttgga acttcctaga    8460
gacttgttca atggctttga ccaaaatcct gataatgata tggacaatga aatccaggct    8520
catgtggtct cagatggaga tgaggaactt gttgggaact ggagcaaagg tgacacttgt    8580
tatgttttag taaagagact ggtggcattt tgccctgccc tagagatttg tggagctttg    8640
aacttgagag aaatgatttt gggtatctgg tgggagaaat ttctaagcag caaagcattc    8700
aagaggtgac ttgggtgctg ttaaaggcat tcagttttaa aagggaaaca gcatgaaagt    8760
ttggaaaatt tgcagcctga caatgtgata gaaaagaaaa tcccgttttc tgaggagaaa    8820
```

```
ttcaagctag ctacagaaat ttgcataagt aatgaggatc ccaatgttaa tccccaagac   8880
aatgggaaaa atgttttccag ggcatgtcag aggccttcat ggcagcccct ctcatcacaa   8940
gcctagaggc ctaggagaaa aaagtgattt catgggccag cccggggtcc ccatgctgtg   9000
tgcagcctag tgacttggtg ccctgcatcc cagctgcccc agctgtggct gaaaggggcc   9060
aacctagagc tcaggccatg gcttcagagg gtgcaagcct gaaaccttga cagcttccag   9120
gtggtgttga gcctgcaggt gcacagaaat caataattga ggtttgagaa tctctgccta   9180
ggtttcaaag atgtatggaa acgcctgcat gtccaggcag aagtttgctg cagggtgggg   9240
gtgctcattg agttcctctg ctagggcaat gtagaaggga aatgtagggt cagagccccc   9300
ccacagagtc cctactgggg caccacctag tggagctgtg aaaagagggc taccattctc   9360
cagacctcag aatggtagat ccacagacag cttgcaccat gtgcctggaa agctgtaga    9420
cacttaacgc catctcatga aagcaaccag gcagtgtgct gtaccctgca aagccacagg   9480
ggcagagctg tccaaggctg tggttgccca gctcttgcat ccgcatgacc tggacatgag   9540
acatagagtc aaaggagatc attttggagc tttaagattt gactgccatg ctggattttg   9600
gacttgcatg gggcctgtag ccccttttgtt ttggccaatt tctcccattt ggaatggctg   9660
tatttaccca attcctatac cccattgtat ctgggaagta actaacttgc ttttgatttg   9720
acaggctcat atgcggaaag gacttacctt gtcttgaatg agactttgga ctggaattt    9780
gaattaatgc tgaaatgagt taaggctttg ggggactgtt gggaatgcat gattggtttt   9840
gaaatgtgag gacatgagat ttgggagggg tcatggcaga atgatatggt ttggctatgt   9900
ccccacctaa atcccatctt gaattcccat gtattgtggg agggacctgg tgggagatag   9960
ttgaatcatg gggatggatc tttcccatgc tgttgtgata gtgaataagc ctcatgagat  10020
ctgatggttt taaaaacgga agtctacctg cacaagctct ttctttgcct gctgccatcc  10080
atgtaagaca tgacttgttc ctccttgcct tctgccatga ttgtgagacc tccccagcca  10140
tgtggaacta taagtccagt aagcctcttt ttcttcccag tctcgggtat gtctttatca  10200
gcagcatgaa gtccagctaa tacagtgctt gaacatgtaa tatctcaaat ctgtaatgta  10260
cttttttttt ttttaaggag caaagaatct gcagagtgtt gtgcttagta aaatgaattt  10320
tgaatctttt gtaaaagatc ttcttctggt tcgtcagtat agagttgaag tttataagaa  10380
tagagctgga aataaggcat ccaaggagaa tgattggtat ttggcatata aggtaattat  10440
cttccttttt aatttactta ttttttttaag agtagaaaaa taaaaatgtg aagaatttaa  10500
ttgtgtttta gtattttaag tagattgtga tagtagaatg gtttgagaca ctttaatagc  10560
aattagcatg tggtttttaa aaagttgcag tttggctggt cgcagtggct catgcttgta  10620
atcccagtat tttgggaggc tgaggcaggt aggttgcctg agcccaggag ttcaagacca  10680
gcctgcccaa cgtggtaaag ccccatctct actgaagata aaaaaattta aaaaaattag  10740
ctggggctat tggcacacac ctgtggtccc agctaatcaa gaggatgagg ttagaggatc  10800
acttgagccc aggaggttga ggttacagtt taactttcag aggccaaggc aggaggattg  10860
cttgagtcca ggagtttgag accaccctgg ggaatgtagg gagatcccat ctctatagag  10920
ggatagatta gatagataat ttctgagggg agggagggg gagggccagg gaaggggagg  10980
gaaaggggag gggagggcag ggccagcagt aaggtcataa tagagacatg tatctgtaag  11040
atccttataa taggtgagga tggcacaaaa ttagcgccac agatttgtat ttttagtaga  11100
gacaaggttt taccatgttg gccaggctgg tcttgaactc ctgacctcaa gtgatccgcc  11160
tgccttggcc tcccaaagtg ctgagattac agatgtgagc caccatgccc aaccacaagc  11220
```

```
atttatttat ttatttattt atttatttat ttatttattt agagacagtc ttgctctgtc   11280
gccaggctgg agtgcagtgg cgccatctgg gctcactgca aactctgact ccctggttca   11340
agcttttctc ccgcctcagc ctcccgagta gctgggatta caggtgcatg ctgcaacacc   11400
cggctaattt ttgtattttt agtagagatg gggtttcacc atgttggcca ggacggtctc   11460
gatctcctga cctcgtgatc cgcctgcctt ggcctcccaa agtgttggga ttacaggcgt   11520
gagccacagc actcagccag ttattttttt ataagaaaac attttactgg ccaggcctgg   11580
tggctcacac ctgtaatccc agcactttgg gaggccgagg caggcggatc acgaggtcag   11640
gagttcgaga ccagcctggc caacatggtg aaacccccatc tctactaaaa atacaaaaat   11700
tagccaggcg tggtggtgtg cgcctgtatt cccagctact ggggaggctg aagcaggaga   11760
atcgattgaa cccttgaggc agaggttgca gtgagttgag atcgcaccat tgcactctag   11820
cctgggtgac agagcaagac ttcatctcaa aaaaagaga aaacatttta ttaataaggt   11880
tcatagagtt tggattttc cttttgctt ataaaatttt aaagtatgtt caagagtttg   11940
ttaaattttt aaaattttat ttttacttag gcttctcctg gcaatctctc tcagtttgaa   12000
gacattctct ttggtaacaa tgatatgtca gcttccattg gtgttgtggg tgttaaaatg   12060
tccgcagttg atggccagag acaggttgga gttgggtatg tggattccat acagaggaaa   12120
ctaggactgt gtgaattccc tgataatgat cagttctcca atcttgaggc tctcctcatc   12180
cagattggac caaaggaatg tgttttaccc ggaggagaga ctgctggaga catggggaaa   12240
ctgagacagg taagcaaatt gagtctagtg atagaggaga ttccaggcct aggaaaggct   12300 cttaattga catgatactg tttcatttaa ggaaaaataa taaaaaaact cttttttttg   12360
tatctaatta aaataatgtt ctgatgttta cagaaacttt gtatatttaa ttggacatta   12420
gaacaagctg tttgttgtgt aagatttatt ttacctcaga tcttttctcc cccctttcct   12480
ttctgtcttg tgttccaaaa gagtaattat tacggtaaat attactgtaa ttatggatt   12540 atcaaataag atgcagttct ttagcatttt ttgataaatc gagtggaact ttagcctgtt   12600
attttactat ttgttttatt ttaactaaat tctgattgtg tcattttttt ttttttttt   12660 tgggaccgag tctcgctctg tcgcccaggc tggagtgcag tggtgcgatc tcggctcact   12720
gcaacctctg cctcccaggt tcaagcaatt cttctgcctc agcctcctga gtagctggga   12780
ttacaggtgt gtaccaccac acccagctaa ttttttgtatt tttagtagag gtgaggtttc   12840
accatcttgg ccaggctggt cttgaactcc tcacctcgtg atccaccac ctgggcctcc   12900 caaagtgctg ggattacagc catgagccac catgctcggc tttgattgtg tcatttgtat   12960
aggcatgtgg tttattattt agttattttt tttttttct ttgaggtgga gtatcactct   13020
tggtgcccag gctggagtgt aatggcgtga tctcagctca ctgcaacctc tacctcctgg   13080
gttcaagcaa ttctcctgcc ccagcaggag tagcttggga ttacaggcat gccccaccac   13140
acctggccaa ttttgtgttt ttagtagaga caggggttcca ccatgttggt caggctggtc   13200
ttgaactcct gacctcaggt gatctgccca cctcagcctc ccagagtgct gggattatag   13260
gcatgagcca cggtgcccag catatttaga ttttttttt tttgagactg agtctgactc   13320
tgtcacccag gctagagtgc agtggcacga tccacgatct tggctcactg cagcctccac   13380
cttatgggtt caagcgattc ttctgcctca gcctcccaag tagctgggac tgcaggcaca   13440
tgccaacacg cccggcttat ttttgtattt ttatagagac ggggtttcat catattggtc   13500
aggctggtct ctaactcctg accttgtgat ccacccgcct tggcctccca tagttctggg   13560
```

```
attacaggca tgagccacag cgccaggcct agatgtttct taaggtatgt atctcccaaa   13620
gattcttttt gtggtcctca agtaccataa gcaccgctgg agataacaca tgtgatgggc   13680 attttttagca tagattgtat ctaagcaact ttccacaagt aatagttctg ttaagggttg   13740
ttattgtggc cgggcgcggt ggctcacacc tgtaatcctg gcactttggg aagctgaggc   13800
ggccggatca cctgaggtca gggattcgag accagcctgt ccaatgtgct gaaaccctgt   13860
ctctactaaa aatgcaaaga aaaaaaaaat ctagccaagc atggtggctt gctcctgtaa   13920
tcctagctac ttgggaggct gaggcaggag aattgcttga acctgggagg cagaggtagc   13980
agtgagccaa gatcgtgtca ccgcattcca tcctgggcga cagtgagact ctgtctcaaa   14040
acaaaaaaag agttgttacc gttgggacta ttttttgaaa gctttatgtg aacgtaattt   14100
tatattttga tgaaaattta gtttattgat gtaaaaagtg tatcagtaca tcatatcagt   14160
gtcttgcaca ttgtataaac atttaatgta ggtgaatctg ttatcactat agttatcaat   14220
gttataattt tcattttgc ttttcttatt ccttttctca tagtagttta aactatttct   14280
ttcaaaatag ataattcaaa gaggaggaat tctgatcaca gaaagaaaaa aagctgactt   14340
ttccacaaaa gacatttatc aggacctcaa ccggttgttg aaaggcaaaa agggagagca   14400
gatgaatagt gctgtattgc cagaaatgga gaatcaggta catggattat aaatgtgaat   14460
tacaatatat ataatgtaaa tatgtaatat ataataaata atatgtaaac tatagtgact   14520
ttttagaagg atatttctgt catatttatc tcaaaaccta aactgtgtat caatgatatt   14580 aagcttttt ttttttttga dacagagttt cacttttgtt gcccaggctg gagtacaatg   14640
gcgcgatctt ggctcaccac atcctctgcc tcccaggttc aagtgatcct cctgccttgg   14700
cctcctgagt agctgggatt acaggcatgt gccaccacgc ctggctcatc ttttttgtat   14760
ttttagtaga gatggggttt ctctatgttg gtcaggctgg tctcaaactc ctgaacctca   14820
ggtgatccgc ccgcctcggg cttccaaagc gctgagattg caggcatgag ccactgtgtc   14880
tggcctattt ttatagttta tgtacttgga attatataat atattctgcc tagcttcttt   14940
cattcaatat ttgtaagatt tatccatatt attgagtgta gttgtggatt tttgcattta   15000
tatttcatag cacgagcatg tcagaattta tccattttac ttcccttctg cccgccactg   15060
ctactctccc cattttacct tttttttttgt tttttgaga tggagtctca gaatttcgct   15120
ctgtcgccca ggctggagtg ctgtggcacg gtctcagctc actgcaactt ctgcctctgg   15180
gttcagctgc acgccaccat gcctggctaa ttttgtatt ttcagtagag gggattttgc   15240
tatgttggcc aggctggtct tgaactcctg acctcaggtg atccaccac cttggcctgc   15300 cagagtgctg tgattacagg cgtgaaccac cgtgcccgac ccccattcta atttgatgg   15360 acatttgggt aattttcatt tttggctgtt ataaatactg ctgcaattac agttaatttt   15420
cacagttttt tttttttttt tttttttttt tttttttga ggtgagtttc gctcttgttg   15480
ctcaggctgg agtgcagtgg tgcgatctca gcccactgca accttcacct tctggattca   15540
agcaattctc ctttctcatc tcctaagtag ctggggttta caggcatgtg ccaccatgcc   15600
cagctaattt ttgtatttta atttcacagt tctggaggct gggaagttca gaattaaggc   15660
actggctgat ctgttgtctg gtgagggccc acttgttcat agataaccat tttctcactc   15720
taacctcaca aggttgaaag ggcctaattt ttgtgttttt agtagagacg gggtttcact   15780
atgttggcta ggctggtctc aaactcctag cctcgagtca tccacccgcc tcgtcctccc   15840
ggagtgcttg gattacagca tgagccactg cgccggccc ccattttagt tttgatggac   15900
atttgggtaa ttttctttt tggctattct aaataatgct gcaattactg ttaattttca   15960
```

-continued

```
ccttgtaaaa accatttttca aatctcaaga gattaacctt tagttttctt ggtttggatt    16020
gggaaggaac accaaggaaa atgagggact tcagaattta ttttcatttt gcatttgttt    16080
tttaaaatct ttagaactgg atccagtggt atagaaatct tcgatttta aattcttaat    16140 tttaggttgc agtttcatca ctgtctgcgg taatcaagtt tttagaactc ttatcagatg    16200
attccaactt tggacagttt gaactgacta cttttgactt cagccagtat atgaaattgg    16260
atattgcagc agtcagagcc cttaaccttt tcaggtaaaa aaaaaaaaa aaaaaaaaa    16320 aaaagggtta aaatgttga atggttaaaa atgttttca ttgacatata ctgaagaagc    16380
ttataaagga gctaaaatat tttgaaatat tattatactt ggattagata actagcttta    16440
aatggctgta ttttctctc ccctcctcca ctccactttt taactttttt tttttaagt    16500 cagagtctca cttgttccct aggccagagt gcagtggcac aatctcagcc cactctaacc    16560
tccacctccc aagtagttgg gattacagtt gcctgccacc atgcctggtt aatttttata    16620
tttttagtag gttgcgggg acagggtttc accatgttgg ccaggttggt ctcaaacttc    16680
tgaccttagg tgatcctccc acctcggctt cccaaagtgc tgggattaca ggcttgagcc    16740
atcgtgccca gccactttt tactttttta gagactgggc ttggtggagt gaagtggcaa    16800
gatcatagct cactgcagta ttgaactcct gggctcaagc gatcttcctg cttcaacctc    16860
atgagtagct gggtctacag gcacaagcca ccatgcttgc ctaattttaa aattttgca    16920 gagttggagt ttcacagtgt tgcccaggat gttcgctcac tcctgacttc aagtgattct    16980
tctgccttag cctctagagt ggtagctggg attacaggca tgaaccacca tgctctgcta    17040 tttttttca aggttttttt ttttttttt tttttgaga gactggtatg actatgtatg    17100
ctccctaggc tggagtgcag tggctattca caggaagtgc catcagagtg tactacagct    17160
tcaaactcct gggctcaagc acttctatca tagtctccaa agtagctggg actacgagtg    17220
tgtctcattg tgccttgctc tcgaattgct tttttttttt ttttctggtt tcaagctatc    17280
tatgtggtat tagtcctcac tttatgaata atttttgtata ctactaatag caatttttt    17340 tttttttttt ttttgagac ggagtctcat tcttgtcgcc caggctggag tgcagtggtg    17400
tgatcttagc tcactgcaac ctctgcctct ccggtttggg caattagctg ggattagagg    17460
cgcctgccac catgcccagc taattttttgt atttttagta gacatggggt ttcatcttgt    17520
tggctaggct ggactctaac tccaggtgat ctgcctgcct cggcctccca aattgatggg    17580
attacaggtg taaccactg ggcctggcct agcaatttaa aatgacattc taagaagttt    17640
tatgtctaaa tctgcagtaa gtggctgggt gacgtggctc atgcctgtaa tcccaacgct    17700
ttgggagtcc agggtgggag gatgacttga ggccaggagt tgagaccagc ctgggcaaca    17760
tagtgagact ctgtctctac aaagaaaaa attagcgggg cttagtggcg tgcgcctgta    17820
gtctcagcta ctcgaaaggc tgaagtggga ggattctttg agccccaagg gttctggctt    17880
gccgtgagcc aggatggcac cactgcactc cagtctgggc aatagagtca gaccctgtct    17940
caacaaataa aataaaactg tagtaattat aaagtggttt tggctggggg agaaatgtac    18000
agttgaacat acggattaag aggttgaaag ttggtcttag gaagaggaac ttttgtgga    18060 aatttcttaa tattgaagaa atattatgtt attgttcctc tgttttcat ggcgtagtaa    18120 ggttttcact aatgagcttg ccattctttc tatttattt tttgtttact agggttctgt    18180
tgaagatacc actggctctc agtctctggc tgccttgctg aataagtgta aaacccctca    18240
aggacaaaga cttgttaacc agtggattaa gcagcctctc atggataaga acagaataga    18300
```

```
ggagaggtat gttattagtt tatactttcg ttagttttat gtaacctgca gttacccaca  18360
tgattatacc acttattgta atatgcagtt ttggaagtat atgttaccat ttaactgtac  18420
agagtacata gtaatagagt ggtaattatt tagattgatt aaagaactca ttttttaaa   18480
taagttttt tttttcact ataaaagttt attttatttg agatggtatg gtatcgaaca    18540
tgttcatatt gtgtgtaatc gtgggtaaat tactcaacct ttatgtcata gtttcttcac  18600
ctttaaaatg acattaataa aagagctact taataggatt ataagcatga gatgatttaa  18660
tatacataaa atacttacag tctgatatat aggaagcact taactcttta tcctagaaaa  18720
gatttaaggt gaccttaaca tatatgtcag aaaatcttta aaattgtgga aataaaaggt  18780
tgtataattc tgctatccta aaattactag tatttcaata tatttatttt tagtcttttc  18840
ttttagatac aagttttaaa acttttaagt gaagtgtaat atacgtaagt actgcttgat  18900
gaatttaagg tgatttctaa agccaggttt gttggggaag aggagtggga tttagtgatt  18960
tagaaccaga aattggggct gggtgcgatg tctcatgcct ataattccag aacttcggga  19020
ggccatagtg ggagaattgt tgtgccccg gagttcaaga ccagcctggg caactcagtg   19080
agacgccatc tctacaaaag aaaaaaaaaa aaaattagct cagtgtggtg acatgtacct  19140
gtagcccgag ctactcggga ggctgaggtg gaatatcac cctggcccag aagtttgagg   19200
ctgcagtggg ctatgattgt gccactgaac tccagcctgg gcaatggagt gaaaccctgt  19260
ctcaaaaaac aaacaaaaaa agaaactgag gctgggcacg gtggctcaca catataatcc  19320
agcacttggg gaggttgagg caggataatt gcttgagccc aggagtttga ccagtctg    19380
ggcaacaaaa tgacaccca tttctaccaa aaaaaaatt gtttaaaatt agctgggcat    19440
ggtggcatgt gcctgtggtc ccagctacat gggaggctaa ggctggagga ttgtttagcc  19500
caggaggttg aggctgcagt gagccatatt catgtccctg cactccagcc tgggtgacat  19560
agtgagacgc tgtctcaaac aaaaatcaac aggccagatg cagtggctca cccctgtaat  19620
cccaacactt tgggaggccg aggtgggtgg attacttgag gtcaagagtt cgagaccagc  19680
ccggccaaca tggcgaaacc ccatctctac taaaaataca aaattagatg gcatggtgg   19740
tgtgtgcctg taataccagc tactcttgag gctgaggcat gagaatcgct tgagttggga  19800
ggcaaaggtt gcagtgagcc aagattgtgc cactgcactc taccctgggt gagaaacgag  19860
attttgtatc aaacaaacaa acaaacaaaa aaagacgccc aaaatcaaca acaacaaaaa  19920
cgatattgga atgattggat ccccaaagat aaatgtttga ggtgatggat atctcagtta  19980
ccctgagtta agtattatac attgtatacg tgtattaaaa tattcaaaac ccccaaatgt  20040
gtacaattat gaggtatcaa taaaagagat tggaaggact gggtaatttg caagtaatta  20100
aggcaattta caattttaa ttttatttg tgaataagta gttatacgtg tcaaaattca   20160
aaaggacag gtggatatac agtgataagt catccccct tctctgtcag ctccataaag    20220
agcccctgtc ttgcatggct ccagggtcac atttcctatt gtattttgcc accacctgcc  20280
ctgggagcaa cagtgttagt ttcttgaaca tccttccaag cagagtctgg gcctacacaa  20340
gcaaaacaag tatgtctatt ctctctcctc tttaattttt ttaaggaag tgattgataa   20400
tttaacactc aagctatagg tcattggtta tatttttaat ttccaattta tgggaataga  20460
ggaagtgtca gtgatcccct tctggtttaa gaactggagg atgcatgtgt ttagacccttt  20520
tagaaacctg aaatgtcacc taatataatt atcagagtaa cacttttag taagcaagct   20580
atctatcaaa gtaggtttt tgaagaagag ggtaaggaaa ggttactttc atgggacata   20640
gcaataattt ctaaaatcta atggttttac aagacttgtt cattagaagt aacatctgtg  20700
```

```
aggatggctt tatgagtcaa aatattatct gcttaatacc ccacctgtag ggtaagaaga   20760
aatgttttt  tcttggtgac aattttttagc agcaagcggg gagggcctgt ggcttccaag   20820
gccaaacgtt gaaataccac agactaggaa gaaaaagatc cactccttat acaggatttg   20880
tttgtttctt ctttttttctt cattttttgta gagatgaggt ctcactatgt tgcccaggct   20940
ggtctctctt ttttttttga gcccgagttt cactcttgac gcccaggctg gagtgcagtg   21000
gtgtgatttt ggctcaccgc aacctctgcc tcccgggttc aagcgattct cctgcctcag   21060
ccttcctgag tagctgggat tacaggcatg cgccaccacg tccggctaat tttgtatttt   21120
tagtagagat gggtttctcc atgtgggtca ggctgctctc gaactcccgg cctcggatga   21180
tccacttgcc tcggcctccc acagtgctgg gattacaggc gtgagccact gagcccagcc   21240
atgctggtct caagcaatcc acacccacct cagcttccaa aagtgctggc attacaggtg   21300
tgagccccccg tgcccagcct gtttcttata attattcctc tttctcaact ctgtctgctg   21360
tggtacctca tgcttcctag tttaagcctt cttgggagtt ctcaggagaa atctgttatc   21420
tcccttacta agcatttggg attgatgttc cttccaggtt actataaaac caagttttt   21480
ttggttcttt ttttttttttc ttttaaaaga aatgagattt tgtcatggtt agcctggttt   21540
caaactccca agctcaagta atccaccttc ctttgcctcc caaagtgcta ggattacagg   21600
catgaaccac tacacccgat ctgtactgtt cctctttcca ttcactaaaa cctacttgca   21660
actatgagca tatgttattg ccatctagaa atgagtttct agggacttgt tcctttttgt   21720
actttattta aacagtcgaa ttagaaatta ttattatcat tatttatttt ttgagatgga   21780
gtcttgctct gttgcccagg ttggagtgca gtggcgtgat ctcggctcac tgcaacctcc   21840
acctcctggg tttaagcgat tctcctgtct cagcctcccg agtagctggg actacaggca   21900
tgtaccacca cacctggcta attttatat tcttaataga aacagggttt cactattttg   21960
gccaggctgg tctcgaactc ctgacctcag atgatccact cacctggcc tcccaaagta   22020
ctggaattat aggcgtaagc caccgtgccc ggccaaaatt atttataata agcaaggcat   22080
ggtggcttgt gcctgaagtc ccagctactt gggaagctga ggcaggagga tcacaggttc   22140
aggtccaccc tgggaaaata gtgagaacct tccctatccc cagtcttcaa aaagaaaaa   22200
aatttgctgg agaaggtcac acaatgctga taggtcccat tgtgctttca tgctttctag   22260
ttttcaatga taactggttg ttacttttat tgtctgactc attatagtga ccaactcccg   22320
atttttact ttgccttaag ccttcagcta tctcctacct ctaagcggat gatttcttcc   22380
ttaacactta aaacctcaaa atttatctgt acttccactc tttactctc tggctctttc   22440
tcagaagaag aaataacact tttatttctt ttcaaagcca acctttccat actttacttg   22500
gagacatatt tcttttttttt tgttttgttt ttgtgagtgg agtctcactc tgtcgcctgg   22560
tctggagtgc aatggcgcaa tctccactca gtgcaacctc tgcctcccag gttcaagcga   22620
ttctcctgcc tcagcctgct gagtacctgg gcttacaggt tagcacacca cccggcca    22680
agttttgggt ttttagtaga cagggtttt tgccgtgttg gccaggctgg tctctaactc   22740
ctgacctccc gatccgcccg cctcaggtgc aagccaccgc gcccagccct agtgtagcaa   22800
tcttaatcag aaatatgtct ctggctgggc gaggtggctc atgcctataa tcccagcact   22860
ttgggaggcc aaggcaggca gatcacctga ggtcaggagt tcaagaccag cctgaccaac   22920
atggagaaac cctgtctcta ttaaaaatac aaaattagct gggtgtggtg gcatatgcct   22980
gtaatcccag ctactcagga ggctgaggca ggagaatcgc ttgaacctgg gaggcggagg   23040
```

```
ttgcggtgag ccaagatctc accattgcac tccagcctag gcaacgagca aaactccatc    23100
tcaaaaaaaa aaaaaaaaaa aaaagattg ctatgttaat cttatttatt tatttattta    23160
ttttgagaca gagtctcaca ctattgccag ggctggagtg caatggcata atcttagctc    23220
actgcaacct ccgcctcccg ggttcaggtg attctcctgc ctcagcctcc tgagtagctg    23280
ggattacagg cgcccgccac cacgcctggc ttattttttg tgttttttag tagagacggg    23340
gtttcactac gttggccagg ctggtcttga actcctgacc ttgtgatttg cccacctcag    23400
cctcccaaag tgctgggatt acaggcgtga gccaccgtgc ctggcttatg ttaatcttat    23460
tttatataaa aagaaataat attaaactag aaggcaataa aaatgccaaa ttcaatacac    23520
aaattatttt gtcagcattt ccacaagaat aaactatttt atatgctaac atatgttcaa    23580
tgttccttac agaattctga cattaaaaat gaaaaattac caaagcttca gatgaatcta    23640
taaatggaca aaagaaaaag cttaaaagga taaagagcaa cactccaagt gcatgtataa    23700
acataaggac tcttgggact taaccttttt aaaaatcttt aggcctagca cagtatttgc    23760
tatttaatgt atcaaatggg tggttttgac ttcattaatc catatatagg acagatgaaa    23820
aaaagaatta tagacttgta attacagttc tttaggaacc atatttgctc tcagccttt    23880 aaatacgctg tcaggcaatt ccagtcagca cttttgaaaa aaacctacct acctacctac    23940
ctacctatct atctatctat ctatctagag actgagttat aagactagct agttttgta     24000 tttttttgcag agacaggatt tcatcatgtt ttcttaggctg ttcttgaact cccaggctca    24060
agccatccac ccgcctcagc ctcccaaagc gctgggatta caggcgtgag tcaccatgcc    24120
caaccaattc cagtcagctc ttaaaatgaa agcctagaaa tggtagggtt aaagagggga    24180
cagaatgttg attttaaaat acctagaatt tggccaggtg cagtggctgt aacccagcac    24240
tttgggaggc caaggtggcc ggattgcctt ggcctgcctc agcctcccaa agtgctggga    24300
ttacaggtgt gagctcagga gttcgagacc agcctgggca acacggtgaa accccttctc    24360
tagtaaaata caaaaaatta gctgcatgtg gcggcgtgca cctgtggtcc cagttacttg    24420
ggaggctgag gcaggagaat tgcttgaacc tgggaggcag aggttgcagt gagctgagat    24480
tgcgccactg cactccagcc tgggcaacag agtgagactc tgtctccaaa aaaaaaaaac    24540
cccaagaatt tgattaattc tgttggaatt ttaagagtta actgatcccc aaaatgactc    24600
agctgtatgc aatttaatgc aatattaatt cgcatgttga ctctcagaat tgcatacagc    24660
tgagtcattt tattgagtag gattgataag tatactatgt tatgccaaca gtaactgtga    24720
tgcttctaaa attgtgattt ttaaattggc attgtcacag aaacagcaga gtagttgttt    24780
ttttctttaa gcttctttta gccagaaaca taaactgaaa ctgtaattat tactgcaatc    24840
gtatgttgaa tagacttgtg aaactagcaa tttattaggc ttttaatgat atctggacca    24900
aaggctgagg gagctgtgct gtgtgtatgt tgctttgtgc tttgtttttt agaagcttgt    24960 cgttctttg ccattttact tctttctttt ttttgagac ggagtcttgc tctgtccccc      25020
aggctggagt gcagtggcgc agtttccgct cactgcaagc tccgcctcct gggttcactc    25080
cattctcctg cttcagcctc ccaagtagct gggactacag gcgcccacca ccacgcccgg    25140
ctaattttct gtattttta gtagagatgg ggtttcacca tgttacccag gatggtcttg     25200
atcttctgac cttgtgatcc gcccgcctcg gcctcccaaa gtgctgggat tacaggcttg    25260
agccaccacg cctggcccat tacccattac ttgtttctta atgttacatt ctctttccct    25320 ctttttttt ttttgttttt tgagatggag tttcgctctt gttgcccagg ctggagtgca    25380
acggtgccat tttggcccac tgcaacctct gcctcccagg ttcaaatgat tctccagcct    25440
```

```
cagcctccca agtagctagg attacaggca cctgccacca cgcccagcta attttttgtat    25500 ttttagtaga gatggggctt tgccatgttg gccaggctgg tcttgaactg ctgacctcag    25560
gtgatctgtc tgcctcagcc tcccaaagtg ctgggattac aggtgtgagc cactgcaccc    25620
agtccttaat gctactttat aggtgaaaat tgtgaaataa cttaaatttc attttaatta    25680
aagttaattt ttgggaaatt aacgaaaggt tgacatttta ttcttttgaa tattgcagtt    25740
gttatttggg tttaaattgg ggggcttagg aaggaaagaa gcctgatggt tgtttctgaa    25800
ttttctgaaa attatgtttg atatgctgta tatgaaatcc agcttggaga gaatatgtcc    25860
attgttaagg aaaaattaat gaagatttga tctagataag gcattccaat catttggaag    25920
tggtttgagt atcttttttt cttttttttaa tttgagacag agtcttgctc tgtggagtgt    25980
agtggtgcaa tcttggctca ctgcatcctc cacctcccgg gttcaatcaa gcaattctcc    26040
tgcttcagcc tcccgagtag ctgggattac aggtatgggc taccatcccc agctaatttt    26100
tttttttgga tggaatcttg ctcccgtcgg gcaggctgga gtgcagtggt gtgatctcag    26160
ctcactgcaa cctccacctc ccagtttcaa gcgattaagt gattctcctt cctcagcctc    26220
ccgagtagct gggattacag gcgtgtgcca ccacgtcgcc accacgtctg gctaatttt    26280 gtattttag tagagacagg gtttcgccat gttggccagg ctggtcatga actcctgacc    26340
tcaggtgatc cacctgcttg gcctcccaaa gtgctaggat tacaggtgtg agccactgtg    26400
cctggcttaa gttttgtatt tttagtagag acggtgttcc atcatgttgg tcaggctggt    26460
gtcaaactcc tgaccatgcg atccgcctgc ctcggcctcc caaagtgctg agattacagg    26520
cgagagccac cgtgcccggc ctgtttgagt atctttaaa accagtaagg acaaactaga    26580
ggtgtcagct ctcttcatgg gctttggaga aacaagacaa aaaggaaaga gatgtttcgc    26640
cgggcgcggt ggctcactcc tgtaatccca gcactttggg aggctgagga cagcggatca    26700
cccgaggtca ggagtcaaga ccagagccat tgcactccag cctgggcaac aagagcacaa    26760
ctttatctca aaaaaaaaaa aaccaaaaaa gaaacaggaa agagatgttt tgatttttta    26820
agtctagagt gttctgttct tactctacag cacttagcag tagtccatct atcctccttg    26880
tttgttcttt acaacaaaac cccattggtt ctctcttacc aagtttgctt tattcttggt    26940
ttatcctttg taagatgtga aagggatatg aagagcaaat aggaagtgtt actcttgctg    27000
cttgagagaa agctgtttta caatttgttg gcaaacaatt tgtaaaagta caacaaaagt    27060
gtgcattttt ggcttcttat ttatgtttta tcattgctat atctcataat ttgtgatttt    27120
taaaataact tttatttga aaagcactac agggtcacgt catgttttta aaaataaat    27180 taagaaggta aacacccgta cttctacttt acctctagtc ctagtctatg gtggtaatca    27240
gtgttaacag tttagtttgt gttcttaccc ttccaggggt tttttttctc tatgtataca    27300
gatatatgca ttttttaaaa catagttaac acttaaaaac aatatgggat cgtattagga    27360
atacaatctg tattccttcc caacagtata tacagttttt ttccatttca ctatgtatct    27420
atttataaat ttttttatttc taataatttc tcttgaatag gtgagacatc atatagtata    27480
aaattcagta gaaaatcagt tttttcagagg tacaaaattg gctgactttg cacagactcc    27540
tttcatttca caggtaggga tgcacagcca cctcttccac cgacgagagg aaaggatatg    27600
tgtgcctgtg ggctcttcaa ctctgttgat tagttatgat ttattttctg gtcagtttga    27660
gaggaaacag tgataaaata ctgggaacag ggaagaagca taagattatt attgttttt    27720 ttttttttt tgagacagag tcttgctcag ttgcccaggc tggagtgcag tggtgcgatc    27780
```

```
tttgctcact gcaagctccg cctcccgggt ccatgccatt ctcctgcctc agcctcccga   27840
gtagctggga ctacaggcgc ccgccaccac gccctgctaa ttttttttttt gtattttttag  27900
tagagacagg gtttcaccat gttagccagg atggtctcga tttcctgacc tcgtgatcca   27960
cccgcctcgg cctcccaaag tgctgggatt ataggcgtga accaccgcgc ccagctttaa   28020
tttttttttt tttttttttt ttgagacaga gtcttgctct gtcgcccagg ctgaagtgca   28080
gtggcgcgat ctcggcttgc tgcaagctcc gcctcccagg ttcacgccat ctcctgcct   28140
cagcctcctg agtagctggg attacaggca cccgtcacca tgcccagcta attacgggac   28200
ctcgctctgt cgcccgggct ggagtgcagt ggcacagtct cgctcactgc aatctggcaa   28260
gtgattctct tgcctcagcc tccagagtag ctggactac aggtgtgcgc cgctacgccc    28320
agctaatttt tgtattttta gtagagatag gtttcgcca tgttggttgg ccaggatggt    28380
ctcgatctct tgacctcgtg atccgccctt ctcggcctcc caaagtgctg ggattaccgg   28440
tgtgagccat cgcacctggc cttcctactt tattaagata cctaagggat ttctgtgatt   28500
gttaggattc aaatttctgt gagcataaga atcaagctgt gtgcataata attgcatggg   28560
atttcacagc tgggccccat tcccagggat tttgtattat ctacctccaa gtgattttga   28620
tgctggtgat ccttggacca gacttggtga agctcaatgc ttagctagga aagccccaaa   28680
aatttgctttt attggattgt gtaatttgac tacatccatt gtttcttttt tcaaatgtag   28740
agttatatgc cacaaaaata ttttccgtag cagtaggcat cctaattaat ctcgatgttt   28800
gtttatagcc ccattgatgg ggctataaac ttggcagcaa attgttttcc cactaatttg   28860
gcattttcca taaatgtttg tttatagccc cattgatggg gctataaact tggcagcaaa   28920
ttgttttccc actaatttgg cattttccat aaaaaacacg tatctgttgt tagctgccta   28980
gacgttagct ggacatggtt taggttactt ttctcttaaa agtaaattt taattcaagt    29040
tcctttaagc cagcagtctc aacctggggc agttttttccc tccaggggac attcagcagt   29100
gtctagagac atttttggtt gtcatgctga ggaagagagt gtatagtggg tagaatccag   29160
ggatgctgtt aagcatggaa cagccccta caacaaaaaa ttatgtagcc taaaatggca   29220
gtgttgccaa gattgagaaa ttatgcttta aatgtgtttt tatatatggc cattttgtgt   29280
ttactctgga gataacatgc ttttcctcat ataacatgct tgataaacat tttggtaaca   29340
caggaattgt aaatgctggt gatgtcagta aatagttaag aaatttaggg ctgtgcgcgg   29400
tggctcacgc ctgtaatccc agcactttgg gaggccgagg cgggtggatc ccgaggtcag   29460
gagatcgaga ccatcctggc taacatggtg aaaccccgtc tctactaaaa atacaaaaaa   29520
atgagccggg tgtggtggca ggcacctgta gtcccagcta ctcaatttag aaagcagatt   29580
tgttccttt ctatacctgt gtaatttgag gtttagttta ctgtcacatc gtttataaac    29640
ataaggaaga tcgttgctca tctgatagca ttccgaacct tgagtcatct gtaatgccta   29700
tggcctccag aaaagcttct ctaatactgt acttagagat gtgtaaaata tgtaggaaca   29760
tttttcccacc ttcgattgtt agtttacctt tcagcttcag taatttacct ttcagctatt  29820
actttagtaa catcttcaac attgtttttc aaactgcaag gtgtgaccca gtagtgggtc   29880
gttaaattag taggtgacag agcatttttg aagaattaaa tacaatagaa catagcgagg   29940
tgggctcacg cctgtaatcc cagcactttg ggaggcgagg ctggcaggtc acaaggtcgg   30000
caggtcacaa ggtcagaaga tcgagacctt cctggctcta acatggtgaa accccgtctc   30060
tactaatagt acaaaaaatt agcgggggtgt ggtggcatgc gtctctagtc ccagctactc   30120
aggaggctga ggcacgagaa tcacttgaat ccgggagctg gaggttgcag tgagccgaga   30180
```

```
ttgcaccact gcactccagc ctcagcaaca gagcaagact atttcaaaaa aaaaaaaaaa   30240 aaaaagaaa gaaagaaaaa aagaaaatag agtgtatcac ataattagag tagcaagtat   30300
tgatttgtga aacctatttt aatcatagat ctatgtatgt atgtgctgga ttgtgatgta   30360
aagacatttc ttgctgtggt tacactgaaa aaaatgaaaa gtcactgatt tccaataact   30420
tacagaagca gtatgaacta catattctgt cgttcttgaa acaagctgag attttattga   30480 cttttgggaag cagtagaatt attttagttt tttaattaac agttttttggc tttgtactgt   30540 caagaggtaa ttttagaaag cattctaaaa atgtaagtac tggatttggc aacattcttg   30600
aactgtaatt ctgtttcgtt aaacatcact atttacatgt gcaacagcgt gtctgtaaca   30660
atgtcccagt aatgaaattc tttcttctat ttaaggcatg tctgtttgat aaaagtcaaa   30720
caaaattggg tatatgtcag tgtcttatga tactgcttaa ttaaacatta atttgactct   30780
tagctaatca ggaaatgttt gcctcacagt cttacagagc tttccacctt ctaaaaaagc   30840
taacgtttca gaatagattc aggattcaac cttctttctg tcttttttttt ttttttgtttg   30900 agacagagtc ttgctctgtt gcccaggctg gagtacagtg gcgctatctc ggctcactgc   30960
aacctccgcc tcctgggttc aagcaattct cctgcctcag cctcccgagt agccggggtt   31020
acaggcgtgc gccaccatgc ccagctaatt ttttttgtatt tttagtagag acagggtttc   31080
accatgctgg gtggccaggc gggtctcaaa cttctgacct tgagatctgc ccaccgtggc   31140
ttcccaaaat gctgggatta taggcgtgag ccaccgcacc tagcctagat tcaggctgct   31200
tctttttttt tttttttttg agacagagtc ttgctcttgt tgcccaggct ggagtgccat   31260
ggcatgatct cagtgcacca caatctctgc ttcccaggtt taagcgattc tcctgcctca   31320
gcctcccaag tagatgggat tacaggcatg agccaccatg cctggctaat tttgtatttt   31380
ttgtacagac ggggtttctc catgttggtc aggccagtct cgaactccct acctcaggtg   31440
atctgcctgc ctcggcctct caaagtgctg ggattacagg tgtgagccac tgcgcccagc   31500
agattcaagc ttttaaatg gaattttgag ctgatttagt tgagacttac gtgcttagtt   31560
gataaatttt aattttatac taaaatattt tacattaatt caagttaatt tatttcagat   31620
tgaatttagt ggaagctttt gtagaagatg cagaattgag gcagacttta caagaagatt   31680
tacttcgtcg attcccagat cttaaccgac ttgccaagaa gtttcaaaga caagcagcaa   31740
acttacaaga ttgttaccga ctctatcagg gtataaatca actacctaat gttatacagg   31800
ctctggaaaa acatgaaggt aacaagtgat tttgtttttt tgttttcctt caactcatac   31860
aatatatact tggcaatgtg ctgtcctcat aaagttggtg gtggtgactc actcttagga   31920
cacattcaga tttcttttttt ttttttttttt gagaaggagt cttgctccgt tgccaaggct   31980
agagtgcagt ggcacaatct cagctcactg caacctctgc ctcctgggtt caagcgattc   32040
tcctgcctca gcttcctgag tggctgggat tacaggcatg tgccaccatg cccggctaat   32100
ttttgtactt ttagttttac catgttggcc aggttcgtct ggaactccca atctcaggtg   32160
acccacctgc ctcggcctcc caaagtgctg ggagtacagg cgtgagccac agagcctggc   32220
catgttcaga cttctaataa caggtttgta ttgactctta gcctcatggc agaagccaag   32280
agacatgaga cagcttagaa attttgtgctt tttggaaatg aatgttagag ttactggttt   32340
gtgattaagg cctattgcac tgacagaggc agtgaaaaag ggtttgattg ccaaggaaga   32400
ttcacagggc ctagaatggc agtggttatg catctacagt ttattacagg agaaggatac   32460
aatccagtag caggattatg gtaaggatat gcatcacagt caaaggctgt catagcaagt   32520
```

| | |
|---|---|
| catccagaga gttcgggtgc aagttccagt tttcctttgt tgtgtaaagt ctgtggtggg | 32580 |
| gtgcattttc tctctcagag caggatgtgt gcacaggaca ccttggaacc taggagccca | 32640 |
| aaatagagtc ttcactggac ttttaatat ttttcttgtc aagcggacat gttcctgttc | 32700 |
| tctaactagc ctcttcagtg gaggtcagag gaagagcctc attgagacca agtgcaactc | 32760 |
| atcaatcaca tgaaacaatg ctgataaata aaccacctaa atatcccctg acccacaaat | 32820 |
| acaaaacaac accattcaat cagtatttt catgccttga tcagggtca ttgccatgca | 32880 |
| ggaactttaa caaaacagta caggctaata atagaattgt tggaattaac tcacacagca | 32940 |
| cacctatgag agagagttaa gatagagggt cttggtggtc tctaacagtt gaattcaaag | 33000 |
| tgaagttacc agagtaaagt gagcaaagac acatattagt acaatattgg tagataaaat | 33060 |
| cacgttgctc taataagcat agttttaaac tttaaccatg tttctccagt aattttagta | 33120 |
| attatattgt tgttatgtct aatacataaa gcatttttta cttttttaaa aaattttag | 33180 |
| gcaatgtggg gtccaaagta attaaaaaaa aattttttta acataaagca tcttaaaatt | 33240 |
| ttacttaatc atgatcactt agaaccatta aaacatacgt tttgatatta tggggaagct | 33300 |
| tcgttgttcc tttgtagaca gacttaaaga aatacaactt tatgatgaca agatataaga | 33360 |
| taattataga tttaaatttt atagaaacct ttcccttat ctagtgcaag aggtagctaa | 33420 |
| gtgcttattt tctcaaagta ctgtgttata aaaagtattc ctagtgtagt caaagcttct | 33480 |
| ctttagactg ataaaactta gagcacctgc atttacttcc aacaaagcag aattaaagaa | 33540 |
| aatgagactt ggccgggtac gtttgtaatc ccagcacttt gggaggccga ggcaggtgga | 33600 |
| tcatgaggtt aggagatcaa gaccattctg gctaacatgg tgaaaccctg tctctaccaa | 33660 |
| aaatacaaaa aattagctga catggtggtg cgcacctgta gtcccagctt ctcaggtggc | 33720 |
| tgaggcagga gaatcgcttg aacccaggag gtggaggttg cagtgagctg agatcacacc | 33780 |
| actgcgctcc agcttgggca acaaaaaaaa aaaaaaaaa aagaaaaaga aatgagtct | 33840 |
| ttactggctg ggcacagtgg ctcacacctg taatcccagc actttgggag accgagacgg | 33900 |
| gcagatcacc tgaggtcggg cattcgagac cagcctgacc aatatggaga accccattt | 33960 |
| gtactaaaaa tacaaaatta gcggggcgtg gtggcgcatg cctgtaatcc cagctattcg | 34020 |
| ggaggctgag gcaggagaat tgcctgaacc cgggaggcgg aggttgcggt gagcagagat | 34080 |
| cgtgccgttg cactccattc tgggcaacaa gagcgaaact ctccatctca aaaaaagaa | 34140 |
| aatgagtcta tactttgctg ttttcatact ctcttagtgt ggtgtaggca gccatgtatc | 34200 |
| cccccttgtgc ctctatttct ccattctgtg aatgagtgtc ttccactgct gtgcttttct | 34260 |
| gattccgtaa cctttgtttg tttgtttgtt tgtttgtttg tttgttttt attgatcatt | 34320 |
| cttgggtgtt tctcgcagag ggggatttgg cagggtcaca ggacaatagt ggagggaagg | 34380 |
| tcagcagata aacaagtgaa caaaggtctc tggttttcct aggcagagga ccctgcggcc | 34440 |
| ttccgcagtg tttgtgtccc tgggtacttg agattaggga gtggtgatga ctcttaatga | 34500 |
| gcgtgctgcc ttcaagcatc tgtttaacaa agcacatctt gcaccaccct taatccgttc | 34560 |
| aaccctgagt ggacacagca catgtttcag agagcacagg gttgggggta aggtcacaga | 34620 |
| tcaacaggat cccaaggcag aataatttt cgtagtacag aacaaaatga aagtctccc | 34680 |
| acgtctacct ctttctacac agacacggca accatccgat ttctcaatct ttccccacc | 34740 |
| tttccccct ttctattcca caaaaccgcc attgtcatca tggcccgttc tcaatgagct | 34800 |
| gttgagtaca cctcccagac ggggtggtgg ccgggcagag gggctcctca ctacccagta | 34860 |
| ggggcggccg ggcagaggcg cccctcacct cccggacggg gcggctggcc gggcggggg | 34920 |

-continued

```
ctgaccccc cccccgcct cctcccgga cggggcggct ggccaggcgg gggctgacc      34980
tccccgcctc cctcccggat ggggtggctg gccgggttgg gggctgaccc cccgcacctc   35040
cctcccggat ggggcggctg gctgggcaga ggggctcctc tcttcccagt aggggcagcc   35100
gggcagaggc gccctcacc tcccggatgg ggcggctggc cgggcggggg gctgaccccc    35160
ccacctgcct ccaggacggg gcggctggcc gggcagagcg gctcctcact tcccagtagg   35220
ggcggccagg cagaggcgcc cctcacctcc cggacgggc ggctggccgg gcagagggc    35280
tcctctcttc ccagtagggg cggccgggca gaggcgcccc tcacctcccg gatgggcgg    35340
ctggccgggc gggggctga ccccccaca tccttcccgg acgggcggc tggccgggca    35400
gagggtctcc tcacttccca gtagggcgg ccgggcagag gcgcccctca cctcccggac    35460
ggggcagctg gccgggcggg gtgctgaccc ccccacctct ctcctggctg gcggctggc    35520
tgggcggggg gatgacccc ccatctccct cctggatggg gcggctggcc gggcggggg    35580
ctaacccccc cacctccctt ccggacgggg tggctgccgg gcgcagacgc tcctcacttc   35640
ccagacggag tggctgccgg gcggaggggc tcctcacttc tcagacggtg tggctgccgg   35700
gcggaggggc tcctcacttc tcagacgggg cggttgccag gcagagggtc tcctcacttc   35760
tcagacgggg cggccgggca gagacgctcc tcacatccca gacggggcgg cagggcagag   35820
gcgctcccca catctcagac gatggcggc ctggtagaga cgctcctcac ttcctagatg    35880
ggatggcggc cgggcagaga cgctcctcac tttccagact gggcagccag gcagagaggc   35940
tcctcacatc ccggacgatg ggcggccagg cagagatgct cctcacttcc cagacggggt   36000
ggcggccggg cagaggctgc aatctcggca ctttgcgggg ccaaggcagg cagctgggag   36060
gtggaggttg tagcgaactg agatcacgcc actgcacccc agcctgggca ccattgagca   36120
ctgagtgaac gcgactccgt ctgacatccc ggcacctcgg gaggccgagg ctggcggatc   36180
actcgcggtt aggagctgga gaccagcccg gccaacacag cgaaacccg tctccaccaa    36240
aaaaatacca aaaccagtca ggcgtggcgg cgcgcacctg caatcgcagg cactcggcag   36300
gctgaggcag gagaatcagg cagggaggtt gtagtgagcc gagatggcag cagtacagtc   36360
cagctttggc tcggcatcag ggggagacca tggaaagaga gggagaggga gaccgtgggg   36420
agagggagag gagggagagg gagagggaac cttttgtttt attccagtag gaccagctag   36480
aaacagaagg tgattgacca gtattaggga tggaatcagg gtacaattat ggagacaggc    36540
tatctaaaca attcactctc accatttaaa tcagctgttt gatcattttt tttccatata    36600
tctttaccat cgcatagtaa ataatatcct ttttattttc aagagggagt attggccttta   36660
agttaggaac tctcttaatt tttttccccc atcatcccac ccgcacttct tactccttac    36720
ttcctacttg cttttattct ttactggctc tttaccactg cgtattttta ggtgcataca    36780
tctatttttt aaaaagcac ccttgttcct gggtcctctt ccagtaccat ctattaatat    36840
atctctctcc ctctttccac tcccagctgg gtttctgaaa gcgtgcactt cccatcttcc    36900
attcattcat ctggtttcca gccctgacca cagtactgaa atggcatttg ctaggtgacc    36960
tttatttttt tttaaatcca gtgaatgcgg tatagtcccc ccgctttttt ctttcttttt    37020
tttttttgt tttttgtttt ttgtttttt gagacagagt tttgccctt g ttgcccaggc     37080
tggagtacaa tggcgtgata tcggctcacg gcaacctatg cctcccagg ttcaagcgat    37140
tctcctgctt cagcctccca agtagctgga ttacaggcac ctgccaccac agctggctaa   37200
ttttgtattt ttagtagaga tgggtttct cgatgttggt caggctggtt tcgaactccc     37260
```

```
gacctgaggt gatccacaca cctctgcctc ccaaagtgct gggattacag gtgtgagcca    37320
ctgcgcccag ccttggtata gtctttaacg aaagttcact gatcttgaaa attttgatct    37380
tgaaactctt tttttttttt tttttttttt ttttgagatg gagtcttgct ctgtcaccca    37440
ggctggagtg cagtggcaca atctcagctc actgcaacct ccacctccca ggttcaagcg    37500
attctcctgc ctcagtctcc cgagtagcta ggattacagg tgcccaccac catgcctggc    37560
taatttttg tattttttta gtagagatgg ggtttcacta cattggccag gatggtcttg    37620
aactcctgac ctcatgatcc acccacctcg gacctcccaa agtgctagga ttacaggcgt    37680
gagccaccat gcccagcctt gaaactctcc taaggttatg ttaaacattt ttgtattctt    37740
ggttttcttt ttgttccatg ggttattct ctttatcctt ctttttagct ttcttaagtg    37800
ttcctttacc ttatcaaatt ctattttgg ctcccatttc acttaataag aggaaaagct    37860
gggattttt tttttctttt gtggagacag agtctcactt tgttgcccag gctggagtgc    37920
agtggtgcga tctcagctca ctccaacctc cgccttctgg gttcaagcga ttcttgtgcc    37980
tcagcctcct gtgtagctgg gattgcaggc atgtgccacc acgcctggct aatttttgta    38040
tttttagtag agatgggggt ttaccatgt tggccaggct ggtctcgaac tcttgtcttc    38100
caagtgatct gcctgcctgg gcctcccaaa gtgctgggat aaatttgagc cattgtgctc    38160
gtctaagctg ggattctttg aatgagttct tagaggcttc ctgaaacttt gtgcaacatt    38220
ttgtgtatgt gtatatttc tggggaaagg atttgtaact ttctattttt tgagagggag    38280
tctctgtggc tcagggtgga gtgcagtggt gtgatctcgg ctcactgtaa cttctgcctc    38340
ctggttcaag tgattctcct gcctcaggct cccaagtacc tggaattaca ggcatgtgct    38400
accacacctg gctaattttg tattttttagt agagacaggg tttcattatg ttggccaggc    38460
tgggaatttg taactttcat cagatatccc aagggatata tgtctttcct ggtagagagg    38520
gaagaaacaa aaacgtgtg taaatacccct cctctccccc agaaggtaag aagtactgct    38580
ctgcacattc cttgggtgat cttctcact ccctgggata attaaggaag ttaggggatt    38640
gggttgaggg taacttggca tccttcccca acctccctgt ataggcacag tctaatatac    38700
ttgatgcacag tttgcaacaa gtcaacaatt tcctactttt ctggtgttag gtttaagtta    38760
tatagaccta tggtgatcat aacattatct aaatcagatg cttcacatta taggtcttgc    38820
agctgatgtc cagtttaggt gtttgaagtg gcttagcctg gaaaatgtta caggggaaaa    38880
tctgctttcc atgtgttatg ctcagagctg tgttcttttc ttttacacaa tatgtttgac    38940
atttgttgaa tttaggtgt accctggtca ttaggaactc cctaaaggat ctctgtgagg    39000
ttttaaaaaa acaaaacaaa acaaaaaaac agtggcattt tgcagaactc agtatagctc    39060
tttaccatac tgactgcaag gagaaagtaa aaagtgagac taattttgca attagtctcc    39120
caagtttctt tacaagaaaa tagaccaaag gtactatgtt taaaagcaaa atcatggctt    39180
aaaagttttt cttttctta atatattaat atattgctat aaattgagta ttgctctctt    39240
gctatcttgt gttttttgg ttttgatta actctaagct taatgttatt cctgacaaat    39300
aaataaataa ataaataaa aaataaataa agtgaattca gagagacagt agagggcagc    39360
agccgtttag aaagtagatt cacattgagt gattacggc cttttaaatc tttctccact    39420
aagagatagc taatttccga aaaggtatac ttggcctccc atattcctta tgtctcttaa    39480
aactaaaaaa gctgggacaa aacttaaaat aacagtattc tacggttagg gcaaatttct    39540
gatactgctt aaaacaattt accgaggtat ctttattttt ttttgagaca gggtttcact    39600
ctgtcaccca ggctggagtg ctggagcctt gacctcctgg gctcagctca agtgttcctc    39660
```

```
tcacctcagt ctgccaagta gctgggacta caggcatgca ccatcattcc caactaattt   39720
tttaaaattt tttgtagaga tgggggtttc atcatgttgc caggctggtc tcgaactctt   39780
gggctcaagc aatctgccca cctcgtcctc ccgaagtaca gggttatagg catgagccac   39840
cactcccagc ctcagatttt tttattgatg aattttatta taacagctac aatactgaga   39900
tgcataaccc ttccctttcc tgatacccag ttatcatctg tttctgttta atacactcct   39960
taagtacctc acatttgcta ttcccctgcc ccccatggtc tatgcatctt cttcattgaa   40020
gtggtagtag tctttgttag ctcatctggt catgtcatca attcagagca cattacctct   40080
ttagttcaga acacattaat tgcttcccat aatcttcagg acacggcccc atttcttcac   40140
gtggcttggc cattgcttcc ctgttcagct tcccccacac tccctcacct acaccttctg   40200
tctcagtata gtactgctag tctccagaca tgccatgcct ttttatgctt ctatgcgtgt   40260
tttcctgtct ttaatgtcct tgtccatgtg atgaacccct actcatttt ccaagattga    40320 actcaaatgt cacctttct gtgagcttct ctgctcttct catgcagagt agaagtgttt    40380
atctccattg cccttgaccc taaataacag tacattagta taataatcac attttttacc   40440
tgtttgtgtg ctttccttct aaatggagaa taagaatata aaagtgattt atttggcatt   40500
tctgcaaagg gagatgataa aaagaatctg cgttacttag cctttttaaa aaacccttag    40560
cctatgaagg ctactattta aggtttggtt ggattttgta tgttggaaat atgttcttta   40620
aatctcatct tcatcagttt ataaaagcaa tataagttct ttgtagatca ttatcatgcc   40680
atccagatgt agtcattatt gttttgatat aggttgtttc agtctttaaa ccaaattata   40740
cactgttccg ctgtaactct tgttttgaaa acagatttgt tccaatgtgg gtggtatatt   40800
agggaacaat ttgagcataa tgtaaatttt gagtttgctt atgcacaaat ccctaggcaa   40860
cactaggtga atgcagaaaa atgcatgcag ctgaactcag cagtgtagat atatacaaaa   40920
gatacacata cacacgctct tcaaatacct accttatttt cctgtatgtg ttatgaacca   40980
tacccattca catctggtat tacaactttg ccacccattt cagacagtat tcctttgacc   41040
attctgcagt aactcagaag ctgcagccct ttagaagtct actccactgt ggctcacgtc   41100
tgtaatccca gcactttggg aggccgaggt gggtggatca tgaggtcagg agatcaagac   41160
catcctggct aacacggtga aaccccgtct ctactaaaaa aaaatagaaa aacctagccg   41220
ggcgtggtgg tgggcatttg tggtcccagc tactcgggag gccgaggcag gagaatggcg   41280
tgaaccgggg aggcagagct tgcagtgagc caagattgcg ccactgcact ccagcctggg   41340
cgacagagcg agagtccgtc tcaaaaaaaa aaaaaagaa aaaagaagg ccactccaca     41400 agcaaaccgc agatgttttg caaggtgact tatttattgt aatagttgtg tatttcttaa   41460
ccatttcaca tgtataaaac tgtgctacta cttttatgag gttcctgtct ttattttttt   41520
taacatgtcg ctggtgaagg ttctgagagt tgtggcttga actccagttt tctcataagc   41580 acggttttt gttgttttt tttgaaatgt tctcgctgtg ttcccaggc tggagtgcag      41640 tggtgtggtc tcggctttct gcagccttgg cctcccagct taagctatcc tcccacctca   41700
agctatcctc ccacctcagc ctcccaaata gctgggactg caggcgtgag cctttgccca   41760
cctaattttt atacttttgt agagacagtt tttccatgtt gccaggctgc tttggaactc   41820
cttagctcaa gcaatcagcc cgccttcacc tcccaaagtg ctgggattac aggtgtgtcc   41880
taccacaccc agacggctct ggtatttact gcatagtgtt ctgattttta ggaatacata   41940
cgttgcatta tatagcagaa ctggctgtat tcaaaagtct aatagaaaat attgataggg   42000
```

```
tgataatgta tatagtacta attgtcagtt gccataattt aactaatatt gttttacttt    42060 ttacttttt  ttttttttgag atggggcctt gctatattac ctaggctggt cttgaactcc   42120
tgagctcaag gaatcctctt gcctcaacct cctgaggatg tttgacatt  tttgactttt    42180 ttttttttt  ttttgagacg gagtcttgct ctgtctccca ggctgagtg  cagtggcatg    42240 atctcggctc actgcagcct ccacctcccg ggttcaaggg ttcaagcact tctgcctcag   42300
cctcctgagt agctaggatt acaggtgtgc accaccacca cggctgattt ttgtattttt    42360
aatagagatg gggtttcacc atgttggtca ggctggtctt gaactcctga cctcgtgatc   42420
ctcctgtgtc agcctcccaa agtgctgtgg gtacaggcgt gagcctccat gccgccggc    42480 tttttggcaa tttaaatagt tacagttacc tattataatt gatatttagc taacatctat   42540
ttttatttta atattccagg aaattattat gcagaaactt taaaggtctg tgtacttctc   42600
tggtgttttg attttttttt tttctttttc tgtgagtaat tttctaaaac tggtttctag   42660
gccaggctat ttatgtcttg cttttttattt tttttggcga tggagtctcg ctttgttgcc   42720
caggctggag tgcagtggcg ctatctcatc ttgctgcaac ctctgcctcc tgggttcaag   42780
cagttatcct gcctcagcct cccgagtagc tgggactaca ggcacatgcc accacgcctg   42840
gctagttttt tgtattttta gtagaggtgg agtttcaccg tgttgcccag gctggtctgg   42900
aacttctgag ctcaggcagt ctgcctgcct tggcctccca aagtgctagg attacaggtg   42960
taagccactg ctcccagcct tattatttta tttttatgga ttcggggtat atgtgcaggt   43020
ttgtcccatg gatatattgt gtaatggtga gttttggact tctgttgtgc ccatgaacat   43080
tgtacccaat aggtggtaat ttttcaattc tcatccctct ctctgcctct gccctttgg    43140 agttcccagt atctgttaat tctctctgta tgtccatgtg tacccattgt ttagctcctc   43200 tatttttat  tttatttat  tttattttg  agacaagagt cttgctgtat cacccaggct   43260
ggagtgcagt ggtgcaatct cagttcactg caaccttggt ctctgggttc agatgattct   43320
cgtgccttag cctcccgagt agctggaatt acaggtccgt gccacgatgc ccggctaatt   43380
tttgtatttt cagtagaggt ggagtttcgc catgttggcc aggctggcct caaactcttg   43440
gcctgaagca atccgcctgc cttggcctcc caaagtgctg ggattacggt gtgagccact   43500
gctcctgacc ccatatttt  tcttttaatt ataaaggtaa taatgtaaaa agaagtcaac   43560
tcccagttta actctagcag agtaaccagt gttaattttt ttttttttt  ttttgagacg   43620 gagtcttgct ctatttccca ggctggagtg cagtgatgcc atcttggctc actgcaactt   43680
ctgcctcctg ggttcaagcc attctcgtgc ctcagcttcc tgagtagctg agattatagg   43740
cgcccagtgc cacgcctggc taatttgtgt atttttagta gagatggggt ttcaccatgt   43800 tggctagget ggtgttgaac tcctgacctc gtgatccacc cgcctcgatg ctgggattac   43860
aggcgtgagc cactgagcct ggccaatcca ttccttttta tggctgagta gtattccatt   43920
gtgtgtgtgt gtatatatac atatatatac acacatatac atatatatac acgtatatat   43980
gtatgtatgc gtatatatgt atgtgtgtgt gtatatatac acatatacat atatatacac   44040
ctatatatgt ggtatgtgta tatatatgtg gtatgtatat atatgtggta tatatatgtg   44100
gtatgtgtat atatatatgt ggtatgtgta tatatatatg tatatatgtg tgtatatatg   44160
tggtatgtat atatatatgt atatatgtgg tatgtatata tgtatatatg tgtgtctgca   44220
tatatgtata tgtgtgtata tatacacgta tatgtgtata tatacgtata tatatgtgta   44280
tatatacata tatacgtata tatatacaca cacacatata tatacacata tgcaggcaca   44340
catatatata catatatata tatacatacc acagtttctt tatccacttg ttgattcatg   44400
```

```
ggcatttggg ttggttccac gttttttgcaa ttgtgaattg tgctgctata aacatccgtg   44460
tgcaagtatc tttttttgtat aatgatatct ttccctgg gtagataccc agtagtggga   44520
ttgctggatc aactggtagt tctactttta aggaatctcc acactgtttt ccttagtggt   44580
tatactggtt tacattccca ccagaagtgt agaagtgttc cctgttcact gcatccacac   44640
caacatctat ttttgatttt tgattatgg ccattcttgc aggagtaagg tggtatcgca   44700
ttgtggtttt gatttacatt tccctgatca ttagtgatgt tgagcatttt tttatgtttg   44760
tttgccattt gtatatcttc ttgagaattg tctattcatg tccttagccc atttttgat   44820 aggattgttt gttttttttc ttgctagttt gtttgagctt gttgtagatt ctggttatta   44880
gtcctttgtc agatttatag attgtgaaga ttttttttccc actctgtggg ttgtctgttt   44940
ttgtctgttt ccttctgctg actgttcctt ttgccatgca aaagctcttt ttttttgaga   45000
cagaatctcg ctctgtcggc caggctggta acaaagacac aggtactggt ataactgcc   45060 atggcttatt gcctacatta atgatgaaag caaatgctaa atttcagcta gaggctagag   45120
aaaataagcc tggaattttc ttttatgttt atatactgct atgaatacca ggagtccttg   45180
ggttaagact gtagggcttt ctaaagcctg tgatcactag tggagaatgt agctttacaa   45240
agtctagttg gaaattggca actggggtt agtacaagtt acaaggaagg gatggaatt   45300 aagatgctag tgaaagcttg gaggataagg gagcaggtga actcataagg aagtttatga   45360
actgagaagg gctgcagcaa agtgggctca tgtgcttgag gagccagagg acatgttgag   45420
ggtgacatag gttctgaagt tcgtacagat acttatgcag tatggattct tggaaaacct   45480
tctttagtca tgtgatagaa aaataacagc ttatggaaaa aacagggttg aggcagacct   45540
gaaaatacat gaaattttaa aaaccgcttc taacagaagc ataacagact gtaataaaaa   45600
ctgtggcctt cctggcattt gcacccaaac aacagcatta gccaactctt tgaagcctta   45660
gatctgtggc tcttgttttc tcctttgagg tgtaggtcct tgagggcatt tgcttctaat   45720
agaggctagt ttcatcagaa ttaaaaatct gaaccatggt atgaaattca attcttttt   45780 ttttttcttt tttgaaaaca ctggcaaatg ttttgtatcc ttgagctttc ccacatatct   45840
taacatagtg agtggaaagt acagtggctg ttaagccaac tactctgagg tcttcactgc   45900
taaggcttac tcttaattgt gtgagagctt aaccttgatc cctttaaaac attaatgggc   45960
tagaaaaaaa accattcata aaccagtgcc acctctgaat tttgctacca caattcctt   46020 atttaccaat agtgcatgag ctaatttgga ataaagaact aggcattgta gcacaacaga   46080
cattatgtgg gcaaagtgtt gtttatattc tgtctaaata gtgcttcaca tgtatgtact   46140
attttctaaa tatgtataga tgcttttgtg attaataata aaacatgaat tcttaaaaca   46200
attttgctga cttcatagta gcttttcacc gtttttttcag tagctgctaa aatttctgga   46260
gaagtttggg aactattgtt ttggagtgaa atgcagtgtg ttagatatca cttgcagaat   46320
tcttctaagg gtatttattg gcgattagaa aaaaatcct tgtgttatac cagtagtaat   46380
acaaagtaat tgttcagctt ctgttaagtg taaaggacta tacaagtatt gtgtatagtt   46440
atctcattta ttatttttctg ggtagctatt gttattatta cttcgtacaa aaagggaaaa   46500
ggaggctcaa agtatcatgc tccagataac agagccagta ggtagcagag ctgggattgc   46560
tacccaggtc tctagtcctg cttttttcaca ctatatactc attgcttcac ttactccttc   46620
atacatgatt ccccagcatg tactctttt tttttttttt tttttttgtt tgagatagaa   46680
tctcgctctc tgttgcccag gctggcaggc agtagtgtga tcttgggcta actgcaacct   46740
```

```
ccatctcctg cattcaagca gttctcctgc ttcaacctcc tgagtagctg agattataag    46800
cctatgctac cacgcctggc taattttttgt attttttagca gagatgaggt ttcgccttgt   46860
tggccaggct ggtctcaaac tcctgaactc aagtgatctg cccacctcag cctccgaaag    46920
tgctgggatt ataggcatga gccatcatgt ccggcctccc catcatgtac ccttaaatac    46980
catcaagcac agttccattg tgtaaaaact tggcttgatt taacctgtta attggaacac    47040
tgtcattaat ggaaattagg aatatgaggt aagctagagg ttttatttta atgactttgg    47100
gttattaaat ctataagaaa tgaaattcat ttagtcataa ttaatgtcat gtttctgcat    47160
ctatattact tgttgggttt acagacgagg tagtgtatta ttagtgggaa gctttgagtg    47220
ctacatcatc tcccttttcta taaaataaat tgagtacgaa acaatttgaa ttaaaacacc    47280
tgagtaaata gtaactttgg agacctgctg tactatttgt accttttgga tcaaatgatg    47340
cttgtttatc tcagtcaaaa ttttatgatt tgtattctgt aaaatgagat ctttttattt    47400
gtttgtttta ctactttctt ttaggaaaac accagaaatt attgttggca gtttttgtga    47460
ctcctcttac tgatcttcgt tctgacttct ccaagtttca ggaaatgata gaaacaactt    47520
tagatatgga tcaggtatgc aatatacttt ttaatttaag cagtagttat ttttaaaaag    47580
caaaggccac tttaagaaag tttgtagatt tttctttttta gtatctaatt gtagcaccttt   47640
tgtggacagt ggatgtaata ttaagtgaca gatgggaaaa ggattttttaa aaaaatagca    47700
actgtttcag tggatgaaat aaagattatt agcagagaaa atgaatattg gcataactg    47760
tcctggtgaa agacaatctc ataaatgaac aatttcataa tttcgtaaat gcaactgcat    47820
tttattttca aagagaagga aaattatagt cactggaaac ggaaagagaa gttagaggta    47880
aacataggac acacaagaaa actttcattt tgtttatttt cttgttttttc ttttgagaca    47940
gggtttccct ctgttaccca ggcttaagtg cagtgacact atcatagttc actaaccccct   48000
caaattcctg ggttcaagta atcctcctgc cttagcctta gtaggtgtaa atacaggtgt    48060
gtaccaccat gcctggcgaa ttttaaaaaa acttttttat agagatgagc tctcgccgtg    48120
ttgcccaagc tggtcctaaa acgctggcct caagctatcc tccggcctca gtcttagcct    48180
cccaaaatgc tggggtttca gtagaagcca ccatgccggg ccacttctgt ttcttttcca    48240
tgtagagttc tttgcaggag gaggttagaa taggtgtgca tctcctaaat agttgtcgaa    48300
tataactaaa aagttaacca ggactctaaa tactatttac ttctaaaatt tgttaattgg    48360
gaacatttag ggtttaactg atctatatct tatgtcttta acaatttga atgataatta    48420
tatgtaaagt aagaacagtt tgtgaaatag ttgaaaatat ccttacatga aagtgaattt    48480
taaagcacag tttatgtaat gttaatgttt tgttttgtat ctgttaaaaa tttgtttata    48540
tgaacaagtt tacaggttta ctgtggtgag cccgttgaat atagtgggtt ttttttgttt    48600
gttttgtttt tgtttttgag atgaagtctc actcttgtcc cgaggctgat gtgcaatggc    48660
gcgatcttgg ctcactgcaa cctctgcctc ctgggttcaa gcgattctcc tgccttagcc    48720
tcccgagtag ctgggattat aggcacctgt caccaaaccc ggctaagttt tgtatttttg    48780
gtagagatgg gatctcagca tgttggccag gctggactca ggtgatccgt ctgcctcggc    48840
ctcccaagtg ctgggattac aggtgtgagc caccatgccg agcctgaata tagtgttttt    48900
aagttgcagg actttaaaaa taatattttg aaattttct aagttaaatt ccctgttaaa    48960
atggtcatgc aggaatatac gcttgcatta ttcatattag ggtaactgtt tggtttgcta    49020
gttgttagat tctttgcatt cctttttttt tttttttttt tttttttttt tgagacggag    49080
tttcactctt tttgacaagg ctggagtgca atggcgctat ctcggctcac ctcaacctcc    49140
```

```
gcctcctggg ttcaagcgat tctcctgcct cagcctccca agtagctgga attacaggaa    49200
tacgccacca agcccggcta attttgtatt tttagtagag atggggtttc tccatgttgg    49260
tcaggctggt ctcaaactcc cagtctcagg tgatcagccc acctcggcct cccaaagtgc    49320
tgggattaca ggagtaatcc cccacccttt taaaaaaatg agacagagtt ttattctgtc    49380
acccagggtg gagtgcagtg gtgcgatcat ggttcaccgc agccttgaat ctgggctcaa    49440
gtgatcctcc cacttcagcc tcccaagtag ttggaaccat agatgtgcat caccacacct    49500
ggctgatttt taaattattt gtagagatga ggtcttgctt gttgtctagg ctggtcttaa    49560
acttctgggc ttcagcagtc ctcctgcctc agcctcccag agtgctgaga tgatagacat    49620
gggccactgc ccctggccgc attttctttt tcttttcctt tcttttttttt tttttttttt    49680 tgaaacggag ttttgccatt gtcgcccagg ctggagtgca gtggcacgat ctctgctcac    49740
tgcaacctct gcctcccgag ttcaagccat tcttctgcct cagccttcca gttatctggg    49800
attacagtca tgtgccacca cgcccagcta attttgtat ttttagtaga aacagggttt    49860
ctctatgttg gtcaggcttg tcccaaactc ctgacctcag atgatccacc tgcgtctgcc    49920
tcccaaagtg ctgggattat aggcgtgagc caccatgccc ggccctaact gcattttct    49980 tagtatttgt ggtttgagtt aatacttgcc ctatgtgatg ttgatttatt attactggat    50040
cattaagtga ggtttaaaga agctaaatgc catttgctct atgccctctg gattttaaaa    50100
gtgcatgggt gtgcacgtgt gtaggtataa atgtttccat attctagtat attctgtgtc    50160
agtgatagag cagtcttaga gctgtctttt ccatttactt gtaggttaag aagccaaaaa    50220
aagttgtgtc atcatcccgt ttaggaaaac ttacattttg gctattgttt cctctagtgc    50280
tgctattagt ggaatgattt taggtgttca actttcagat caatgggaga cagaaatatt    50340
gttctgagac atctggaagc cgaatgtgtt ttattcctgc ctgtctgagg atgtggtctt    50400
gcctttgata gggcaaagtt atttgtaaac attgctttaa ataaaaacat gtaaggtgt    50460 ttttgatggt taacaaaaac tatgagtata atagagccta gtccctatta cggactggta    50520
ttgatctggt gtgggaagag tattgagctt ttcagtgtca cctacctgta ttcccttgaa    50580
gggacccaga gcccaggcaa agctctgctg aggtcgggcg tggtggttca cgcctgtaat    50640
cctagcattt taggagacca aggcgggtgg atcacctgag gtcaggagtt caagaccagc    50700
ctagccaaca tggtgaaacc ctgtctctac taaaaataca aaaattagct gggtgtggtg    50760
gtgcatgcct gtaatcccag ctatctggga ggctgaggca agagaattgc ttgaacccag    50820
gagacggagg ttgcaatgag ccgagatcat gccactgcac tctaggtggg tccctgagtg    50880
agactccatc tcaaaaaaaa aaacaaacaa aaaaaaaaa aaaaaaaaac ctctgctgaa    50940
atgctacagt taattttgcc atttgtggtc agcattcttc ttctaaattg ctataatctt    51000
gccttcatat tatgtgtctc aaatttaagc aggtatcaga atgtccacgg gaacaaattg    51060
ccatggctct aagcccagaa tcagattctt cagatctgga gtagggctgg ggaatttgca    51120
tttctaacac acaagtttgt tgatgctgtt tgtctggggt ccacgcttgc ctaacttctg    51180
atgtgattta tttctgccag tttctttttt tgttgttgtt ttatttttt gagatggagt    51240 ctcgctctgt cactcaggct agggtgcagt ggcatgatct tggctcactg caaccctgc    51300 ctcctgggtt caagcgattc tcctgcctca gcctcctgag tagctggggt tataggcaca    51360
ctgcaccaca cccagctaat ttttgtattt ttcgtagaga cagggtttca ccatgttggc    51420
caggctggtc ttgaactcct gacctcaggt gatccattgg cctcggcctc ccaaagtgct    51480
```

```
cggattacag gtgtgagcca cccaccatgc ctggcccttc ctaccaattt ctatcctccc    51540
tgaaatgctg cacacttagg cagtcactgg acaatatctg ccccaaaatt ggtttgtata    51600
attgagaata tttaagaggt tgttaaaatt tgaaccactt tctattcttc tattaagtgt    51660
acacatctat taaagatccc cttgtagctc tttttatctg ggccatcaca tttctgccca    51720
gcagatgcag aggccctgtc ctctcttcca cctccccact acctctcctt ccctactttt    51780
ggactgtaaa agctgtcttt ctgcagttaa ttgttttatt ctttgtaggt tctactcgtt    51840
gataatgtta tctactgcta taataattac agacggcaac aggatgatca aatcttggat    51900 atttttaaatt tacattatgc ctttttttatt ttatttttttt aaagtctctg cttgacagca    51960
aataagccta acgttcccta acaaatgatg atgtcccatt aatgatttga tgacttcctg    52020
tttgtagttt ttatttagag tgcttgtggg tagttttttca taacgacatt taaaaatcag    52080
gatataaata atttttttaag ttttttttttt aggcggggca cagtggctca cacctgtaat    52140
tccagcattt tgggaggctg aggtgggcag atcttgtgag gtcaggagtt caacaccagc    52200
ctggccaaca gggcgacacc ccatttctac taaaaataca aaaattaggc cgggtgcggt    52260
ggctcacacc tgtaatccca gcactttggg aggccgaggc aggcagatca caaggtcagg    52320
agatcgagac catcctggct aacacggtga aaccccatct ctactaaaaa tgcaaaaaat    52380
tagccgggca tggtggcagg cgcctatagt cccagctact cggaaggctg aggcaggaga    52440
atggcttgaa cccaggaggt ggagcttgca gtgagccgag atgcgctgc tgcactccaa    52500 cctgggcgag agtgcgagac tctgtctcaa aaaataaac aaataaaaaa taaaaaaatt    52560
aaccaggcat ggtggcgcat acctgtagtc ccagctactt gggaggctgg gacagtagaa    52620
tcgcttgaac tcgggaggtg gaggttgcag tgagctgaga tcacccactg aactccagcc    52680
tgggcaacag agcaagactc tgtctccaaa aaaaaaaaat gtattttct ttgaagcttt    52740 tctactttta aatgtaatgt atagtattat aacaagtgaa caaaatgata caaagaagta    52800
tggcgggaaa ggtgtggtag agatgggaaa acatatttcc tccagcctct taggttcatt    52860
ggaggagctt gggaattcaa ctgacacacg acagatttac aggagaaaag ttttatttca    52920
agtacacatg agagcttcat agaaaagaag tgaagaccta agaaacaga ctggagagtt    52980 catatgccat tttaataaag gataatgtat tagtctgttc tcatgctgct aataaataca    53040
tacccaagac tgggtaattt ataaagaaaa agaggtttaa tcgactcaca attgcacatg    53100
gctggggagg ccttacaatc atggcagaag gtaaggagg agcaaaggca catattacat    53160
ggtgtcaggc aagagagtgt gtgcagggga actgcccttt ataaaaccat cagatctcga    53220
gagacttatt caccatcaca agaacggcat gggaaaaacc tgccccgtg attcaattac    53280 ctcccaccgg gtccctccca tgacacatgg ggattatggg agctacaact caagatgaga    53340
tttgggtggg gacacagcca agacatatca gataataaat tgtggagagg cagtaagatt    53400
gaagaaaaga ggtttgagct tcgagggggtg gtaaattgtg ggaaggtaat tatttggggc    53460
aaactaatgg cacataagga ttgttttagt aaggcttgtt atgcatacccc aaaacaagtg    53520 ccatctccag taatttaaga gtctatggtg atcaagagta gttctcttcc tgctagaaga    53580
ggggtgggga agaacacctt cacaaaggga aatttatatt ctgccttcat gcagaaaggg    53640
ggcgagcaga gagttcctac gtatactgtt tcttcattat cttcctctca aaagaatact    53700
taggctaaag tggcatgatt tggggtgaca ttctgatcct cttcagtgac aatccttgat    53760 attttttcctt ctttctctcc aggtaaacag tgttaacatc ctggtatgct tccccccaatt    53820 ccattatact aactctgtat tgtgggttaa agatttttta cttttgatcag cagtatttga    53880
```

```
aacatacctg ttatactaga tgtactctga ctgtaaaata gtggtcagtg ttacttcttt   53940
aatgatgctg tgggattaaa ggattttatt ataaatgctg ggaagagcct ggatttgagg   54000
aaggtaagca gtgcagttag gtggatgtag actagaagag gtcatttgtt ctcatttcat   54060
tgttgcccct atgacatgcc cgtttctttc ttttttttct tttttttttt gagacggcgt   54120
cttgctctgt cgcccaggct ggagtgcagt ggcgcaatct cacctcactg caagctctgc   54180 ccccgggtt catgccattc ttctgcgtca gcctcccgag tagctggaac tacaggcgcc    54240
tgccaccatg cccagctaat ttttgtatt ttcagtagac acggggtttc accatgttgg    54300
ccagggtggt ctcaatctcc tcacctcatg atctgcccgc ctcggcctcc caaagtgctg   54360
ggattacagg cgtaagccac tgcacccagc ctacgtgccc atttcttaaa gtagaaaatt   54420
tagtagttga tgatgtcagg gaagaaaagc ttttctctg ccttacgtta agtagttggg    54480
ggcaaattaa attaataaaa gacagattag tgagagaaaa ggctgtaaga atttggactt   54540
tatataccat cataatagag gaagtaaagg gagatgaagg gcacttaagg gaaaacagat   54600
gacttgtagg aaagataaat gaacccttaa gagaatagat gagaaatatg aaggttttgt   54660
gacaatgtct gtttaggtgg ttacttctct tcttgttatg agagtcagtc ttctggttgc   54720
tggaaactgc taggagattt ataacaattg ggctcttttcg agaggctctt cttttaagca   54780
gataagggag ttcacaaaaa agcctgttct caaatgattt cagcacacac acacacacac   54840
ttacgacaca gttaagtact gtgccagtaa gatgtgagtt gtgcatttct ttttttttctc   54900 tgagtagact gtttgaggtt atttatatca ggacttgtta tgcaggtaac tgaaaactca   54960
acataatcta ggttatgtag ttaaaagtat ggagagaagg taggctttat ttagagttgc   55020
ttgatcctgt agatctcttc tacctttgt aattttaatt tcaaccaagg atggttccct    55080
ttttggccct aggaccagtt agcagttggg gcaccattcc aagcaagagt cctgcagttt   55140
gtagtgatgg gaccatttaa acagtgattg tgaccaggga catagaatgg gatgattggc   55200
ccgaggtaac catggttggg tatggagtca gcttccctgt aggaagagat agacaaagtc   55260
tgagcactcc tgggaagggg gaggaaggga ataactgttg tgtaaatcat cagcagtgtc   55320
tactaagata ccatctgtaa ccataggctt ctatgtttta taatataagg ctgtctttta   55380
aataaatcag attccctgtt aaagatctgt tctagattcc ctaggggggtt gacctcatat  55440 agtatcttct ttttctttgg ttacaaactt ttaaacttgt ctgaggttat aaggtgaatt   55500
caactgtcca ctgtcaatgt agatattttt aatggattta gggatttaaa ttacatgatt   55560
cagaaccact ttgaggaagt ctagggaata tcagttgttt ctgtataatt tctgaaagct   55620
tcactgtttt ctaggtgtgc acttaattca tgtgatgaag ggaacagtat ttacatgagt   55680
ggtttggtta atttttcccc tcctaagctt agctttgtgt atcgtgcgtg cttccagtgt   55740
ttttgtggct gctttacata agtctttttag aagtattttc tattttttgaa gtaaatgtgg  55800 atcaaaacca ccccaagaca ggattgaaaa aaagacagtt tttcgcaaga aagtaaataa   55860
ttttatttag cttgggactt taaatgatat gtcttaaatg taaacatttc tatactgcat   55920
tttggccatc ttttgatact agttttcaga tgcatattgt tatttcattt attattggaa   55980
aagtagtaac tttaaacaaa ttttttattga aaatgctgac agaggccgag tgtagtagct   56040
cacacctgta atgtcagcac tttgggaggc cgaggcgggc ggatcacgag ctcaggagat   56100
caagaccatc ctggctaaca cggtgaaacc ccgtctgtac taaaaataca aaaaattag    56160 ccgggcatgg tggcaggtcc ctgtagtccc agctactcag gaggctgagg caggagcatg   56220
```

```
gcatgaatct gggaggcgga gcttgcagtg agccaagatc gcgctactgc actccagcct   56280
gggcaacaga gcaagactcc atctcaaaaa aaaaaaaaaa aagaaagaaa atgctgacca   56340
aaaaaaatga aatagtttta aagaagccac agttgtgtga tcctgataca actatatcat   56400
tattgtatga gtatatatga gttataaaaa tagtatatgt aaatgcttca taattttttat  56460 tattagaaat gaaaaagtat aacaaggggg gtattcatat tctctccact tagaattaac   56520
cctcaacatg ttgacatctt tgtttatagt aatccttttt tgttttttt gtttttatt     56580 atactttaag ttctagggta catgtgtaca atgtgcaggt ttgttacata tgtatacatg   56640
tgacatgttg gtgtgttgca cccattaact cgtcatttac attaggtata tctcctgatg   56700
ctatccctcc cccctccctc cacccctcaa caggtgtgtg atgttcccct tcctgtgtcc   56760
aagtgtcctc attgttcaat tcccacctat gactgagaac atgcggtgtt tggttttttg    56820
tccttgcgat agtttgctga gaatgatagt ttccagcttc atccatttcc ctacaaagga   56880
catgaactca tcatttttta tggctgcata gtattccatg gtgtatatgt gccacatttt   56940
cttaatctag tctgtcattg ttggacattt gggttgattc caagtctttg atgttgtgaa   57000
tagtgccgca ataaacacac gtgtgcgtga gcctttatag cagcatgatt tataatcctt   57060
tgggtatata cccagtaatg ggatggctgg gtccaatggt atttctactt ctagatccct   57120
gaggaatcgc cacagtcttc cacaatggtt gaactagttt acagtcccac caacagtgta   57180
aaagtgttcc tatttctcca catcgtctcc agcacctgtc gtttcctgac tttttaatga   57240
tcgccattct aactggtgtg agatggtatc tcattgtggt tttgatttgc atttctctga   57300
tggccagtga tgatgagcta tagaaatcct ttttagaaac aacagagcct tgttgtaaaa   57360
caggtaaatg tacgtgagga cttcaaaaag tttgtggaaa aatggaatta aagataaaa    57420 tttaaaaaca cattttaaat ttatttccca acataagctc ctcaagttca agacacttt     57480 ataaatgatg atctcagctg tttagttcat ccgtaaagaa ctgagggtac tagaaatttt   57540
accatgtcaa tgcagtctct ttacattact aactaaagaa aaataggtgc tctttaaaga   57600
tcttttaaga ttaggaacaa aaagaagtca gaagaagcca aatcaaggtg gatgcttaac   57660
gactttccat agaaacttac aaaattggcc ttgtttgatg agaagagcgt gcaggaacgt   57720
tgtcatggtg gaaaaggact ttgatgatgc tttccctggc atttttctgc aaaaacttgg   57780
gataactttc tcaaaacact ctaataataa gcagagctta tgttctttat ccccccagaa   57840
catcagcaag caaaatgcct gaacatccca aaaaactgtt gccatgacct ttgcccttga   57900
ctggtccact tttgcttcga ctggaccact tccatttttg gtagccattg ctttgattgt   57960
gctttgtctt caggatggca ttggtaaagc catgttttgg ctcctgttac agttctttga   58020
agaaatgctt caggatcttg atcccttgtt taaatttcta tggaaagctc tgctcctgtc   58080
tgcagttaat ctgggtgcaa cagttttgtc acccatcaag tgaaaagttt gttcagcttt   58140
aatttttcag tcagaattgt gtaaactgga ccaattgttg agatgcctgt agtgttggct   58200
attgtttctg ctgttagtca ttagttctct tcaattaggg aatgaacaaa attaatttt    58260 cctgaaaaat tgatgtggat ggtctgccgc tgtgggcttc atcttcgaca tggtctcatc   58320
ccttgttaga acaagttatc cgtttgtaaa ctgctgattt cctaggagca ttgacccat    58380 aaaattttca taaagcatca gttatttcat tattcttcta tgcagacttc actataaatt   58440
tgctgttggg tcttacttca attttagcag aactcatact gctctgacat ctaaactgat   58500
gtcttagcct tcatagtgtc tctgactaga tcctattcag acgtgttata gcaaattagt   58560
aaagtttatt ttggtgccaa aaactttgga atccacgcat agttttttca caacacattt   58620
```

```
tccatgaact ttttgaagac ccttcatata ttataagaag aaagttaaaa atatcccctg    58680
catctactac tcagaaataa ccactgttaa cattaagtct gttctcaact ctaggcatta    58740
ttgagggttt tgaggacagg tcttgaaaat ttctatggct accttttact gggtggagac    58800
tagcatgtat agttgaccgc ataggttaat ccctccactc aaaaagccac aattttaaag    58860
tgtagtattc actagcattt agtatattca cagtgttgtg aaatgaccac caccatctag    58920
tttgaaaata tttcatcaca accaaaagaa aacctcatat ctattagcgg tctctcctgt    58980
ttccccagac accggcaacc actaatgtac ttttttgtctc tgtggacttg tcagttctgg    59040 acatttata taaatggaat catgtgacct tttatgattg acctctttca cttagtataa    59100
tgttttagag gctcatccac attgtagcat gtgtcagtac ttcatttcct tgtgtattgg    59160
tccattcttg tactgctata aagaaatagc tgagactgag taatttataa agaaaagagg    59220
tttaattggc tcatggttct gcaggccgta caggaagcat gatgatggca cctgctcagc    59280
ttctggggag gcctcaggaa atttaaaatc atggcagaag gggaagtgcg gcgtcttaca    59340
tggtggagca ggagcaagag agagaagggg gaggtgctcc acactttaa acaactagat     59400 ctcaggacaa gtcagtcact ataatgagaa cagcacccag gggaaaccgc cctcacgatc    59460
cagtcacctc tcaccaggct ccacctccag cactggggat tccagttcca attcaacatg    59520
atacttgggt gggggcacat atccagacca tatctcctcg tatagctgaa tagtattccc    59580
ttatatggac ataccacatt tattattaat ttattgattg attgacagga tcctgctctg    59640
ttgtccaggc tggagtgcag tggtttgagc atagctcact gcaggccttg aattcctggg    59700
ctccagtgat cctcccacct cagcctcctg cgtacctgag attataggtg tgtgccacca    59760
cacctggcta atttttttta ttttttagca gagacagggt ttttgctatg tttcccaggc    59820
tggctttgaa ctcctgggct caagcaatcc tcctgccttg gcttcccaaa gttgtaggat    59880
tacaagtgtg agtttagaga ggtataattt cttactcaac ttcaagtatt ttatttctct    59940
tatcatttgt tgtttggttt gttaattatt tggaagtata tttttaaatt tccaagctta    60000
gtgtgtgtca gttcataaaa agttccccat gtatttaaaa attggatgtg tactctaatt    60060
ttgggattgc ttttttcattg tctatatatg cttgctaatt tttgatctgc tgggttactg    60120
agaaggatgt gggtttctcc atctagttct attttttggtt aatatgttag gcacagagct    60180
gttgtttttt tgtggtgaat tgaatcttca tcattcttta gggactctgt ccttaataat    60240 gcttttttg ccttacattt tgtttcattg taagagagct atgtcagagt acttttaaa      60300 acactttta atatggtata tattttttc tttttaatg aggttttta accgtaagtt        60360 taagcaaaat aaagcttaat aactggattt tatttagttt taaatttaat ttgatttttt    60420 ttttttgag actaagtctc actctgtcgc ccaggctggg gtgcagtggt gcgatctcag    60480
ctcactgcag cctccgcctc ccgggtttaa gtgattctcc tgccttagcc tccctaggag    60540
ctgggattac aggcgtgcgc caccacgcct ggctaatttt tgtattttta gtagaggcgg    60600
gctttcacca tgttggccag tctggtctcg aactcctgac ctcaggtgat ccacctgcct    60660
cagcctccca aagtgctggg attacaggca tgagccaaca ctcctggcta atttaattcg    60720
atttttttag tagcagtttt agtctattat gtttgttgta gttactagta tctttggatt    60780
tatttctacc taattatttg gtgattcctc ttcttcctgg ttccacttac acattaaaaa    60840 aaaaacaaa aaaacttag aatagagatg gtgtctcact atgttgttca ggctgctctc     60900
aaactccagg gctcaagtta tcctcctgcc ttggcctccc aaagtgctgg gattacaggt    60960
```

```
atgagccacc atacctggtc ccccttgccc attctgtttt acttttgtat tgcttgggtt    61020
tctaaaattc cattttgtcc tctcccttttg ctcttcccca atcctatctc atcacacaca    61080
ctggtttgga agatagccac ttttttttt ccaatgtgtt tacttatctt atcagagtca     61140
aaagcctatc agtatcttct cagatatccc aaaaaatact aggaccttaa gacacctaaa    61200
atcaggttac atttcttcat aattgtctag tattctagtt ctatcagttt tacctctcag    61260
atctccattc tgtaagtcaa tgttaagttt agatttgtcc atatgcatac gagtttcttt    61320
ggtattcaat acttcctgta tattttttaag aagttccttt gttggaggtc tgttaggttt    61380
tatttgtttg aaaatgtctg tatttcaccc ttgttcttga aggatggttt ttctaggtat     61440
acagttcttt ttttttttttc tttgatacag ttttgctctt gttgcccagg ctggagtgca    61500
atggtgcgat cttgactcac tgcagcctcc acctcccagg ttcaagtgat tctcctgctt    61560
cagcctctcg agtagctggg attacaggtg cccaccatca cacctggcta attttttggta   61620
ttttttagtag acggggtttc accatgctgg ccaggctggt cttgaactcc tgacctcagg   61680
tgatctacct accttggcct cccaaagtgc tagggttaca ggcgtgagcc accgtgcctg    61740
acaaaggcct aactttcctt cctcattctt ttcatcttgt ttcttggttt catcatccca    61800
ttttttagtt tcttttcagt ctccttttgt gtagcctgaa gcaataactg tgtttctgat    61860
gcctaggtaa gtatactgta ggtaggctga tactgttcag ctagtacata gtagaagtca    61920
gatgtcacat ttttagaata ctccagttct agataagaat accttgttgg gtgatatatt    61980
ttattatcct ggattgtttg gcggatgtaa tggattgctg aagacgccca gtttcctgtg    62040
tggccccttga gtatttattt tagtaagtta gaggctagtt gttcactttt cccttgttta    62100
actggggact cctcagcagc cctttcaaaa cagtataacc tcatctgaga aaggaaaatg    62160
taaggatatt cattaagttt tcttctctcc agatttggga ttattttag gaattctcaa     62220
gagttttgtt gacttaccaa ctaggtttct tgaagatggt gagtgaggat aggaacttgg    62280
cctggtttgg ctcacctctc agattcattg gaagaggcaa gttcattagc acagtttcag   62340
tccaccatta cagcattttt ttcctgaatt attataagtc ttagtcaata tttccagata    62400
atcatcatta tctgttttaaa ttactgcaca gtattctatt ttactgatgt accattgtgc    62460
aaatactatg atgttttatt atttttaagt tttgctataa cagataagtc tgcagagatt    62520
ttattcagct ctgtattgtt ttgcttctgt tgcattgttt cctcagattg aatttctagg    62580
agtagaattg ctatgtcaaa gagaataaca agtatctctg agccttgccg catactgctt    62640
ttttcattttt taaaggttat accaagttag agtctcacta gaactgaatg agtgtactaa    62700
ttttactgta gctagtttct tttttttttaa aaaaaaaaaa agctgtagaa taatctcaag   62760
gttgcttaaa tatttctgtc ttttattctt acagcatttc ctgtggatta gttcactact    62820
tatttctta tctgtgagtt gtaagtgctt acacatgccc acttgatgac cttgatgttt     62880
tcttacacat ggaagcaagt gcttttttgta aaagaatata ttaaccttta tcttttttaca   62940
ttttgtgaag cttttttttt aatgtttcat ctttaaaaaa ttaggtttat tcagaatttt    63000
aaatttttaat attatattga atttcttttg gttggtttaa attgagaaag ttatttttatg  63060
tatattctct tttttttgcta gctttctgta atttgatttt aattccttat tccttgcata    63120
gtttgcttct ggtatgttaa agtgtgctct ctctaagtgg gtagtaatta ggaacaattt     63180
atctcaacct catttattga atgttttaaa tcaagagaac ggactctgtt atattaagct    63240
tctatatata attgtctgtt tcactgtaat gcctagtaag gatacacttc attcttttt     63300
tagatgttct ttcacaattt catgtaaatt ttagttgttt tgtttcaaaa aacaattcct    63360
```

```
attgaacaat ctctaggaat agatagctta ataataatat tagatctagt tttctctttt    63420
catagtttac ctcttctttc ttttcttttct tttttttttt ttttttgagac ggagtctcgc   63480 tgtgtcgccc aggctggagt gcagtggtgc gatctctgct cacagcaagc tccgcctccc    63540
aggttcgcgc cattctcctg cctcagcctc ccaactagct gggactacag gtgcccccca    63600
ccactcctgg ctaattttttt tttttttttt ttttttttttt ttttgtatt tttagtagag    63660 acagggtttc attgtgttag ccaggatggt ctcaatctcc tgacctcgtg atccgcccac    63720
ctcggcctcc caaagtggat tacaggcgtg agccaccgcg cccagcctct gtctctcttt    63780
tctttttctt tttcttttct tttcttttct tttcttttct tttcttttct tttcttttct    63840
tttctttcct ttcctttcct ttcctttcct ttcctttcct ttccttttct tttctttctt    63900
ttcttttctt ctctcttctc ttctcttctc ttctcttctc tgtctttttt tgacgagtct    63960
cagtatgtca cctaggctgg agtacagttg cacaatgttg gctcattgca acctctgcct    64020
cccttgttca agtgattgtc ctgcctcagc ctgccaaata gctgggacta caggtgcgca    64080
ctgctacgcc cggctaattt tgtatttttta gtagagatgg ggtttcacca tgttggccaa    64140
gccggtctca aactcctgac ctcaagagat ccacctgcct cggcctccca aagtgctggg    64200
attacaagta tgagccacga tgccagtcca attcttgtgt agttttttaa tcagctgaat    64260
ttaacattca aattcttctt ttaaatcttc aataggcag ttatctttat aaagatccta    64320
tataatcaag actttgtttc tgaatatttt atgtatgttt ttgctactgt aaatgagatc    64380
tatttctcat tgtggtttct tgctgttatt actggtaaga atttagtgaa acaaagtact    64440
taagagtatg tctttaaatt gtgagatttt gatgaacttt taagaaataa aattctttag    64500
tttcttagag cttttgaga tttctaaggt agatccttgg tttgggcaac atataactat    64560
tacaagtttt gcacattgaa cgttatttgg taattttttag agaggacatt ttaaatgttt    64620
aggaaaaata taaataaat gtagaatact attgggggca tatacatcat cagcactgta    64680
actgtttcat atgaatcatt tttgtacata tagaactcta aagtcctaat gaacagaatt    64740
ttacatttct ataaatagaa agtccttaat agttgtgact gaataactta tggatagcaa    64800
attatttaac tgaaaacagt aaaatttaag tgggaggaaa tatttgcttt ataatttctg    64860
tctttaccca ttatttatag gattttgtca ctttgttctg tttgcaggtg gaaaaccatg    64920
aattccttgt aaaaccttca tttgatccta atctcagtga attaagagaa ataatgaatg    64980
acttggaaaa gaagatgcag tcaacattaa taagtgcagc cagagatctt ggtaagaatg    65040
ggtcattgga ggttggaata attcttttgt ctatacactg tatagacaaa atattgatgc    65100
cagaattatt ttataagttc cctgtcccca agatgatgac ttcacatctc tgtcaaacag    65160
aaatcgccca acaggccctt gtatgatgtc atttaaacaa gccctatttt aaatgtcacc    65220
tccactggta acaggatact cctaggagga tcaccaagcc caattcttct aggagtagtg    65280
cattgattag gctttggggt ttccaagcag ttcattaatg tcacttttgg aaaaagtctg    65340
tctttcatac cagcttatta attccctatg ggttcacacg gttttttttc ctggattttc    65400
atcaaacatg tgtaaggtac tcagtacaaa gaagtttaga aatccagaac aaagcagtgt    65460
atttaagtag tagtaaactt ccagataatc tgatgcccat atctacatat ataaaaaatt    65520
tgcaaatagt tctgtagaga gtccaaacat ggagtagatc cctaattaag agcctttgca    65580
ttaaagtcca ccttcctcat ttcatagcta aggatattga ggctcagaga gtttatgtgt    65640
ctggagttaa agttatttg tgtttcctta attttgact tactagaaag ttaaagtacc    65700
```

-continued

```
tacagatttc tgtgtttcac tatatgttaa cttgcttggc tggaagtttt tctgctgata    65760
attggtttta tgaaggaaga atcctgttaa gaatgcatca ttggactggg tgtggtggct    65820
cacgcctgta gtgatcctag cagtttgaga gaccgaggtg ggcagattgc ttgagtccag    65880
gagtttgaca ctaacctggg caacatgatg aaaccctgtc tctacaacaa atacaaaaat    65940
tggccataca tggtggcacg cacctgtggt cccagctact caggaggctg aggtgagagg    66000
atcacttgag ccagggaggt tgaggctata atgagccata attgcactac tgcactccag    66060
cctgggtgac agggtgagat cctgtctcaa aataagaaaa gagaatgcat cattggccag    66120
gcacagtgac tcatgcctat aatcccaata ctttaggagg atcacttcag cccaggagtt    66180
caagactagc ctgtgccaca tagaccacat ttctaccaaa aatcaaaagg aaaaaacttg    66240
ctgggtgtgg tgatgcacac ctgtggtccc agctactcgg gaggctgagg tgagaggatt    66300
gctttagctt aggtggttga ggctgcagtg agccatgata gcaccactgc attccatcca    66360
gcctgaggga cggagtgaga gcgacaccct gtctttaaaa aaaaaaacag aggaatgcat    66420
catagtatat attaaattat tgcctatttt tttatctatt ttattgagtg ctaataagaa    66480
aattaatggc aaaaacttgt ttttttacagt ataaattaag tttaatttca ttttaaaatt    66540
aagtaaattt gttttattaa aaagtatgtt gaaagcaaca taaatagcac tcaaattgag    66600
acagaaactg taactgtagt ataagaagca ttaggctggg aattgggaaa cacgagttct    66660
agttgcagct tggaaacttt ttctgaagct ctttacaaat tacttaatttt ctctggtttt    66720 caccacattg ttctatagca ttaacatgtt ggattcattg ctttaattct tagacctacg    66780
tgtcatcaga aatgccatta cactttgagg atttgagcct tatttttaaat aaagttgtga    66840 tcctcatggc agcctaggtt tacatgtgtt aaataaacag tattctgtaa ataccattgt    66900 cttttcatgtt tagtgatgtt gctgttgtta acactgcagt gaaatgcata tataagcaaa    66960
ctacattaca tactcatgaa catggtcctt tgttttgaaa cttttgatcac tgattgttcg    67020 cagtctttca ttgtggaact actctttcac tttgaatgtt ttgagaggtt cctttgttca    67080
gatcagtccg atttcgtttc tgggtgggtc tctactttcc cttttctcac tggtcaagcg    67140
aggtctgtct aattgttttgc tactactaac atttgatggc cacgcttcag caagtacatt    67200
tgtagattct ctctctctgt ctctcttaat ttgtggtcta gagatcatat tggttaatga    67260
aattatgaag agggaatgta tttataaaaa ctcaaattct tgatgcagaa ggtctagctg    67320
attgtgaacc caaaatatcc gagacaggtc acaaccaatt tagaaacttt attttgccaa    67380
ggttaaggat gcatccatga catagtctca caaggttcta atgacacatg cgcaaggtgg    67440
ttagggtaca gcttggtttt atacatttta gggagacatg agacatcagt caacatgtgt    67500
aagatgtaca ttgattctat ccagaaaggc aggacaactt gaagcaaggg gctttcaggt    67560
aataagtaga taagagacaa aaggttgcat acttttgagt ccttgatcag cctttcactg    67620
aataaacaag cttagtcttg ttagtgaatc tgcgttttta cataaacagt aggtcagagg    67680
aagcaatcag aaatgcattt gtgtcaggtg agccgaggga tgactttctg tccctcacct    67740
gtgaagataa gctatcagtt tccattgcta gggtgaaatt caacagaatt gtttgagagt    67800
gaacatctgg aggcccacaa ggactttcct tgtgaggggg aagtatgtag tgagggaagt    67860
atgtagtttt taaatctttg tcgctatctt atttagaaat aagatggaag gcaggtttgt    67920
ctgacatagt tcccagcttg acttttccct cggcttagtg attttgcggt tccgagattt    67980
attttccttt cacatatcag tcagatcatt tggtttgtga agtttcctat gcttaacaga    68040
aaatatgtgc actagttttc ctagagtttc attgtcagag tctcaagttt ttgtttggaa    68100
```

```
attgtatttg gtcacattaa ttatactcta tgttagttcc aaagaaatac ctttggttaa    68160
gaaaagaatt ctcatgcata actcctcgag ggtggggtta caccttaatc catcctcagg    68220
tgctcatggt aattggggca aatatgttgc ccagtgctgg tgctctgcag ccttggatgg    68280
gtttacccag aaagcagctt tcaagtcaga aactaacatt cataagggag ttaaggattt    68340
tataaataga tatccataat tcatgtagtt ttcaagtaag tagtatttga atcttttctg    68400
gttagataat aattgtgagt atgttgtcat ataataacag tatgttttc actatttaaa     68460 taattttaga attacattga aaaatggtag taggtattta tggaatactt tttcttttct    68520
tcttgattat caaggcttgg accctggcaa acagattaaa ctggattcca gtgcacagtt    68580
tggatattac tttcgtgtaa cctgtaagga agaaaaagtc cttcgtaaca ataaaaactt    68640
tagtactgta gatatccaga agaatggtgt taaatttacc aacaggtttg caagtcgtta    68700
ttatattttt aacccttat taattcccta aatgctctaa catgatgtga atgttctatg     68760 ataagttta ctaatgtagt catcaggtaa gagtcaagct ttcttccata gagcagtcag     68820
ctgtcgcaac accatttgtt aaatagtccg tctgttctcc attgactgaa gtggtacttt    68880
gggtctattt taaagactct acttttacct cgtctcacca ttcttttgtc tacacaaaat    68940
atattttatc gcttattctg tgttaccata tctattagag ctagttcccc ctcatatctc    69000
tgctttagtt attttcacat gtttctttta tcttttttt ttttggagat ggagtctcgc     69060
tctgttgccc aggctggagt gcagtggcat gatctcggct cactgcaagc tccgccttcc    69120
gggttcacgc cattctcctg cctcagcctc ccgagtagct gggactacag gcgcccgcca    69180
ctgcgcccag ctaatttttt gtattttag tagagacggg gtttcaccgt ggtctcgatc     69240
tcctgacctc gtgatccgcc tgcctctgcc tcccaaagta ctgggattac aggtgtgagc    69300
caccgcgccc agccttatct tttttttt tcccctgag acagagtctt gctgtgtcgc       69360
ccaggctgga gtgcagtgac gcgcagtctt gactcactgc agcctccacc tcccggattc    69420
aagcgattct catgcttcag cttcctgagt agctaggatt ataggcatgc accaccacgc    69480
ctagttcatt tttgtatttt tagtagagat gggttttcac catgttggac aggctggtct    69540
cggactcctg gcctcaagtg atccacctgc ctcagcttcc caaagtgctg agattacagg    69600
tgtgagccac cgtgcctgac ccacatgttt attttttcta agaaaacttt actatcattt    69660
atcaagttaa gaaaattatt ctgatatttc aattgggtgt ttaaattagt tgagggaaat    69720
atgaggccat tcactagatg ataggttttt tttgttttaa tcatgtttca tgttgaaaca    69780
aaaaagtttt ttcctgccag ttttctggct aatctcagga agtccctgaa acaaattatt    69840
gataagtaaa aaaaattatt taaaaaattt taaattatat ttaaaatctt ctgtgactta    69900
tggtgggggg aggctaaagc ctttctcctt ctgtactgtt ctggaaacta tggcctgttc    69960
tactccctcc cctcctgaat tttcccagaa ctttacaggt agcttttata tatatgatcc    70020
cctgtcgtct gtttaacaag tactttgagt gtctattata tgcagacatt ctaggtgttc    70080
agacacccta gtaattagtt tgttcctcat aattctcagt aaagaagaca tgtatatttc    70140
tcattttata ggtgaagaag ctaagacttt acttttcctc agttagacag ctagtgctgg    70200
tgggtgccta aacttagatc ttccattgcc aaatctaggt gtgttgtttt tccagcacac    70260
tagaatcctc ctggttcaag aaatgtatat attttagctt ggataagata caacttttgg    70320
agtgttctaa tcatcttcaa gtttttcgtg gattagttat aacatatgaa aaagatagg     70380 gctgaatggg ccacatgatg ccaaaagtga aaaagtcact cactagatta tgacctgcag    70440
```

```
aatctggtcc ttgcctgcct ctgcttttat attttgcagc ttgtcccttc acacagtggt      70500
ctcactttta taatgtcttt ccctcatgca tttctttaat tcttttattt tgcctgttcc      70560
atagtagtct gtttgtgctg ctacttgccc ctgtactgtt cttgagctat acatatacat      70620
gtctgctgtg ccattgagtg attccatcaa ggccacaatt atcatcttga tgaactgatt      70680
ttctcccact gctgataatt acttctctct cctttctttc tcctttacat cacctctttt      70740
tgttcttaat ttcattccct ccttgatgcc agtgagtatt ttttcttat tttattctca       70800 tcttccttga gtattgttta tttcaacctc tttttttttt tttttttttg gagaagggtt      70860
tggctttgtc gctcaggctg gagtgcagtg gcacaatttt ggcccactgc aacctccacc      70920
tcctgggctc aagccatccc acctcagcca cccaagtagc tgggactaca ggtgttgccc      70980
actgctttgt attttaata gacacaggat ttccccatgt tgctcaggct ggtctcgaac       71040
tcctgggctc aagcagtcca cctgccttgc cctcccaaag ttctgggatt acaggattac      71100
agatgctgtg cccggcccaa cctctaattt taattttctc ttcaaattgt tcaataagat     71160
ttagtttcaa gacattttcc tggccgggca tggtggctta cgcctataat ttcaacactt     71220
tgggaggccg aggcaggtgg atcacttgag gtcaagagtt caagaccagc ctggccagcg     71280
tggtgaaacc ccatctctac taaaaaatac aaaaattagc cgggtgtggt ggtacatgcc     71340
tgtaatcgta gctattgtgg aggccgaggc atgagaatcg cttgagcccg ggaagcagag     71400
gttgcagtga gttgagatga caccactgaa atccagcccg gcaacagag tcagactacg      71460 tctcaaaaaa aacaaaacaa gctgggcgcc gtggctcacg cctgtaatcc cagcactttg    71520
ggaggccgag gccggtggat cacgaggtca ggagatcgag accatcctgg ctaacacggt    71580
ggtgaaaccc tacctctagt aaaaatataa aacattagcc gggcgtagtg gttggtgcct    71640
gtagtcccag ctactcagga ggctgaggca ggagaatggt gtgaagccgg gaggcagagg    71700
ttgcagtgag cctagatcgc gccactgcac tttagcctgg gtgacagaac aagactccgt    71760
ctcaaaaaaa aaaccatttt tcttattttg aaaacttttg gtattgaaag atattttatac    71820 tacagtaatg agaaatactg tgtgtgtgta tatatgtttg tgttttttt tttgttttttt    71880 tctttctctc tctctctttt tttttttttt gacagagttt tgctcctgtt gtccaggctg     71940
gagtgcagtg gtgctatctc gactcaccac aacctctgcc tcccgggttc aagtgattct     72000
cctccctcag cctcccgaat agctgggatt acaggaatgt gccaccacac ctaactttgt     72060 attttagta gagacggggtt ttccccatgt tggtcaggct ggtcttgaac tcctgaccctc   72120 aggtgatcca cctgcctcgg cctcccaaag tgctgggatt acaggcaccc tgcctgtgtt     72180
tgtgttttaa aagggtaat agcttcagtc tttttttttct ttctctgaga cggagttta      72240 gttttgttgc ccaggctgga atgcaatggt gtgttcttgg ctcaccacaa cctccatttc    72300
ctgggttcaa gcgattctcc tgcctcagcc tcctgagaag ctgggattac aagcacgcgc    72360
caccatgctg ggctaatttt tgtatttta gtagagacgg ggtttctcca tgttggtcag     72420
gctggtctcg aactcctgac ctcaggcaat ccaccgacct caggtgatcc acccgcctca    72480
gcctcccaaa gttctggggt tacaggcgtg agccaccacg cccggctgtc ttcaatctta    72540
aataaggatt ccatttaaat atttttgtaaa aggacacaga tcacagtttt actcagggga    72600
atataattgt tatagcagga attgtgccat tgcgctattc caaacagtgt aaaagaacat    72660 taataaaattg aattctaact acatttgtcc ctaaggagtt gttcgttttc cacttgtatt    72720 tccatttttaa ttatcattat ttggatgttt cataggatac tttggatatg tttcacgtag    72780
tacacattgc ttctagtaca catttttaata tttttaataa aactgttatt tcgatttgca    72840
```

```
gcaaattgac ttctttaaat gaagagtata ccaaaaataa aacagaatat gaagaagccc    72900
aggatgccat tgttaaagaa attgtcaata tttcttcagg taaacttaat agaactaata    72960
atgttctgaa tgtcacctgg cttttggtaa cagaagaaaa atcatgatat ttgaagtgtg    73020
ttttgttatt ttcgcaagcc attacattct gactatttaa tatgttaggt ttcctatata    73080
aaataaggca tggtatgtta cagtaggaca cataactgga agttactctt gcacatagaa    73140
acaaaaaatg gcagaaaagc acaaaactta ctatagttgt aacagggaaa ggaaacacta    73200
gggcctacaa cgtactaatg tcttgggtca tctatgggct catgaggctc taggttatgg    73260
aagtaaatac cactgaaaag caaatattaa ttacacatga ggcaagcctt tttgagttct    73320
gtatgtcatt ttgtagattt tgagttcatt ctagtggcac catttgagat cattttcatg    73380
taattaaagg aacacagcaa cctggcactg tgttattgcc cttagaatgg aatgaatata    73440
tgtttagcac aaggtaggaa gtgatgcgtt aagttggaag gctttgccga tcatggtgtg    73500
tatgttgact aacctttatt gtgccttta aaaatatact caagaactac cttaaccaag     73560
taattaaagt caagattacc agttgtggga caaatgacat gtacttcctg gtgtgatata    73620
gaaggaagga cacagtatca cctatatagt attcttgacc agaatattta acctgatttt    73680
aaacaagaag taaaaattca aataaattta gattgtggtg cattcaaggc ctgaacttta    73740
ataaatgtcc atgtcacggc agcaaaaaag aaatcaacag gtcttaaaga gacagggcaa    73800
ccaaacgcag taggcagtag ttgattagat cccaatttag aggttggagt tggggaatag    73860
ctatagagga cactattggg gcgaattgag aaagtttaat atgagacaat atggtgttag    73920
tgtcagattt cttgtgtgaa atggtagtgt tatgattagg agaatgtcct tgttctcagg    73980
atatgcatgc taaattattt aaggacaaat attttttaa aaggttatgt gcatgagtaa     74040
ttctataaat tgtgttgcta ttatgaattg tcatggtaaa tcaaaggaa acataaaact      74100 caaaaggttt tattttaata cactttatgt attgaaatga atggaattga tttgtaaaga    74160
ttacattttt gcttgttggt gtcagataac tgtgacgtaa taatcttttg ctgaattatg    74220
tttcttaggc tagatttcat tttaaagaac cctgtaaata ccatttattt gaactgtgga    74280
tcttccttaa aaaataatat ttattaagca cctagcaggg taaagttttt agattttaac    74340
atttaaattg aaggttttat attagaagtc aacctgaatt taaatgaaac ttcttcttgg    74400
tctgatatta catattatga gctatttta tttaaaaatg taatggcggc cagacatggt     74460
gattcacacc tgtaatccca gcactttggg aggctgagct gggaggattg cttaagccca    74520
gaagtttgag accagcctag ccaacatagg gggaccccaa ctctacaaaa aaatccaaaa    74580
aatattagcc ggctgtggtg gtacatgcct gtagtcccag ctactcagga ggctgaggca    74640
ggagaatcac ttgaacccag gaggtcgagg gtgtggtgag ccataattat gctactgtac    74700
ttcagcctgg gcgacagagc aagactccca tctcaaaaag tgtaatggat cactttaata    74760
attttctatc atacaattaa gtcataaaag gtcatgctat taagagccag ttatgtgaca    74820
tgccaagtat agactcttaa ttaagatgct ttggtttgct ttttatttat ttatttattt    74880
ttcagatggg gtcttaccat gttgcccagg ctttagtgca gtgatgcgat catgactcac    74940
tgcagcctca acctcctagg ttcaagggat tctccccact tagcctccca agtagcttgg    75000
gactactaca tgtagtagtg ccaccacacc tggttaattt ttttttaatt atcttttgtg    75060
gagatgaagt ctcactctgt tgcccaggcc agactcaagc agtcttcctg ccttggcctc    75120
cgaaagtgtt gggattacag gcgtgagcca ccctgcccag cctagttttc ttttttttac    75180
```

-continued

```
tataaactta ttcttgtcag tatgctagca attttacaag ttttaaagta gttatagcaa    75240
gtacttcact catgtttaat tcttaaaggc ttctattgct atataatagg gtagtctgaa    75300
ttcttcaaaa gtgtactgag gccaggtgca gtagctcaca cctataatcc cagcattttg    75360
ggaggccgag gcgggtggat cacctgaggt caggagttcg aaactggcct aaccaacatg    75420
ttgaacccct gtctttacta aaagtacaaa aattagctgg gtatggtggc aggtgcctgt    75480
aatcccagct actcaggagg ctgaggcagg agaatcgctt gaacccagga ggcggaggtt    75540
gcagtgagcc aagatcacac cattgcactc cagcctgggc gacagagcaa gactctgtct    75600
ccaaaaaaaa aaaaaaaaaa aaaaaaaaaa agtatactga acagaggaa gataattagg    75660
tctgcttggc cattgttaag ttgattttta ttttcaaaac atttgatcac tgttgtgggg    75720
aacaagggaa taaaaaataa gttaaatttc cagcccctag attaaactaa taattttgg    75780
ttttcctaga attaaatgct tttatcttga atgttctgtg aagcttttga catgattgat    75840
agctgtatga tagtctgaat gacatgtggg tcatgcacca gcccctccaa cctgttaaca    75900
tttagaatct attcagaaaa atttaagcat tgttaatttc ctttgttttt tgtctagcat    75960
gtgtcagatt ttttaaatg tatttattaa tagcttttaa tgttaatact ctagaacagt    76020
agaatcttga aaatgtttta agtgacaatt agagatttaa atttatgctg acatcctctg    76080
catgtgatac tgatgaggaa agaaagccaa actgtcttac ggtcagttcg tacaatatac    76140
caggccttga tggtcacatt tcaacttgct accttttgc ttacattttt cttatggtga    76200
ttttgaggtg tcattctggt ttctcagata cttaaaatat aggaaaaggt gtgtcttaaa    76260
attgagagaa tgtcttggat aagcagctgt gtagttttat attttgctga taagggaagg    76320
tactctattt ttgttttttg tgtgttttg tttgtttgtt tttgagacag aattgcccag    76380
gctggagtgc tgtggcgcaa tctcagctta ctgcaacttc caccttctgg gttcatgcaa    76440
ttctggtgcc tcagcctccc aagtatctgg gtttacagac atgcaccacc atacctggct    76500
aattttgta tttttggtag agatgggggtt tcgccgtgtt accaggctgg tcttgaattc    76560
ctggccccat gtgatccccc ggcctcatgc gatctgcccg cctcagcctc cctaagtgct    76620
gggattatag gcgtgagcca cccaacccag ccagtactct gttttgata gctattcaca    76680
atgggaaagg atgtagcaac acattttaac cctatgttga gttttaggtg ggttcctttg    76740
aaattttgtt aaggctaact tttgttaatt ttttaaaaa agtgtaaatt aggaaatggg    76800
ttttgaattc ccaaatgggg ggattaaatg tattttacg gcttatatct gtttattatt    76860
cagtattcct gtgtacattt tctgttttta ttttatca ggctatgtag aaccaatgca    76920
gacactcaat gatgtgttag ctcagctaga tgctgttgtc agctttgctc acgtgtcaaa    76980
tggagcacct gttccatatg tacgaccagc catttggag aaaggacaag gaagaattat    77040
attaaaagca tccaggcatg cttgtgttga agttcaagat gaaattgcat ttattcctaa    77100
tgacgtatac tttgaaaaag ataaacagat gttccacatc attactggta aaaaacctgg    77160
tttttgggct ttgtgggggt aacgttttgt tttttttttt ttttttttaa tcttggagta    77220
gaaatatatt taaaattgat ggagaaaatt cccagttctt aacattagaa agggaatata    77280
ttattcttac cagttagtaa tctattcaca tttggtttag agggaagatt tagaaggtga    77340
gataaaagct tgtgagagaa tagtgtattc atgtgaaact tcttccatgg gttcagagca    77400
tttagaaaca aacatcccct cacactcaaa gcttaccttt gagccagtcc tccaatagtg    77460
aggtctttga aggtcaggcc aaattggctg tgggaggacc tcaggttagg ataggaatta    77520
ttttaagaca tggcactata ttcatgtgaa actcgcaaaa actagccttg catataggct    77580
```

```
catgtatcat gtctcagctg agatgtttga gagatcttaa ctagattcta gaaaacaaaa    77640
aaggaagtag ttttggggca aatatatttg ggaaacagtt tattgtattt cctttcccca    77700
aatggatttt caagttcttc atataatcta accccaacaa ataaattgcc tgttttcaa     77760 aagaaagatc atgtcttcag gttttgtgt ggggtttaaa tgattcgaaa gatttgacca     77820
tactgataca ttcactagta accttagtta ctaatgagta atggttttga gttaatcagt    77880
taggcctgaa ctacttttct ggaagttagt aaattatctc acaggcagcc ctgtgagcca    77940
tgggaaaatg tgtatatggt cttctaggc cacagtcaaa ttacaggtat atttgtcatg     78000
gcttctcttg atgaaaggcc cagtatcggt ttgtctgaag atatataata gcattgcttt    78060
tgggggtaat atgggcagta actctgtcca catctttggg caggctgtgg ttctgccttt    78120
atatgctatg tcagtgtaaa cctacgcgat taatcatcag tgtacagttt aggactaaca    78180
atccatttat tagtagcaga aagaagttta aaatcttgct ttctgatata atttgttttg    78240
taggccccaa tatgggaggt aaatcaacat atattcgaca aactggggtg atagtactca    78300
tggcccaaat tgggtgtttt gtgccatgtg agtcagcaga agtgtccatt gtggactgca    78360
tcttagcccg agtaggggct ggtgacagtc aattgaaagg agtctccacg ttcatggctg    78420
aaatgttgga aactgcttct atcctcaggt aagtgcatct cctagtccct tgaagataga    78480
aatgtatgtc tctgtcctgt gagaaggaaa agtatatttg cagattctca tgtaaaaaca    78540
tctgagaatg tttgtcttag tttaatagtt gttttcctgt ggactttata actttgtat     78600 tgtcttaaaa gagtgattga tggtagctac ggaaaacttt gattttaaa attgtctctt     78660 taagtagaca atttataagc tactggtacg agttcacctt ataaatctcc actaccatgt    78720
ttttgcttgg actgttcaca cttcctggaa tggtccttct tgccgtttat ccaacttctt    78780
tctaattttt aagtccctaa tgatgggaat tctatttctg tagtgatttt tctggtcata    78840
cgaccgtaag gtcatgggtg ttttttctctg aattcctctt gagatgcctg taacttgaac   78900
cacgttttta ttctagacat tactgaaatg ttttgtcttt atttcacttt ttaggagctt    78960
ccttgaaggt agggactata ccttctattt cttggtatct tttctttct ttttttaaaa     79020 gtttttaga gagacagggt ctcactcttt tgcccagact ggtctcgaac tcctgggctc     79080
aggtgatctt cctgccttgg cttcccagag tgctgggatt acaggcatga accaccgtga    79140 tcctcccttat ttcttagtat cttctaaaga acattaaata tagtaggtgc ctagtaaatt   79200
atgtattgat ttaacttctt tgaggttctg ttgtttgtga agaattataa aagcaataca    79260
aatgtttgta tagtaattaa gcaacaggtt aatattcatg acttaaaaga ttaaagaaat    79320
aagcaaaaca tgttagctgg caactcacag aaaaagaatt aaattgccaa tgagcacacg    79380
agcacatgaa aaattagcaa aagtttcacc cctttacata tatttggtta aaattgagaa    79440
aagaatagta atagatggta ttggtaggac tgtggcaggc acacaattta catgaccacc    79500
aaaagtgtat gcaggtatcc atgtcaccac accctggtct catcttcatt cagttttatt    79560
tatttttttt aatctcggcc tatttgattg gcacgaaatg aatgatagct gccttatttg    79620
gaattccttt gattactact agtgtgcttg ataatgtaaa acaatattca aaatctgttt    79680
ttcctttcat ccgttgtttg ttcatgttca tgacctttt tttttttcc tattctcctc      79740 cctccctccc tccctccctc ccttccttcc ttccctcctt ccctccttcc ctccctccct    79800
cccacacaaa ggtgtgtgct accataccctg gctagttttt aatttttttt tttttttttt   79860
tttttagagg caaggtctca ctatgttgct caggctggtc tgggctcaag tgatcctccc    79920
```

-continued

```
acctccgcct tccaaagtgc tgggattaca gacgtgagcc atcatgcctg gcccttgccc   79980
atttttctat tgaagtttta gtgctttttta ttgactttgt ttatatatta agataatcca   80040
ttatgtttgt ggcatatcct tcccaatgta ttgtcttaat tttgtttttg tatgtgtatg   80100
ttaccacatt ttatgtgatg ggaaatttca tgtaattatg tgcttcaggt ctgcaaccaa   80160
agattcatta ataatcatag atgaattggg aagaggaact tctacctacg atggatttgg   80220
gttagcatgg gctatatcag aatacattgc aacaaagatt ggtgcttttt gcatgtttgc   80280
aacccatttt catgaactta ctgccttggc caatcagata ccaactgtta ataatctaca   80340
tgtcacagca ctcaccactg aagagacctt aactatgctt tatcaggtga agaaaggtat   80400
gtactattgg agtactctaa attcagaact tggtaatggg aaacttacta cccttgaaat   80460
catcagtaat tgccttattc taagttagta taaattattg atgttgttat agaacccatt   80520
taccccttaa ttcacagtct gggggtagga acatgtacat catatttctg tatctcatag   80580
taggaccact cattctaaag cattcacaga aagaattatc tgtactcttt ttgggacaga   80640
atctcgttct gttgcccagg ctggagtgcg atctcggctc actgcaacct ccgcctcccg   80700
ggttcaagcg attctcctgc ctcagcttcc cgagtagctg ggattacagg cgcctgccac   80760
cacacctggc taattttttat attttttagta gagacggggt ttcaccatgc tggccaggct   80820
ggtctcgaat tcctgacctc aggcaatcca cccgtctcgg cctcccaaag tgctgggatt   80880
acaggtgtga gccaccacgc ccggccagaa ttatctgtac tcttgaacat caccatggag   80940
gcattttctg ctacctccca tggcagtatg ttttcttgtt gaattaggat aacaaacaat   81000
atgctttcaa gttccaaagt tctagctgtt attgtttaac aaaatcttca ttataattag   81060
cttatttttgt gtttaagagt gtgttataga aacaggttca tttaaagctg ggggttccag   81120
aaatcttgaa atagtagtta tcacatgcag agtgacttat ctgttgttgt ttcatccttt   81180
caggaaagtt tgtcattcgt gggcttggga tctagtcaga tccctgtatt gatgagattc   81240
acatgttata aggctttcaa aggttttaaa aatcatacta taaggattga tttcactagt   81300
caccagaata acttttttcag atagcgctct gattttccac gaacacgttt ttctgcatca   81360
gttggttgca catgagtgag ataatcttgg ttctttatcc tttgttattt gtacttcatt   81420
gggaatcctt ttgagttagt atatttgagt cattattatt attgctgtag aattcaggaa   81480
cttttagtag atctggcagc ataaaatttt gcttttaaat cattgtttgt gttttgtatg   81540
ctatagaaat gggttcagaa tattttttaa aaggccagat gaagtgtgaa gatagaaaaa   81600
cttcatcctt cactgtgaat gtttaacaaa catttgcttc tactttatttt ttgtttgctt   81660
cctttagttg tgcaaagtat tcagttctag aatgcatgag atatatgaca aagccaaaaa   81720
attcttata gttgataaat aattgtggca aaaacagctg tatagtaact ttgcaagcat   81780
catttgatta aatgcttaaa aagtcttgac tcagttttaa ctatttcctg caaataatca   81840
atatttaatt aaagctactc caaattagtg acactttacg tgtctgtctt tctccctccc   81900
cttctccctt ctcccttccc ccttctccca ttctcccatt ctcccttctc tcttcttcct   81960
ttcctcttcc cttcccttcc cctttcccctt cccccttccc tcttctcttc ccctccccct   82020
tcccatcccc catcccttcc cttccccat ccctttcctt tccccttccc ttccctcctc   82080
ttcctccttc ccttcccccct tcctccttcc cttcccccctt cctccttccc tttcctcttc   82140
cctttccct tccctccccc cttccttcc ctcttccctt cccttccc tttcccctcc   82200
ccctctcctc ccctccctta ccttcccatg aaatgagaaa gctcagaga tagtggcttg   82260
attaattttt ctttagatta agatatttgt ctaagccttt aaggtttatc tattgagctt   82320
```

```
ttttgtctcc tatttttatt tttcctacta tgtttgtcga ggataaaata cagcactgtg    82380
tgccaagtca taatcacttt tcatttgaga cttaattaaa atgcctttat tttaatgata    82440
tatttggcta atgtatttga agtaatccga aattaagttt tctaatgaca aggtgagaag    82500
gataaattcc atttacataa aattgctgtct cttctcatgc tgtcccctca cgcttcccca    82560
aatttcttat aggtgtctgt gatcaaagtt ttgggattca tgttgcagag cttgctaatt    82620
tccctaagca tgtaatagag tgtgctaaac agaaagccct ggaacttgag gagtttcagt    82680
atattggaga atcgcaagga tatgatatca tggaaccagc agcaaagaag tgctatctgg    82740
aaagagaggt ttgtcagttt gttttcatag tttaacttag cttctctatt attacataaa    82800
caggacacta agatgaaggt ttttgttgt tgtttgtttt cctctgtgtt tctagtgctt    82860 atttttaat cagttttttt gatggcaaag aatctatctc tgtgttattt tgatttctgc    82920
agtatataca tctgcatgat caatattcga tttcaagtac caaagtagga gtaaaggaat    82980
attaacctag gttaaaatt agtcatttca ctaaaattag ttattatgga cgatagatgt    83040
ctaggtatat ctttgttcat aaacgaatat atcaagttca gttattaaat tacacattag    83100
gtaagaaaag gacaaagaaa taaaaaagca tgattcataa ttcctgccct ctatttgtct    83160
agaatttagt tgggaagata agaataacga acgtgacaca gagaataaag tggcatatga    83220
caaatattta ttcaagaaag ctatatgtgg acgggatgtt tcagttctca tgggagaagt    83280
ggattttatg gtgcctttga gtaatgggtc atatttgggc gttcacacag aaagacccaa    83340
gcatatgcct aatttttat tattattatt ttttatttat ttatttattt tttagacgga    83400
gtctcgctct gtcgcccagg ctggagagca ggggcgcgcg atctcggctc actgcaaact    83460
ctgcctcctg ggttcacacc attctcctgc ctcaggctcc cgagcagctg ggactacagg    83520
cgcctgccac cacgcccggc taaatttttt gtatttttta gtagagatgg ggtttcaccg    83580
tgttagccag gatggtctcg atctcctgac ctcatgatct gcctgccttg gcctcccaaa    83640
gtgccgggat tacaggagtg ggccactgtg cccggccctt tttttttttt tttttttaa    83700 attagaggat tactagttct cttcaattat aaaaataaaa gaatcttatt tcactgcctg    83760
gtcctggaaa catgtactgc aatatacatt gtgacaactt tttacctgtc atgttttag    83820 cttttacctg tgaatgtctt atcattgttc ttatctgaag gatagatagt tgctacaata    83880
ataatagatg gtgtgtatgg tttttgagcc taaaagtgt agtttttatct gttgtaccta    83940 tacaagcagg agaaatataa cttgttaata attttaggta tggcaggctg ccatcctaaa    84000
tatgaagtgg tctttgtatt tgcactttaa tgtgttgaaa tcatagcttt cagtgatcca    84060
ggattaggca gactctttta tgcaatctct tgtttccagt tagaatagaa gtcgtgtact    84120
tttgataaca ttaattataa tatattttga gccctgtgag gttggtaaca ttattcccat    84180
tttatgaatg aggaatgtgt gttaaggagt ttgcccaaga gtcacatagc aagtcatagt    84240
catgctctct gaagcagcaa taacttggca ataaaataaa aatgaagcat cttctgtatg    84300
tgttaacttt tcagtgactg tttatgcctt ccagtattct ttgtaaacct tgaattcttt    84360
ttttcacaga tgattaaagt ttatcaattg taaaggtgga ggaatttggg aactagacag    84420
tgcacacata aataataaat atgttcttca aatattgggt gggctaatgt gggaggagtt    84480
tgagaccagc ctgggcaaca tagtgagacc ctcgtctcta aaatatgaa aaataaaaaa    84540 aaaattttt aaatgtgtga tatgtttaga tggaaatgaa acaatttgtc actgtctaac    84600
atgactttta gaaaagatat tttaattact aatgggacat tcacatgtgt ttcagcaagg    84660
```

```
tgaaaaaatt attcaggagt tcctgtccaa ggtgaaacaa atgcccttta ctgaaatgtc   84720
agaagaaaac atcacaataa agttaaaaca gctaaaagct gaagtaatag caaagaataa   84780
tagctttgta aatgaaatca tttcacgaat aaaagttact acgtgaaaaa tcccagtaat   84840
ggaatgaagg taatattgat aagctattgt ctgtaatagt tttatattgt tttatattaa   84900
ccctttttcc atagtgttaa ctgtcagtgc ccatgggcta tcaacttaat aagatattta   84960
gtaatatttt actttgagga catttttcaaa gattttatt ttgaaaaatg agagctgtaa   85020
ctgaggactg tttgcaattg acataggcaa taataagtga tgtgctgaat tttataaata   85080
aaatcatgta gtttgtggaa tttgagatgc attgtagttc ttcgcagtgt gacttcaaat   85140
attttggaag aaacaaatag ctcagagacc tcgtaaaata tcttaaactg gagggctcca   85200
tggagatcat tgcgagtgac tcccccagaa tgtccatctg ttgacaggag ccaggctggc   85260
tgcatacgaa ttagctaagg agcttattat atatccagag tcctaccgtg agcctccatc   85320
ccgtctgcca ttctcccatc cctggtctat gataagactt agaaatctgg attttaacaa   85380
aacgtttcag attgagaacc ttgatttagt ctacttctcc tattttacaa taaagagatg   85440
aagcggttaa gaattagcta atcctacgca aagtgaggga aaaaggacag tcttttttaat  85500 aaatgcggcg ggctggtggg gtatccatat aggaagaaat gacattggac ccctactcca   85560
tgtcatatat aaaaacctcc actttgggag gcgaagcagg caatcacttg aactcaggag   85620
atcaagacca gcctggacaa catgacgaaa ccccatctct acaaaaataa atgcaaaaat   85680
tagccgggca tagtggtgct tgcctgtagt cccagctact caggaggctg aggtgggagg   85740
atcacgtgat ctgggagagg ttgaggttac agtgagctgc actccatcct gggtaataca   85800
gtgataactg tgtctcaaac aaaacaaaac aaatcacctt cagtgatttt tagaccaaat   85860
gtacaaggta atactctcaa ggttttaatg ttttatagtt ctgcagaaga taacatagga   85920
aaatattttt atgtccttgg ctttgggaag aatttaagtc acagaaaaac accatccata   85980
aagtttgact tatttagcta tttgaaatta acaacttcta ttaaaaggca ccacaagtga   86040
aaagacatga atcgtaatgg aagaacatac tggtacgtta taaaatatca aagagttggg   86100
catggtgtcc catgcttgta gtcccagcta ctcaggaggc tgaggcagga ggatcacttg   86160
agcccagcag ttcaagtctc agcagttcaa gtccagcctg ggcaatatag caagactgca   86220
tttcttttct tcttcttttt taatacctgg aataaagaac tcctataaaa tcactaagaa   86280 aagggg tcac ttaagaatct cattaacaaa aagaatttga atattttttcc aaggaagata  86340 tgcaaatgga ctgtaagcac atgaaaagat gcagatcagg gaaatgcaag tcaaaaccac   86400
aatgagctac aacttcacac tgattacgat agttaaaatc aaaaagtcag atggtaagta   86460
ctggcaagga agtggagaaa ttgaaactgt catgcgctct tggtgcgaat gtaaaatggt   86520
gcagctgctt tggaaaacag tctggcagtt cctcagacaa ttccactcca acgtatatcc   86580
aagtggaatc acaacatatg tccccacaaa cttgtacata aatgtttata gcaggattat   86640
tcataatagc caaaaggtgg aaacaacccg aatgtccatc agcagatgaa tgcataaatg   86700
aaacgtggtc tatccataca atggagtata ttattgagcc attaaaggaa tgaagtactg   86760
gtacatggtg cagcttagat gaaccttgga acattgtgc taaatgaaag aagctggtta    86820
caagagtcaa cacgtatgat ttcattcatg tgaaagttca gaatagagac agcagtagag   86880
acaaagtagc agttcagggt tggtgccagg aataggggg taggtggggt gaaagctaaa    86940
ggatacggtt tttctttgtg agatggaaat tctaaaatag gtgatgttta tacatgtctg   87000
tgaatatact aaaaaccatt gaattgtaca cattaaatgg atgaattgta taggaattat   87060
```

```
attttaataa agctatttaa aaaaatccag acacttcacc caagaggaaa tctaagtggt    87120
ccataaacat gaaaaggtct ttaatcacca gtcagaaaaa tgaaaatgaa aaccatgcca    87180
ggccacctcc caccaccata gtgacaagca tttcaagtgt ggcagttcca gctgttgttg    87240
aggatgtgga ataacactgg tagggtgtt aagattatct ggtgaaattg aaaagacgca     87300
tacgacccag caattctgct cttaagtgca tactctggag atgcttttgc ccattgtgct    87360
gcgagatgta tacaagaatg ttcctaatac ctccacactg gaaacaactc atcagtgaaa    87420
atgaactaca gctacacaaa atgacataga tggaatctta aaacgtttag taaaagaaat    87480
gatacaaaag gatacagttt ttttttcatt tatgtgaagt ttaagaatag gtggtattgt    87540
ttagggatgc agtctttggg atggcaactg taaagaaaaa gtgattgtgt taatcagagt    87600
gattgtcttt agggaaatgg agtgctgatg gggagggggc acattagggc ttctggaggg    87660
ccacagttct ggttttaac ctgagtggtg gttttgcacg tgcttgcttt atagttagct      87720
gcaattttt tttttaatgc agttaaagtt tggtatgaga acaaatgtat gaccgatgag      87780
tcctttcagt ttaccaagtt ctttttcgtc atcgttaatt tagagtgggt tacatcagtt    87840
tttcttttct ggctgccaaa ggcttaggaa aaaggcaaac tgacagagga agattttaaa    87900
tgtagaaata tttattggtt tacaaatcct tttaatcact tatacatgaa aagctttcat    87960
ataattcaaa aagcaaattt taaattccaa tgaaatagtt catcccgtgg ttgtgaaaga    88020
gtgtttttag attgctgcac agaagcatgt ttaacgtgga aatcagctca tggttttagt    88080
tgttagggct acaagaaatt gggggagact tcattccaag aaaacatgta gtctgtcagg    88140
ctgttttcat tcctctaaaa gagacagttt tctaagatgt ttttgaaaat gagaaaatac    88200
gtaatagatc tgcttaagaa gtttcaaact taatctgtgc ttattacatg aatatgctaa    88260
tgtaaaacca ggccttcagt tagtgtttcc ttccttttag aatggtgtat gtaaagcaaa    88320
atataaaacta atttctgacc tgtcaaaggt ttttcttaa aatttaaatt tataatgtgg    88380
tttggttttt ctttcccact caaacatgaa tttgggtaat accagaataa agctggatat    88440
ataaatttta tccaaaattt agaactctgt tgttaagaaa tctgttgacc acataaccat    88500
gtttctgaga aaatacatga tttttttgcat cttaaaaaa aattagcact aagaagctaa     88560
gatgaagttg ttttttgtaat ttgatttttt tttccttaaa atactgtttt ggagttaaaa    88620
gttgtagcaa aactggtata agaaagatgt tttaagatat atttaagtct tgtctcatac    88680
tctattgact aagctagccc ggtgactagg gtagatgtat ttaaagaata acttttcccc    88740
cttaaaatct caatattcca catcctgtta gacttcttga gtattaaata catcttctat    88800
ccttggtctt tctgcattta gctttttgg gaagtatgtt tttacccaag catatggtat    88860
gagctgctga ttcagtattg agtggctctt taagcttgtt agttacattc tgctgattaa    88920
aatggtgtac agaatagtca ggaaaaacca gtccctggtc tgaaataaac aatgttaatt    88980
agcttatggg gaagaacaaa tgagtaagga gaattttcat atacaaagga aatctctgat    89040
tgtctttctg gactcagtgt gtttgggtta aggagatagg gtgcggctgg agaaaatgat    89100
gaaaatgttc agaatgttac atgtattttt acactgaaac tggaagtgga agcccagtgt    89160
gatagttttc tgcccgatgt tggcctgtct tcacacccac accacttatc ttgattgata    89220
gagctactac ttcctcttat actgcttcag aagttaacct ctgtggtgca gtgctaggat    89280
atcacagagg aaataatccc ttgtagacag tgtcttgttg ctgggagtta tcagtgcctc    89340
ctgttctctc taaggagggc aatgggaagc ccttttccttg catttgctac agccgtttcc    89400
```

```
ttgacctccc tggaagaaca gtatttcatg gtgtcagaca acattcagaa catgctcaaa    89460
ttaaatgtat gtcagtatgc atttgctttg gtgtgtggtt tgtccaaacc aaagtgccca    89520
tacatgtctc tggtccagcc atgtgggaaa ttcagcagtg gggtgaacca tatggaaatg    89580
gcaggtgttg ggcagccttg actggactgc cctggtctta cttctggatt tggtgagtag    89640
aagatcacac tgttgcttgc tgccctgggt tcacctcaaa gagggaaaga agaattagca    89700
acttaaatgg ttaaatttag aaacaagaaa aagttctgtc agtgggcagt ttcttacgtc    89760
taacaaaaaa aacaacagca gtgaattctt ttgtgttcag aattaaccag taaacacaac    89820
cttagcaatt aacctatcac tatcacgatt gtttatttcc tggaattttg ttgacagaat    89880
tagtccaata aatgttatga ataataattt tatgaataga gataggttaa tgccaaatta    89940
agtataattg aatctgagac attaatgcaa ctgttttaaa ttcaaccact gacctgcaat    90000
ttttatatgc cttgtccatc cagcaagata cattttgtcc attttttttca tgtttaaaat    90060 ttaatattta ttgtcaattc cagtgtgttt cattgctaaa catcaggctc agccaaagca    90120
atcacgaaaa tgactccacg ttgaatcttt aacatcacaa tgtggattaa caatttggca    90180
acatttggct gggcgcggta gctcacctat aatcccagca ctttgggagg ccgaggcagg    90240
tggatcacga ggtcaggaga tcgagaccat cctggctaac acggtgaaaa cccgtctcta    90300
ctaaaaatac aaaaagccat gcatggtggc gggtgcctgt agtcccagct acttgggtgg    90360
ctgaggcagg agaatggcat gaacctggga ggtggagctt gcagtgagct gagatcgcgc    90420
cactccagcc tgggcaacaa caacaacaac aaaattggca acattaaata ctttgtcagt    90480
atctgaaaag tgcaaagtac tgtgcttggc tcccccaaagg ctcctcttaa tcctgaaagg    90540
caggtgcttt tattatcttt tatcttatta tctacatttt ccagatgagg aaacgtaggt    90600
acagaggttt agtaacttgc ccaggtcaca tagccagtaa gtggcagagc tgggatttga    90660
accccagtac cctatctcca gcgaatctga gatgtacatg tgataaattt aatctttctc    90720
aataaattat taagtgtcaa agcaagtggt atgggcaatg caccaggatt aagaaaaaca    90780
gtgtgtggta aagatgtaaa atatttctaa ttctgttgtg ggctgtggca ctcccgtgga    90840
aggcttgcca cagacacagc cagaggcatc cacgtgggcc cctgctgcac acctggtttg    90900
ctgctaccaa ggctgctctc ccgaggcttg ttcacacaaa ggaaagtgag cagctaggaa    90960
gctgcatatt tgaaagttga ctagtcacca aatgctggca tccaaccaag tgattgcatt    91020
gtaccctgtt tggatgaaag attgtgttta aatgaaaaga gagatgatga gccagaagtg    91080
tggcaaatga gttaaaataa attgtcagca gtgtttgaag caggttgctg agggctggtg    91140
tcctgaaatc cggtcacttg gaggatgtat atgttccatc aggggccgga aatgtttat     91200 ccaagcttta gggaataacc ctggagattc tcttcgttac tctactgtta agtacgtgct    91260
tacggagtaa acttcgcatg actaaggttt acaggcctga atgtgcaact gagttcaagt    91320
aagcagcaat gtggtgtatt aggaagactg cttgacttgg gttctaatcc ttgcttcacc    91380
acctagctgt gtgactttaa acatcactgt tttcctcct gccttccttc tgtaacttaa    91440
gggggttgga ttattagagt tctcaaatgc cataccttca aggccaggtg caggatgcag    91500
agaatagtgg gttaaagtga acacctcaat gtaaaatcat tcaaaaattt aaaaacatca    91560
cggaccaaac aaatatgtct ttaaatctga atttggttaa aggtcacaag tttatgccct    91620
ttggagtact ctctgacatt ttcatgatga tatgaaagga ttttccata catactcaaa     91680 aggcgctcac gcctctgttg cagtcagtct ggccacttcc aaatagccac cccatgttgg    91740
tctccacttc ttccctccct ctttaagtgc tatgttaata atctagctta taattctcta    91800
```

```
atcagcagta gagcactttg ctactttatt ttttattgtt aggggtgatc ttagcagccc    91860
aagtatgcta agtcttagaa atattcatca gtgatgtttt tccctgaagc tcgtttggtg    91920
actgctaaac tagaaccaga attggagaaa aacgaccctg tgaattccaa gccaacaaag    91980
ccggggaaga ggcattgagc aacctgtggt tgcctgagaa acaaaaggca aggtggttgg    92040
atgaaagcaa cacttccaag ccttttccag cttaacgaac ataagtctag gttttgggga    92100
gagcctatct tagtgagagt gaacaaataa agtaggctgt atctttcaga attgggtatg    92160
actcaaataa cttttttttt tttttttttt tttttttttt ttgagacagt ctcactctgt    92220
tgcctaggct ggagtgcagt ggcatgatct cagctcactg caacctccac ctcctgggtt    92280
caagtgattc tccggcctca gcctcccgac taactgggat tataggcgcc caccagcacg    92340
cccagctaat ttttgtagtt ttagtagaga cagagcttta ccatgttggc caggctggtc    92400
tggaactcct gacctcaggt gatccacccc cctgggcctc ccaaagtgct gggattacag    92460
gcgtgagtca ctgtgcctgg cctcaaataa ctttcaagat tgaataatag tagcttgaag    92520
caagtctaga gacgagccag ctggaggaca gggccagcag gaaggaggta tgcaaggaaa    92580
aacctgcaat gaatggacct actgtgtttg agggtactga gaggagtttg gggttgaatt    92640
aatacctaca aagcatccac aaagcaattg ggaagaaagg gtaggggac tattaggcct     92700 agtcatatca aacttttttt tttttaaaaa agagtaaatg tcatgatagt atactgccca    92760
cctcaattgt aaaattttat tttatttcgt ttttagatgg agtcttgcac tgtcgcccgg    92820
gctggagtgc aatggtgcga tctcggctca ctgcaacctc cgcctcctgg gttcaagcaa    92880
ttctgctgcc tcagcctccc aagtagctgg cattgcaggc acccgccacc acgcctagct    92940 agttttttg tgtttttgt ttttttttt tttttttt tttgagacgg agtctcgctc         93000
tgtcgcccag gctggagtgc agtggcggga tctcggctca ctgcaagctc cgcctcccgg    93060
gttcacgcca ttctcctgcc tcagcctccc aagtagctgg cactacaggc gcccgccact    93120
acgcccggct aattttttgt atttttagta gagacggggt ttcaccgttt tagccgggat    93180
ggtctcgatc tcctgacctc gtgatctgcc cgcctcggcc tcccaaagtg ctgggattac    93240
aggcgtgagc tactacaccc agccaattgt aaattttatt catttaaaca ccaacaagtg    93300
atttaagaac aataataaaa taactgtagc tggtatgatg gctcatgcct gtaattccag    93360
ctactcagga ggctgaggtg agaattgatg aggccaggag ttcaagacca gcctaggcaa    93420
catagtgaga cccccccca ccccgtctc taaaaaaata attaaaaaaa aaataactgg       93480
gcatggtggt agtcccagct acttgggagg ctgaggtggg gaggtttgct tgagcccaag    93540
agttaaggct acagtgagct gtgatcactg cactccagcc tgggtgacag agcaagaccc    93600
tgtttctaaa aaataaaaat tatattggga tgatggaaag gtataaatct gctctttctg    93660
taagatgatg tctaaaattg gaaaataaat agtggtataa gcatgttatt taaaaattta    93720
gaggtaagtg atagaggatt gtgaaagtgg ctacctctgg gacagtgaac agggcagcat    93780
tgagaaggga gctgccattt ttcatcataa gcctcatgat gatcctatt gatttttttt     93840 aaagatttgt gttcataaaa atgaatattg aaagtgaatg caggaaaaaa actgtctaaa    93900
agtatattta aacagtgaca ttcactttgc acattgacac cttaagataa atccaatgca    93960
atgtcatact cttaccccaa ataagttgca ttgtaatgta aggtcattct cttggggaga    94020
atctaaactg acagaaaaat ctgtcttaag gagtacctat gatcacaaag tacttcaagc    94080 acccttaaa ttgtgattaa agataatttg ttgtttagaa atatatatac ctaggtctgg      94140
```

```
ggaggaatag aagggaaatg gagagtgact gttaaggttt ctttgaggga tgatgaaaac    94200
gttctaaaat taagttgtga taattgcaaa actataaata tattagaaac cactgaattg    94260
cacatttaag tgggcaaact attacggcat atcaattata tcccagtaaa gctgtttaaa    94320
aaatagtagc ataaataaga tgtaataata gccaacattt gttgggagcc aatagcctga    94380
gtgaccagct cagcattctt gataaccacc cccttctccc tatctccttt actcaataaa    94440
tatgaagggc tctagaagct cagggccctt gttccctaga agcaaggagc ccccgacccc    94500
ttcttccaaa cacactcttt tgtctttgtc tttattccca tgttcatcct cctttgttca    94560
gtccagcatg gtctgtggca aacattcaac aatctctaag gtagataata ttatcccatt    94620
ttataaatga aacgggccta gaggagctaa atgactttct taagaccatc agacatgaat    94680
agattagaaa ttatttttct ttcatgtaaa agaagtctgg aggtaggctg tctagggcta    94740
gtaaggtggc tccacgatta tgcagcagag accctggaac ctttgagttg gtttctccac    94800
tgtacatggc ttctctcaag gtcacctcat ggcccaagat gactgccagg gcttcaacca    94860
atgcatccac attttaggca gcaagaacga tgagagtgca aagatgctta tcccacccttt   94920 aaagaaacaa aagtacacag cttccacttg catcttccat gggagaactg agtcacacat    94980
ctatgctgtt ggagcctagg aaatggagtc ttcactccca aaactcattt tgaaaagcat    95040
tcgcgttttg tgaatggcaa ggagtttccg gtttggtgct tggtaaatgc tttgagatga    95100
tgatgtctct tctgcccacc atcttcacag cctcacctag tctttcatat ttatttccgc    95160
tcaaagcttc atttggcctc tggtcttcct tctctttctc tcacagcttt tttggactct    95220
atcctgtaat cgcttttcca ctgaatccaa ctaaacactc agtaccttgt ctgtctcgtt    95280
catcgtgcta ggcacagtgc taggctctca ggaaacatgc atggagtgta ggttccttgg    95340
gggatgtgaa ttatcaacac ccttgagcat ggctggaacg aatcgcccct cccgaggaca    95400
gacaggtaga gccagagtgc agggcagtct cccagctcgc tggaggcaga gctggcctgg    95460
agcctggcct cctgaccctc aagtgcctcc tctcaccctg agcttcccaa caccgatttt    95520
ccaggcaaag cctcatcaca caacgatatt aagtaaagta aaataggaac ggataataaa    95580 ttttatgta tgcagaaatt gtttctctcc tcccctcctc ttggggttga ttaacttagc    95640
tggaagtaat gaacctgaac tgattttttg agcaccagat ctaagtggta attactgagt    95700
tggtaccttg tttatagact ttcagaagac cgtaatactt actaagagaaa tccttttctc    95760 ctctactccc accagtttct cccttggcat gagaaccgac aaaccagaac ataaatgagc    95820
tggaggagag agccctttct ttttttttcta ggagttgtgt catatttcta aagggcagca    95880
ctgtaagtac tctgctccct tcagggaaga aattgtgctt ccaggacccc tcactgagag    95940
caacgccagg gaaagaatgg ccggctcagg acttccatcg cggtcattgg ccaaactcct    96000
tccttctgag aatcttactg acagaggccc cagggtcatc tcatgggct ttctgaggcc    96060 agtactgctt tcttctgact ttcctcagta gacatctatg gctctttttaa tgacattctc    96120 tctccaacct gcttggactc catccacatc tttctttggg ttcctccttc tatgaaggag    96180
actcctgttt gtcctcaact ggcctctcct ggggttcaaa ggcagccctt ccttcgagtc    96240
tctcgtgggt tcgtgagcac tctacctgct tgttttttggg tacttggtaa gcccggcatc    96300
acaatctccc ctggagctag tcccatggtg acacctgccc agattctgtg gtcaccagag    96360
gtttcaggtg atggttcaga gagggcaccg tttcccggga ggcttgggga cttggcaatt    96420
catgggcttt atattctctt gtatatccca cctgggccct ggaagcccag tagctaagtg    96480
aggagaggca caacctcctg gcctgaagct gagttgcttc tattccacct acaggttttc    96540
```

```
ctctccctgt tccctctcct ggagcttcca gatctctgcc accctgtccc cctattcacc    96600
ccagtgatac aggcagcccg agggctgagt tctgtgacag caccctcacc acttcaaata    96660
tgctgacatc ggttcttcag gcctgggcca ctcactgagc aatttgatct tccatttatg    96720
cctctgccca gctgcgtcct gatcggtggc tctggcctgc tctcttcttg tcctggcttc    96780
agcccttgcg cctgcctctg gccagccgag cttcaacagc cagagcacca gctcctgcac    96840
aggtcgaggc tcaagccgtg gcagggcccc ttccccaagc agtcttcatc tcatgtagct    96900
gtgacagtcc ttggatgatc cgagctggga ggggcttcaa acaactgtat caagttcaaa    96960
cccttgattt aaatgtgagg aaaccaccga cccaaggcca cacaggtagt gtgaggtggc    97020
cattgccagg aaaggaggga tgggcagttg tgtgccccat cctgagtgtc tctggcagct    97080
ggactggatg accaccacta agccttccac aaactcaaat ctgctttgac agtgaggaga    97140
tacctgatgt cttgtttgtt ccccagtccc tccctgtctt tgctggttgc tgctgctacc    97200
aatcacatgg cccgttgtcc tgcccacaga agtggaccaa tgacccaagc catgtcatca    97260
gctttagatt ctgggaacga gaagctctcc ttcctccatg attattgagc ttgtatgctg    97320
ctatagccgt ctgtgggcat accccacctc tacctcttct catctttgtg taccctaccc    97380
agccatcccg gggagcctat cagcagtggg aaagaatgag atcaacatag acgaactatt    97440
ccatgttgat ggggaagggg gcatggtgga gcaaaagtga gctgagcaca ttattggagt    97500
ccttgggcta cgtcagggag tctctaggtc accaagccaa ccagttcctt tttggcttaa    97560
gctgctctct tattctccta caccaactgg gtatccaaca atgcaaccca atcctgacaa    97620
taactatccg gacggcatag gttaagggct tggtcccaca agactgtccc cacttcagac    97680
atcagctgca aagaaggtgc ccaggctacc cacatttctg cccaactgac tataaatttg    97740
ggggttccca ccagccctct tcatgtttga taatttgcta gaacaactca ccaaactcag    97800
gaaagcactt tacttactat tattggttta ttataaaggc taaaactcag gaacagccaa    97860
atggaagagt tgcataggc aaggtatggg gatgggagta ggggtggctc agaactacca    97920
tgtcttcttg ggatgcatta ccctcccagc accttgacat gctcagcaac ctgtaagctc    97980
cctgaaactt tgcttgggaa ttttttttttt tttttttttag attccattaa gtaggcatga    98040
ttgatgaaat cactggccat tagtgattga actcacactc cagactaggt gtggtggctc    98100
ccatgtgtaa tcccagaact tgggaggct aaggcaggag gattgcttga ggtcaggagt    98160
ttgagaccag gctagccaac atagcaagac ccgatcttga caaaaagaa aaaaattaa    98220 ccagtcatgg tgatgcaaac ctgtggtctc agctacctgg gaggcggagg tgggaggagc    98280
caaggaggtt gttctctctt gagattggag ggtgggctg aaaattccaa ccctctacac    98340
acagggttag ttctggctac caaaccctgt cttgaagcta tctagggtca cctcattagc    98400
ataaactcaa gtatagttga aaggggctca ttataagtaa gaaaatacac ttccatcatt    98460
caggaaattc tcagggtttt aggagctctg tgctaggaaa tggagacaaa caccaaacaa    98520
attttatata ccagaaatgc tataagtgca gtttctgttg cctgtgacca aagggtccct    98580
ggatggttca ggcactgatg gagccagaat gaaaacccat gacaaccaac tcctaatggg    98640
cctcatgttc tgtgaactac tcagattcca aatgcatcaa agacaccact attgaaggca    98700
agtctgattg ttttgtgggc tcttgcagac cataaatgta gccttgcacg cgtgggtttg    98760
atcgaagtga ggttctatca gtaacatgtg actatgcctc tttcataggt tgttgcttca    98820
aagagaaaaa taaccacttc tgtgctgttc tatgtgtacg gcatccagca tgggtgctca    98880
```

| | |
|---|---|
| agtagaatga aataaattca cccaagggtc cctactctgc ctctgcacct cagacctttta | 98940 |
| acctcatttg tagaaggagg gtgacaatcg aatcgatgta atttacctat ctactaataa | 99000 |
| tcagaactct tttgctttca ggtgagagaa atgcaaccca taccaccttc taccctaaga | 99060 |
| accatctgag gttaggggtg ctgatcccag gcccagctgg gttctaaaac tggaggggggg | 99120 |
| catgcggcct catcctccct cgcttcctct ctcatcctga gtgtcatctt tgtctttcgg | 99180 |
| ttccttcatg tggcagggga cgtggccact gaaagcaata gggtcagatc cttacagtat | 99240 |
| cttcttttc ttttctttt ttttttgag atggagtctc acactgtcac ctgggctgga | 99300 |
| gtgcagtggc acgatctcgg ctcactgcaa cctccgcctc ctgagttcac gtgattctcc | 99360 |
| tgcctcagcc tcccgagtag ctgggattac aggcacacac caccatgccc ggctaatttt | 99420 |
| tttttttttt gggggacag agtcttgctc tgtagcctcg gctagagtgc agtggtgcga | 99480 |
| tcttggctca ctgcaacttc tgcctcccgg gttcaaataa ttctcctgcc tcagcctcct | 99540 |
| gagtagctgg gattacaggc gcctgccacc atgcctggct aattttttgta cttttagtag | 99600 |
| agacggggtt tcgccatgtt ggccaggatg gtctcaaact cctgacctca ggtgatctgc | 99660 |
| ccgccttggc ctttcaaagt gctgggatta caggcatgag ccactgcgcc tggcccttac | 99720 |
| agtattttct cagagggaaa gaaggcctct gtcttcaggg gccacctttag atcccagaag | 99780 |
| gattctgaca cctggaccag aggcagagac cgccagggca actctacccg aaccaagagg | 99840 |
| aagtggggac agatactctc ctttgaccaa aactttaatg aggctcgtct gagaccttcc | 99900 |
| tgaccaggcc cagcctatgt ccttgcagaa ttcagtttga gcaagaatcc tgccgagtca | 99960 |
| gggcagggaa acgcccccag ccttggtatc tgaccactgt ctacatctta tcagcctgat | 100020 |
| ctgccttcag caagagtcct attgggttgg tctaacagga ttcccctctc cccgatgttt | 100080 |
| tctctcagtt attttccatt cactgacctc caccctgctt catggctgca agtccccact | 100140 |
| tgcccatgct gtagtcagaa tcgagtgcaa tctctcccca caactgcaag accacactgc | 100200 |
| agtgcagctt gttcctctga ccatggctcc ccttgtgtag tctgccttac tatccataac | 100260 |
| aagtgtcatg aataattttt tctttaacaa tacccccctc caggctgggc acggtggctc | 100320 |
| acacctgtaa tcccagaact tgggagact gaggcaggaa gatcacttga gcccaggagc | 100380 |
| tcaagaacag cccaggcaac atagtgaaac cctctacaaa aaatgcaaaa attaatgggg | 100440 |
| tgtggtggtg tgtacctgta gtcccagcta ctcgggaggc tgaggtagga ggatcacctg | 100500 |
| agcccagaaa tttgaggctg cagtgagctg tgatcatgcc actgaactcc agcctgggtg | 100560 |
| acaagagtga gaccctgtcc caaaacaaac aaaaacaata aaataaaata tcccctcca | 100620 |
| aaaaagtgaa gggttgacag tctgaggaaa acagcttgtg tctgcacata tatttttt | 100680 |
| tttaggtaga gtctcactct gttgcccagg ctggagggca atggcatgat cttggctcac | 100740 |
| tgcaaccttt gcctcctggt tcaagtgatt ctcctgcctc agcttcccaa gtagctgaa | 100800 |
| ctacggggta catgccacca cacctggcta attttttgtat ttttagtaga gatgggatt | 100860 |
| caccatgttg gctaggctgg tcttgaactc ctgatctcaa gtgatccacc catctcagcc | 100920 |
| tcccaaagtg ctggggttac aggtatgagc caccacactc agccatctgc acattctttt | 100980 |
| ataggagact tgtgaggatt ctaggagaga aggcatgagg aaagctgagt acagtgtcca | 101040 |
| gctcccagca aatcctcaac caatgtcagt tgctgccaca atgatgacgg cagtggtgat | 101100 |
| gaggagggga ggtgggatgg ggagttggga gttaatgtgc cctgtgcttt gatgagggcg | 101160 |
| gccagcgtgt agcccagtgg aactgcactc cagcctgcaa gctgctacat gccagggtgt | 101220 |
| gtgtggtttg tctgctcaga ggggtgcctt gttctacttc atgctaaggc actgcaggag | 101280 |

```
ctctcaatgg tcctgggaaa aagaggatct ccttgtacta aggtatgaag agctaagttc    101340
ctttgctcat caaaggccag aagtggggaa atgattttaa tgtcttgtaa gagattgccg    101400
aattggagca caatttgcaa ctgatggtgt agtgaaatga gaaaggtttt ggaaaatcat    101460
ttccaaggcc ccagaagctg ctgagcctgg atggctttct aagtgggaac tgaaactggc    101520
ccagttgtcc tatagaactg atgtttactg tttttttgtt tttattttg ttttttttt     101580 tttgatagac tgtagaaatg gagcctcctg ctctgaaagg ttgaaactta catttgtctt    101640
atctgagttc cttcctcagg aaactgaccc tcaggcctgg cagatgttat taggaactga    101700
aacttaccag atcaccacat cagggcaatg agacaccaga cccctcacgc atcatgattg    101760
cctaagcaac catctgttgt ttgaccaact cgttttcctt acctctccct aattcctgtt    101820
ttcccacatg tagttacaat tcttccctgc cacatgaact cctaaattca gctggtccag    101880
ctgatcaatt tgagactgat ctcccatctc cttggctgca gcacccaaat aaagccttct    101940
tccctagcaa tgttccttgt tcagagatc agctttctgt gcggtgagca gcaggaccta    102000
gactgaagcc ctggtgtttc ggcaacagaa tcagccgcag gcatcagagg cagtgggcac    102060
ctaacaatat tctgttgttt tgagcttggg gatccaggca gatcctttgc ctcctgaact    102120
cggctgaggg aggctctgct gagtgaggac ggcaaacatc tctcagaagg gaactaaaat    102180
ctattgcaca cttggtttgt ggtctacact ctgcatggat gatctaattt catctgtaca    102240
caaccggtaa tgctcacaga caagaacaag gaggctcaga aaaggaaagt tattcactca    102300
aggacactga gtcgatggaa ggaaggagga ctggcttcca ctgtgcctcc tcacctcctg    102360
ggagtggctc acagaacagt cacgatcact gtcactctgg cactcagaca agctggttgt    102420
gtaggcaagg tgtgtgaagt cctcacagcc aagtaagata atacacagag atgtatatat    102480
gtatgtattt atttatttat tttgagacag tctcctctgt catccaggct ggagtgcagt    102540
ggtgcagtca tggctcactg cagcctcgac ctcccaggcc cgagcaatcc tcccgcgtca    102600
gccggccaag tagctcggac tacaggcaca cgccaccaca tccagctaat tttttatttt    102660 tcattttaa cttttttttc agagatggag tcttgctctg tcaccaggct agagtgcagt    102720
ggtgtgatct cagctcactg caacctccac ctcccgggtt caagcagttc tcctgcctca    102780
gcctcccaag tagctgggac tacaggcgtg cacctccttg cctggctaat ttttgtattt    102840
ttagtagaga tgggggtttca ccgtgttagc caggctggtc tcaaactcct gacctcaggc    102900
aatccacctg cctcaacctc ccaaagtgct ggaattacag gcataagcca ctgcgcccgg    102960
cctatttttc tattttatt tcttttgaga tggagtcttg ctctgttgcc caggctggag    103020
tgcagtggca cgatctcgac tcactgccac ctctgcctcc tgtgttcgtg tgattctcct    103080
gcctcagcct cctgaatagc tgggcctaca ggcatgtgcc accatgcctg tctaattttt    103140
gtatttttcg tagagacggg gttttgccat gttggccagg ctggtctcaa actcctggac    103200
tcaagtgatc ctcctacctt gacctcccaa agtgcaggga gtacaggtgt gagccactgt    103260
gccctgccta cacagagatt tagaaagcta aaaggactca cccaaactca cacacttgag    103320
aagtggcaga gttgggtctt ctgtctctaa atctaccaca ccaaacaact caactggcag    103380 catttctca gcaacatctt tgcaggaacc ttgtggtcaa ttcctcctgc aggggtgagt    103440
ggcagcctgc agagagttct gtgagtcaag tgtttcaaca tatggatgga ttgttgtttt    103500
ttactgtggc aacaaaaggt gtgagatttt tgtctttcat cagctacaaa ctacactgtt    103560
ggtcaggcac ttttactggg agatgttttt cccccgattc ttcctggggt gacttgaaat    103620
```

```
gtgggcagga tccaggaggt ggagagagag gggtctttga aggggtggag gtgggctgct   103680
gacactgaag agctctcagc tgattgactc acctgcacat gactgtgtag ggaatgtctg   103740
gcccaaggag gcttcctgta atgtatctat catctcttca tttagctcat ttttttgggtt 103800 tcagaatccc tcgtggaagg tccatttaaa atcttggaag aaacctgggc tctgcagatt   103860
gtcctcagtg gagcaactaa gagctgaata cagtaaaatg aaaggcaaga caaagtcatt   103920
tcctgggtta ggataattag aatttgagtc accttcctgt gtaaaaggaa acaaacattc   103980
tgatggtctt catcagggaa agagaaatgt tttatcaaat aaagtgtaat cctggcagtt   104040
ggcttcaact gaggcttgaa gagaggcccg gggtgtttaa tctcctgaca tttcccctgt    104100
acctctttta tgacactttt cactttttgc caagttattt ataccatagc ctttatagtt   104160 aattttgct tctagattat atatttccac ttctgtggac aacttgcagc agtttgtgca    104220
tagtatgtat tcaaaaaatg aaaaaatata atacatggga tgaattactg aatggatgga   104280
taggtgagtg aatggatgga tgagtggatg gatgggtgga tgagtggatg gatggataaa   104340
tggatggatg ggtggatgga tgtatggatg gatggatgga tggatggatg gatggatgga   104400
tggatggata aatggatgga tggatggatg gatgagtgga tggatggatg gatgagtgga   104460
tggatggatg gatggatgga tggatggatg gatggataaa tggatggatg gatggatgga   104520
tgagtggatg ggtggatgga tggacggatg agtggatgga tggacggatg gatggatggg   104580
ccctggtcat gttcacataa gaaaggttga acttgtggga gaggaggcaa aaagaggaag   104640
tgatagtcac tgaatgtgtg tgctagacag tatgtctggc actttataat cattttagtt   104700
aatcctcaca acaatgcaat aaggtagatt gcttgtttcc ccatttcaag atgttgaaac   104760
tgattctcag agaggttaaa gaatttgctt aatgggaccc tcatctagat cagtctgaat   104820
agaaagaact accagactct taaagtcagc ctagcaccaa gtagacacta aaacattgat   104880
ttttgtgatg ttgtttccca gaaacattga gtcagaaagc atgtggatgc agattaaagt   104940
ggaacaggct cggccatgac tgagcatctg caggaggagc tgaggaaaga gctgcctcc   105000 tcaaggcctg ggtgactcaa ctgtcagcct ccaaagccca ttcccctcct tcattggaga   105060
ggagtttgag gacagttgtg gttgaacccc cagcaaaact attccaaaac gccgtgtgct   105120
ggggcaggtg gggcctaggc caaggccatt tggccctgcc tgctgtggcc cttctcccct   105180
cccatgtctt ccagccttgc ctcccccaca ggctgcagat gacacccttc gcagtgctta   105240
ttctggagtg taagagctga gagcaggagc tacctggggg ttgagggggtg ggcaggcttt   105300 agagaagggg agagaagagg cctcactgtg ggagctgggg gctcccagga gccacatttg   105360
ccaggcttgg cttcaagctg acatcactat cagagaagac aggtctgggg aatgagaggg   105420
cccaggagtt caggagccca aactgtcatt cagttttgga agccgaatcc ccagcacaat   105480
tgtccacctt gctggcagca tcctggttcc caaagcctgt cagcccgggg ctgcgggcct   105540
ctctctcaca aagccttgtc taggtgactt gggaggtgag gccctgttg gtcagccccg    105600 ttcctgatgg aacaagccac cctaaccgct ctgtcctctc aggtcaggct tctgacaagc   105660
cacaatgtgg gtgagccttt gtgcactgcc tgcccacctc tcaccaggag ccctctctcc    105720
ccatggcctc aaggtaccag tgaggctttt ttctgtctca gcctggccat aagcagccct   105780
ctgcaagagt tccgttacca gtcatttgca ttgtagtata agtggaaacc acagaatcgc   105840
cttcctcccc agttatttat acttcaagtc atattgtaga gagaaaattt ctgtcagcaa   105900
aaatctcagg aatcctcctc atttctattt gtatggcttt caatcgttga catgattttt   105960
tcacatatgt catcttctgg ggatggattc gtataaccct gcttcacttg cttccctgtg   106020
```

```
ggaggctcac ttgcttctcg acaggctctg gaagaactag gcagtctggt acatggttgt   106080
gcaagaaccc ttgagggggc cttggagtgt gtgcttgggc cctggaactc atgcctagga   106140
tggagggctg agattgcccc ttcccatcca ccagggagtt gacaagggga agaagaaact   106200
tcttgtgagc ttgcgatgac ttgtggcact tgcatcagac cttggagttc cctggggaga   106260
ggcactcttg ggtatgacac tgtatagtgc cacctgattg ccatttgacc cagtttggcc   106320
ctggatcctt gagcaagagg gctggaaaga aagacaggcc cacttttkgg gacactatta   106380
gggtctgtag cattggtggg gagagaattc ccccaaccccc caaaagagct gaaaatgaga   106440
cacgcgtgga ggggtgaaag tggagtgtgg tcaacagtgt ggttacagag atgtgtgtcg   106500
gggccactcc cactcaccag ggagactcat gaagcagaag ggatggggca caatgtggct   106560
tccataggca caccaagcca cctggagagc gcatcagccc tttgggtacc cccaagcgga   106620
aggaggttgg gtctttgggt ctggaacttt tggtgcttgt tctggtggga agggcaggga   106680
gtcaagacca gctgtgtctt ccactgctct tcttgtccac tttggttact ggcctctgtt   106740
ggcatgaact ggggaggcag aggctaccta cagacgagga actgtgtgga gtgcgagtgt   106800
atgcagtaaa gggttagctt agctgacttg aggtactcac acccatattc cgaagaaaag   106860
actggccctc agcctgagcc tccgaaataa tctctaagcc cttagaatac cctgctttgt   106920
attcaaagag tatctttgaa tgctgaactt agaaccactc tagaaaatgt atgctaacaa   106980
tgcgatttat gatgaacact tgtctttgtt cccctggggc cctgggccac attgtatcag   107040
tttgagccct agagggacag agaatgagaa actaagatca gtcatgcagg tgctccaggc   107100
ctatgtgacc aaccaccaat aaaaaccctg aacatcaagg ctcaagtgag caatacagct   107160
ggtcccaact tacagtggtt caacttgtga gttttgcact ctacaatggg tttattggga   107220
cataacccag tggaggagga tctgtacttc attcacatgt gttgtcacat cattactggg   107280
agaattaagc actgtccacg tgaatccact gggagaggat aactggaagc ttgcacctgg   107340
cttctcctgg attctgctct gtacgccttt ttcccttgtt aattttaatc tgtattcttt   107400
cactgtagta atctacaact ataagcagaa tagcttttct gagttctgtg agtctttcta   107460
gtgaatcatt gaatccaagg tggtcttggg gacctctaac aaaagatgtc tggacctgaa   107520
cttcctgttg tttcaaagat cctatagcag gctgtcttac caactttcag catcaagaag   107580
ctggtggaga gtgggttagt ttaaaaatga aactggggag agagatgaag ccggggggaag   107640 atgccgtgaa atctcacctt ataggcagcc tctgattcac ctgagggttt ttccttgaat   107700
actttctggg tacaagtatt tgagacaggt gatgtgctgg tcactttatt ctcagctgct   107760
tgtggcctag ccctaacatg ggcactggaa acaatggggg taggggttga tgatggagaa   107820
atggggagta aagggattta aaactttgaa aaactgagct gtttccatga tttgtctctt   107880
ttgattctca caaaaccttt atgaaatatg tgctgacatt ttaagctctc acttatagtg   107940
agaaaagcaa tcttcagcaa ggtgatgact tgtccaaggg aagacatggt cgcccttgtt   108000
ccttgggaga ttttgtgctc ccaggggaaa gcataagccc tcaggagcca tgatgagaac   108060
agctgtagaa cagcaagtga acaggtgtgt atcagtcagg ataggcaagg ctaagctgca   108120
gtaataaata atccccggat ctcagtggcg gaacattgag gaggtttatt tcttctttat   108180
acaaatatgc tgtggatcag gatgactctc caggcaactg tctgtgggac tgtccaggtg   108240
ggcttggatc acctggtgtt gggccttgaa gtcggtaatg gagaggacat gttagaagag   108300
aaggaactta caagcagtgg gagtgcagcg ccctttgtg gataggggtc aaggcaatgc   108360
```

```
tttccaaggc tatgacttgg tgtggtcgaa aaagtcaagc agtcttcact ttttgctgtg    108420
gtcccagcaa atctgcttcc aatccaggct tctcccatat aaaaagcctc ctttgtgtac    108480
agtgagtgaa ctagaacagg gaggagatgc cagtggagct tggcttgctc cttctgtggc    108540
cagctggctt gttttaccac tgcctttggg gtacagtggc agctgtggca atctctctg     108600
gagtttctct agcgggagcg aagcacctaa agcacatggg tgcaggagca gccaggcctg    108660
cacccataga catggtacag agaggagcag ggaagcccgc tgcctgcaga cttcaggagg    108720
agagaggtag gggtggtgca ggggagaggg ccttaatgcc ttcagggaaa ggagtcaaag    108780
aggaataccc aggagacaac tagactttag aattcttggg gccagaaact tgattccacc    108840
tctagtgctt tcttttagat ttctttctct ctttactttc tttctttctt tctctttctt    108900
tctctctctc tctctctctc cctccctccc tccctccctc cctctctctc tctctctctc    108960
tctctctctc tccctccctc tctctccctc tctctctctc tctcctttct ctctctctct    109020
tcttaagact gggtctcgca gttgggcaca gtggctcata cctgtaatcc cagcacttta    109080
ggaggctgag gtgggtacat cacatgaggc caggagttca agaccaggct gggcaacact    109140
gtgaaaccca tctctactaa aaacacaaaa atttgccagg catggtggca gatgcctgta    109200
atcccagcta ctcaggaggc tgaggcagga gaatcgcttg aacctggcag gtggaagttg    109260
cagtgagccg agattgcact actgcactct agcctgggta acagaacaag actctatctc    109320
aaaaaaaaaa taaataaata aaataaaagg gataccgggt cttgctctgt gtcctaggct    109380
ggagtaccat ggtgtgatca tggctcactg cagcctccac ctcccgggtt caagcaattc    109440
tcctgtctca gcctcccaag tgagtacctg ggaccacagg catgtgccac catgcctggc    109500
taattttaa atttttgta gagatgaggt cttgatacgt tgtccaggct ggtcttgaac    109560
tcctgggccc aagcagtcct cccactttgg cctcctgaag tgctgggggt acaggcgtga    109620
gcctccacct ggccagcctc cagtgctttt gcatccttcc tgttaacttg tgtaggaata    109680
aaacattgtc acaataagat tttttccctt tttattgttt tgattttta gccaatgaga    109740
aggaaaattc cttattaggg agggcgaggg tgaggatatg tggggtgggg agaagcgaac    109800
gttccaagtt tcgaaaacag cgactctctc ttggactctc tagccagtag aaacctccct    109860
cccactctct tgccccaaga tctggtgctt agaagagaat caagggaagt tggaacccag    109920
aagacggaga cagattgagg gactgctgtg aaatgttggg gtgtttggtg aataatatta    109980
gaagttgggc tggcagagac cctgtcacat aaacattaaa tcaacactgg agactgagca    110040
tttgttagaa atgtaagcgg gaatggcaga aaacttgttt ttaagggaaa gcatgttacg    110100
gcttatgttc agcctccatc ctctgaaggc aaaagttagc aaagttgatg tatggcgttg    110160
cttttttctgg gaactttatc tcgtttggtg gggttcccat ctctgtctcc caggagccaa    110220
gactttcccc tccctctgct ccagcagaag ccagtctcag gcaaggctcc ctgtacctca    110280
tttacacttt ggtgtgaata tgttattgta acctctctcc tggaggtgtc tgcattccaa    110340
gactgaactt ttctgtgaaa gttactgtca ctgtgaaagg cagttcagcc cccagggatt    110400
gaaaaggaa atcattttgg gtaagggac agttagtcca gatttttttca gttgcaagta    110460
aacctaactc agccagtagg caaagggga aattgctggt ttgaactggt gggaagaaag    110520
ctgaggaaac tcctacactt gggggaagaa ctgcaggtgc ctggctgcag gaacgcagc    110580
gggggctcag gaccaggcag atgccctgcc tctgcttccc ttggcacagt ggcctccttc    110640
tcccttcaag taggcagatg ctgcctgtgg cagaggacag cagctgattg cagcccagc    110700
agggaggatg tggtagacag gcactgagca tctcttctac cctccttcta gagggctatc    110760
```

```
ctgtactgtt gaggctaaaa gactgaaaac cacatttccc agcctctctt gcagctacca    110820
atctggatga gagttagatt ctacacatta gatgcacttt agcaagattt tcaaaagcag    110880
attggagaag gagcccatgc ttctgctggt ttttttttgct ggcaagtgag gggttctgtt   110940
tttcctggag tgactttatc atggtggcat ctgaaaaagg ctatttcttg atcagagaga    111000
cagcaaccct ctcagtgacc tagttctgtg ggtgtgtctc tcctgagagt taatcccaga    111060
gctcaaacta gagctcaacc ctagagtctc ttcaggcttc ccaggggtgg gggtgcattt    111120
aacagtccaa gttaaagaga aaataaaggc cattaaagac caaacattga gcactgagtg    111180
aaaaagtttt attgccaaac aggaaacctg attcaggcca gggtcttgga aggttgttca    111240
ggatgagatg ggggaggtga aatggggtag gtctttgaaa accaacagat tgcaaattct    111300
ctgtcccata gcaggaaacc acagtctctg atgtcagctg gctgccaaca cgtcagttgt    111360
atcagcatta gctggctgga ggtggcctgc tgtgtgcaga tggtacctgg tgcaggattg    111420
tggtgtccag gtgtctctcc ttagcacata agaccctgtc cgaggactgt ggcatgacgt    111480
gctggagtca cgattctgtc acccagtcag gtcatcagtg tcagagagct aggtggccag    111540
gttggagtta attgccaatg ataggtcttt ttctgcttaa atcagctgga ctggattcta    111600
ttgcattaac ttgaccctga ctcatgccgc caggcctaat ttataaacca agacaagaaa    111660
gggctactcc acccccctcca atttgtgtaa ggccagggga cttccccccc actcccaac    111720
ctgaggcatg caccctccct tagatcaatg gctgtttctc tgagaatgcg gaaccgtgat    111780
taatccagcc ttgatgggga ggcagcagga actgtaggca ttctcacttc acacccatcc    111840
caatcccctc ccccttgctg tcctcttgta cagaggactg aaagcacaac actctctccc    111900
tccctccctt ataggtggtg acgatcatgt gactctcttc tggtcaatga gatgcagcag    111960
aaagtcctag ggaggtctag gaaaagtcct gttgggagag agcattttt t accttctccc   112020
tgctacttct tgctactagt aacatggatg tgagccttgg aggggtagct accatctggc    112080
acctggggtg gcaagccaac atggaaagga tggcagagcg ggaaggagga gccagcctta    112140
ccgatggcat cactgtcact gcgctagccc cagaccacct gctccagagt tctggttatg    112200
gtaatgaaat aaaccttgat ttttattcct taaaactacc cttcaatggg ttttctgttc    112260
attacagttg aatgctttca taactgatac aggagggacc ctgtgattgg cagttccact    112320
agactgcatg gagatgggtg gagttatcta aaagaacaga gatagtgtcc ctagaagaag    112380
gggacaggaa agcatcctgg gtacacaaaa gtcaaggctc caggatctgc cctgggggct    112440
atctcaacac ccctacactc tcaccgcacg tatttggtca gctatgaata tgaccaactc    112500
tcgtcgttta tctctattca gtggaacaca gcagcactgt gacctgccca cgagaagaag    112560
gatttttaga acttatctta gggcaatttt aggtagagga gcagacaaga tggtgtacag    112620
gagaaacagg tctattaacc ctggtattaa tattaactgg ctgcccagaa taaatgaaga    112680
atagcttatt ctttgccagg ttgaagatag aaaaggaatg aagggccgga gaagtacagc    112740
tgggtgaagc acagagcagc ctagtgcttg gcatgggact cagatctgaa gcagcctctc    112800
cgggacttct ctgagcctgc ccctggtggt atgactgtga tatccctgct tctatagttg    112860
gcaaccaaca tgtcctagct cctagaccat agagggccag attcatgtct cattgactgt    112920
gtaatctctg tgtggcccag tacagagcat gcacaccgta ggttctcaca tatgtttgtt    112980
gagtgaatga atacaatacc aaacgaatgg acaggacaga gctgtgggct agcaggaagg    113040
atatctggct tttgcttgaa ttagctagtg aattgctgtg tggcctcctt actgagcctc    113100
```

```
atttccctct gtctgcagag tcaagcaaat cttccatttt ttgttcccct gctgccagag    113160
catggcagag taaatgtgtg agttgaaggg agcaacctca tgaggttttg ctttgtgtct    113220
taattacagc catttgtgga attaggcttt taatataaat atttgtgtgc ctgcgcctgc    113280
atatatgtat ttggaccaat gctctcatgt gtgcaaatac atgtattcta aagaaatctg    113340
tccagaaccc cagcatctgt ggtgtctgtg gtgggagggg cttccatatt acagagagat    113400
gcccacagtg catgacgtta cccgcacagg tgtgacatca cagggtaacc aaatgctttt    113460
gccctggggg tgggagaggg atgggtgcac ggtgaacagc aggtgggggt ctttccatag    113520
gggatgagga agacaaggcc acttggaggc agaggagacc acagtgggc atgatggttg     113580 gggaaggcct tttacttctg ccccttaagg atgccctgga attcaggctt tcggatccca    113640
gagctctcat tagagcagcc ctgcgttgta gactttctg cagtgacaga aatgttctat     113700
atctgtgcta tccaatatgg tagccacaag ttacatgtgg ctattgaaca cttgaaatgg    113760
ggttagtgca attgacgagc tgaaaatgta gtttaaattc acttacattt aaatagctgt    113820
gtgtggcttg tggctgccta ttggactgtg cagttctgga gaatggtact ttacttgtcc    113880
ttggggaagc agaaacaaat gaaaacgagg atctggagct catgaagttt ctcatggggt    113940
ggggtatgtg tgttgaagct gcaccttcag caggaacctg gccagtcctt agtggaggac    114000
atttctttcc atcctgcatc cagatggctg gtcctgctcc tcccagtcca tggagaaaaa    114060
agaattgaac aaactgtcta agctgggtca ggtactctgc agatgtttgc tgagtatcgt    114120
tcttgatgga aatcccgtg gaactcctac attttctcct ctcttctcct tcctttcaga     114180
acctcagagt gacagagcca aaagaccagt gcctcatttt gctgacatgg aaaaggaaac    114240
ttcgtggggg aaagagatct gcttgcagtc ggccagagag acagaaccag ggcagtggtg    114300
agctctcatg acctggtgtc tgttgccttc tggttaagtt tttcatttgt aattctacaa    114360
acatcccttc tgtaaacatt tccctcaaaa tggagcagga agctctcaaa aatggaccag    114420 aaagggtca ggaatataac tttctctgcc cagattccag gacttacagt gagaaagcgc      114480
cttctgggaa cttcacaatg gctaaagtgt gctaatggga tgatgtgccc ttgtacaccc    114540
actgcctctg aactctgctc tgcattgctg agcaaactac atttcccaga actccttgtt    114600
ggattccttc caaacaggtt taccactggg agagcctgtt ggttggggag ggcaggaaga    114660
gggaggaaag aggaagggac tcacttcctg tttccagctg aagtctaaat caatcccacta   114720 tcaacaggta gctatcatac taccctcatt gtcacccctc agaggtccca ctgcagctgc    114780
ataatgtccc ctcagtggcc tgaacatgag atgaacaaca ctcttcttgg gagtaccagc    114840
cttgcttggt tcatggccac ttttcctgat tatcttgcag ctatattagg tcatgtgaca    114900
aagttctggc cagtggcaag ggaacacaag tgataggtac agatagaagt gtctgatact    114960
acatagatta tgcttgcact cactcttaag agagagacat gaacttttac caacggaagc    115020
cagtattatt ttgaacctct gttagagtgg cttgaatctg tatcctaact tgtatcccta    115080
atgtgtgacc catgaaaatt agccaggcag caccagttcc aaagaagctc acactcccct    115140
gcggctgctt ctgccaaggt cactgatatt tccctttgct aaatcttgtg ggtgttttct    115200
tcagtccttg tcttaatcac tcagtggcac ttggcactta ttccttcttg aaaccctgt    115260 ttcccttggc tttgtggcat cctgtgctct tggttttctc ccatatctct gaccctcttt    115320
ccttagtctt ttttcttctt cctcctgtcc cttaaatgct ggttgtgatc ctcttttat    115380 ctcattctac acactcacag cctgagtaat tcacaccatc ttgatgctga aacttccaa    115440 aatgttggtc tagcctgggt cattgttatg agctctagac tcacaaggcc aattgcttgg    115500
```

```
tgggaacccc tccccatgg ttatctcatg ggtccctgaa gtccaacttc tccttcattg   115560
aactcatcac ctcttctgtt cctcctcctg ggttcccagg ctcagtggtg gcaccactgt   115620
ctacctggct gcttagcctg agacctggct ccgtcccaat tcctctctct cagtcttatc   115680
atccccatcc aggcaaatca ttgattctgt ggacctactc tttcgggtgt ccctcaaatc   115740
tctccacgtc tctgtgttct cactagcact accttggtcc accctgccat ctgctttcct   115800
cctccactcc tgcattctga gtcatttttcg gcagcacacg catccttaaa acccctccac   115860
tggcttgcca gtgtcctcag gattaggcga aaagtctttg ctttgtttta caaggccctt   115920
cgctatctgg ccccctcatt acctcccttg ctctgcatgc tccagtcctg cagaactaca   115980
cacagttccc ccaacaaggc cctgctctgt tcttcccaca cactgctcct ctgcctgggc   116040
cactcttcct gctccttgtc agcaggcttg ctgctctcag gctcagcatg gacagctgct   116100
tctgagagcc ttctctgcct acccaggctg ggtggctgcc tctctttggt gtgcccatgg   116160
cagcccagaa tgcctggtgg acagggagcc ctcagcaggc cgtactgcag cgccctgccc   116220
ccgtcagcct ccaggagcct ggagtccagg gacatcaagg gcggtcctgt ctttctcacc   116280
cttgtctctc cagcccctaa cacaggggat gcctgacccc aaactagacg agttacttga   116340
cctctctgac ccaagacaaa atgggaggaa agtgccaaat ttccaagatt ggccagggga   116400
ttaaataaga taaatatgca agtctcttat ctgggggtct ggcttggtaa atataaagtt   116460
cttttttctt ttcttccttt ttcttttttt ttttctttc ttttgagac agggtcttac   116520 tctgtcacca aggctggagt gcagtggcat gatcatggct caatgaaaca tcgacttcct   116580
gggctcaggc gatcctccca cctcagcccc ctgagtctct tggactccag gcgtgcacca   116640
ccatgactgg ctaattttt gtattttag taaagacagg gtttcgacat gttgcctagg   116700
ctggtctcga actcctaggc taaagtgatc cacttgtctc agcctcccaa agtgctggga   116760
ttatagacat gagccaccat gcccagctaa aagttccttt ttaaaatctg cttgttagat   116820
acactcatag aaaggtaact ggccacagaa gggagaggaa tggcagtcca tccagggatc   116880
actggagtgt catatgaaat gttataggaa tcacaggcct tagaacttga aaggaaccca   116940
aggatcatct aggctacttt atgcaggtaa acagccacc tgtgcccatc acatagctgg   117000
ggcacagctg gagaccccaa cagagaggag agctgatggg tgacgagaaa tcaggcctct   117060
ccgccacggc agcctagcta atgggtcttg gctggaagct aacaggaagg cctcttttcca   117120 gaaacactgt aagccagtgt ttctcagatt gctgggtgta attcataggc agatcatgaa   117180
atcagtttaa tagctttgac cagcattaac ctatttatgc ctagcgttcc cttattgaa   117240 cactaagtct gtgagagtta tttacatcct actgcttaag gtcatcgcca aaatctgatt   117300
ttttacacaa aaaatttgca acctccagca taaatgggtt aaaacaagac aaaacaaaac   117360
aataccagaa tggaaaatag tgcatgatct gtacagtata gttgtagaaa acttcttgtt   117420
ttatcatttg atgtcatgaa agtccctgct gtagataaaa gatggagctt gtgcttctga   117480
gtggtcatgc tcaacagggt ggggagccca ggggagtggg gagtgatcgt atagacagag   117540
gtgggtgggg ccagtgtgag cctgatggtc aattacttct catttctagg gaaaattgaa   117600
ggaaaagaag gaggggggatg tggaggggag agaaggcctc agtagagttt gcactattat   117660
tagggcaagt aagctgcttc tgaaaagaag gggtttgcaa agccaaccca ggcaaaagca   117720
atctgctgga agaacttcat ccccagctga cactgtggga aggaccccat gcagaagcaa   117780
tagggcagcc tggtcccata tcctcatgaa atgcctctta taattgtgac atcttgcaat   117840
```

```
tgtggaggac tttacactttt tcggagttcc tagcccctca cttatttctc gtaagaccgc  117900
tgggaggtgg ggggatggta tcatcatccc actttagaga tgaggaaaca ggatcagagt  117960
gagctaaatg actgccagat ccaaaactag aattcagacc tcctagtttc taagtggacg  118020
ctctttctac accaccataa tgtgagtgtt ctgtgtttac agggtgtatt caagtccatg  118080
actgcccatt agaatccccc caaaaaattc caggactggc ctgagttgct ccttagacca  118140
atgaaatcag actcctggga gtacggcccg ggcctcggga tcctttaaag ctccatttgg  118200
agagcctcgg gcacagccag gttggatcca tctcccagtc ccccagcctt ggctcagcct  118260
ggccaagctg cccaggaggt cccttggtgc cctgggctct gtttcactgt tgttttgtag  118320
agcaacttcc cagtgatgct gccactgggc cccatcctaa cagtgaagtc ccccgggccc  118380
tcctgagagg aggtgtgaac tggaagatgg ggaggcaggc ggctctgaca gacagaaagc  118440
aaacagctca gaggggtggc aggctgcatt ttattcatcg ttaatttaaa cacccttcaa  118500
gtcctctctt ggaatgctgc tcagaaaaat agatgtattg tttgagaaac cctgcaggct  118560
tgtcccgcat gctctagccc cctcctgaga gaacagatag cataaaaaat gatttgtaaa  118620
gcaaggggga gcttccttag ggaagaaggg gaaggggaag agggtttggg gccaggtccg  118680
agtgcagaaa tcctcaatgc atgagactag cgtggaaggt gtagcaattg tgctctgggg  118740
tgcctgaaag tgccagagct gcttcagggg caagagtcca ggccccaagt ccatgctgat  118800
gagcccaccc tggggtcag gaatggcctc agcaggccct ccctccctcc ctctccaccc  118860
tacaaagtga ggagccttga gtcaccacca gcacattata caacaataca agaaccctgc  118920
aacagataaa gccccagcgc ctcttctgga ctcagatgcc ctaggctggc tgtctggctg  118980
tgctttccag acagtgtgta tgtggaattg tgcttttttgt tttttaagaa tgtaaaaagt  119040
tacagtaaga tcgaaccaca gggcccgtcg ctcctatggt ctctgcctga ctgggctgcc  119100
gtctgcctca gttccccaga agcttctcct ttggccatga gggctcagtc atccctcacc  119160
ccagagtcca caggaagagg gggtctgctg ggaggcctgt ctgaaggacg aggatcctg  119220
ggtcaattta gcagctattt tccagggttt ggcttgggtt tggatgctgg cttctgtgtg  119280
aaacctgaat acatgcaaat tgtacataaa actcccccaa ggcagagagg gattttccag  119340
gccctggtac atctctagag agttaaaaat gggaaatctt tcttcttaaa gtggcccaga  119400
ctgagacttt tccttgggga aaagggttag tagctctttg taaggctggt gtgtatgtgt  119460
gtgtgtatat atatatacat atatgcatga tgctgtgcaa atgcccaggg ctgtctggca  119520
ttttccacaa aatgagagcc tgagattgcc taagccttct gatgccttct ccaggcctgg  119580
aggcactgct tcattcagag gacacaaagg cctgaccacc tggctttagc aagctaggac  119640
acccagggtg gcttctttac ctttctcctc agctctgaga aggctgctag ccaagactct  119700
ggattctctg tggccacagt catatggtga gggcctcttg gagttcattc aaactttaag  119760
ggagccccac agcaccggca tgatgggtaa gtccaggcct aaggttagga agcaaatcct  119820
ggagcatgag gaaattgtag gctacagtga gctaccagtg gtgtgcaaac tggagacccc  119880
caagacagtg agagaggcca cagcatctga gggaatggag ctctttcttg gcctgaggtt  119940
cagaagaacc tgcaccaaag aaaggcatcc ctatcaatgt cactgttcct gaaatgatga  120000
gagaaccaca tccctgcttc agggaagcag tccctgtcgt ctggggcgct gagccctttg  120060
gcctgagatg aaggatgatg gtgtgatgta tcatggcagt gtgactgaga ctggattggg  120120
ggatggggac aggggaacat aggcaaaaat acacatgtgc cactggatcc tgagctgcca  120180
ttgtaccttg gaggactggc gtttctctgg gaagttggga ggtgggaaga ggaagggtct  120240
```

```
cattttcctg ccccttgaaa ccatgcttac cattccttta gaagattgct caagctgcct    120300
ccaattgcct ctttccaaaa ccaaagcata ggaaaacaag taaaaacagc tgaggctgca    120360
gcataagcaa cttaggatag agtctaggaa gcaccgccaa cagagaagac tgccaagaaa    120420 catttгgagt ttttcttctc tggaggtggg tcctggttcc tcccatggag accacgattc    120480
tgtgtagtcc tgcacgctgg gcggggatt gcctggaggt ttctttagac ctgtctagct     120540
cacacagtct tgatgcctgg gttttaggct gctgtactgt tgctgggct cacttcctgt      120600 gggtaggctg ttattttgcc cgcagatcaa gtcctcactg tctagatgcc tctatcatgg    120660
ggatctcttc ttccctctct ggatggctct gatccccaag ttatttcctg ttgcctaggt    120720
aacacctcta attggatgcc ttttaatcgt tccctttttt aaagggataa atgtggattt    120780
tatttccagg tcctgtcaga gggccctgcc ctagagaaca cgtgcgcccc tgcgtgggca    120840
atcccttcac tgtgaccgca accatggggtt ggatggggg cactcactgg gctggcctga    120900
cagtcacagt gaatcctgaa agcatggttt tcacaggaac ccaccttcag gatttagcaa    120960
gactgacgtc tctcctggcc agcgctgctt cactggcttc accccagatt agggcctgtg    121020
tttaaaaacc aatcccaact caaatcagaa attacccaaa atagctggag agtcactgag    121080
atctcaggta agctttccct tcctgccatg aactagaagg ggaaagaaga gtttgacatt    121140
caagtttgac tctaatgctg ggtgcgtgag cgcatgcgtg catgtttgtg tgtgtgtgtg    121200
ttccacgcac atttgccagg gagagagatt tcacagcatg gctccagctg gaggcggtga    121260
ggcggtgctt ttctaagact tcctatcaga agctgtgcat actggtgggt cacgccgtgc    121320
ctgtataaac tctggcacct gtccttgccc tcatcatata tgagaaaaat gggcagagag    121380
agtgttcgtt tacaccccca gaccactatc ctttcaatga agcctgggta tctggccttc    121440
ctccaggtca gggacccct atgctgcaga aggcaagtct gggagaatct gtccctcagc     121500
ccgagagcaa aactgtaatc ctaacattac ttccatccac cagtttcacc agctacctcc    121560
ctcctgcctt cctctgcctc caataggctg tgcatggaga agacaaatcc tcttgataaa    121620
caatatttag aaagggattc tatctttcct gaccccaaac acatcatggc ctctggagcc    121680
aaataccctg acatttgcaa gatggcttct tttgggttcc tggtgctgca ggccctggtt    121740
cccaaggacg cagctggcag aggtgcctcc ttcagaggag gaggaggaga agctggaggg    121800
ctgcgcccgg caaccccatg atctcttaaa ggggaaaag ttgaactgat caacagtagt    121860
taagaaaaaa aaaatccaca ccaacaaata aatatcttgt ctgagaagac tcagatattc    121920
ctggttaata ttgaaaagca ctgctgtgga tgagcttgtg aaagaaagga cggttggggg    121980
attcaagatc tgccgatccg agcctggaga tcagccagct aaaagcccag cagggctcct    122040
gcagcctcac cgctcccctc ctcacaggtg ccctggaccg cccaccatta gaagtagctg    122100
ccctgtgctc tgtgctaaat ggactaactc tgagctgaga aaggccagct aagcccctca    122160
ccactgcaat ttccaaatct gggggaaatg ccacagtccg caagttggtg ctatgtttca    122220
tctcattgca taatactaca ccattctctg tgtgtagtgg ctgttctata tatatacatc     122280
gggaggcaac atatggctgt cccaaccccc acctgtcaaa actgtgacta tatcacttct    122340
gacgaccaga aggaagctgc taggctgggc caggattcta aatgctgagg aggtaattca    122400
gagccacgaa aagttgcacc atatgctttg ggggttgccgg ctgcttctgt gcatggggac    122460
ggggtttagt gccagtctgc aaaaccctcc tcgctgcggt atgccctggg tgtgggcctg    122520
gggggccacg ttttctctcc ctgaaggaga atctgctggg ggccacggtt ctccaagagg    122580
```

```
ggactcacaa ggaacacagg cgtccccaaa acctgcccct gataacatca ggcctggcca 122640
aatagtattt ctttaaaaaa attttttttg tttcatttta ttggataaag attaagaaag 122700
cgccagcagt gactgagaga agcaaaccac gcccggcggc cccgcggcct ggagagggtc 122760
cccggcgcgg gcggacgggc ggtctacctg gaggcgctgg tctcggccag ccggttgttc 122820
atgatgccca gcgcgcccac gccgcccgag aagccgttct ggcgcgtgtt gacgcacacg 122880
ctgcgcgggt agccgttggc cgtctccgac agctgcttct gcagcagcgc cagcgacacc 122940
ttgttggagg ccgtgaggtc gcgcatggag atgagctcgc ccgagaggcg gcggccctcg 123000
gcgtcgctgt cgcgggccgc ggggtcggca ccgagcgcgg ccaggcggcg gcgcagccgg 123060
gagcctgggg tgatggcatt gcgccgggcc aggggcgcgc caggagccgg gcagcagcgc 123120
gcgcagcagc ggcagctcag cttgcgcagc atccagttga gcacctgctt gatgaggatg 123180
gagatgacgt tgaagagcga gtaaatgcag cacacgccga gcaggatgaa gaggaagttg 123240
cccaggcggt agagccctg gttccggtag gcggcgtgct ggctgctcac caggtccccg 123300
aagccgatgg tgctgaaggt gacgaagcag aagtagagcg agtccacgta gtcccagccc 123360
tccacgctgg tgtacatggc cgaggcgcag caggacagca gcacggcgaa caggcccagg 123420
atgagcagca cgtggtacac cgagggcttc cagcccgcca ggctgtcggc ctccgagagc 123480
gcggagccgc ggcggaaggt ggcgggcagc aggccgctgc ggcgcagctg gcgctcccgg 123540
caggcgcgca tgatgaaggc cagcagcgag atgatgcgct ccaggaagag gttgaagaac 123600
aggatggtcc cagcgcagcc gaacagcccg taggcgatga ggaaggcctt cccgcccacc 123660
gtcgcggggg tggtcatgcc gaaacctgtg agacagggc agggtcagcg cggtcctggc 123720
cgcgcaggtg gtcctcactg ggcgagggtg ggggtgtgg gggcggggc atgcaggtgc 123780 ttgcgcggct cctatctcga gtggcaccac tcaggtggag gaagaacagc acttagtcat 123840
ttatctccct tggtggcact taataggttt cctgatcttg gcagccccta aactgatgga 123900
ggagacatgg cccttcatct tggggaccta taaacccaag tggttgggac aggtagtcac 123960
taggaaggac ccatcatgac acaaaaaata gaaaccactg ctgcacaggt gcaaaccact 124020
gagctaccca caaagccaac aagggacacc tgctctccca ctcctccaaa tttttttta 124080 aaaactgtca tctttatttt agttcataaa tacattaata tactagtcta ggtgagtttt 124140
gttgggtgaa ttacaaatat ttacattaga aatcaaaacc aacatagatc tcttcaaaga 124200
tatctagctt cttatgtgct tgtgcacttt ttataccagt cttgttactt ggaaactcca 124260
ctgcctactt gagaatggtg aaaaaagcca agtaatctta gtgctgtgac taattttcac 124320
tttacaggca cttcgaaaag gcctttggtc aaacgatcat attttctttt ttgggggat 124380 aggttctttg tcacccaggc tggatgcagt ggtacaatca tagctcactg cagctttaaa 124440
ctcctgggct caagtgatcc ttccacctca gcctcccaag tgataggact gcaggtgtat 124500
gccaccatgt ccagtgaatt cttgtgttatt ttttctaatg gcagagaaag gaccatattt 124560
tcttagtctg ccaacatttc atgcctctgg aattgggcct aaggccaagt gggtagtccg 124620
tcacttccct agttcttaca gtgtgaatat ggggtgacaa gaaaatgtgc atttcaaatc 124680
aattcccaga tgactccaaa gtcttacata ctagaatagc agacttttct gttcaaaggg 124740 cagttttaa agagttgtca tatgtgccca attttttttc ccaagtgtgc catagatttt 124800
cggtccctcc ctgttattaa aaaaaaaatc agtttaccaa ctctgcctac taactaaagg 124860
accccaaaat taagtgtcag tgctcaaaag tcaactgcag ctcctcttct ttcctcaagt 124920
tatttggaat tgtgagtgaa tccgagccga acaactgttg actacgagtt tttctccaaa 124980
```

```
agcctggttt ttaaatgtaa cctgtagtac acctgggcag acagccttgt tagggaagca  125040
ttccataggg cttTgcctta attgggattg ttcactctgg gaccaggtag agtgtaacca  125100
ggtagctaga gttaatggtc tctgaaaaga gctttgtgag gctgacaaaa ggattgcttg  125160
agagtagtcc acccacaccc ttcagagact gagcatggct ctgccattgg gtgccggctc  125220
cttctcaacc aaggatcacc atcagtcatc cttgctcaca cttgtggcca agaaaggct  125280 ctggcccagc tgggtcctgt gctgctggta tatcaaattg ctttgttctg ggaggtctat  125340
acaactgcgt attgcttcag gcccttatcg ttgttaactt accacttgtt caaagcacag  125400
gctttaaggg tgtctttatc aattgatttc tgcagaaggt gtggctgcct gccagtgtgc  125460
tcgcccatgc catccagggc agtgcagagt ggcagctctg cctctcaact gagctccctg  125520
cccagtgctg gctgtggtct gtgggacccg tggttgcctg actctggtta tgggaggggg  125580
tttcatctct tggtggaaag attcacttac tgcttggagt ctgagctgaa aaatggatc  125640 atttgagcag caccatgata ctgttcagca agtctggcag cgatcagggg catccctgtt  125700
taatttgtgc cctatggcag aagggctacc tgtgctctgc cagtggggtg gggccagccc  125760
tgggaaagtg gagaagagtt tgtcctatgt ggcttactag tttcctaaac agactataga  125820
aaatatttct tgtaatactt tcagagtaca ttccttaagc ctatgtgcta acaatcattt  125880
tctagactgt ctgaaggaaa tgcccagttg cccgagtgtg tgttgatct tacgcttaat  125940 gactcaggtg agggggaaaat cttatgatgt tacccatgtt gaggaagatg gattatgtcc  126000
ctagatttac agaaagtgaa aaaaaccaaa atagctgtgt aaccaagaac ttgatagagg  126060
gattttgcta cattttaaag ccacactcaa gttcttgagt ttataaagaa atcagctctg  126120
aatttacatg gctataagtg gagtgggagt atatgtgtat atttataaaa cgttttagac  126180
cagtaaccta aatgtctaac aacacaacta aatgattgtc tattcataaa aaggaaaact  126240
atacagcaat taaaaagcat gaaccatagc tacttgaaac aacatggata aatctcacaa  126300
aaagaatgtg gaacaaaata agctggacac aaaataatac attctgcatt attccattaa  126360
cataaaattc aaaatcaggc caaactacag ccttttttag ggatgcatgc atggttggta  126420
aaattataag ggaaagcaag gaagtaattt tgataaaagt cagaattggg atttcctcta  126480
gagcatggca gggggtagta gctgagaggg gacatagggg acctctgggg tgctagaaat  126540 gttttgttg acctgggtgg tagttacatg tgtgttagct gtgtaataat ctgttaaatt  126600
gtatgttttg tgagttttttt tgtactcata gtgagaaaaa aattttaaac ttctagactg  126660
ttagaactct cagatacca attctgacgt acccatcact gtataggtga gggagtaggg  126720 gctgagggggc tgtgacctgc atgttgggga cagactccca cctctttgtc ctggcttcaa  126780
gcctggtgca tagatcggta tacagaacac tgcatctact cactgaggga acacaaagtc  126840
tcttatagaa ggataactct gttaaattcc taaggtaatt gaaaatcctg ggcctggaaa  126900
accaatactt tgtctaacta agaaaatact gaattggatt tttcagctaa agcctcaaag  126960
ctgagaacag tatgtgtaca tttctcccca ttctaaagag aagttccaga cacatccatg  127020
ctggacttaa taaaacagca aaacaggtct ggggctagca accccccaca ccccacctc  127080 caggctgtac ggaaaggctg gggattgatg ggatcttcca tcagttggga agttgttatg  127140
ggtagttgtt gtggcagtgg agagtgctgt ggattctttc actcacccc aggccagggg  127200 atggttggag cagggaaggt caagaggact tatgagtgt cagcaagagc ccggcagctc  127260
acttcctagc tggctgggca cagccgctca caggcctacc cagagtggag catggtgagg  127320
```

-continued

```
gttctgggag aacccggcag tgtcccctgg agtccagagc tgtgctggag agttctctgg   127380
gtgggaggct gactgggca gcccccacag gcagggagg aagagggcag tcccaggggc    127440
catctgtact tcaagggctt gcttcatcag gagatgtgag ggtgacatgg gtcaccagag  127500
ggtgacaagt ggatactgaa aggaagagat ctgaagagac tgctcaagag ggctgcctgc  127560
tggagcaagg gggccctagg aagaagaggc tgaggggcag agggctgggg acagcatgag  127620
agggagtcac aggaggaggg atggagaggg cagtgcccac tcaggggaatg ggcagggag   127680 tggtccctgt gcagggctcc caaggaccca taaatagatg ccgtgaaagc acatatgcct  127740
gttctaacag ggagccttgc agccccacca gcaaaagtta agaaggaatg atagtggctc  127800
cagtgatgta agatcacccc catgcccat ccactgcggg tcccctgagc catgtgtcag   127860
cccagagcta gaggggagg ctaaataagc tctgattaga agtgaatttg aagatttgat   127920
taaacaactg agaacgagtc tcaatcttaa aactggtact taattaacaa caacaacaac  127980 aacaaagag gccgggcgtg atggctcatg cctgtaatcc cagcactttg ggaggccaag   128040
gtgggcaggt cacttgaggt caggagttca agaccagcct gaccaatatg caaaaacccc   128100
gtctctccta aaatacaaa aaaaaaaaaa aaattagcca ggtgtggcgg cgggtgcctg   128160
tagtcccagc tactcgggag gctgaggcag gagaatgccg tgaacccagg aggcggagct  128220
tgcagtgagc cgagattgcg ccactgcact ccagcctggg caacagagtg agactccctc  128280 agaaaaaaa aaaaaagag aagaaagaa aagaacaaa gaaactggct gagcctggtg     128340
gctcacgcct gtaatccca gcactttggg aggccaaggt gggtgcatca cttgaggcca   128400
ggagttcaag accagcctgg gcaacttggc gaaactccgt ttatactaaa aatacaaaaa  128460
ttagccgggc atagtggagt gcacttgtaa tcccagctac ttgggaggct aagccaggag  128520
aatcgcttga atccgggagg cagaggttgc agtgagccaa gatcgcgcca ctgccttcca  128580
gcctgggcga cagagcgaaa ctccgtctca aaacaaaca aaaacccaa aacacaaaaa   128640 gacataaaaa ctatttggat aactctagca tttacccaag atgttaagga atctaaaagg  128700
gagttcttaa agacaataga tgagacaaag ccatttccag tgtcggccca tttaataaac  128760
tggttccacc tggattttct cttcattgtg gtgaaagcca ccacctaaca atgctggccc  128820
tgcctgcatc atcgcatgtc atcatgacaa cctatggggg agaacagctc cattcaacag  128880
atgcagaaac tgcaggttaa agggtgaaaa gcagttgcga agtccccaca gcttggaaat  128940
ggtggagccg agactgaaac ccaggtgtgc tagcatctaa agttcatgct cttttccacca 129000 cattagactg tattctgagg gcaccaagga agctccattt ttcttaagaa accaaattgc  129060
agtcctccag gaccacagcc aggggagcat cttcgtggga gagtggctgc tgctcagagt  129120
tgtgactccc atccttaaga gtcctctgtc ctctctggcc tcctttctac tgatcattgc  129180 tgtcccttc acagggaga ggggccatgg cctatcccct aaagagtctg ccaaggtaga   129240 ctcataaccct ccccgtggca cagctcagac aagctgggct atttacataa gacttgaccc 129300
agggcttgag gacagcgcga ggaatgaggt gcagaggaga ctgctgcttc tgggtgacag  129360
tctgcctggc tgaccacagc tggggtactc attggcctct tgaggccccc cacaggcctg  129420
ccctgcctga cctactcttg tgaggccaag gccatctcct ccactctctg ggggcctctt  129480
ctgactcctc caaactcttc catgtctgga ctcctggctt ctgcccaagg ccatctattg  129540
gagtttgggt ttccagttga ggatctgcct ttttcctgga tgaccaaacc tagaatgtga  129600
ccggcctcat gctccctcct cacaagggtg tggctttatc cgagggcctc agcaaggcaa  129660
ccaacaccag acatgaagct ggtaagacca acatccacct attcattcct tcagcaaaca  129720
```

```
tttactgtgg acagcatcag gttggcagta tcatgcaagg ctcagaaata tggtggaaaa   129780
ccagacagat gcagttcctg tcctcagtct ctaggctgcc ttcctagagg cccctcactg   129840
ggtttcttag cagttttgta cagatcctac cccctttgct gccagcaggc tcacctctgg   129900
gacagggcgc atatagtctg ggccagaact tgtcctgggg tcttcttacg gccctggttc   129960
agcttgcatt cagcataaca acttagctag ggagtgctgc aggccccaaa tgatgctaaa   130020
tactagacta gctgtgtaac accatctgcc cagaatgaag ggacaggtga ggcagaaggg   130080
tctccgacag cgcacagggc aaccagtgaa agcgtcctta ctgtcctgtt cctgaggtct   130140
ctctgtgcct gctttactgc ccttcgcttt cctacagagc acactcagct catcctggga   130200
gacaaggtgg gggtggagga tggtccatcc ttcttccgca tcaaggtcag taggttcaga   130260
gctctggggg ggtgctgaga ccctgggaca ggcttcctgc tgagggcact ggggcctatg   130320
cttgtgccac tgcctagcca gttgcctccc agagtagaga agcagtctcc caagctcttg   130380
caatttgtgg ggagccaagc tgctctggag aggggcctca aagcttcagc cagagaaaag   130440
gcaaacccag ccaccctgag aatctcctcc tcccccctcaa tcacaccctg cagaggcgtg   130500
atctgtccct gggttcgcac caagcctgct attttgttta tgccacaatt gatctgccat   130560
cccagtttgc aaagagcaga cacttggggg ctttattatg ccactttgac aaaagctgtg   130620
aagctcgttc ccacagcctg tctggtgccg ccttcgcaaa tggggccctg gtgatggggc   130680
cttcggagtt cagctcagag agcatggaag tgagatggag aggccagcac tgatctgtat   130740
cgtgcagccc tgggcggcag cctcggttgg gcccttgaca cactcctccc atccaggccc   130800
ccagccaccc tgtgagggag gcactattac gcccaaaaat gcaggcaagg aaatgggctg   130860
agggagggga agcattcact gaagttagtt tgtacgtggc tgagctggcc ctgaagccca   130920 tgcccttttcc acttgccaga cagatgggaa gtcttgactc attcccgct ggagactttt   130980 cctgctgggc tctgcactgt caactgtgag agagggaaat aaaacgtact gtacagtcca   131040
atctgggata cttctgagag tgaaagtggc tctactagta attccccag acagcatgt   131100 ataaaccagg gctgttccaa gcaactggga cacatgatta aaatgcagat tccatggcag   131160
gtcccgctca gaggtttatt tagtgggtca gaaaatgggc ccaggaattt cattttaaca   131220
aatgtctcca gataaatctg atgtaaatgg aatattcctt taagaatgcc attcctttaa   131280
gaaataatgt taataaggta ttccagatga ccctattggt tggaatctgt ccaactacaa   131340 atatttgat ttaaatttcc attgacctaa aattttgtg gtgggcactg cagctctctc    131400
cttaccaatc attctcccag cctgtactat attgagtagc agccaggcta cttggagaac   131460
agactgaact ccaggaatgg gctctattag tctaggccaa tcaggataat ccagttcctt   131520
accatgactg gctcaagaat gggtagacct aagtcaatca gtgcagagca ttttcatgac   131580
tacagagaaa ccatgggaag gctgaggcgt ggactcagtg ggcagggatg gaaaaagact   131640
cagaaatact gggcatggcc catggctcat tagggttgcc aggtaaaata cagaacaccc   131700
agttaaatat gacttgggta aacaagaaat cattttttaa gtataagtat gtcccaaata   131760
ttgcatagga catacttata ctaaaatata gttgattatc tgaaattcaa atttcactgg   131820
gcatgctgtc tttttatttc ctaaacctgg caacccctact catgactcca cttgtcagct   131880
tggtacactc ctctgagaag cttctcccaa tattcccatc tcatttgatc cttcctgact   131940
ggccagtgtt gggattaaga gcctcacttt aatcaaggaa cccaaggctc acacaaggct   132000
gagccctgcc cagccaggcc agcggccagg cctccccatg tccctctctc tcctaacagg   132060
```

```
gaggagtggg agatggggga gggctgtggg atggagggcg gggctgccaa cagcctgctc    132120
cgtggctgga actgcgacat cgcctctctg ggagtaggag tgggcttctg gccagactca    132180 gtggggagg  actggacact tgagagggca ctgggccaaa gacttccctg ggacatgtgc    132240
cccagccctg gtacctcagg gctgcacatg tcagccatct ccatgtcaca cccccgggga    132300
ggacaaccga ccaccgtgga caagccctga acctttgggg aaagctggtg ctaaaagaat    132360
agctggagaa gtcactactg aggactgaaa atgcggaggg tataataact gctgttgtgt    132420
atcgagcctc actatttcca cgcaccgtgc caagtgctgc acgcgtatca attcatttaa    132480
tcctcacaac aactgcatga ggctccatgt tttcactgat ccaagtcac  agcttttttc    132540 ctctcatgtt aacatctcta aaatcgtgca tcttacagtc aatggcctga tagtttattt    132600
ggcagtattt taaattccta atggtacgta ccatgatggt gtgttcataa ccaatagtgt    132660
cttagatttg atgaactata gtggggatga ttattgtccc cagttgtgag attagtaaac    132720
tgagttgcat ttaacagata aagacattga agttcagtaa cttgcccaag atcacaaagc    132780
aagcacatgg cagagatttg aaactagagg aaggagcttg caatgtgata aagcagcaaa    132840
tgtacaagag tttggaagaa ggagaggtag gttgcttttg gcaagagcag caattctcaa    132900
ttctggctgc acaatagaat cacctgggga actgaaaata tccccaatc  cccgggtgca    132960 tccagaccag tttaggtcaa catcagaact gaggccttcc tggtggaatg attaggaaag    133020
acatatggaa gaagagatat ttgtgttcag tcttaacaac tgggtggggc cgggcacggt    133080
ggctcacacc tgtaatccca gcactttagg aggctgaggc ggttggatcg cttgagccca    133140
ggagttcaag accagcctgg gcaacatagt gggaccccat ttctacaaaa aatttgaaaa    133200
tcagctgggc gtggtggcgt gtgcctgtgg tcctagctac tcaggaggct gaagtgagag    133260
gatggcttga gccctggagg tcaaggctgc agtgagccat gactgcaccc ttgcactcca    133320
gcctgggtga cagagcaaga ccctgtttaa aaaaaaaaa  aagattaggt gggatttcaa    133380
gagattgaca gggagcagag gcctaggctt gggaaaggca tccctgctg  ggacagtgca    133440 gtgcccaggg ccactgggca gggtgagggg gttcagcctg ctggtgaagc ctggcccata    133500
ggaaacgtcc agtgactctg gctgatggag caggggaatc tgtggaagaa ggcaagggac    133560
aatgctggtg aggcaggaga agagggaatt ggggtaacca aaggttaagg cgtaaaaaca    133620
gtgggtgcag ccagttctag gcaagattag gcagcacata ggccacatcc tcactcctgt    133680
gataagacag aagtttccac ttcagcctct gattgattgt gggccaagct gtcacttcag    133740
cctctgattg gtcacaggcc agtccttcat ggggtgtaac taaccctagg cctctaaagg    133800
gcacctaggg gtgctagcaa attctttag  ctttataaaa accctgggga gaggcagagg    133860
ttgcagtgag ctgagatcat gtcactgcac tccagcctgg gtgacaaagc gcgactccgt    133920
ctcaaaaaaa accccaaaa  acaaaaaaca atattcattc attcaacaaa catttatttg    133980
cacacggtgt agcaggctgt cataggcatt agggatacag ctttaaacaa aacagacaac    134040
attgactatc ctggagcaca cattctagta acaataagca aacaaacaaa tttgtaaata    134100
gcataaaaaa aaaaaaccct ggggagcact gcagtagaga ggctcttggg ccacctgctt    134160
gagtctgctc ccactttgtg gaatgtactt ttgcctcaat aaatctgtgc ttttattact    134220
gcttttttct ttttcttttt ttaaagttta ttctttgaga caggatcttg ctctgtcacc    134280
caggctggag tgcagtggta tgatcttagt tcactgcaac ctctgccccc tgggctcaag    134340
tgatcctcct gcctcagcct ccagagtagc tgggactaca ggcacccacc accacacctg    134400
gcaaccgttc ttttgttgct ttgtctttca ttgctttatt cttttgttgc tttgtaaggg    134460
```

```
tttttctatt ctttgtttaa cgtgccaaga acctggacaa ctcacagtca aggcgttcca    134520
tctggtaaca ttgggagcac ctcctagcca cctgggactc aggttgaccc tacaggagct    134580
ttgtgaagtg agcattgcct ggcactttta ggtgccagca tccaagccta gcacctggca    134640
ttgtgccctg ctctgtagaa acttctagga tctggtaagc ctcatgttca gaagacaaac    134700
tcagcaagtc ttaactcctg caggcttggg aagggcctcc ctcggagagc tgagagcaga    134760
actaggaaca gggacggtgg tttcaggctc tggcgcctcc acctgctaag gaggtgacat    134820
ggacacattc cttaccttct cggaccctcg cttctccctc taaaaatggc ccaatgccct    134880
acttatttat ttatttttta tttttttgag acaggctcac tctgtcgccc aggctggagt    134940
gcagtggtgt gatcttggct cactgcaacc tccacctccc aggttcaagc cattctcctg    135000
ccacagcctc ccaagtagct gggactacag gtgcgtgcca ccacatctgg ctaattttg    135060 tatttttagt agagacgggg ttttaccatg ttggccaggc tggtctccaa ctcctgacct    135120
caggtgatct gcccaccttg gcctcccaaa gtgctgggat tacatgagtg cgccactgtg    135180
cccggcccac tgccctacct ctgaatgtca ctgtgaagat taaatgagga tgtagttccc    135240
acatgcatcc cacagtgccc gggacatagt aagctcccca aaagcaccaa gcttagctgg    135300
gaagcacgat gggtgaggca tggaccttat ttcacagcaa agtggctcag gtgaggcagg    135360
caaggaatgg gcaaatcacg acatgacata tggatttcca tggcagggaa atgccccgt    135420 aggcacagtc aagcctggct ctaccattgg ctcgccgttc tcctacctcg ctgggcctcc    135480
atctccccac ctctggctca cttcctgctt tggcccctac gctgggtagg aggcccggct    135540
agaggttagg caccatcttt tccagtcccc aaagtgagag tgtgtgtgtg tgggagagat    135600
atttttaaat ggggctgttg tggaaaagct gagaccgtgg gctgctctat tgttggcgc    135660 ttgctggttt gtctgatttg cagagctgga tggactgctc cctgaggaca gaagctcttg    135720
gttttcttcc ctccgaagcc aggcgtgggg tgggagcatc cagtgcaccc ctcttgcatt    135780
gggtgcgcag tgatccggac agagaggctc cagtcagcca ggcacagaga aaatggccct    135840
ctgcccctgt tctgcttgtt tttgtcttgt tctctggggg cctttgaggt gactttcttc    135900
atttgatgac aacaagatgg gaggcgggga cagctgaggt ggcaggagta ggggagctag    135960
ggacagagga tgaaccccac aggctcaggc cagtgacttc taacattaga gaggttttgg    136020
ttaactggga gcaaatgcaa gtgacttctt tgaatcgact ttgtacctcg gcacagcctt    136080
ccttgctagc agggctgact tcaaccaccc cccactctgt gctttatctc tgggattaag    136140
gttttctctc ctcaccagaa atcattcagc aaaatgagtt attaaaagcc ggttaaccac    136200
tcctgcctcc gggtagctcc cgtttaacaa cctctcctgg ggagcagctg tcaagctcgg    136260
ccctgagctg gcgggaagat gactcattta catacagccc gtctccaggc cccccccacc    136320
gccaccccaa gatctgtccc tgtctccctg atgactaatc cttttccaggg atgagatcac    136380 tgcccctttc aaccccccccc cccgccccca cacacagaaa gagcagagcc ctcatctcag    136440
cccagaattt tgggagaaga ctaaatccaa gaccaaggga ggcctttgat gggacaaaga    136500
cgtgactgat gaacccggag tgaggagcaa tgagatgaag aaagctctgc ccacctaccc    136560
cgtccctcac tcctccctcc cacctcaggg cgctcatgtg gggcttgtgt ggggaacagc    136620
tccagggtca taccacctct cagaagggag acagaccagc caggcgtgag gtgacagacc    136680
agcgggcagc tcagagcagc aagacaatgt caattcaatc actttacctc aattcctcta    136740
tcacacagga ggagatttta aaaggaagtc tctggtggtt tgtaaagcaa caaatcctgc    136800
```

```
tctcaagtgg atagttccaa gccctctcaa tgaattcagt tttatacacc tggagaagca   136860
cagcctcgtc ctttccatgg agctacaagc cacatctggg ggcgtcagt gcccaggctg    136920
aggggggcacg cagagccctc ggggacgact caatgcacag aggccactcc ttaagggccc  136980
ggctccctca aactgaggtg tccccatgct tggtcttccc acagaagcca gcctggttgg   137040
ctgcttcaaa ggaggaataa agatgaggag ccatgatgca aacaaaccca caccttttcag 137100
ctgcagccag ggaggtgctc tagaggccca cggagagctg tgtgtctgct ctgctagccc  137160
gacctgcacc tgccctatgg gctggtaaag gggctgccca cagcacctca gcacatgggt  137220
ctctctctct tttcatccag cccaaaatgt caaagcacaa gggtctctgt cagggcctgg  137280
ctgtggtcac tggactgcgg ctgaggggta aggtgcaccc ctcctctaat gggggcgcac  137340
ccctcctcta atggggggtgg ggctggagct aatggcacat tccactctca gctgccacac 137400
acagatgggg aggttgatgg cccgcacaca ggaagtgagg gatggtgggg actgaattta  137460
tggagcccct atcccagacc aagcactctg ctggtacttt cacaggtgta atccccagag  137520
cagctcctgg gggaggtgtc attatgccgg tgaggaaacc aaggctcaga gaagtaaggc  137580
agcacaggtc ccagccccac tccacctctt gaggcctgac tcagccttag gttcagagaa  137640
tgcaactgtg attttttccct gagatgagca ttcaatcata ctgcgccagg gtacttgctg  137700
tggccaaaac gcctgccctg gatctgtggc atgactttgt gtcagaccct gtgcgataga   137760
aggagatgga agctgaggtt cagagacgtt aatgaccttg aaggtcaggg tcacagaaaa  137820
tggcacaacc gggattgcaa ctcagttctg cccaatttca aatctaccct cctgccacct   137880
ccttgccttg cctattgtcc ccctcccttc atatgacctg ggacccagac tccctggttt   137940
tctggaaata ttctctctcc ttttggctca ttctgtgcac tgtcccagtt ggtggtattg   138000
aggcacagct ctgccagat cactctccag ctcagctgcc ctgagctccc cagccccacc   138060
tttcaaggtc aggaatgact tatttccttt tctcttcgcc tgtctgaatc ctcgccatca  138120
tctgacagca ctttcagctc accaggcatt taactgtgtg ctgtcttgtg acagcccctg  138180
tcctgaccat tgtcccagag atttaaccct ttgtgttttt ctatgttagc ttgccagtga  138240
ggacatggcc catgtcttgg acttcttgcc accctccaga atgcaggtcc tcagggagca  138300
gctgctaaat tcccaacaga actgacagtt tgtccagtga tcaccagcag acactgtacc  138360
agaaacattg tctccatctt agtttcagtt aactcaacat gttttgaga cctgctgtgt   138420
gccagacatg agggcagggg aaggaagact atggtgaata agattgccca cagacctcca  138480
ggaacacacc tgtagtcaaa acacaattga gcttactggc tcactgcaat gaggaagctt   138540
ggccaccatg gattctgggg catctcagtc agagggtatc aaagagggct aattctagga   138600
gttgggcttg agttcttgag ttaggtgatt tatggaggac ttaaggaagc aggcttcgct   138660
ctggatggga tgctgccaaa gagcggaagt acttctatga ctgggcatct taattcttag  138720
ctggaagatg ggaacgacat agcgaggcca agctgtgatt ggccaagaag cagcagttgc   138780
tcatactaac cagatgaggg atgttggtc ttttagtgg tttggacgat gttcttgttt     138840
tggtctgtgt ttggacatga ttatggggtg aatggtcttg ttttctctc actccatctt   138900
ggtcataagg cggccttgcc tgatcagggg ttctgtgaaa tgcttatgct ccatggcaga  138960
tcctcccagc cccactgtga gtgccaggcc agctctcggc gctcagggc tgccttcatc    139020
tttctcaaaa tgctgctgtg ctttgcagcc cataatagca ttttactgga tgccattcat   139080
tatttttgt aaatgaaatt cttttccaagt gttccaattt acttggctat atatgtgcat   139140
gtgtgcacac acgcgtactt aattccgtac atggagcaca ctgctcagtt gtgaaaatgg   139200
```

```
gtgattttct ttcttttttt tttttgagat ggcatcttgc tctgtcgccc aggctggagt 139260
gcactggcgc gatctcagct ctctgcaacc tccgcctccc gggttcaagt gattctcctg 139320
cctcagcctc ctgagtagct gggattacag gcgcccacca cgacgccag ctaatttta 139380 tattttaat agagacaggg tttcatcatg ttggccagga tggtctcaat ctcttgacct 139440
cgtgatccgc ccgcctcggt ctcccaaagt gctgggatta caggcgtgag ccaccgcgcc 139500
cagctgtgat tttcatttta agtttcttct atttgctttt ataaatattt cacatttct 139560 gtggtgcaaa taggatagtt gctacttttg aaaccgtaag ttcactccca acaagcactg 139620
ttaagtttat aaataaaaat gaataagata tgatccctgt cctcatacat aatgaccaca 139680
atgccctatg aaaatgacag taagggagat gtcagggat tccgggaagc aagagaagcg 139740
gtttgggagg gtgccccaga gcaggtgcca ttggaactga gtagtgaaga tgccttagcc 139800
aggagatgga ggcagttggg cacaaggtct gcaaggtcca ggttggcatt caagggttca 139860
ggtgtcatgt ggataagact ttccaggag cacgtgtggt atgagaatga aggccctga 139920 ggaacttcag tatctaaagg gcagaagagg agtctatgaa ggagaccaca ttcattcaac 139980
aaacatttat tgagggccta ctgtggccag gaactgtgct aggcccttgg gattcaacag 140040
tgatctaaaa gacaaagtcc cctaccctca agaagcttac atttcagtat gggagatgga 140100
ataataaact acaaacaatt acgtggcctg tgagaaagtg gcaagtacta caaaaaataa 140160
aaaatagagc aggctaagag ggtgaggagt gtgcgggcag ggaggaggca ggtcatggtt 140220
ttaagtgggg tgggtccagg gaggcctcgt taaggaacgg atgtttgata aaggactagg 140280
gtaagagtgt ttcaggctag tcaacagcac gagcaaaggc cctgaggcag aggggctgga 140340
aacagagaag aaaagagtga aaaaggactg ggcatggtgg ctcatgtctg taatcccagc 140400
actttgggag gctgagacag gtggatcact tgaggtcagg agtttgagac cagcctggcc 140460
aacatggtga aacccgtct ctactaaaaa tacaaaaatt agccaggcat ggtggtgcat 140520
gcctgtaatc ccagttactt ggaaggctga ggcaggagaa tcatttgaac ccaggaggca 140580
gaggctgcag tgagcctaga ctgcaccact gcactctagc ctgggtgaca gagaaaacaa 140640
tggacaaaga gattagccag caaatccctc ctgcacactt tcaggcaaa gtttaggtga 140700 tataaatgtc cctgaaatga gaaaaaccat gactttcatt tgattttaat gtgagggaga 140760
aacataaact agtagtttta caaaagaaa aagaaatata atattcaagt agatttcaag 140820
caacagcaga tatgctgaat ttatttgata actgtcttct ttttctctgt cagcagagtc 140880
tcatgcaatt ttaaaaggaa attcgatgaa acgaacaccc atcaacatct ttaatagctg 140940
caagcaatgt ggagcaaatt ttttgtctta tttaatgtgg tcatcaccat aacccagtaa 141000
agacaatatc atcattgctc ccattttgta gacaggaaa ctgaatccag gataaataat 141060
gtagcttgca tgacaccaat cttcctcaag tctgagccag aatttatatc tcccatttct 141120
caacctcatc tctcaagcct ataatctttc agttataaga agggaaacac ttgagggtgt 141180
atcagtttgt gttttgttca tagtgtttat atgctctcaa tcaaggactg tttattaaaa 141240
aattttagga ggtggtagtc aaaaagtgtc tctggctgca gtactgggga cagactgcag 141300
gggtgagttc agcgagtcta gttcagaggc tgtggatcaa acaggtgggg tggcccgac 141360 caggagagta gccaaaaggg gactaaggaa gggaggccaa agggaggcca caaacgcagg 141420
agaggatgaa ggtgctgaag ctagaggcca ttcaggaagg aaggaatgac ggggcaaggg 141480
gtcagaaatt tctagaagaa tctagtaaga tggaaaccta acagtcctac tgggatttgg 141540
```

-continued

```
caactgggag gaagctggct ctgtgcagga aagaagggggg caccgctgtg cggacgccag   141600
actgcgaagg gctgcagaag gagccgaaag gggaagaaac ggacgcaggt aggggtggct   141660
gctgttaaag ccgcttcccg gggaggccaa ggacatccac agctgaagtg ctcaggacca   141720
tccacagctg aagtgctcag acactgcgtt ttctttatct cagagaggct gtgtgacttg   141780
cccacgtatg agtacagtgg ctaaatcaca agccctggag tcaagggttt aggttgatcc   141840
agcccccact actcactggt ggctgtcagc aagctactcg ctgtgcctca gtttccccat   141900
ctatcaagta gacagcactg ccttacagat ggttgtgggg atcagagggg aggggacagc   141960
tggcggattt agcagagtac gtggcacaga ggaaacacta aatatgcttc ttcagctcct   142020
tatcaaggtt aggcctccac aaagggtgga gcagggaaga gaaggcctca ccgggcagac   142080
ctatcttgga gaagatacaa gcaatggtgc tgaagtttca caacagtgtc aaccccctcc   142140
ctcatgtgtg tactcacagc tactcacttt cctactctgt gccagccatg aggtgtagtc   142200
actgtgccag ggggctgagt gtccggcctg ggacgtgaga gggcatgggc tcacctgctc   142260
agggtttgaa tgagaccccg gtaaccgcag cagtaaagac ccctcaaatg ccatctctaa   142320
attaaaatgg gtgatcagaa aatagcaggt gaacgatagt gccctcactg cccacagaag   142380
tgccttcagt cagatttagc gctccatctt ctgccttcct gaagggacag tggaagcatc   142440
catttgaaga ctcttcctgt gtcttctgca aaaccaaaga aaagccatca ctgccgatgt   142500
ctctcttttaa agatctgtta ggctaggcac ggtggcttat gcctgtcatg ccagcacttt   142560
gggaggccaa ggcagggggga ttgcttgagg ccaggagttt gggaccagcc tgggcaacat   142620
ggtgagactc catccctaga aacaattaaa acaaacaaa caaacaaaca aacaaaagca   142680
agctgggcat ggtggctcac acctgtagtt ccagctactc aggaggctga ggcaggattg   142740
tttgagccca ggaggtcaag gctggagtga gctgtgattc taccactgca ctccagcctg   142800
ggcaacagag tgagaccctg tctctacata aatcagtaag atccatctgt gcaattcctt   142860
cctcctagaa ttcagaatct gaggtgctgg tttcctgagg acacttgtga cttgctgcct   142920
tttattgaac tctgagtgcc ctattgccca gtttgagtgt tccaatggga agtgcagagc   142980
caccgtggcc attcattgct gtagagctgc gccccagtac ctgatacatc cctcacccct   143040
ttccaattga tttttagctt ccttcatccc tccctctttc ccttgtcctc ttcgtgtcca   143100
caggaagcct gttgggagcc tgctatggca agtgctgtgc taggacacgg tcctgcactc   143160
ttagagtttg tggttcagtt attccagttt cagcacttac attcattcaa atgctttgtg   143220
gaagcaagct ggcttttagt caccagcaat agcaatttct gaaatcacc aagccacacc   143280
aaatatatga aatatctttc tctaaggtgg tctttaaaat ttgggctgac tctcctccct   143340
ctaggaatgt tctgatgagt ttcagtctga aggcagggag atggtctcgg tgacctcctg   143400
ggcccctgtt ctgcactgaa ctgtatgccc atacattcat aggttgagat cgtaacactc   143460
cagtacctca gaatgttact gcattggtag aaaggctttt taaaaaaggg aatcaaggta   143520
aaacgaggcc attagggtga gccctaatcc aatatggctg gtgtcctcac aggaagagtg   143580
tattaagata cagacataca caaggaaaac cacgtgaaga tatggagaag gtggttgtct   143640
gcaagccaag gagagagtcc tcaggagaaa ccaaccctgc cagccccttg atcttagact   143700
tctggcctcc agaattgtga gaaaatacat ttccattgtt taagtccccc agtccgtggt   143760
actttgttat ggcagccgga aggagactgg ggccgcctgt ttgcttggct gcagaagccc   143820
cacgtggctg caccctggct cattctgttt tctgtagcag cagcagcagc agcagcggca   143880
gcagggagcc caggatgcaa agcttggttt ctgagccctg atcaggaggc tgtgtttata   143940
```

```
tttatcctgc taactgcagg ggactgttta ttcccagaga aataacctcc tgggcaggat    144000
aggggcagcc aaggaaccag ctgcttccat caggcctgct gggctcctcc aggttctcat    144060
cataccactt ctgtcgaggc tctctctgac gcagctctcc tcactccaca ccaggcttgg    144120
gcccagggc acagcctggt cttcctgagg atgctcagac gcagggaccg actgctcctc     144180
acaagcaccc tggcacatgc acagcccagg gactggagcc ttcgcaaaca agtcacagtc    144240
ctagtctgag attcagtgca acactaggcg cttagtagat gctcagtaaa cagaacaaca    144300
aggattttct tttttagttt taaaacatta gtctacccat gccttgataa actgtaaaat    144360
gcctctgcca cccattctcc cttcttgctc cctttcatgg gagctctgag gggaaggtct    144420
ctggggtggg ttccagcaac cctgggcctg ttctggggtc ctgcagccag gttgggcttt    144480
caggagccta tatttcatct gggcccagt cacactacat agattttgt tttatcacag      144540
aaatcactgc cacactgtga cccttaaggt cctcagcagg gatggcgcga ggtgagagta    144600
tcaaagccag gtgagagcac tcagatggct tctgcctttg aacgtgtgag aagctcactc    144660
atgcacagcg acaagcaaga aagacatggg aaactgacag gttttcatca ctggctagtg    144720
aaaacacatt ttatacttct gggccaacaa atacttgggt caattcacac attggcttga    144780
gaatgagttc tttttctttt tctttattta tttagagatg gggtctcact gtgttgccaa    144840
gcctggagtg cagtggctac tcacaggcac aatcataacg cgctacagcc tcaaacctct    144900
gagctcaaga gatcctccca cctcagcctc cgagtagctg ggactgtagg tgtgcactac    144960
tgtgcttggc caacgtgttc tttttgagg tgggaacttt aatttacttg agcagatgta     145020
tcaacgtagc tgtgaataag gagctaccag ggcattagac tgcagactct gacacaacca    145080
ccgtcaccac aataaatagc aacaaccacc accacaacaa gcacagacac ctacatttt     145140
ttttttttt ttagctttga ttactacact gtgttgcttt cctcactgag gcttatgtgg     145200
ggttttctgg ttttaggaat cattttcaca cacggtttat ttacatttct tcacaaccac    145260
ctagtgaggt aagcattatc ctcggttttt agatgcacaa tctgaggctc agaaaagtgc    145320
agtgtgaggt cactttgtga ataagtcata gaggtaatgt cagaatttgg gtcagagact    145380
ccacaagggc tgaccctcct tgcggttctc tgaagacact gtagaaaccc gtgggaagct    145440
ctgctgtatt gctgggtgct cctgttctgt ggcaagacaa cctagaaggt gatgggggt     145500
cttctccgag acatgtgctc tgctggctct ttggcagaaa gggcagagtc ggggatcagg    145560
acggtcatgc aggctggcac tgcccagggg ctgatcttcc aggagctggg ctagcaagct    145620
cgggatgggg gatgggtcat tccctccttc tccccactgt cactataatt ctggagatct    145680
gtaaaaggat gtttaacatg tttaaagtct tgtttccca tccttctgcc aaggattgag     145740
acatcgccca cccagcttca atcctcatag ctacttctgc cactgatggg aggaggattg    145800
aggttctttc taccaaggag ccaggaggat ggctgtcact gctcctggaa gcagggactc    145860
ccagatgtgg ggataagtac gcagggcctg ccttccctcc actcttggtg gcttccaaag    145920
gccaacattc tagaaagcca accacccatg tctcctctct ttctattgga gtgactctgc    145980
tgcttcaaca gagtattaaa aacaaagaca gccttccacc ctgacgtcag acacacagac    146040
acacgagcac gagcatcttg tactaccctg tgccccatt ccccatcagc atacgcgtgg     146100
tgtttcgggg ataaagctac accaaaggaa ccctcccata caggcttggt acagtctcag    146160
cctgtaacgc ttccctttcg aagagctgtc cctccagcaa ggcctcataa cccagggaac    146220
ccctggcatc tctgccgagg gcataaacca tattagctct gaatcataaa gaatgtttac    146280
```

```
tgagaaccac atttgggaag acctttctct ttcaaaccct ttcttcccag gcccccagtg   146340
atggctaaca ccattgttcg cagcgttcct actgaaacac attggtcgtg tgtactttct   146400
tgtctaactc atagattgca aaagctataa tttcatggga tttgttttaa gcgccctttt   146460
ctggcagatg taggctcagt atgagcactc tgtaattttc cagcctccta aatggccccc   146520
tggcagctta cataccacat ggtgtaaccc acccttttcc tatcctgcag acaacccaat   146580
tactcacaca gtcttcacca gggcctcct aggtgggtcc cccaggctag gtcctgtggg   146640
ggatgcagtt gcacttataa caaaccatgg cacatccttt ctgaggaata ctatgcatcc   146700
aacaagaggg atgcttagaa agttgattct gacatcacat accaatacac aaaaacaaaa   146760
cccaaaattc atccagaaaa tagactcaag gacaaaaaaa tccctggagt actattttag   146820
tggtgaagct aaaggctttt tttccctgtc acttttttg agcttctctc ttttcaaat    146880 gttctataag aagtatctgt tattcgagtg aattaaagac cactcgtttt gtcattattt   146940
ttaaaggcag agtctcaccg tctgggtggg gagggaagtc atacacaaga gaggagatgg   147000
caaggtgcta ggaggttaga tcatcactgg cagaaggcaa atgaaggagg aggctccatg   147060
aagcctggat gatgaaggtg ggctctgaag agggagtggg ccttagatac atgaagggta   147120
aaggacaggc agggatgctc caggcaggga gaatgctatg aatgaagact ggaggacag    147180 ttcagggtct tgctgactag tttggctgga ggaaaggctg cagtgagggt agcattagcc   147240
acacttgggc ttgaaaaggc tgggggaccac tgaaatgcaa agtagcttcc cctgaaagaa   147300
accagggagg ctgctgtcag agagtggacc ctttgggaag cctggataca gatggatgtc   147360
ttttcccaat tcagtcattt ataagtagct catatgtctc tcaattcctc atcattttcg   147420
cagcaccaac tttgtggggg agtagggga ctagctgtgg agtcagggac acctgggcta    147480
gaatctcagc tctgtcactt gctggctctt tgatctgaga aagccattga gcctcttttt   147540
gcctcaattt cctcatctgt aaatgagatg tgagctgtgc tcacctccac aggatgctga   147600
tgaggattaa atgagaagaa gtgtgtaaaa tgctcagcat agtgctaata gcatgaccac   147660
ctcaaaatgc aagccatttg tgctaactga tggacagcaa ggaacagaat ttctaaagag   147720
agtagataag aaaaaaatag agaagaggag gtcatggaat ataaagccga gactgaattg   147780
cacttaactt cttttttttt ttttctcaa ataatttgct caggggctggg gcagccagta   147840 tcatctacat gctctctccc tcagggagga acccatccaa cactaaactt ccagagaaag   147900
aggcaactat ggacagggaa aagctgtaaa tgaagcaagt gtcataagtt cttcagtaac   147960
accctctctc ttattcaaaa acttccagtg gcttcctagg gtctagaact gtgagtccca   148020
atgatcaggc ttggaatcct ttgggaactc tgcagttatt gcaaaggcat atcaatctac   148080
ttggtcacca attgttgttt gcaaccttaa ctttctccta catggttatg ctattacttt   148140
ccaaaaatat gtaaatggtt ttctgatgaa gatgcactta aaagtgctac tgaattaatt   148200
cagaggactt tgtgtgtcaa tatgcatttt ccctattaat taacggatac tgaaagtaca   148260
tgtaacttcc atcatacagg tgctgtgaaa ctattcctcg catttaaagc gattctcatg   148320 tttaaaagt tggaagcagc ctaagcaaaa tggcaaagcc ccatctctac aaaaactaca    148380
aaaattagac aggtgtggta gcgagcacct atagtcccag atactgggga ggctgaggtg   148440
ggaggatctt ttgagccagg gaggttgagg ctgcagtaag ctgtgatcat gccactgcac   148500
tccagcctgg gtgacagaga gagactctca gtgtcaaaaa aatagttggg agacttctgg   148560
ttcaagatga ttatttaatt acctcaattt acctactctc cctcttaaga tcctatttaa   148620
atgatggtaa aaggacataa aggtgtaaac tagcaataac acagggaatg ggcagagggt   148680
```

```
ttacagtgga agggcccgag aagtttcaac atgcttgtgc aagatggaca gcttgagaga  148740
gctgtaactg atgaaggcag gtggagaaac ccacagctca gagggagtac agctgagaag  148800
gggagggagg gaggggaact gccctgaaga accctggaga gacttgggtg tgggaaaggc  148860
catatagata atgggtagct gcccacccte tgccccaaaa agaaagcccg cagtccacaa  148920
gccccaccta tgcacactga gtttccagtc caattttcta tttttaattc ttaaatgtga  148980
gtggacagcc acagttcaga catttgagga aagcctgtaa gccctctctt gcagctcctc  149040
ctagcttagc ctccttcatc ttcaagggca ctgcggctca atcttcagat ctcttctttt  149100
ctggctccca cgaacacgcc ctgggactct gtggttctaa ccttgacagc aactgaaatt  149160
actctcatga ggagttttac aaaatgctaa ttcataagcc cccacttcca gagagaatga  149220
tacagttggt tagggcacaa cctgggcatc aaggcttaaa aactcccagg taattttaat  149280
atgcagccag ggttgagaac cactctccta ggtgatcttt tcttttctt tttgcgtctg   149340
ggtctggctc tattgcccag gctggagtgc aatggcacga tcatagctca ctgcatcctt  149400
gaattcctgg cctcaagtga tcctcccacc tcagcttcca gagccccta gctgacattg   149460
gcagggcttt atttatttat ttatttactt ttgagatgga gtctcattct gtcacccagg   149520
ctggagtgca gtaccatgat cttgactcac agcaacctct gcctccctgt ttcaagcgag  149580
tctcctgcct cagcctccca aatagctggg attagaggca tctgccacca tacttggcga  149640
attttttatat tttttagtaga gagggggttt caccgtgttg gccaggctgg tctcgaactc  149700
ctaccacata taagtggttc tcactcctgg ctacatatta gagttgatat ggtttggatt  149760
tgtgtccctg cccaaatctc atgttgaatt ataatcccca atgttggagg aggggcgtgg  149820
tgggaagtga ttggaacatg ggggtggatt tcccccttgc cgttctcatg atagtaagtt  149880
ctcatgagat ctggttgttt aaaagtgtgt agcaccttcc cctttgctct cttcctcctg  149940
ctccagccat gaaggacgtg tctgcttcct ctttgccttc tgacatgatt gtaagttccc  150000
tgaggcctct cctgccaagc ttcctgtagc ttgcagaacc gtaagccaat taatcttctt  150060
ttctttataa attacccact ctcaggtatc ttcttcagtg atgataacat tgctttagcc  150120
agggttaaga accagtggtc tataggctgg caaatcccaa atttgtatct caaacccaac  150180
ctgtcccttg agttctagac tggcctatcc actatctaac tggcacccgg cttggaagtg  150240
gaaaagtcat ttcagaatta acatttccaa aaccaagctc ttgattctcc ctcccaacca  150300
gcccctcctt gattccactt cagccttccc tatctcagta aatggcaaat ccatccttgc  150360
agttgctaag ggcaaaagtc ttagagccct ttttattct tttgctttct ctcacaccct   150420
acatctgatc caggaacaaa tcgtgccacc ctactgtcaa cacttatcca gattctacac  150480
actgactttc gcttcaggcc acgagggcgt agctgaatcc agcttccct cccaccataa   150540
tcaaccagga aaccggaaaa agtctatgag ataattattt tcagacattg gaaaaaaggt  150600
agttcaggat tatggtccct gagagaaggg aaacaaacaa ggtgagccct tcaaaagccc  150660
tggttttgc ctggtggcag ctttcagaca gccatgggag tggagagatc cagacagagc   150720
ccagaactct tgctgaattg aggggagaga aattcaggtt cagggaggat aaagcagctg  150780
tcactgctta actgctgtaa ctactgtgga gcactggaga ggaaggaacc atcaagaaaa  150840
aggactccag aaatctacta ggggtccctc tttgttactc gcaaaggtct gaataacaat  150900
ctgtgcaggt acagggtaaa acctagaaaa aaataagacc aaggaaaaca acttccagga  150960
aatcacaatt tccagagagc tgtaaaccaa acaatttcca gagccctcac aaagccagga  151020
```

```
atcacctgag ttcctatcag tcaaaggagg aaaggtttca ctgaatccac aaggcattca 151080
gtagagaccc caaaaaggtt attctttaat agtgtggctc atctagtccc agagaaaaga 151140
ctcctttaga cctgccttta aaaagcttaa aaacaagtct ggaaaatatc aactgatcta 151200
taaagaactg tctggcagaa caaagtccaa ccctgcttga aagagtacaa aacaatcaag 151260
catcaacaat gtaaaattca tgatgttctg atctctaata aaaatcaga tatgcaaaga 151320 agcaggaaga tgtgacccag aaataagaga aaaatagtca atagaaacag acccagaaat 151380
gccagagatt atggaattag caaaggcatt taaatacctg ttaaaatatg taaaatatgc 151440
tcaagattta aaggagaaac ataatgatga gaaaaatggg aaaaatttt ttaaaaccaa 151500 gtagaatatc tcgagatgaa aaatataggg ggctgggtgc ggtggctcac gcctgtaatc 151560
ccagcacttt gggaggccaa gatgggcgga tcacgaggtc aggagttcga gaccagcctg 151620
gccaaaatgg tgaaaccccg tctctactaa aaatacaaaa attagccagg cgcagtggcg 151680
ggcgcctgta attctagcta ctcaggaggc tgaggcagga gaattgcttg aacccaggag 151740
gcagaggttg cagtgagctg agatcgcacc actgcactcc agcctgggtg actgagcaag 151800
actccacctc gaaaaaaaaa aaaggaaaa atatcatgtc tgaaatgaaa aattcactga 151860
atagagttaa caacatacta aagactgctg aaaaaggttg aacttgaaga catagcaata 151920
gaactattca aaataaagca ctgtaaccaa aaaaagactg aaaagagcct cagctacctg 151980
cagaacaatg taaattaaga ctaacatatg tgcagttgga gttcaaaaag agaggatagg 152040
gtagcaaaaa taatatttga agcaataatg tcaatctttc caaatttgag aaaatttata 152100
aacacgcaga tccaaggagc tctataaaca caaaggaaac tacacaaagg cacatcaaaa 152160
tcaacttgtt gaaagtcagg aatgaagaga atcttaaca gcagccaaag aaaggaggca 152220
caattactta cagatagaga aaaatattca cagacttttt tttttttttt tttttttgag 152280
atggagtctt gctctgtcac ccaggctgga gtgcagtggc atgatcttgg ctctctgcaa 152340
cctctgcctc ccgggttcaa gtgattctcc tgcctcagcc tcccgagtag ctgggattac 152400
aagcgtgtcc caccatgccc ggctaatttt tgtacttta gtagagacag ggtttcacca 152460
tgctggccag gctggtctca aactcctgac ctcaagtgac ccacccgcct cggcctccca 152520
aagtgttggg attacaggtg tgagccacca cacctggcca cagacgtctt atcagaaact 152580
atgcaagcca gaaacaatc tttaaggtgc taaaagaaac aggaaaacaa acaatgaaa 152640 aaaccccac acttcagtaa atatgcattt cttttctgaa agatataatc acttctcact 152700
gcctccacca aacatgcccc ggtccaaatc atcatcatct ctcacctgga atatttcaaa 152760
agcctgctaa tgagtcccca cacttctata tttccccgt acagtttttt ttgaacagca 152820
atgagtggtc ttagaaatca gatcatgtta tgcctcttt gtctccctgc ttttttaac 152880 ctaagttttg cctcaggatc taatcatgct tcttctcaaa atcctcccgt ggctcccat 152940 ttcactcaga gtaaaaccca aaggtcttgc cgtggcctgg agaccctgca tgacctagtc 153000
tctggctact gctctgagct cacattctaa ctcccacttg cccctcctcc aaacactatt 153060
ccagacacac tggcttcctt gcggctcctc cagcaaaccc tgcaagctcc tcctaaggga 153120
ccctggcact ggctggagcc ctcttcctcc aggcagccac atggctcact cccttacctc 153180
attccaagcc tccactcagg ggtcacatca tccaagagac cctttcagac caccctactt 153240
ccatcacttt attcttaccc tggttttgtt ctttttgcag catttaccac cacctgacat 153300
ttatttgtat gtttattttc tatctccccc aactagaatg ttagctccat aagctaggga 153360
ctttgtctac ttgttcactg ctgtatccct ggggattttc agttgctggc acatagtgga 153420
```

```
gcgctcaaga aatatttgtt gaataaatgg atcaatggga atcatgtttt ctggatgcca    153480
aattagaata cagggcctgc taactgttct ggaaagtatg acgtgtgaaa tcagtattac    153540
cccctacccc acacggcacc atattttct ggagctctcc agttctagac tcgttgacac     153600
ataaaaatat tttggtgcta gtcctgggga aggcagatta ttggtttaag attcagttct    153660
agccacaggc tgcactgtgc ataaatctag gggactacat ggagttctga atgacatgtg    153720
tctcactaca gtggcattac agagaaagcc tggaaacatt acaagggagt agagccaggg    153780
ccttgtagat actggctcat tcaatcctgc aacccagagg agctgggcct cctcctgaag    153840
ggcctgcatc acctccttcc ttcttgtttg ccctgggga cgaccggtgg tggggaggtg     153900
gggggaaggt caggaactga gatagaattt atcagcgtgc tggctccgag tctgcagcta    153960 ggatgcccctt tagccacaaa cagctataaa agaataagct ttatggaaaa acattaaaaa   154020
agaaataaag caagaatgta gatggaagtg aagggactc tagggacaaa aatgctatga     154080
attaaggtca ttgccacaca ccaacctctg ctgcaccccc gcctccacca atggtagtgc    154140
ctttcccacc tgcagggcac aggggctgc cctcagcaat ctccgagcag tgaggggagg     154200
gctgccctgc tgagcccagc tttggaggag gggtatcctc ctccagcctc agcctgcttc    154260
attccccact tcctttgtgg ctgcagcatc ttcaactgcc ttcccccat tatgagacat     154320 gcccacaaat ctccagatgc attgttagaa accctgggc cctgtagagc ctggcggctc     154380
atgcctgtaa tcccaacact tgggaggct aaagtggaca gattacttga gtccaggagt     154440
tcgagaccat cctggccaac atggtgaaac cccatctcta ctaaaaatac aaaaattagc    154500
tgggcatggt ggtgcatgtc tgtaatccca gctactcagg aggctgaggc acaagaacca    154560
cttgaaccca ggaggcagag gttgcagtga gcagggatcg caccactcca ctccagcctg    154620
gatgacagag tgagactctg gctccaaaaa aaagaaaaaa aaggaaaga atcccccagg     154680 cccacggtca gcccctttgc ctagatcttc ctgtgtgggc atgatgtcaa gaatgagg     154740 gggaatggag agcaagaaga cccaagatca gcagaggtct tgttgagtct tgttgagtgc    154800
cgataaccaa attctgtctt tggctcctga aaatatctct taccccttt cttttgctcc     154860 tttccaaagg ccacatgatc ccccagttcc tatccctagt cccctctacc caattcatcc    154920
tgccacaaat attcagcatc ctgggctgcc atataaacaa atgaacaaac atttactggt    154980
tctcaggcta tgcaagggtc ctccccatga ccctgtgagg tagacctcat tgcaagagta    155040
tatagctctt cagtccaatg tgacgaattc tgctctttgt ttaaagtgtg aacaccagta    155100
gctataaaat aaaattataa cgcatagatt atgaaccact tagagcgcgt aaagaaacaa    155160
gtcatgttgg cagtcctctt gaataagttt ggaatcatat agcagttcag agctgaatat    155220
acaaactaag cacatattcc tcagtgattt atcactgata gagatatata agctgttttt    155280
tttggtgggg tggggggca cccaggatct cactctgtca cccaggcaga agtacagtgg     155340
taagctcttg ataaagtgag gggacagttg ataatggcct gatttaatgt ttgaggtgaa    155400
cagccaaaac aagggacttc acaattatct ggttgtttga aggtagttct agagactaac    155460
agtttagact aacgaggttg cctgacttaa cggcataact atatagtgac taaagtgcca    155520
gaatcttctt ctaaaatagt catgatcaca ttacacccct gttcaagaac tccagtggtt    155580
tcctgttgcc cccataccaa gtttaaatgt ttccacctgg ctttcaaagc cctccaatat    155640
gaccttaacc tattgaagca gtttcacctg tcattgttcc ttaacttgct taaggcaggc    155700
tggtcctgac ctcactcaca ctgttctttc aaacctgcct accctgcaac ctgagaggtg    155760
```

```
gcatcagaca tactggaaag aacaaaagat ctggggtcag agaactcagc tcagggttta    155820
gctttgccac ttacatgtga actcagccag attatctatt aataaaaata taagcccaca    155880
ttaaagtgct tatgaaatac cagggccaga ctaagtacct gcattcattg tctcatataa    155940
ttctcccaac caccacatga tacaggtgtt attatgattc ccattttata aatgttaaaa    156000
tggaagcttt ggaagttcat ctattcaaca aacacaaggt actgtgctag gcaatgggaa    156060
tataatagtg gacaagagag acaagaaccc tgttctcatg gagcagggag tgagcagagg    156120
tcagggaaca aacaaacaca taaacacgtt atttgctcat gaacaggatg atttccaaaa    156180
acggtacatg ttctaaggac aataaggcag aatagtgtga gggacagtga ctagggggtta   156240 gtgggggaca ctactgtaat caggggggacc agggaaggct cctcaagggt gacattttag   156300
ctttagatat gaggcttgaa tgtggttaag agaagtcagc catgccgtga ctcacagagc    156360
agtgcgccag gcagcaggaa cagcaagtgt taagtgccca gaagtctgat ctgggtaagt    156420
ccagcgtggc tgtagtgcat tgagtgaagg ggaaagcagt gccagtgagg ctaagagggg   156480
tcagggccaa attatgcagg gccttgagtg tcatggtgaa gagtcagatt ttttgcaaca    156540
ggaagtcact gaaggatttc aaacaagcaa aggacttggc ctgacttccg cttttaaaga    156600
tctctttggc tgtgtgtgaa gaacaggctg tcaaggagca tagagaaagc tgggggattg    156660
gttagaacgc taacttagtt gccccagcaa gaaatgatgg tgacagctgg agtagactgg    156720
tcgtgatggg cagcgagaca agtggatgga atcagaatgt attatgcgga ttgagctgac    156780
aagagttgat gatgaattgg atatgaaagt ttaggaaaaa aagaggaatc aggacaactc    156840
tttatatgga tgacatttat tgatatgaag actcatggag cagtgtacca aggagcagga    156900
acagcttgtg aggggaacag tcaagagtgg gatatagcag gaatcaggag ttctattttg    156960
ggcttttaaa agttttgata catattgaat atccatgtgg agatgtcaag tgggcagttg    157020
gacccatggt tctgaagctt agtgtagaag atgggttatt catcaataga taaatggggtt   157080 taaagccaaa gggtgtgagg gggatcagag tatgccatcc ccaaatatgt cactttagca    157140
caaggattgt tttgagctgc aggcaatttg gaagcagcag atgcaaagaa agctccttat    157200
cctcccctat ctgcctaaag gcaggacata aatttcccctt tgccaaggtg tcctccttac   157260
cctctctgta ctcttaatca ctggggaccc cactgtcact ctagagattt tacaagattg    157320
agtctgcata acaaacctta ctaaaaccaa agcttattct ccattagttt ccctcctata    157380
tttatcttcc cataatttac cacttctaga agtccaaact ccttttatct catcattact    157440
tcacaattta tcactctttg ttaaaatggt atacaacttc ttttttaggta attccttttc   157500 tatgaaggcc tccatatgta tatgcaataa atcttttctc ctattaatct gtcttttaat   157560
tcagggccct agcggctgaa aataagaaaa tgtaggggaa aagcttttcc tctacaggtg    157620
agagattgtt tggagacagt ccagagtgag gactgagcat ggggccctct catactgaaa    157680
ggtcacatag agatccagca aaaaggacca aggaaagcag ccagtgagga tcaaggacag    157740
catgatgttc tggaagccaa gagaaaagag gagtttgagg ataaatggtc agccatgtca    157800
aatgttgctg agatgctgag gacaggcaag tcatcactgg atttttttag gaagggggcc    157860
actagggacc ttacaataac gtagtcactg gaaaggtggg gctggactcc tgattggagt    157920
ggatccaggg gagaagggca ggtgagggag aggttgacta ctcttctcag aagctttcct    157980
gtaaaggagg gcagagaaat gggaaagtag caggagggtg atgcagggtc tattaagaag    158040
gaagaatata catgtttgca taccgatgga gtataaatta acaatgcatg gggagtgggt    158100
aatgacagga actaagccct ggaggaagtt agaggaagtg agacccagtg aagctggcat    158160
```

```
ttgtaagtgg gcacttcatc cactgccaca ggagagaaag cagctccaca tggtgggtgg 158220
atttaggggt gtgaagatta cttctgatta cttttattac ctcaatggag tgtgaaagaa 158280
aggtagttag cagagagtga ggggaatggg aggctaaaga tggaagaggg aggataagtg 158340
gtggacacag taggaagtac agtgggatgt gggggtgct gccagtgtgg agtgtccagc 158400
tggtactcag ggtcaccaat ttaaagttgg accagtcagc atctctgcat agtttgttag 158460
ccatattcag ctgcttgagg gcagatgaag aatacgtggg aagttggtat tttgataggg 158520
gtacaacata gggagagagg ggcaaggaag ttaagggtct ctgaaaaggg aatgaatcca 158580
agctgagtta aaaagaaat gcaggctcaa agaagatggt ggaaaataa gagtgggagt 158640 gtaaaggacc tgtaggtctt acagccaaag gattatgatc tcacccaaac agggtgatat 158700
cagaggatgg gagctggaag catgggaggt ggtggtcaga ggtgagatgt ttagagtcaa 158760
aaactttgaa ggtaatgcag ttactagtaa tagcaaggac atacatagat agaaccaaat 158820
gacctgctgg ggtgggatgg aaagaaatat ggttatagat gagatggtta aggagcccag 158880
ttcttggatg catcatctgt gggaggctgg agaaggctgg agaggaactc agtgaggcag 158940
acttcagtga atgggcagga gatgcatgct ggcaacccca atgacagagc ttgctatggt 159000
ttgaatgtct cctccaaaac ttacgttgaa atccaatggc tattgtaaga cttttaagag 159060
gtgagaactt taagaggtga ttggatcatg tgggttctgt tctcatgaat ggattaatgt 159120
catcatcact ggagtgggtt ggttattgcg ggagtgggct cctgataaaa ggatgagttt 159180
gggctgattc tgtcctgcac ttgctcacca tgtgatgcct tccacatgga tgactcttgc 159240
cagatgccag agccctctat cataaacttc ccagcctcca gaatggtgag tgaaatcaac 159300 tttttttgt ttgttttttt ttaataaatt acccagtctg tgatattctg ttatggaagc 159360
agaaaacaga ccaagacaag ctaaaattca tacccaagac cagggccccc agcattctct 159420
ccctaaccac tacattgtac tgcaaattgt cacttggcaa tgcagatttc ttcattctta 159480
aaatggatac atgaataatg catacctgcc cggctgaaca atgcacatca aggagctttg 159540
taaggcaatt tccgtatgtt aggcatacaa tccaatctct gcttgactgc accaagaggc 159600
ccgaacaact ccaatcagta caggtgtatg acccacttca gctcttgtta tatactctgc 159660
tgaactgcct tctgggtcat gtatattgct cactaatttg atgttaggaa ctgagatgcc 159720
ttagggattc ggggactgtg aaggtagaaa cggcagtaag gtggacttca tgcagctgct 159780
gggttcctga cattggttac aagttacatc tctctttaaa tataatgggg tatgttgctg 159840
cttacaggag ctttggaatg aatccctttg agaagcaaag ccttctttta caaagcaggt 159900
catcatctga tcatcatatt ttactttta taaaacaggt gcctaggtag agttgggaat 159960
cttggaaacg gccattcatt caaatttaca ttgattctga aaatatttct gtagcccctc 160020
ccatgtgcca tgccctgtgc caggcactgg agacatggag gggaatggag gagatagcgt 160080
tctcatcttc caggaaccca gaatctggca agagaagcag atgctaagca cacagtcaca 160140
caagtgattc catgccaaac cagcaggaag tgtgggagt gacaaagagg gtgctggcag 160200
gggcaggccc tgcagtccca cttctgcact gacacaggca aggacctctt ccctgcctgc 160260
cactgaggct gccagacctt cagaattagc tcccatgcaa tctcagcttt cttcccgac 160320 cttccatttt agaagagaac ccagcaatcc aaacctgcat ggcctccaaa atgcaccccg 160380
cccctaggaa atgccaacac actcagcaca ggcagaggcc cgtgcctacc tttcccctc 160440 gcacctgggc tgtccctgca gaattcctgg caggtcctgg tgttagcagc taaacaggct 160500
```

-continued

```
cacacgaggc gctcagaatt cagaacactt ggcagcaggg aagaggatca tggccatttg    160560
gaaaggatta gagaggagtc acgcggagtg cgattcggag tttgcgttta tctcaactga    160620
aactttccag aaagctagga caactgattc caataaaagc ttccccaagt attttggag     160680
gcattgtgat ggtgctgggc cgtgtgggtg ggggtggctt ttcctggttt gtggaattgc    160740
atttcattac tgattaaact tccgtcaaat gtgtgaagca acctccagtt tctaaggaat    160800
gtgtcctggg caggtgaaga gaaaaggcag aaccactgga ctgagaggtg gaattgagca    160860
gggcctcttt atggctaaga gatgtggcca aggccagggc cagataggaa atctgagtca    160920
gtgggaaaac taggaccaga agccccccta gttcagaact gaacttttcc tactgctttc    160980
tgagggtaac aagggctgag cttagaatt gtctagtttg gtttcagtcc agggcagggt     161040
caggataagg acccagctga ctcagagagc catggaaacg cactgccagg agggggagct    161100
ccagaatgag ctggctgccc tgctgcacac ctgccagcca ctgagagagc attaaagcaa    161160
cggcccagca gaggggctca tgcacagcca gcccctccag ctgtaggagt ggggagccca    161220
gcagggaggc cctgggaggt tctggaaacg tggtctgggc ccagcttgct cagtttttat    161280
tttttgttgt taatttccag cagtccaggg ttttcagtta ctcattcatt ccatccactc    161340
aacatatgtt gattaatcac ctactttgtg ccaagtatta tgctccatga ttgacagaaa    161400
ttacctcttt gctgcacttc gaagtagtca ttcaatgcat agctgctgcc atgatggtta    161460
ttatcatgtt attaattgta acagtgacaa gcactactaa gatgtagctt ctgaggtgga    161520
gaaagaagaa actacgtttt ctgcatacct actatgtgct gggccctggg ccagctttag    161580
acacatctta acccactgaa cggtggctta cttcgcagat ggggaagctg gcatagaaac    161640
aaatgattgg cacaggtctg agggcagtaa gagggacttc acagtaggtc cctctctagt    161700
ggcaccattt gagctggatc ttgaagactg atttcacctg gtagaaaaca gggaggaagg    161760
gaagggcatt ccaggtggag agtacagcat atgtaacagc ctagaggctt aaagtgcgag    161820
gtaaggggga cagaagttaa gggtggctag agaagagagt agcactggca ggcgcttggt    161880
gcaaggtcta ggcagggtct gtttcaggac atgaccttag gcagagtctc cctcaagcca    161940
accacccttc aggaggcgag ttctgagctg gctatgtccc caggcttttcc ttgctggtgt    162000
gcttaaggga ggccctcctg tttttttggt tttctgtccc gcctgtccat gcccactgca    162060
gctgttttcca gtgcaaggct gagggttctc aggtctgggc gggagctcgg tcctcttcaa    162120
caagttccca gagttctggt gagctctgtg ggaagcacgt gctctaccct ctccgatctg    162180
gttggcagcc tccttcacag agaggtacta ggtggcgaag gatgggaagc aggcagccct    162240
cgctttagtg tagccactga cactgccaga agcacagcac agccaaatcc cagagtcccc    162300
aaactgtgct tcagctctca ctgatgcctc ctcatcctcc tcctccaccc acacaaccct    162360
gcagaccca ggctgggcta tggttcttcc ccctctgtgg aactgcacaa ttcagagaca     162420
gcagagatct tgagcagtca ggagccgtgg atcctctatt ctgccattga ctgacttgct    162480
gtgtgatgcc aagaaagttg cttaacctct ctgagcctgt catctgtgaa atgggatata    162540
attttctttg ctgtcctagg attttttggga gcttactgag taaacacaga taaaaacaca    162600
gtgaactgga aaacatgaca tgtggcaggg aggggagtca atcagggaga ccaacaatgc    162660
ctcagttatc ccctcactc cccagaacaa aggcattggc tgctggcatg atggagagtt      162720
tggaaagggg agatactggt gggctctgtg gcctcccctg gccccagatc ctgtcctgct    162780
ccgggaggct tctgcctggg aagggggtcc cggtgcttcc tccacccacc agggagtcat    162840
ggtagccctg gggtgcaggg agcagcagcc tggcacccac acatgggct atttgctgca     162900
```

```
gtgccttcct tcagcgacct tcacccagca gccatgacac tggacccacc tcagagaagt   162960
gtggcgggac ctggcctcag ccagcatctg gcttccctgc tactcttcaa ctccatgacc   163020
tcctcctcag cctaagcact gccaagaggc ctcagcacac ctggaaacaa ggagggtggc   163080
caggattgtg gctgcccagg gctctgctcc gggtgtgggg ggcagagaag cactggatgt   163140
cactggtcta actcaccact caatcattca ttcagttatc caccaattac atccttgaca   163200
atgattaaag agcactgcgc ctatgaggga tgattaagat attctagttg aggacccaaa   163260
gaaaatgcat tttcaaaagt acccttccag gctggttatg taacagcata ggacacaaca   163320
cacccgagag gcagtgacca accagagtgc agcaggtgcc acacagcagg ggggctgagg   163380
cccagaggac tggaccatgc acagggtggt gtggccgggt gagctacagg gaaggaaatg   163440
tgccttggcc tcccctcctt cacagagagg cagggcaggg ctcaccaaca gggttgccga   163500
gatctgggga gcagatgcta ctcatggtta ccaggcactg cacccatggg ttagagcctt   163560
cagtctttaa agtaaccccca tggggtaaga accatcatgg tcttcacttt agagaggagg   163620
caactgaggc aaggagaagt atatccactc accagaacca cacagtttga atacttaaga   163680
attaggacgt gaatccaggc aagcaggctg gctgcagtgc tggtgtgttt agagtcgaca   163740
ctaaactata ctggaaggaa ggatatgagc caatagtctt cccagatata agaacatctg   163800
agctaagaag gggctcaaag gaccttgggc attcccttct tttagtaagg agaaactga   163860 ggcactgaat ggtgatatgt cctgcctaaa gccacgcagc cagttagtgg cagagccagg   163920
tctagactcc tagtgcctga ctcaccgctg ttctctctac cctagcgact ccaagtgcat   163980
cagcataggc attgccagga gctcatgagg aatgcagact gtcaggtccc accccagacc   164040
tactcaacag aaactacttg gtaagcagat tcccaggtgg ttccaggcac cttacagttt   164100
gaaaagcact gctgcatgct atcctacctt cctggtctgt aacatctgtt gctgttgagt   164160 ataagacac tgtgaacatt gtaaaatctg caattacaag attctggatg cttcatcctg   164220
aggtcacctt ggaatgagat cctctgggat ctggaggaag cagatggagg agaaacccca   164280
gggctcaatt tttctaaggg cccaggcaca ccagttacca ctgacctgct agtaagccag   164340
gaacttagcc ccatgttggg ggttggccaa gcgcagggag gaggcagcac tcacaagaca   164400
gagtccggag cattctccac cacagccagt ggccacttgg agagggacc tagagtcccc   164460 tggtaggtgg ctagggaatg gcagggtttg gggtagaact tcctgggggcc agagtctcat   164520 agcagtggta gccaagagtt ggcttagggt gagagccaag gggcttcagt acccttcttc   164580
attctctacc agcacctccc caacctcctg gaaactgctg tgcttcctgc agtttcaagc   164640
ccctccaccc cctgttcctc accaactctc cccgtgtaga aactctgcag agagtatgac   164700
cgtgtctctt aaaaaaactt tggtgaggat cagaggctgg actctgccca aagcacccac   164760
cttgggctcc acacactttc cggattgctg gctggtggcc ccatgcagag cccccgaccc   164820
cggaaagtca gtgaactgg acggaaaaaa tggaagggcc agaaaacttg gggaggactc   164880
cagagctggg ggtgacacag gaatagacca acggcctttt gttgtttcca agatcctctg   164940
aatctgaggc agccaaacaa ggcatgggag tgctgctcca ggtgtcaggg atgggtacac   165000
ttactgaaca cttacccaag gctaccacca ccatctccag atcaagcagg agtttttacc   165060
caaagccccc tcacaagtca ctcagcctgc cttctgctcc tcagataccc acccttctct   165120
ccagctcctc ccctctgtgc gtagcgcaac actcacccct tctgggaagc cttggtgccc   165180
tctcagaact gtactggatt ctctacttgt ctatgtgagc agtgtgtgtg tgtgtctgtg   165240
```

```
tgtgctgttt gtgtgagaat tatgtgtgta agaaagggtg tgggagagtg agagagatac    165300
acctaccttt ggcaatattg atgtaactct tctagggagg atgagagcgc aagctctcag    165360
ggaatccccc tttgacttgc tgggtaactt gggcaacctc tcctcctctc tgagccttgt    165420
gtaaaatgag gaacaagggt aaattcaccc gctttgggct ggtcttggag atgctctagg    165480
gctcttcaga gaagacttca gggagcgggc ggcaactgag gaaaggccca ctggtccgga    165540
ctccagcccc cacccctaat tacagcagct ctgctcctat ttgctataat gggctgattg    165600
ttggcttttg ttgacaaaat ggtctacatg cctggggaaa gttatgaagg atctttgtgg    165660
tgcttccagc tagaatactc taggagtgta cctttgctcc attcggcaca attctgagct    165720
gttcgacgcg gaggcccttg ggcatagtca agactgagtg gaaatatgtt ctctctcagc    165780
tggcttggcc caggaatagc ggcagaccat tcctgggagt ccaggggaga gcaggggat    165840 ccaggtacct ttcttgtctc agttttgat ggcctggcag tgcccccacc tgtttttct    165900 tcttaccttt ctccactctc ccagaacttc ccaaaggaag ctgctctcat taaaacaagg    165960
gaggttgaag atcctaacgc cacaggcttg ttcggggaggc agctccactc ctggaactga    166020
gtgcagtcct ggagaaaacc aagtggatgt gcggcccctt tccatggagc aattaggtgg    166080
ataactgtcc agtcgctcct aggctttgta gaggcatagg ctcagataca aagagaccag    166140
acagtctctc gctccaaagg ggctggccac aagcaccatg aagacagc                166188

<210> SEQ ID NO 6
<211> LENGTH: 32772
<212> TYPE: DNA
<213> ORGANISM: Homo sapiens

<400> SEQUENCE: 6
ctccttggtt caagtaattc tcctgcctca gactccagag tagctgggat tacaggcgcc      60
cgccaccacg cccagctaat tttttgtatt tttaatagag atggggtttc atcatgttgg     120
ccaggctggt ctcgaactcc tgacctcagg tgatccacct gcctcagcct cccaaagtgc     180
tgggattaca ggagtcagcc accgcaccca gcccaactaa tttttgtat ttgagtagag     240 acagggtttt accatgttgg ccaggctggt ctaaaactct tcacctcagg tgatccaccc     300
atctcagcct cccaaagtgt tgggattaca ggcgtgagcc accgtgcctg ccctggatt      360 tcactcttgc ccaccataa accattcact cttctgtttt aaaactctct tggccgggcg     420
cagtggctca tgcctgtaat cccagcactt tgggaggcca aggtgggcag atcacaaggt     480
caggagttcg agaccagcct ggccaatatg atgaaccccc catctctact aaaaaaatac     540
aaaaaaatta gccgggtgtg gtggcacatg cctgtaatcc cagctactcg aaggttgag      600 gcaggagaat cacttaaacc tgggaggcgg aggttgcggt gagctgagat ggtgccactg     660
cactccagcc tggacaacag agcaagactc tgtctcaaac aaacaaacaa aaaaacctc     720 tctcatggcc tggcatggtg gctcacgcct gtaatcctag cactttggaa ggctgaggca     780
ggtggatcac ctgaggtcag gagtttgaga ccagccaggc caacgtggca aaacctgtct     840
ctactaaaaa tacaaaaatt aagccaggcg cggtggctca tgcctataat cccagcactt     900
tgggaggccg agaccggcgg atcaaatgtc aggagtacga gaccatcctg gccaatatgg     960
taaaaccccg tctctatttta aaaaatacaa aaattagct gggcatggtg gcgggtgcct    1020
gtaatcccag ctactcggga ggctgaggca ggagaatcgc ttgaatccag gaggcagagg    1080
ttgcagtgag ccgagatcac gccattgcac tccagcctgg cgacagagc aagactcgtc    1140 tcaaaaaaaa aaaaaaaaca cctctctcat gacttcccaa ataaactcca aatgccttac    1200
```

```
ccataagaac caacacgacg tggctgctct tctctgtcct cacccctctg tcccctcac    1260
ttgcctcagt ctggctatac cagcattctg ggttttttgt tttgtgtttg tttgtttgtt   1320
tgtttgtttg tttgtttgtt ttgggatgga gtctcactct gtcacccagg ctggagtgca   1380
gtgacatgat cttggctcac tgcaacctcc atctcctggg ttcaaatgat tcttctgctt   1440
cagcctctca gtagctggga attacaggca cccaccatca cacccagcta attttgtat    1500
ttttgtagag atgaggtttt gccatgttgg ccaggctggt ctcaaactct tgacctcagg   1560
tgatctgccc acctcagcct cccaaagtgc tgggattaca ggtgtgagcc actgagccca   1620
gtctgttttg ttgttttttg agatggagtc tcactctgtc gcccaggctg gagtgcagtg   1680
gtacaatttt gtctgactgc agcctccacc tcctgagttt aagagattct cctgcctcag   1740
ccacacaagt agctgggatt acaggcgcgt gccaccacat gcgtctaatt ttggtatttt   1800
tagtagcgat ggggttttgc catattggcc aggctggtct cgaactcctg gcctcaagtg   1860
atctgcacac ctcggcctcc tgagtagctg ggattacagg cgtgagccac catgcagggc   1920
cttctggtc ttttaacgca caaagctatt tcccagttct gggtgtttat agtatcattg    1980
ccagttcctg gaaagctctt tccagaagcc ttcacatgac tgatccctta tcctccttca   2040
ggtcttagct caaatgcctc cttttcagag agctccttcc tgaccatttt atgcaatgtg   2100
ctttcctcta gttagtctct cttcattctg tgtatttcct tcagagcatt tatcatcatc   2160
ttggtcctga tgcttgctgg tttacatgtt tgttgtctgt ctcccacaca gaaagcaaac   2220
cagcccttca tctgtcttgt ccaccacttt atcccagcac agtgactaac atatatcagt   2280
agtcaatcaa taaatagcta taagccaggc acggtgactc acacctgtga tccccgcact   2340
ttgggaggcc aaggtgggcg gatcctctga ggtcaggaat ttgatatcag cctgcccaac   2400
atggcgaaac cccgtctcta ctaaaactat aaaaattagt cgagtgtgat ggcgtgcgcc   2460
tgtaatacca gctacttgtg aggctgaggc aggagaatcg cttgaacccg ggaggcagag   2520
gttgcagtga gccgagatca caccacagca ctccagcctg ggtgacagag caagaccttg   2580
tctcaaaaaa ataagaaata gaaatatata tatgctgcca caagaaattc actacttttt   2640
agcaaaaaac acagattcct aattaaagaa aggggaaacc tctctctaaa taacttcaga   2700
attcggggca gaaacgcta catgtggaaa ctcgtcttga aaaacagtcc cgtttgtgaa    2760
caggaaacac ttggactaca ctttttccat ctccacgaag gacttaaatg tgcagcattg   2820
atgaagaggc agttagcccc agtccttacc atttctgcat attccacctg ctcccccctca  2880
tggtacagct ctgggggcag gttataaatt cgcaagatgt tatcagcact attggtcaag   2940
atgcaggaac cgtcaggagc cctagaaaca ggggagagtt agaaagctgg ccagacctat   3000
gcttttcaag tgtagggcta gggctgagcc tgcctctggg gtaggtaagc cccctgaat    3060
ccttgaggga agtagaagac acaaactgct agataaaatg taagctcagt ctaaagggc    3120
tacgtgccgc ttctcccagc tctggggcat ccctctccta gaaaactgga ctgttttaca   3180
gtgaaaatct cgggggtggt cagctccctg ccccgttgtt atccttacca cttacagcct   3240
ttcaagaagt tctcaggttg ggtgctgaac tctgaccagg aaccactgag aaatcgaggc   3300
agctgggaga agctgtagtt ccaagcgctg aaaggaagat gggggacaat aaacctgggt   3360
cgccaagcaa aggggggcaga ggcctggaga agtgggtctc aggaccagag gacagatcga  3420
cctcacactt catctcccca gactccacac tccactgcca tcaccactta cgtgtctccc   3480
tcgtcctctg cagcgggttc cccagaggta tcttccatgg cttttccaga ccccaactct   3540
```

```
ggcccgttcg cttcttcttc agaaaggctc ccgtttgctt cttctgcagg aaggcttgta    3600
tttcagaaa gttcttgctc ctcgattcga ggactcaact cactagggga accaaactct    3660
gtttccaggg gagtggagag agaaactggg tcccctccc gtagctcctg ggacacagct    3720
gagccagcca caggatctgg ggacaaccgg ggcggatccc ccctttcggg aggcggtggc    3780
atcagttcag agtccgcatt tttattcatc ggggaagcgt ggggagaagg atgggctgga    3840
gctgggtcct ggtctgaagg acagcagtcc ggagctaacg gttgagtctc caaagtcttc    3900
atactgcaga ggaagcacag cggagattag cctcagccag gatggcttcg aagttctcag    3960
ggatccgacg cagagctaaa gaaacccacc tgtgcttccc tcctcttctg ggagtaggca    4020
gaagactccc gggaggagag gcgaacagcg gacgccaatt cttttgaaag cactgtgttc    4080
cttagcaccg cgggtcgcta cgggcctctt gctgtcgcgg gatttcggtc caccttccga    4140
ttgggccgcc gcatcccgga tcagatttcg cgggcgaccc acggaacccg cggagccggg    4200
acgtgaaagg ttagaaggtt tcccgttccc atcaagccct agggctcctc gtggctgctg    4260
ggagttgtag tctgaacgct tctatcttgg cgagaagcgc ctacgctccc cctaccgagt    4320
cccgcggtaa ttcttaaagc acctgcaccg ccccccgcc gcctgcagag ggcgcagcag    4380
gtcttgcacc tcttctgcat ctcattctcc aggcttcaga cctgtctccc tcattcaaaa    4440
aatatttatt atcgagctct tacttgctac ccagcactga tataggcact caggaataca    4500
acaatgaata agatagtaga aaaattctat atcctcataa ggcttacgtt tccatgtact    4560
gaaagcaatg aacaaataaa tcttatcaga gtgataaggg ttgtgaagga gattaaataa    4620
gatggtgtga tataaagtat ctgggagaaa acgttagggt gtgatattac ggaaagcctt    4680
cctaaaaaat gacattttaa ctgatgagaa gaaaggatcc agctgagagc aaacgcaaaa    4740
gctttcttcc ttccacccttc catatttgac acaatgcagg attcctccaa aatgatttcc    4800
accaattctg ccctcacagc tctggcttgc agaattttcc accccaaaat gttagtatct    4860
acggcaccag gtcggcgaga atcctgactc tgcaccctcc tccccaactc catttccttt    4920
gcttcctccg gcaggcggat tacttgccct tacttgtcat ggcgactgtc cagctttgtg    4980
ccaggagcct cgcaggggtt gatgggattg gggttttccc ctcccatgtg ctcaagactg    5040
gcgctaaaag ttttgagctt ctcaaaagtc tagagccacc gtccagggag caggtagctg    5100
ctgggctccg gggacacttt gcgttcgggc tgggagcgtg cttccacga cggtgacacg    5160
cttccctgga ttgggtaagc tcctgactga acttgatgag tcctctctga gtcacgggct    5220
ctcggctccg tgtattttca gctcgggaaa atcgctgggg ctgggggtgg ggcagtgggg    5280
acttagcgag tttgggggtg agtgggatgg aagcttggct agagggatca tcataggagt    5340
tgcattgttg ggagacctgg gtgtagatga tggggatgtt aggaccatcc gaactcaaag    5400
ttgaacgcct aggcagagga gtggagcttt ggggaaccctt gagccggcct aaagcgtact    5460
tctttgcaca tccacccggt gctgggcgta gggaatccct gaaataaaag atgcacaaag    5520
cattgaggtc tgagactttt ggatctcgaa acattgagaa ctcatagctg tatattttag    5580
agcccatggc atcctagtga aaactgggc tccattccga aatgatcatt tgggggtgat    5640
ccggggagcc caagctgcta aggtcccaca acttccggac ctttgtcctt cctgagcga    5700
tctttccagg cagcccccgg ctccgctaga tggagaaaat ccaattgaag ctgtcagtc    5760
gtggaagtga gaagtgctaa accagggggtt tgcccgccag gccgaggagg accgtcgcaa    5820
tctgagaggc ccggcagccc tgttattgtt tggctccaca tttacatttc tgcctcttgc    5880
agcagcattt ccggtttctt tttgccggag cagctcacta ttcacccgat gagaggggag    5940
```

```
gagagagaga gaaaatgtcc tttaggccgg ttcctcttac ttggcagagg gaggctgcta    6000
ttctccgcct gcatttcttt ttctggatta cttagttatg gcctttgcaa aggcaggggt    6060
atttgttttg atgcaaacct caatccctcc ccttctttga atggtgtgcc ccaccccgcg    6120
ggtcgcctgc aacctaggcg gacgctacca tggcgtgaga cagggaggga agaagtgtg    6180 cagaaggcaa gcccggaggt attttcaaga atgagtatat ctcatcttcc cggaggaaaa    6240
aaaaaaagaa tgggtacgtc tgagaatcaa attttgaaag agtgcaatga tgggtcgttt    6300
gataatttgt cggaaaaaca atctacctgt tatctagctt tgggctaggc cattccagtt    6360
ccagacgcag gctgaacgtc gtgaagcgga aggggcgggc ccgcaggcgt ccgtgtggtc    6420
ctccgtgcag ccctccggcc cgagccggtt cttcctggta ggaggcggaa ctcgaattca    6480
tttctcccgc tgccccatct cttagctcgc ggttgtttca ttccgcagtt tcttcccatg    6540
cacctgccgc gtaccggcca ctttgtgccg tacttacgtc atcttttttcc taaatcgagg    6600 tggcatttac acacagcgcc agtgcacaca gcaagtgcac aggaagatga gttttggccc    6660
ctaaccgctc cgtgatgcct accaagtcac agacccttt catcgtccca gaaacgtttc    6720
atcacgtctc ttcccagtcg attcccgacc ccacctttat tttgatctcc ataaccattt    6780
tgcctgttgg agaacttcat atagaatgga atcaggctgg gcgctgtggc tcacgcctgc    6840
actttgggag gccgaggcgg gcggattact tgaggatagg agttccagac cagcgtggcc    6900
aacgtggtga atccccgtct ctactaaaaa atacaaaaat tagctgggcg tggtgggtgc    6960
ctgtaatccc agctattcgg gagggtgagg caggagaatc gcttgaaccc gggaggcaga    7020
ggttgcagtg agccaagatc gtgccactac actccagcct gggcgacaag aacgaaactc    7080
cgtctcaaaa aaaagggggg aatcatacat tatgtgctca tttttgtcgg gcttctgtcc    7140
ttcaatgtac tgtctgacat tcgttcatgt tgtatatatc agtattttgc tccttttcat    7200
ttagtatagt ccatcgattg tatatccgtc cttttgatgg ccttttgagt tgtttcccat    7260
ttgcggttat gaaataaagc tgctataaac attcttgtac aattctttt gtgatcatat    7320 gttttcgtgt ttcttggaga aatacttagg aggggaattg cgagtttgga agtaaaaagt    7380
agctgtattt tgaactttt cagaagctct gagttttcca gagcggttgt accatttac    7440 actccaacta gcaaggtatg ggagttatta tggttgtgcc acagccttcc ggacattagg    7500
tattgtcagt ctttctaatg tggtatatcc ttgtggttgt aatttacagt tctctattga    7560
ctaaggatgt tcagcatttt ttcatgtgcc tattggccat tcgtattttg tttgtaaagt    7620
agctcttcga gtcttttacc tgttatttg gttttttgtt tgtttttatt gttcagttgt    7680
gggactgctt tatacattct ggatacaagt cctttatcag atccatgtgt cgtgaatgtt    7740
ttcttctgat ctgttgcttg cctatttgtt tgctttacag agtttacagt atcttaagag    7800
gagtggattt atctttttta tgttcagtat ttgccttgtc ctgtttagga catcttttttt    7860 tttttttta accccagggt catgaagata ttatcttaca ttttctttta ggacctttat    7920
ggttgtaagt tttacagtaa ggtccttgag ccattaatta attcttaaaa ttaattgttt    7980
atggtgtgag gtgtaggagt cagtctctgg tatctttcct gtatggaaat ccagttattc    8040
tgtctccact tgttgaaata ggcttccttt ctctactgaa tgcttttaat tttaattatt    8100
ttacagttgg agtatagggc taccattta gtgctatttt ctttttttct ttgttaattt    8160
ttgagacagg gactcacact gttgcccagg ctagagtaca atggcacaat caaggcttac    8220
tgcagcctcg aaccctggg ctcaagcagt cctctagcag cctcacgagt agctgggatt    8280
```

```
actccaccac acccagctaa ctattttatt tttttgtatt gacaggatct cactatgttg    8340
cccaggctgg tctcaaactg ctggcctcaa gctttcatcc catctcggcc tcccaaagtg    8400
ctgggattac aggtgtgagc caccatgcct gacctcttag tgctattttc tatttatctc    8460
ctctgttctc tgctctcttt aaacgttgga ggaagaaaca gtaccatct tacacaaact     8520 cttcagaaaa cagaggaaca gactgggcgc ggtggctcat acctgtaatc tcagcacttt    8580
ggtacgctga ggcaggggat catttgaggt cgggagttcg agaccagcct ggccaacacg    8640
gcgaaacccc atctctacta aaaatacaaa aagtagctag gcgtggtgac acatacctgt    8700
aatgccagtt actcaggagg ctgaggcaca agaatccctt gaacctggga agcggaggtt    8760
gcagtgagcc gagattgcgc cactgcactc cagcctgggc aacagagtga daccctgtct    8820
cagaaaaaaa aagaaagaaa gaaaaaatag aggaatattt cccaacttgt tttcgaagcc    8880
agcataatcc tggtaccaaa accaaacaag gacattataa gaaaagaaaa tatagaccaa    8940
tattcctgtt agcatagaca tgcaacagct aaccaatttt agcaaaccaa acctggtaat    9000
atagaaaaaa ggataaatag gccagtcgcg gtggctcacg cctgtaatcc cagcactttg    9060
ggaggctgag gcaggcagat cacttgaggt caggagtttg agaccagcct gaccaacatg    9120
gtgaaacccc gtttctaata aaaatacaaa aatcaggctg gcacggtgg ctcacgcctg     9180 taatcccagc actttgggag gccgaggtgg gcagatcacg aggtcaggag ttcaagacca    9240
gcctgaccaa tgtggtgaaa cgccatctct actaaaaata caaaaatcag ccggtgtggt    9300
ggcacctgcc tgtaatccca gctactcagg aggctgaggc agaattgctt gaacccggga    9360
ggcagaggtt gcagtgagcc aagatcgtgc cactgcactc cagcctgggc gacagagcaa    9420
gacttcatct caaaaaaaaa aaaaaattag ctgggcatgg tggtgggcac ctgaaatccc    9480
agctactcgg gagtctgagg caggagaatc gcttgaaccc aggaggcaga agttgcactg    9540
agctgggatc acaccattgc actccagcct gggcaacaga gtgagactcc atctcaaaaa    9600
aagaaaaaga aaaaggataa atacattcta accaaataat gtttatctca tgattgtagc    9660
tgattcaaca ttcaaaaatt ggcctggtgc agtagctcag gcctgtaatc ccaacatttt    9720
aggaggctga ggcaggaaga tctcttgagc ccaggatttc aagaccagcc tgggcaacat    9780
agtcagactg gtctttactg ggggaaaaa aatcagtctg tgtaattcac cacattaaca    9840
aagggaaaca taaaaccct atgatcattt caacagatgt agcaaaagca gttaatgata    9900
ttcaacacat atgcatgatt acaaaccaac caacctccta gcaaactagg gaaaggaaac    9960
ttaacctagt ttgataacag ggcgtccaca gtcggagttc cactagcagc atacataatg    10020
gtagaaaact cagtgctgcc gggcgcggtg gctcacgcct gtaatgccag cactttggga    10080
ggcctaggcg ggcggatcac gaggtcagga gatcgagact gtcctgacta gcatgctgaa    10140
accccgtctc tactaaaaat acaaaaacaa aaaattagcc gggcatggtg gcgggcgcct    10200
atagtcccag ctactcggga ggctgaggcg agagaatggc gtgaaccgg gaggcggagc    10260 ttgcagagcc tagatcgtgc cactgcactc cagcctgggt gacagagtga gacttcgtct    10320
caaaaaaaaa aaaaaaaaa aaagaaaaga aaactcaacg cttttcctc taagatcagg     10380 aactagaaaa ggatttgact ctcacaacgt tgataccata ctggaggttt taaccaggca    10440
agaaaaagaa ataatgaggg ccgggtgcgg tggctcaggc ctgtaatccc agcactttgg    10500
gaagccgaga cgggtggatc acgaggtcag gagatcgaga ccatcctggc taacacggtg    10560
aaaccctgtc tctactaaat atacaaaaaa ttagccgggc gtagtggcgg gcgcctgtag    10620
tcccagctac tcgggaggct gaggcaggag aatggcgtga actcaggggg cggagcttgc    10680
```

```
agtgagctga gatcgagcca ctgcactcca gcctgggcga cagagcaaga ctgtgtctca   10740
aaaaaaaaaa aagaaaaaga aataatgatt agtggcccga tgtctcacgc ctataatccc   10800
agcactttgg gaggccgagg tgggcagatc acctgaggtc tggagttgga gaccagcctg   10860
acaaagatgg tgaaacctcg tctctattaa aatattaaaa aaatagccag gcgttggccg   10920
ggtacagtgg ctcatgcctg taatcccagc actttgggag gccgaggtgg gtggatcacc   10980
tgaggtcagg agttcaacac cagcctggcc aacatggtga acccatct ctactaaaaa    11040
tacaaaaatt agccgggcgt agtggcgggc gcctgtaatc ccagctactt gggaggctta   11100
ggcaggagaa tcgcttgaac ctgggaggcg gaggttgtag tgagccgaga ttgcaccatt   11160
gcactccagc ctgggtgaca aaagcaaaaa ctccgtctca aaaaaaaag aattagccag    11220
gggtagtggt gaacgcctgt agtcccagct actcaggagg cagaggcagg agaatcactt   11280
gaacccagga ggcagaggtt gcagtgagcc gagattgtcc cattgcactc cagcctaggc   11340
gacaagagca aaattccatg tcaaaaaaaa aaaaaaaaa ggaaagaaaa aaaataacga    11400
ttagaaagga agaaataaaa cacattcaca gccagtatga ttctatacat acatgtccta   11460
atggggccag gcgtggtggc tcatgcctgt aatcctagca cttttaggag gctgaggcag   11520
gtggcttccc tgggaccagc ctggccaaca tggtgaaacc ccaactctaa taaaaataca   11580
aaaaatcagc caggcgtggt gacgggcacc tctaatccca gctactcagg aggctgaggc   11640
aggagaattg cttggacctg ggaggcagag gttgcagtga gccgagatcg cgctattgca   11700
ctccagcctg gcaacaaga gtgaaactcc gcagggtgt ggtggcttac gcctgtaatc     11760
ccagcacttc gggaggctga ggcaggccga tcacctgagg tcaggagttt gagaccaacc   11820
taacatggtg aaaccccgtc tctactaaaa atacaagaat tagctgggtg tagtggtggg   11880
cgcctgtaat cccagctact tgggaggctg agacagaaga attgcttgaa cccaggaggt   11940
ggaggttgca gtgagctgag atcatgccat tgcacaccac gccggcaac agagcgagat    12000
tccgtctcaa aaaaaaaaa aaagagtgaa actctatctc aaaaaaaaa aaaagtccta     12060
atggaaaatc cataaaaagc taccaaaact aataaataaa tatagcaggg ttgcaggtta   12120
cagggcaata tagttatccc tctatctgta ggggcttggt tctgggactc ctcacacacc   12180
aaacccacag atgtctaagt cccatatata agacggtata gtatttggat ttaacctaca   12240
catatcctcc catatagttt aaattatctc tagattactt acattacccc catacaatga   12300
aaatgctaat gtacatgcaa gtatgtatgt aagtacttgt actatattgt ttagggaatc   12360
actggacata taggccttca agactgatac cagcagccac tgttaagatt ctggtcaggc   12420
ctgcccctgt ttggggtctc agttgatctc attgccttcc cacccagcca agggcacctg   12480
catttctctt ggctccctgg ccatttggaa ggcctagttc agcctggcac atttgtatcc   12540
tggcccactg atgctggtac ccctgggaag gtcctgctct gaaaaacacg gagattttag   12600
ttgctactga agatttgaga gataaagaca gggagacctg tctgtagacc tgtgtccctc   12660
caagtgggat tgagactttg gccccccat ttcaggacag cacctcctgg cctgttgact    12720
gaatagatcc ctgaaggagg tgtacttgca ttaatggagt gggggtggga gcagtaccac   12780
agatccgcac taacaatcac acagttctct ctagaataat aatatagaac aagtgaaata   12840
gaacaattgc agaaagagct aacctttgtt gagctcttac tgtgtgccca gcactttcct   12900
caactctaca tttcccataa tacacagagt actaggtagg ccaggcttgg tggctcacgc   12960
ctgtaatccc agcactttag gaggccaagg ggggtggatc acctgaggtc gggagttcaa   13020
```

```
gaccagcctg accaacatgg tgaaaccccg tctctactag aagtacaaaa ttagccaggt    13080
gtggtggcac atgcttgtag tcctagctac tcagcaggct gaggcaggag aatcatttga    13140
atccgggagg aggttgcagt aagcggagat agtgccactg tactccagcc tgggcaataa    13200
gagctgagac tccgtctcaa aataaaataa aataaaataa aataaaataa aataaaataa    13260 aaaagaaaa gagcctgcca ttaaaggagc tgtttggtag gggatgtttt gtcagtgcaa    13320
acaacagaaa agtgggctgg gcacagtggt tcatgcctgt aatcccagca ctttgggagg    13380
ccaaggcggg cggatcacct gaagttggga gttcaagacc agcctgacca atatggagaa    13440
accccgtctc tactaaaaat acaaaattag ccgggcgcag tggcgcatgc ctgtaatccc    13500
agctactcgg gaggctgagg caggagaatc gcttgaacct gggaggcaga ggttgcggtg    13560
agccgagatc gcaccattgc actccagcct ggacgagagc aaaactctgt ctcaaaaaaa    13620 aaaaaaaca gaaagtgta acaaacactt acagtaggca tgtttcttag caaatctgat    13680
gacaaatttg gcataagaa agagagcatc cctgaaaaaa aaaaaagaa aaagaaagag    13740 agcatcctgc ctgggcaaca tagtgaaacc ctgcctctac aaaaaaactc aaaaattggc    13800
cgggtgcagt ggctcacacc tgtaatccca gcactttggg agtcggaggc gggaggatca    13860
cctgaggtca ggagttcgaa accagcctgg ccaacatggc aaaacccat ctctactaaa    13920 aatacaaaaa attaatcagg cgcattggtg ggcgcctgta atcccagcta ctcaggaagt    13980
tgaggcaaga ggatcgcttg aatctgggag gtggaggtta cagtgagtcg agatcacacc    14040
actgcactct agcctgggtg acagggcgag actccgtctc caaaaaaaaa aagaaaaaga    14100 aaagactaa aaaattagcc aggcaggcct ctgtggtccc agctacttgg gaggctgagg    14160
caggagaatc actgagccca ggagtccgag gctgtagtga gccatgattg caccactgta    14220
ccctagcttg ggcaacaaag caagaccctg cctcaaaaga aaaagaaag aaagaaagaa    14280 catggcgggc caggcacagt ggctcacacc tgtaatccca gcgctttgag aggccgaggc    14340
aggtggatca caaggtcagg agttccacac cagcctggcc aacatggtga aaccctgtct    14400
ctactaaaaa tacaaaaaat cagccaggca tggtggcagg ggcctgtaat cccagctact    14460
cgggaggctg aggcaggaga attgcttgaa accagaaggc agaggttgca gtgagcctag    14520
actgcaccac tgcactccag cctgggcgaa aagagccaaa ctccatctca aaaacaaac    14580 aaaaaaacaa aacaaagaa aacatggcaa agcctttgaa agcttgtctg ggagaaggtg    14640
cgatgatagt tgcataactt cgtgcaagat gctggtccac acaggggctg ccccttgctc    14700
tttctcgctc tcttaacctc tcatataaca ggcttgtgtg ttattcacat ttattgagcc    14760
caagcaggtg caaggcattg tgatctaata ctttggtcag caagacaaca agatagatca    14820
ctgccctgcc cttaggaagt gtatatgcta ttagaggaaa cagataaaat aaacaaggaa    14880
aagtatcaga caatgtaagt gctatgagaa tgcaaatgag gtgatgtgaa ttaaaatagg    14940
atgacttaaa gtctgcacgg gaaggagcct acccccatgt tcctggctag ccaaggaacc    15000
accagttgat tagcagagaa gggcagccag tctagctaga gcttttgggg aagagggagt    15060
ggttgttaag agatgagatt aaagaagccg agacgggcca ttcgtgaggg gtttgtaatg    15120
cagggctgag gagtgtccga agagaatggg caggtgagcg tgagacagt tgttcttcca    15180 gaagctttgc agtgaaagga atcaaagaaa tggagccgtg tatcaggtgg ggaagggtgg    15240
gggccaaggg ggtgtccttc cccatacaga gattgcaggc tgagaatgac tatatccttg    15300
ttaacaggag gtgggagcag ggcacggtag ctcacacctg taatcttggc actttaggag    15360
gctgaggcgg gccgatcacc tgaagtaagg agttcgagac cagcctggcc aacatgcaaa    15420
```

```
gccctgtctc tactaaaaat acaaaaatta gctgggtgtg gtggtactcg cctgtaatcc  15480
cagctactcg ggagactgag gcaggagaat ggcttgaacc cggaaggtag aggttgcagt  15540
gagctgagat catgccactg tgctccagcc taggtgacag agagagactc catctcaaaa  15600
aaaaaaaaaa aatacaggaa gggagttggg aatagggtgc acatttagga agtcttgggg  15660
atttagtggt gggaaggttg gaagtccctc tctgattgtc ttttcctcaa agaagtgcat  15720
ggctggtgag gggtggggca ggagtgcttg ggttgtggtg aaacattgga agagagaatg  15780
tgaagcagcc attcttttcc tgctccacag gaagccgagc tgtctcagac actggcatgg  15840 tgttgggggga gggggttcct tctctgcagg cccaggtgac ccaggggttgg aagtgtctca  15900 tgctggatcc ccacttttcc tcttgcagca gccagactgc cttccgggtc actgccatgg  15960
aggagccgca gtcagatcct agcgtcgagc ccctctgag tcaggaaaca ttttcagacc  16020
tatggaaact gtgagtggat ccattggaag ggcaggccca ccaccccac cccaacccca  16080 gcccccctagc agagacctgt gggaagcgaa aattccatgg gactgacttt ctgctcttgt  16140 cttttcagact tcctgaaaac aacgttctgg taaggacaag ggttgggctg gggacctgga  16200
gggctgggga cctggagggc tgggggggctg ggggggctgag gacctggtcc tctgactgct  16260
cttttcaccc atctacagtc ccccttgccg tcccaagcaa tggatgattt gatgctgtcc  16320
ccggacgata ttgaacaatg gttcactgaa gacccaggtc cagatgaagc tcccagaatg  16380
ccagaggctg ctccccccgt ggcccctgca ccagcagctc ctacaccggc ggcccctgca  16440
ccagccccct cctggcccct gtcatcttct gtcccttccc agaaaaccta ccagggcagc  16500
tacggtttcc gtctgggctt cttgcattct gggacagcca agtctgtgac ttgcacggtc  16560
agttgccctg agggggctggc ttccatgaga cttcaatgcc tggccgtatc ccctgcatt  16620 tcttttgttt ggaactttgg gattcctctt cacccttttgg cttcctgtca gtgtttttt  16680 atagtttacc cacttaatgt gtgatctctg actcctgtcc caaagttgaa tattcccccc  16740
ttgaatttgg gctttatcc atcccatcac accctcagca tctctcctgg ggatgcagaa  16800 cttttcttt tcttcatcca cgtgtattcc ttggctttg aaaataagct cctgaccagg  16860
cttggtggct cacacctgca atcccagcac tctcaaagag gccaaggcag gcagatcacc  16920
tgagcccagg agttcaagac cagcctgggt aacatgatga aacctcgtct ctacaaaaaa  16980
atacaaaaaa ttagccaggc atggtggtgc acacctatag tcccagccac ttaggaggct  17040
gaggtgggaa gatcacttga ggccaggaga tggaggctgc agtgagctgt gatcacacca  17100
ctgtgctcca gcctgagtga cagagcaaga ccctatctca aaaaaaaaaa aaaaaagaa  17160 aagctcctga ggtgtagacg ccaactctct ctagctcgct agtgggttgc aggaggtgct  17220
tacgcatgtt tgtttctttg ctgccgtctt ccagttgctt tatctgttca cttgtgccct  17280
gactttcaac tctgtctcct tcctcttcct acagtactcc cctgccctca acaagatgtt  17340
ttgccaactg gccaagacct gccctgtgca gctgtgggtt gattccacac cccgcccgg  17400 caccccgcgtc cgcgccatgg ccatctacaa gcagtcacag cacatgacgg aggttgtgag  17460
gcgctgcccc caccatgagc gctgctcaga tagcgatggt gagcagctgg ggctggagag  17520
acgacagggc tggttgccca gggtccccag gcctctgatt cctcactgat tgctcttagg  17580
tctggcccct cctcagcatc ttatccgagt ggaaggaaat ttgcgtgtgg agtatttgga  17640
tgacagaaac acttttcgac atagtgtggt ggtgccctat gagccgcctg aggtctggtt  17700
tgcaactggg gtctctggga ggaggggtta agggtggttg tcagtggccc tccaggtgag  17760
```

```
cagtaggggg gctttctcct gctgcttatt tgacctccct ataaccccat gagatgtgca    17820
aagtaaatgg gtttaactat tgcacagttg aaaaaactga agcttacaga ggctaagggc    17880
ctcccctgct tggctgggcg cagtggctca tgcctgtaat cccagcactt tgggaggcca    17940 aggcaggcg atcacgaggt tgggagatcg agaccatcct ggctaacggt gaaacccgt     18000 ctctactgaa aaatacaaaa aaaattagc cgggcgtggt gctgggcacc tgtagtccca    18060
gctactcggg aggctgagga aggagaatgg cgtgaacctg gcggtggag cttgcagtga    18120 gctgagatca cgccactgca ctccagcctg ggcgacagag cgagattcca tctcaaaaaa    18180
aaaaaaaaaa ggcctcccct gcttgccaca ggtctcccca aggcgcactg gcctcatctt    18240
gggcctgtgt tatctcctag gttggctctg actgtaccac catccactac aactacatgt    18300
gtaacagttc ctgcatgggc ggcatgaacc ggaggcccat cctcaccatc atcacactgg    18360
aagactccag gtcaggagcc acttgccacc ctgcacactg gcctgctgtg ccccagcctc    18420
tgcttgcctc tgaccctggg ccccaccct accgatttc ttccatacta ctacccatcc      18480
acctctcatc acatccccgg cggggaatct ccttactgct cccactcagt tttcttttct    18540 ctggcttttgg gacctcttaa cctgtggctt ctcctccacc tacctggagc tggagcttag   18600
gctccagaaa ggacaagggt ggttgggagt agatggagcc tggttttta aatgggacag    18660 gtaggacctg atttccttac tgcctcttgc ttctcttttc ctatcctgag tagtggtaat    18720
ctactgggac ggaacagctt tgaggtgcgt gtttgtgcct gtcctgggag agaccggcgc    18780
acagaggaag agaatctccg caagaaaggg gagcctcacc acgagctgcc cccagggagc    18840
actaagcgag gtaagcaagc aggacaagaa gcggtggagg agaccaaggg tgcagttatg    18900
cctcagattc acttttatca cctttccttg cctctttcct agcactgccc aacaacacca    18960
gctcctctcc ccagccaaag aagaaaccac tggatggaga atatttcacc cttcaggtac    19020
taagtcttgg gacctcttat caagtggaaa gtttccagtc taacactcaa aatgccgttt    19080
tcttcttgac tgttttacct gcaattgggg catttgccat caggggggcag tgatgcctca    19140 aagacaatgg ctcctggttg tagctaacta acttcagaac accaacttat accataatat    19200
atattttaaa ggaccagacc agcttttcaa aagaaaattg ttaaagagag catgaaaatg    19260
gttctatgac tttgcctgat acagatgcta cttgacttac gatggtgtta cttcctgata    19320
aactcgtcgt aagttgaaaa tattgtaagt tgaaaatgga tttaatacac ctaatctaag    19380
gaacatcata gcttagccta cctgctttt ttttttttt ttttttggaga cagagtctca     19440 ctctgtcacc caggctggag tgcagtggcg ggatctcggc tcactgcaac ctccgccttc    19500
tgggttcaag cgattctcct gcctcagccc actgagtagc tgggattaca ggcacctgcc    19560
ccgacgccca gctaattttt tgttatttat ttatttttt ttttagtaga gatgaggttt     19620
caccatgttg gccaggctag tctcgaactc ctgaccttgt gatctgcctg ccttggcctc    19680
ccaaagtgct gggattacag gcgtgagcca ccgcacccgg cctgcctagc ctactttat    19740 tttatttta atggagacag catcttgctc tgttgcccag gctggattac agtgatgtga    19800
tcatagctca ttatacccct ctgggctcaa gcaatccccc taactctgcc tccccagtag    19860
ctaggaccac aggcatacac caccataccc agctaatttt taaaattttt tgtagataga    19920
tagagtctca ctatgttgcc caggctggtc tctagcctac ttttttgaga caaggtcttg    19980
ctctgtcacc caggctggat agagtgcagt agtgcagtca cagctcactg cagcctccac    20040
ctcccaggct ccatccatcc tcccagctca gcctcccaag ttgcttcaac tacaggcctg    20100
caccaccatg cctggctaat ttttattttat ttatttttat tttatttat tttattttt    20160
```

```
tgagactcag tctcactctg tcgcccaggc tggagtgcag tggcatgatc tcggctcact   20220
gcaacctctg cctcctgggt tcaagtgatt ctcctgcctc agcctcccga atagctagga   20280
ctacaagcgc ctgctaccac gcccagctaa tttttgtatt tttagtagag acagggtttc   20340
accatgttgg ccaggctggt ctcgaacttc tgaccatgtg atccgcccgc ctcggcctcc   20400
caaagtgctg ggattacagg tgtgagccac cacgcccggc taattttttat ttatttattt   20460
aaagacagag tctcactctg tcactcaggc tagagtgcag tggcaccatc tcagctcact   20520
gcagccttga cctccctggg ctccggtgat tcaccctcc caagtagcta ggactacagg   20580
cacatgccac gacacccagc taattttttta ttttctgtga agtcaaggtc ttgctacgtt   20640
gcccatgctg gtatcaaacc cctgggctca atcaatcctt ccacctcagc ctccccaagt   20700
attggggtta caggcatgag ctaccacact cagccctagc ctacttgaaa cgtgttcaga   20760
gcatttaagt taccctacag ttgggcaaag tcatctaaca caaagccctt tttatagtaa   20820
taaaatgttg tatatctcat gtgatttatt gaatattgtt actgaaagtg agaaacagca   20880
tggttgcatg aaaggaggca cagtcgagcc aggcacagcc tgggcgcaga gcgagactca   20940
aaaaaagaaa aggccaggcg cactggctca cgcctgtaat cccagcattt cgggaggctg   21000
aggcgggtgg atcacctgag gtcaggagtt caagaccagc ctagccaaca tggtgaaacc   21060
ccgtctctac taaaatacaa aaattaaccg ggcgtgatgg caggtgcctg taatcccagc   21120
tacttgggag gctgaggcag gagaatcgct tgaaccagga ggcggaggtt gcagggagcc   21180
aagatggcgc cactgcactc cagcctgggc gatagagtga gactccgtct cagaaaaaaa   21240
agaaaagaaa cgaggcacag tcgcatgcac atgtagtccc agttacttga gaggctaagg   21300
caggaggatc tcttgagccc aagagtttga gtccagcctg aacaacatag caagacatca   21360
tctctaaaat ttaaaaaagg gccgggcaca gtggctcaca cctgtaatcc cagcactttg   21420
ggaggtggag gtgggtagat cacctgacgt caggagttgg aaaccagcct ggctaacatg   21480
gtgaagcccc atctctacta aaaacacaaa aattagccag gtgtggtagc acacgcctgt   21540
agtcccagct actcgggagg ctgaggcaca agaatcactt gaaccccaga ggcggagatt   21600
gcaatcagcc aagattgcac cattgcactc ccgcctgggc aacagagtga cccccatct   21660
caaaataaat aaataaatat ttttaaaagt cagctgtata ggtacttgaa gtgcagtttc   21720
tactaaatgc atgttgcttt tgtaccgtca taaagtcaaa caattgtaac ttgaaccatc   21780
ttttaactca ggtactgtgt atatacttac ttctcccct cctctgttgc tgcagatccg   21840
tgggcgtgag cgcttcgaga tgttccgaga gctgaatgag gccttggaac tcaaggatgc   21900
ccaggctggg aaggagccag gggggagcag ggctcactcc aggtgagtga cctcagcccc   21960
ttcctggccc tactcccctg ccttcctagg ttggaaagcc ataggattcc attctcatcc   22020
tgccttcatg gtcaaaggca gctgacccca tctcattggg tcccagccct gcacagacat   22080
ttttttagtc ttcctccggt tgaatcctat aaccacattc ttgcctcagt gtatccacag   22140
aacatccaaa cccagggacg agtgtggata cttctttgcc attctccgca actcccagcc   22200
cagagctgga gggtctcaag gaggggccta ataattgtgt aatactgaat acagccagag   22260
tttcaggtca tatactcagc cctgccatgc accggcaggt cctaggtgac cccgtcaaa   22320
ctcagtttcc ttatatataa aatgggggtaa gggggccggg cgcagtggct cacgaatccc   22380
acactctggg aggccaaggc gagtggatca cctgaggtcg ggagtttgag cccagcctga   22440
ccaacatgga gaaaccccat ctctactaaa aatacaaaag tagccgggcg tggtgatgca   22500
```

```
tgcctgtaat cccagctacc tactcgggag gctgaggcag gagaatcgct tgaacccggg    22560
aggcagaggt tgcggtgagc tgagatctca ccattacact ccagcctggg caacaagagt    22620
gaaactccgt ctcaaaaaag ataaataaag taaaatgggg taagggaaga ttacgagact    22680
aatacacact aatactctga ggtgctcagt aaacatattt gcatggggtg tggccaccat    22740
cttgatttga attcccgttg tcccagcctt aggcccttca aagcattggt cagggaaaag    22800
gggcacagac cctctcactc atgtgatgtc atctctcctc cctgcttctg tctcctacag    22860
ccacctgaag tccaaaaagg gtcagtctac ctcccgccat aaaaaactca tgttcaagac    22920
agaagggcct gactcagact gacattctcc acttcttgtt ccccactgac agcctcccac    22980
ccccatctct ccctcccctg ccattttggg ttttgggtct ttgaaccctt gcttgcaata    23040
ggtgtgcgtc agaagcaccc aggacttcca tttgctttgt cccggggctc cactgaacaa    23100
gttggcctgc actggtgttt tgttgtgggg aggaggatgg ggagtaggac ataccagctt    23160
agattttaag gttttactg tgagggatgt ttgggagatg taagaaatgt tcttgcagtt    23220
aagggttagt ttacaatcag ccacattcta ggtaggggcc cacttcaccg tactaaccag    23280
ggaagctgtc cctcactgtt gaattttctc taacttcaag gcccatatct gtgaaatgct    23340
ggcatttgca cctacctcac agagtgcatt gtgagggtta atgaaataat gtacatctgg    23400
ccttgaaacc acctttatt acatggggtc tagaacttga ccccccttgag ggtgcttgtt    23460 ccctctccct gttggtcggt gggttggtag tttctacagt tgggcagctg gttaggtaga    23520
gggagttgtc aagtctctgc tggcccagcc aaaccctgtc tgacaacctc ttggtgaacc    23580
ttagtaccta aaaggaaatc tcaccccatc ccacaccctg gaggatttca tctcttgtat    23640
atgatgatct ggatccacca agacttgttt tatgctcagg gtcaatttct ttttctttt    23700 tttttttttt ttttctttt ctttgagact gggtctcgct tgttgccca ggctggagtg    23760 gagtggcgtg atcttggctt actgcagcct ttgcctcccc ggctcgagca gtcctgcctc    23820
agcctccgga gtagctggga ccacaggttc atgccaccat ggccagccaa cttttgcatg    23880
ttttgtagag atggggtctc acagtgttgc ccaggctggt ctcaaactcc tgggctcagg    23940
cgatccacct gtctcagcct cccagagtgc tgggattaca attgtgagcc accacgtcca    24000
gctggaaggg tcaacatctt ttacattctg caagcacatc tgcattttca ccccacccttt    24060 cccctccttc tccctttta tatcccattt ttatatcgat ctcttattt acaataaaac    24120 tttgctgcca cctgtgtgtc tgaggggtga acgccagtgc aggctactgg ggtcagcagg    24180
tgcaggggtg agtgaggagg tgctgggaag cagccacctg agtctgcaat gagtgtgggc    24240 tgggggggccc agtgcccggg ttccgggagg ggaacaaagg ctggagactg ggtcagtctg    24300
cgggctgcat gacaacaagg gaggggtgg ctccattcat aactcaggaa ccaaccgtcc    24360
ctcctcccct ccggccacgg ctggcacaag gttctctccc tcccctgctt ctaggactgg    24420
gctgcttccc cctcggcagc ctctcaccaa ggattacggg attttaaatgt ctgatttagc    24480 aaggctgagc ctccagggtg gccatctgct ccatcagaaa gtggcaggat acctgggttc    24540
ccaaggggaa caggggtggg tgctactgga tggagagagg ccagtgggag gcctgctagc    24600
cagggtccca ggaaagtggg ggcagctaag gtaagagtag gggtgtgggg ctaggtcctt    24660
cccagcatcc cctcatcctg ggcctcatgc caggtagctg aatgaattga agctttaaac    24720
tctgccagga aaacctttca aagggcttct tgggatagg agagagtcg ggttgaggag    24780 ctcagtactg cctgcccatg ctcctcaggg ctgctggctc ccaggagggg gggctgggag    24840
caggcaggct cttccccatc acccactgct ctcttggagc cagtgcttga aggggcagtc    24900
```

```
agacatggct tgcccttcct cctccctggt ggtggagatg ggtgttaggg tccagtgggt   24960
gctactgtcc aggggggctt ctggggccac cagcctgtca gctcatcaac caggctgaag   25020
gtgcaagcag gagccccttg ccttgcccca aggatcccag acagctatga agccaccagc   25080
cttcctgacc tcaagaccac cttttttttt tctctttctt actagggaat gccaaacact   25140
ctccccagga gatccagacc cgcctctttc agagactttt aacttaaaca tctgtcccta   25200
cccagcaggc aaactagagc tcctgaagct cagtccctgt ccttgcctct gtagacaggt   25260
caccttgatg agcttccttt tttttttttt aattttttt tattttaggc tttattgggg    25320
cataattgat cccccaaaat tgcatacatt caaggtatgc agtgtgatga tttgatatgg   25380
gggtatattg tgaaaccatt accacaatca aattaatcag cacgtccatc atcacacaca   25440
gttaccattt gtgtgtgtgc acgtgtgttc acctacgacg aggacacttg gacctactct   25500
gcagatctca agtaaacaga aaatctccct ttttgacaac catcctccac cctttcaatc   25560 ccaaccttt cctagattat gtccctagct ctgtttttat ttctgctgtg ctgcttcaga    25620
tccattctga ctctgccaaa cccttctttg tgagctgata gattgctgga ttgagaatta   25680
cagctgggcg cggtggctca cgcctgtaat cccaacactg tgggaggcca aggccggcgg   25740
atcacttgag gtcaggagtt ggagaccagc ctgaccaaca agatgaaacc ccatctctac   25800
taaaaataca aaattagctg gcatggtgg tgcacgcctg taatctcatc ttcttgggag    25860
gctgaggcag gagaattgct tgaacccggg aggtggaggt tgcagtgagc caagatcctg   25920
ccattgcact ccagcctggg caacaacagt gaagctccat ctcaaaacac acaaaaaaaa   25980
gaagtacaaa gtctgagact tcaggccagc tctgctacac tatatactct aacctctctg   26040
gtcctacttg gtgacttctt tccctctggt cgtgttcaag ttcccgtccc atccagtcaa   26100
gcaggtactc attggtacct taccctgtgc caggagctgt tctaggccct ggaaacctat   26160
ggcagacatg ttccctaccc tcccactcaa agagcccagg ccttatccta atgagatctg   26220
aaatcaaatc tcccaatttc ctcatggctt cagtctaaac ttgtaattca aaccttaaa    26280 tcaatatgtt ctatttttt atttagaaaa catttccggc caggcacggt ggatcacacc   26340
tgtaatccca gctactcggg aggctgaggc aggagaatcg cttgaaccca ggaggcagag   26400
ggttgcagtg agccgagatt gcgccattgc actctagcct gggcaacaga gcaagactcc   26460
atctcaaaaa agaaaaaaaa atggaagaaa aaaaatttc cccctcattt taggaacacg    26520
aggtctccaa atctaaaatt cgtactctga ggagattgaa tagccttaaa tgctttcatc   26580
attaaaaaga aagaaagga acctggtatg catcctaaaa atgaaaaata tacctacctg    26640
taatcccagc acacagcaca ttgggaggct aaagcaggag gataacttga ggccaggagt   26700
ttcagatcag cctgggcaac atagcaacac cccatttctt tttcttttct ttttttttg    26760 gagacacagt ctcgctctgt tactcaggct ggagtgcagt ggctcaatct cagctcactg   26820
caagctctgc ctcccaggtt catgccattc tcctgcctca gctcccgag tagctgggac    26880 tacaggcgcc cgccaccacg cctggctaat tttttgtatt tttagtagag acagggtttc   26940
accgtgttag ccaggatggt ctcgatctcc tgacctcgtg atccgccagc cttggcctcc   27000
taaagtactg ggattacagg cgtgagccac tgcgcctggc cacaacaccc catttctatt   27060
ttaataaaat aaaatactgt gaaaaacatt tacaattttt aaattttaat tttaaaatta   27120
aacttatatt tattcatttg tgtgtgtggg ttttttttt tttttttttt tgcttttttt    27180
ttgagatgga gtgtcactct gtcacccagg ctggagtgca gtggcgtgat ctctgcctcc   27240
```

```
cggttcaagt gattctcctg ccatagcctc ccaagtagct gggactacag gtacacgcca   27300
ccacgccggg ttaattttg tattttagt agagacagga tttcactgtg tcgccaggct    27360
agcctcgaac tcctgacctc aggtgattcg cccaccttgg cctcccaaag tgctgtgatt    27420
acaagcgtga gccaccgtgc ccagcccaaa gttggtttta atagcagaaa atctatcaac    27480
ataattcaat atattaaatt tagaaagaaa aattatctat catatcaaca gatactgaaa    27540
ggaatttgat taaatttcag tagccatttc cttaaaaaag aaaacacttt aacacagtaa    27600
tagactgata atggaatacc aattttccta ataagttaaa cattaagata atttcaatta    27660
aggtcaagag ctgggccagg tgcagtggct cacacctgta atcccaacac tttggaggcc    27720
aaggtgggtg gatcacctga ggtcaggagt ggagaccagc ctggctgaca atagtgaaat    27780
cctgcctcta ctaaaaacac aaaaaattag ctgggcatgg tggtgggcac ctataatccc    27840
agctactggg aaggctgaga caggagaatt gcttgaacct gggaggcgga ggttgcagtg    27900
agcaaagatc acaccattgc actccagcct gggcgacaga gccagagtca gtctcaaaaa    27960 aaaaagagg tggccacacc tataatccaa acattttgtg aggccaaggc aggagaattg    28020
cttcaggcca agagttgaac acctcgtcaa catagccaga cctctctcta gatagataga    28080
tagatgatag atagagagat agatagatga tagatagaga gatagataga tgatagatag    28140
atagatagat agatagatag atagatagat agatagatag atagatagat aatctggccg    28200
ggtgtggagg ctcacgcctg taatcccagc actttgggag gctgaggcgg gcagatcacg    28260
aggacaagag attgaaacca tcctggctaa caaggtgaaa cccgtctctc actaaaaata    28320 caaaaatta ggcgggtgtg gtggcacgcg cctgtagtcc tagctattca ggaggctgag    28380
acaggagaat tgcttgaatc cgaaaggcgg aggttgcagc gagccgagat cgtgccactg    28440
cactccagcc tgggtgacag agcaagactc catctcaaaa taaataaata aataatcaag    28500
aacagtataa ggggctgtat ggtggctcat gcctgtgatc ccagcacttt gggaggccaa    28560
ggtgggagga tcccttgaga ccagcccagg caacagagaa agaccctgtc tctatttaaa    28620
aaaattaaaa actggccggg cacggtggct cacgcctgta attccagcgc ttgggaggcc    28680
aaggcaggca catcaggagg tcaggagttc gagaccagcc tggccaacgt ggtgaaaccc    28740
cgtctctact aaaaatacaa aaagtagcta ggcgtggtgg caggcacctg taatcccagc    28800
tacttgggag gctgaggcag gagaatcgct tgaacccagg aggcggaggt tgcagtgggc    28860
aaagatcgtg ccattgcact cagcctgggt gacagggcaa gactccatct caaaataaat    28920
aaacaaagta attaattaat taaattaaaa actgtgggga tatagactta ctctggtttt    28980 atttttctt ttcttttctt ttcttttttc tgagacggag tctcgctctg ttgcccaggc    29040
tggagtacag tggcgtggtt tctgttctct gcaacctcca cctcccggat tcaagcgatt    29100
ctcttgcctc agcctcttga atacctggaa ttacaggtgc ctgccaccac ccccggctaa    29160
ttttttgtat ttttagtaga cagggttt caccatgttg gccaagctgg tctcgaactc    29220
ctgacctcat gatccacccg cctctgcctc ccaaagcact gagactacag gagtgagcca    29280
ctgtgcccag cctactctgg ttttagtgca ttcaagagga acaaaaaagg aagaaaatca    29340
ctagtaaata tacctctttc tggttagagt ggatgtttgg aaattatata tatattatat    29400
tatattatat atattatata tatacacaaa cacgtacata catgcacaca catatatgcc    29460 ttttgatta taggatagta taccaaaact cagaaatatt atggaattaa cagaatttag    29520
taaggcagat aagtagtagg tagaaaaata ttaattttat cttccagcag aagcactgtg    29580
aaaaattaga caacaagaaa acattccatt caaaataatg acaataaggc cgggcatggt    29640
```

```
ggctcacacc tgtaatccca gcactttggg aggctgaggc aggaggatca tctgaggtca    29700
agtttgagat cagcctggcc aacatggtga caccctgtct ctactgaaaa tacaaaaatc    29760
agccagctat ggtagtgtaa gcctgtaatt ccagctactc gggaggtcga agcagaagaa    29820
tcacttgaac ccaggaggca gagattgcag tgagccaaga tcctgccagt gctttccagc    29880
ctgggcaaca gtgtgaggct ccatctcaaa aaaaaaaaa aaaaaagac aatagcaata      29940 aacattaaga aatgtgtaat aggaatggca cacacaaaga aggaatggca cagagcctgt    30000
atgcagaaga ccacaaaccc ttatttaacg acgtaagcca agatccaaag aaaatgatag    30060
attctcagat gggaaaacta aaaaaataag aaaaatcaat tatctcgaga taaatataat    30120
ataatgcaat ttcaattaga atcccaaatt ttcattgtgt gtgtgtgtga gttgggtaaa    30180
tttatcataa atgtatagga acgagtaagt gtcactagtt gtttaaataa atactggatt    30240
tgggccaggc atggtggctc acgcctctaa tcccagcact ttgggagacc gaggcgggca    30300
gatcatgagg tcaggagatc gagaccatct ggccaacata gtgaaaactc gtctctacta    30360
aagatacaaa aaattagctg ggcatggtgg cacgtgcctg tagttccagc tactctggag    30420
gctgaggcag gagagttgct tgaacccggg aggtggaggt tgcaatgagc cgagatcctg    30480
tcactgcact ccaccctggc gacaaagtga gactccgtct ctctctctct ctttaggcca    30540
aggcaggtgg atcacctgag gtcaggagtt caagacagcc tggccaacat agcgaaatcc    30600
catctctact aaaaatacaa aaattagcct ggcagtggtg gcccacgcct gtaatcccag    30660
ctactaaggg ggctgaggca ggaggatctc ttaaccaggg aggaggaggt tgcagtgagc    30720
agagattgtg ccactgcact ccagcctgtg caacagagtg agactctgtc tcaaaaaaaa    30780
taaataaaca aaatactgga ggccgggcac ggtggctccc gcctgtaatc ccagcacttt    30840
gggaggccaa ggcgggtgaa tcgctttcag ctcaggagtt ccggaccagt ctgggcaaca    30900
tggcaaaacc ccgtctatac taaaaataca aaacttagcc aggcgtggta gtgcatacct    30960
ataatcccag ctactcgaga ggctgaggca ggagaatccc ttgaaaccgg gaggcagagg    31020
ttgcagtaag ctgaaatcgt gccactgcac tccagcctgg acgacacagc gggagactgt    31080
ctcaataaat aaaataaata atataaaata acataaataa taaaattgta aataataagt    31140
aaataataag caacagaatg gagaggggt cctatttgcc ttgccagatt ttagagaact     31200
tagtataggc taggcaggtg cagtggctca cgcctgtaat cccagcactt tgggagtcca    31260
aggcagtgga tcacatgagg tcaggagttc aagaccagcc tgaccaacat ggtgaaaccc    31320
catctctact aaaaatacaa aattagccag gcatggtggc acatgcctgt aatcccagct    31380
acttgggagg ctgaggcagg agaatcactt gaactcgaga ggtggaagct gcagcgagct    31440
gagatcacgc tactgtactc cagcctgggc aacaagagtg agactccatc aaaaaaaaaa    31500 aaaagaaac gagaaaaaaa aaagaaaac ttactatata actgctggaa tgaggtggat      31560
gtgacatatg gagtggtaga caaaccaagg aaagcaagta acaaatacag gagatgttct    31620
catacaggag aattattaca tggccaaaat tagcatttca atttaattgg aacacattag    31680
atatatttgt tctttttgttc ttttttgttat cttttttttt tttttttttt tttttttttt 31740
gagacagagt ttcgctctca ttgcccaggc tggagtgtaa tggtgtgatc ttgactcacc    31800
gcaacctccg cttcctacgt tgaagtgatt ctcctgcctc agcctcccga gtagccggga    31860
ttacaggcat acgccaccac acctggctaa ttttttttgc attttcagta gagacagggt    31920
ttctccatgt tgatcaggct ggtttcgaac tcctgagctt aggtgatccg cccacctcag    31980
```

```
                                                                           -continued cctcccaaag tgctgggatt acaggcgtga gccactgtgc ccggcccta  tctctttttt   32040 tgtttgtttg ttttctgaga tggaatctgg ctctctcacc caggctagag tgcaatggca   32100
cgatgttggc tcactgcaac atccacgtcc cgggttcaag cgattcttct gcctcagcct   32160
cccaagtagc tgggattaca ggtgcctgtc gccacatcca gctaattttt tgtatttta    32220 gtagagacag ggtttcaccg tgttccccag gctggtctca aactcctgag ctccggcaat   32280
ccacccgcct cggcttccca aagcgctagg attacaggcg tgagccaccg cacctggccc   32340
ctatctctta aaaatatatt tttttgccca acacacattt ccaagttgcc ttgggggaaa   32400
aaaaataaat gaagctggca caactgaaaa aataaaactg gggccttggc caggcacagt   32460
ggctcaggcc tataatccca gcactttggg aagctgaggt gggaggatca cttgaggtca   32520
ggagttcgag accagtctgg ctaacacggt gaaaaccctt ctctactaaa aatacaaaag   32580
tcagccaggc gtagtggtgt gcacctgtaa tcccagctac tcaggtagct gaggcatgag   32640
aatcacatga acctggaaag tggaggttgc agtgagccga gattgcacca ctgcactcca   32700
gcctgggtaa ggaaatgaga ctctgtctcc aaaaaaaaaa aaaagatact acaaagtcaa   32760
gagacaaaca at                                                      32772
```